US010913706B2

(12) United States Patent
Malkas et al.

(10) Patent No.: US 10,913,706 B2
(45) Date of Patent: *Feb. 9, 2021

(54) PCNA INHIBITORS

(71) Applicant: City of Hope, Duarte, CA (US)

(72) Inventors: Linda H. Malkas, Duarte, CA (US); David Horne, Altadena, CA (US); Robert J. Hickey, Duarte, CA (US); Long Gu, Duarte, CA (US)

(73) Assignee: CITY OF HOPE, Duarte, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/714,062

(22) Filed: Dec. 13, 2019

(65) Prior Publication Data
US 2020/0216386 A1 Jul. 9, 2020

Related U.S. Application Data

(63) Continuation of application No. 15/760,959, filed as application No. PCT/US2016/052310 on Sep. 16, 2016, now Pat. No. 10,550,070.

(60) Provisional application No. 62/340,964, filed on May 24, 2016, provisional application No. 62/313,592, filed on Mar. 25, 2016, provisional application No. 62/220,014, filed on Sep. 17, 2015.

(51) Int. Cl.
| | | |
|---|---|---|
| *C07C 233/76* | (2006.01) | |
| *C07C 237/22* | (2006.01) | |
| *C07D 217/26* | (2006.01) | |
| *C07D 401/12* | (2006.01) | |
| *A61K 31/4418* | (2006.01) | |
| *A61K 31/4725* | (2006.01) | |
| *A61K 31/4409* | (2006.01) | |
| *A61K 31/167* | (2006.01) | |
| *A61P 35/00* | (2006.01) | |
| *A61P 35/02* | (2006.01) | |
| *C07D 213/68* | (2006.01) | |
| *A61K 33/24* | (2019.01) | |

(52) U.S. Cl.
CPC .......... *C07C 233/76* (2013.01); *A61K 31/167* (2013.01); *A61K 31/4409* (2013.01); *A61K 31/4418* (2013.01); *A61K 31/4725* (2013.01); *A61K 33/24* (2013.01); *A61P 35/00* (2018.01); *A61P 35/02* (2018.01); *C07C 237/22* (2013.01); *C07D 213/68* (2013.01); *C07D 217/26* (2013.01); *C07D 401/12* (2013.01)

(58) Field of Classification Search
None
See application file for complete search history.

(56) References Cited

U.S. PATENT DOCUMENTS

| | | |
|---|---|---|
| 4,030,910 A | 6/1977 | Johnston |
| 4,269,829 A | 5/1981 | Seidel et al. |
| 5,783,597 A | 7/1998 | Beers et al. |
| 6,090,854 A | 7/2000 | Epperson |
| 7,067,506 B2 | 6/2006 | Keegan et al. |
| 10,550,070 B2 | 2/2020 | Malkas et al. |
| 2001/0049374 A1 | 12/2001 | Steele et al. |
| 2007/0155727 A1 | 7/2007 | Chen et al. |
| 2007/0191378 A1 | 8/2007 | Campbell et al. |
| 2007/0208166 A1 | 9/2007 | Baly et al. |
| 2009/0048226 A1 | 2/2009 | Wannamaker et al. |
| 2011/0301188 A1 | 12/2011 | Shankar et al. |
| 2012/0015962 A1 | 1/2012 | Arora et al. |
| 2012/0108562 A1 | 5/2012 | Chen et al. |

FOREIGN PATENT DOCUMENTS

| | | |
|---|---|---|
| EP | 1 291 341 A1 | 3/2003 |
| EP | 1 291 341 A4 | 3/2003 |
| WO | WO-2005/117867 A2 | 12/2005 |
| WO | WO-2005/117867 A3 | 12/2005 |
| WO | WO-2012/004554 A1 | 1/2012 |
| WO | WO-2012/173677 A2 | 12/2012 |
| WO | WO-2012/173677 A3 | 12/2012 |
| WO | WO-2015/129860 A1 | 9/2015 |

OTHER PUBLICATIONS

Buckner, J.C. et al. (Oct. 2007). "Central nervous system tumors," *Mayo Clin Proc* 82(10):1271-1286.
Capdeville, R. et al. (Jul. 2002). "Glivec (STI571, imatinib), a rationally developed, targeted anticancer drug," *Nat Rev Drug Discov* 1(7):493-502.
Chemical Abstract Registry No. 1295611-89-0, indexed in the Registry File on STN CAS Online May 16, 2011, 1 page.
Chemical Abstract Registry No. 1298989-51-1, indexed in the Registry File on STN CAS Online May 22, 2011, 1 page.
Chu, J.S. et al. (Sep. 25, 1998). "Proliferating cell nuclear antigen (PCNA) immunolabeling as a prognostic factor in invasive ductal carcinoma of the breast in Taiwan," *Cancer Lett* 131(2):145-152.
Ducoux, M. et al. (Dec. 28, 2001, e-published Oct. 10, 2001). "Mediation of proliferating cell nuclear antigen (PCNA)-dependent DNA replication through a conserved p21(Cip1)-like PCNA-binding motif present in the third subunit of human DNA polymerase delta," *J Biol Chem* 276(52):49258-49266.
Extended European Search Report dated on Feb. 15, 2019, for EP Patent Application No. 16847479.9, 7 pages.
Friesner, R.A. et al. (Oct. 19, 2006). "Extra precision glide: docking and scoring incorporating a model of hydrophobic enclosure for protein-ligand complexes," *J Med Chem* 49(21):6177-6196.
Gavett, S.H. et al. (Nov. 1, 1995). "Interleukin 12 inhibits antigen-induced airway hyperresponsiveness, inflammation, and Th2 cytokine expression in mice," *J Exp Med* 12(5):1527-1536.
Grivennikov, S.I. et al. (Mar. 19, 2010). "Immunity, inflammation, and cancer," *Cell* 140(6):883-899.

(Continued)

*Primary Examiner* — Po-Chih Chen
(74) *Attorney, Agent, or Firm* — Mintz, Levin, Cohn, Ferris, Glovsky and Popeo, P.C.

(57) ABSTRACT

Described herein, inter alia, are compositions of PCNA modulators and methods for treating or preventing cancer.

42 Claims, 15 Drawing Sheets

Specification includes a Sequence Listing.

(56) References Cited

OTHER PUBLICATIONS

Gu, L. et al. (Apr. 11, 2014). "A PCNA-derived cell permeable peptide selectively inhibits neuroblastoma cell growth," *PloS One* 9(4):e94773.

Hoelz, D.J. et al. (Sep. 2006). "The discovery of labile methyl esters on proliferating cell nuclear antigen by MS/MS," *Proteomics* 6(17):4808-4816.

International Search Report dated Dec. 12, 2016, for PCT Application No. PCT/US2016/052310, filed Sep. 16, 2016, 7 pages.

Ito, N. et al. (Jan. 2003). "A Medium-Term Rat Liver Bioassay for Rapid in Vivo Detection of Carcinogenic Potential of Chemicals," *Cancer Sci* 94(1):3-8.

Lehmann, B.D. et al. (Jul. 2011). "Identification of human triple-negative breast cancer subtypes and preclinical models for selection of targeted therapies," *J Clin Invest* 121(7):2750-2767.

Malkas, L.H. et al. (Dec. 19, 2006, e-published Dec. 11, 2006). "A cancer-associated PCNA expressed in breast cancer has implications as a potential biomarker," PNAS USA 103(51):19472-19477.

Mayer, M. et al. (Jun. 27, 2001). "Group epitope mapping by saturation transfer difference NMR to identify segments of a ligand in direct contact with a protein receptor," *J Am Chem Soc* 123(25):6108-6117.

Müller, R. et al. (Jul. 31, 2013). "Targeting proliferating cell nuclear antigen and its protein interactions induces apoptosis in multiple myeloma cells," *PLoS One* 8(7):e70430.

Münch, G. et al. (May 2003, e-published Mar. 5, 2003). "Microglial activation induces cell death, inhibits neurite outgrowth and causes neurite retraction of differentiated neuroblastoma cells," *Exp Brain Res* 150(1):1-8.

Nurden, A.T. (May 2011, e-published Apr. 11, 2011). "Platelets, inflammation and tissue regeneration," *Thromb Haemost* 105 Suppl 1 S13-33.

Phillips, J.C. et al. (Dec. 2005). Scalable molecular dynamics with NAMD, *J Comput Chem* 26(16):1781-1802.

Pubchem CID: 16794268, CTK6A1088, (Nov. 13, 2007). located at <http://pubchem.ncbi.nlm.nih.gov/compound/16794268> retrieved Nov. 3, 2016, 9 pages.

Punchihewa, C. et al. (Apr. 20, 2012, e-published Mar. 1, 2012). "Identification of small molecule proliferating cell nuclear antigen (PCNA) inhibitor that disrupts interactions with PIP-box proteins and inhibits DNA replication," *J Biol Chem* 287(17):14289-14300.

Raschle, M. et al. (Sep. 19, 2008). "Mechanism of replication-coupled DNA interstrand crosslink repair," *Cell* 134(6):969-980.

Scott, H.R. et al. (Jul. 29, 2002). "The systemic inflammatory response, weight loss, performance status and survival in patients with inoperable non-small cell lung cancer," *Br J Cancer* 87(3):264-267.

Shen, F. et al. (Mar. 2011). "Nuclear protein isoforms: implications for cancer diagnosis and therapy," *J Cell Biochem* 112(3):756-760.

Shibata, A. et al. (Mar. 16, 2011, e-published Feb. 11, 2011). "Factors determining DNA double-strand break repair pathway choice in G2 phase," *EMBO J* 30(6):1079-1092.

Strzalka, W. et al. (May 2011, e-published Dec. 17, 2010). "Proliferating cell nuclear antigen (PCNA): a key factor in DNA replication and cell cycle regulation," *Ann Bot* 107(7):1127-1140.

Stoimenov, I. et al. (Jun. 2009). "PCNA on the crossroad of cancer," *Biochem Soc Trans* 37(Pt 3):605-613.

Tan, Z. et al. (Jun. 2012, e-published Mar. 7, 2012). "Small-molecule targeting of proliferating cell nuclear antigen chromatin association inhibits tumor cell growth," *Mol Pharmacol* 81(6):811-819.

Wang, J.L. et al. (Apr. 1, 2004). "Predictive significance of the alterations of p16INK4A, p14ARF, p53, and proliferating cell nuclear antigen expression in the progression of cervical cancer," *Clin Cancer Res* 10(7):2407-2414.

Wang, X. et al. (May 15, 2011, e-published Oct. 28, 2010). "Elevated expression of cancer-associated proliferating cell nuclear antigen in high-grade prostatic intraepithelial neoplasia and prostate cancer," *Prostate* 71(7):748-754.

Warbick, E. et al. (May 5, 1997). "Homologous regions of Fen1 and p21Cip1 compete for binding to the same site on PCNA: a potential mechanism to co-ordinate DNA replication and repair," *Oncogene* 14(19):2313-2321.

Written Opinion dated Dec. 12, 2016, for PCT Application No. PCT/US2016/052310, filed Sep. 16, 2016, 40 pages.

Yu, Y.L. et al. (Apr. 8, 2013). "Targeting the EGFR/PCNA signaling suppresses tumor growth of triple-negative breast cancer cells with cell-penetrating PCNA peptides," *PLoS One* 8(4):e61362.

Zhang, Y. et al. (Jun. 1, 2004). "Intravenous RNA interference gene therapy targeting the human epidermal growth factor receptor prolongs survival in intracranial brain cancer," *Clin Cancer Res* 10(11):3667-3677.

Zhao, H. et al. (2011). "Targeting Tyrosine Phosphorylation of PCNA Inhibits Prostate Cancer Growth," *Molecular Cancer Therapeutics* 10(1):29-36.

Molecular Weight: 396.44

AOH1160: IC50 = ~200 nM

PCNA1: IC50 = 371 nM

PCNA2: IC50 = 405 nM

PCNA6: IC50 = 198 nM

AOH1996: IC50 = 216 nM

PCNA INHIBITORS

CROSS-REFERENCES TO RELATED APPLICATIONS

This application is a continuation of U.S. patent application Ser. No. 15/760,959, filed Mar. 16, 2018, which is a national stage application filed under 35 U.S.C. § 371 of International Patent Application No. PCT/US2016/052310, filed Sep. 16, 2016, which claims the benefit of U.S. Provisional Application No. 62/220,014 filed Sep. 17, 2015, U.S. Provisional Application No. 62/313,592 filed Mar. 25, 2016, and U.S. Provisional Application No. 62/340,964 filed May 24, 2016, which are incorporated herein by reference in their entirety and for all purposes.

STATEMENT AS TO RIGHTS TO INVENTIONS MADE UNDER FEDERALLY SPONSORED RESEARCH AND DEVELOPMENT

This invention was made with government support under R01 CA121289, R01CA120954, and P30CA033572 awarded by the National Institutes of Health; and W81XWH-11-1-0786 awarded by the Department of Defense. The government has certain rights in the invention.

REFERENCE TO A "SEQUENCE LISTING," A TABLE, OR A COMPUTER PROGRAM LISTING APPENDIX SUBMITTED AS AN ASCII FILE

The Sequence Listing written in file 048440-512C01US Sequence Listing ST25.txt, created on Nov. 12, 2019, 4,953 bytes, machine format IBM-PC, MS Windows operating system, is hereby incorporated by reference.

BACKGROUND

Originating from neural crest progenitor cells of the sympathetic nervous system and accounting for about 15% of all pediatric cancer deaths, neuroblastoma (NB) is one of the most common childhood neoplasms [1]. The single most important factor determining the treatment options and prognosis of NB patients is risk stratification. Survival is excellent in low and intermediate risk groups [2]. Localized perinatal adrenal tumors often regress spontaneously. Current treatment for high-risk NB consists of induction treatment, high-dose chemotherapy and autologous stem cell transplantation (HDCT/autoSCT) as a consolidation treatment, and maintenance treatment by 13-cis-retinoid acid and immunotherapy to reduce relapse from minimal residual disease [3]. Despite aggressive therapeutic regimens, which often cause severe side effects and possibly secondary malignancy [4], approximately 50% of patients with advanced diseases either resist treatment or relapse. The survival outlook for high-risk NB patients is dismal [5, 6]. Thus, there is a significant medical need for new therapies to improve the treatment outcomes of cancer. Disclosed herein are solutions to these and other problems in the art.

BRIEF SUMMARY

Provided herein, inter alia, are ligands for the proliferating cell nuclear antigen (PCNA), and methods of using the same.

In an aspect is provided a compound having the formula:

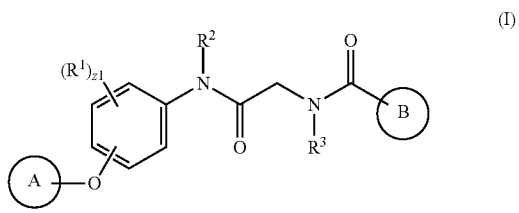

(I)

wherein
Ring A is substituted or unsubstituted phenyl or substituted or unsubstituted 5 to 6 membered heteroaryl;
Ring B is substituted or unsubstituted naphthyl, substituted or unsubstituted quinolinyl, or substituted or unsubstituted isoquinolinyl;
$R^1$ is independently a halogen, $-CX^1_3$, $-CHX^1_2$, $-CH_2X^1$, $-CN$, $-SO_2Cl$, $-SO_{n1}R^{10}$, $-SO_{v1}NR^7R^8$, $-NHNH_2$, $-ONR^7R^8$, $-NHC=(O)NHNH_2$, $-NHC=(O)NR^7R^8$, $-NR^7R^8$, $-C(O)R^9$, $-C(O)-OR^9$, $-C(O)NR^7R^8$, $-OR^{10}$, $-NR^7SO_2R^{10}$, $-NR^7C=(O)R^9$, $-NR^7C(O)-OR^9$, $-NR^7OR^9$, $-OCX^1_3$, $-OCHX^1_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^1$ substituents may optionally be joined to form a substituted or unsubstituted cycloalkyl, substituted or unsubstituted heterocycloalkyl, substituted or unsubstituted aryl, or substituted or unsubstituted heteroaryl;
$R^2$ is independently hydrogen, halogen, $-CX^2_3$, $-CHX^2_2$, $-CH_2X^2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^2_3$, $-OCHX^2_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^3$ is independently hydrogen, halogen, $-CX^3_3$, $-CHX^3_2$, $-CH_2X^3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^3_3$, $-OCHX^3_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^7$, $R^8$, $R^9$, and $R^{10}$ are independently hydrogen, halogen, $-CX^A_3$, $-CHX^A_2$, $-CH_2X^A$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^A_3$, $-OCHX^A_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^7$ and $R^8$ substituents bonded to the same nitrogen atom may optionally be joined to form a substituted or unsubstituted heterocycloalkyl or substituted or unsubstituted heteroaryl;

z1 is independently an integer from 0 to 4;

m1 and v1 are independently 1 or 2;

n1 is independently an integer from 0 to 4;

$X^1$, $X^2$, $X^3$, and $X^4$ are independently —Cl, —Br, —I, or —F.

In another aspect is provided a pharmaceutical composition including a compound as described herein, or a pharmaceutically acceptable salt thereof, and a pharmaceutically acceptable excipient.

In another aspect is provided a method of treating cancer in a subject in need thereof, including administering to the subject a compound as described herein, or a pharmaceutically acceptable salt thereof.

In another aspect is provided a method of inhibiting PCNA activity in a subject in need thereof, including administering to the subject a compound as described herein, or a pharmaceutically acceptable salt thereof.

BRIEF DESCRIPTION OF THE DRAWINGS

FIG. 1A depicts the AOH1160 chemical structure. The ether oxygen in AOH1160 is indicated by a dashed box. FIG. 1B is a line graph showing that human NB cell lines, SK-N-DZ (circles), SK-N-AS (squares), and SK-N-BE(2)c (triangles tip up), were cultured in the presence of various concentrations of AOH1160. The non-malignant 7SM0032 cells (triangles tip down) and human PBMCs (crosses) were also cultured under the same AOH1160 treatment. Cells cultured in the absence of AOH1160 were used as control. Cell growth was measured by a CellTitor Glo assay (Promega). The average of luminescence signals in triplicates normalized to the control for each cell line was graphed plus/minus standard deviations. FIG. 1C is a line graph showing TRβ reporter cells were treated with various concentrations of T3, AOH39 (N-(2((2-benzylphenyl)amino)-2-oxoethyl)-1-naphthamide), or AOH1160 for 24 h. The effect of compounds on TRβ activity was examined by measuring the relative luminescence units (RLU) in a luminescence plate reader. Circles: Signals from T3-treated cells; squares: overlapping signals from AOH39 or AOH1160-treated cells. FIG. 1D depicts a computer modeling image of small molecule binding to PCNA. The model was initially built by AAD methodology and further refined by 50 ns metadynamics simulation. Shown are small molecules (in stick) and PCNA surface around the binding pocket. The loop residues of L126-Y133 of PCNA are indicated in black to gray shading. The image shows AOH1160 as varying shade gray sticks and AOH39 as grey sticks. FIG. 1E depicts a series of spectra from STD NMR experiments using 1 μM of PCNA. The T3 compound structure is shown on top along with proton labels. Spectrum 1) is a T3 reference spectrum; spectrum 2) is the saturation spectrum of 30 μM T3 in complex with PCNA in the absence of AOH1160. Spectrum 3) is a reference spectrum of 30 μM T3 and 2.9 μM AOH116; and spectrum 4) is the saturation spectra of 30 μM T3 in complex with PCNA in the presence of 3.2 μM AOH1160.

FIG. 2A depicts a series of spectra showing 7SM0032 (bottom series of spectra) or SK-N-DZ (top series of spectra) cells were fixed, stained by PI, and analyzed by flow cytometry after being treated with 500 nM AOH1160 for the indicated time. FIG. 2B is a series of images of gels showing extracts from 7SM0032 or SK-N-DZ cells treated by 500 nM AOH1160 for the indicated time were analysis by western analysis. FIGS. 2C-2D is a series of images showing TUNEL analysis. 7SM0032 or SK-N-DZ cells treated by 500 nM AOH1160 for 24 h were fixed on slides. Cell apoptosis was analyzed by a TUNEL assay. FIG. 2C: The TMR fluorophore attached to the free ends of DNA indicates cells undergoing apoptosis. DAPI stained nuclei are observed. FIG. 2D: The abundance of apoptotic cells relative to the total number of cells in six randomly selected fields were averaged and graphed plus/minus standard deviations. The dark and light bars represent results from 7SM0032 and SK-N-DZ cells respectively.

FIG. 3A depict images of individual DNA strands being elongated from their origins of DNA replication (a DNA fiber assay), and FIG. 3B a histogram showing the inhibition of replication fork extension by AOH1160. Synchronized cells were sequentially incubated in the presence of CldU and IdU before and after AOH1160 treatment, respectively. Cells sequentially incubated with the same two nucleotide analogues but without AOH1160 were used as control. Images of FIG. 3A depict representative images of the labeled DNA strands from cells treated with or without AOH1160. FIG. 3B depicts the lengths of CldU (light gray) and IdU (dark gray) incorporated DNA segments measured from more than 30 independent DNA strands in cells treated with or without AOH1160 were averaged and graphed with standard deviations.

FIGS. 6A-6B depict measurement of the inhibition of tumor growth by AOH1160 in vivo. Histogram FIG. 6A depicts mice bearing SK-N-BE(2)c derived xenograft tumors that were given vehicle only or 30 mg/kg of AOH1160 for 4 weeks. Tumors were isolated from these mice at the end of the experiment. Tumor masses were measured and individually plotted. Circles represent mice treated with vehicle only and triangles represent mice treated with AOH1160. FIG. 6B depicts animal body weights over time. Circles represent mice treated with vehicle only and triangles represent mice treated with AOH1160. FIG. 6C depicts Tumor volume based on the length (L) and width (W) of the tumors (V=L×W²×0.5) at various time points after tumor implantation. Black triangles represent tumor volumes from mice treated with 30 mg/kg AOH1160 and black circles represent tumor volumes from mice treated with vehicle only. * indicates p<0.01.

FIG. 8A depicts an illustration of AOH1160 degradation by amide cleavage in mouse plasma. FIG. 8B depicts the stability of AOH1160 in human and animal plasma. AOH1160 was quickly degraded in the plasma collected from a wildtype Balb/c mouse. Liquid chromatographymass spectrometry (LC-MS) analysis of AOH1160 metabolites found that the compound was degraded by amide cleavage as illustrated in the left panel. This amide cleavage was catalyzed by the carboxyl esterase, ES-1, which is highly expressed in rodents, but not significantly expressed in the blood of higher mammal species. AOH1160 is stable in the plasma of canine, monkey, and human, as well as in the plasma of ES-1-deficent mice (Es1e/SCID). The stability of AOH1160 in Es1e/SCID mice not only proved that ES-1 was responsible for the quick degradation of AOH1160, but also identified a mouse model which mimics the human enzymatic environment for pharmacological study of AOH1160.

DETAILED DESCRIPTION

Figure 1A:
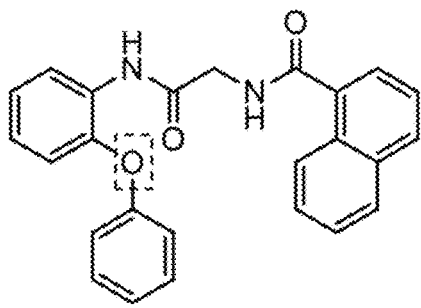
FIGS. 1A-1E depict data on the development of AOH1160, a potent PCNA modulator.

Proliferating cell nuclear antigen (PCNA) plays an essential role in regulating DNA synthesis and repair and is indispensible to cancer cell growth and survival. Previously a novel cancer associated PCNA isoform (dubbed caPCNA), which was ubiquitously expressed in a broad range of cancer cells and tumor tissues, but not significantly in non-malignant cells was reported. It was found that the caPCNA-specific antigenic site lies between L126 and Y133 inside the interdomain connecting loop of PCNA. By computer modeling and medicinal chemistry targeting a binding pocket partly delineated by the L126 Y133 region of PCNA, AOH1160, a potent PCNA inhibitor, which selectively kills neuroblastoma (NB) cells without significant toxicity to a broad range of non-malignant cells was identified. Mechanistically, AOH1160 interferes with DNA replication, blocks homologous recombination mediated DNA repair, and causes cell cycle arrest. It induces apoptosis in NB cells and sensitizes them to cisplatin treatment. AOH1160 is orally available to animals and suppresses tumor growth without causing death or significant weight loss in mice. These results illustrate the favorable pharmacological and therapeutic properties of AOH1160 and demonstrate its potential as a novel therapeutic agent for treating NB.

PCNA lies at the center of essential cellular processes, including DNA replication, cell cycle control, and DNA damage repair [10], which are fundamental to the proliferation and survival of cancer cells. Inhibition of PCNA is viewed as an effective way to suppress tumor growth and several attempts have been made in recent years to block various aspects of PCNA function [13, 19, 39-42]. Distinctions in structure and accessibility in the L126 Y133 region between nmPCNA and caPCNA [16] and studies showing that the cell permeable peptide containing the L126 Y133 octapeptide can block PCNA interaction with its interacting partners and selectively kill NB cells without causing significant toxicity to non-malignant cells [18], the L126 Y133 region on PCNA is an attractive target.

Described herein is the successful identification of small molecule compounds that inhibit PCNA function, including AOH1160. The compound is chemically novel in the drug discovery space. AOH1160 has especially remarkable favorable therapeutic properties. AOH1160 is a small molecule PCNA inhibitor that is orally available and kills tumors in vivo without causing significant toxicity after being systematically administrated to animals. Therefore, successful translation of this compound into the clinic may lead to a new class of anti-cancer drug and significantly improve NB treatment options. In addition to the potential of AOH1160 as an effective monotherapeutic agent, its ability to sensitize NB cells to treatment by DNA damaging agents (e.g., platinum containing compounds) may significantly improve the efficacy and reduce the dose-limiting side-effects of traditional chemotherapies in the clinic.

A. Definitions

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e., unbranched) or branched non-cyclic carbon chain (or carbon), or combination thereof, which may be fully saturated, mono- or polyunsaturated and can include di- and multivalent radicals, having the number of carbon atoms designated (i.e., $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkenyl moiety. An alkyl moiety may be an alkynyl moiety. An alkyl moiety may be fully saturated.

The term "alkylene," by itself or as part of another substituent, means, unless otherwise stated, a divalent radical derived from an alkyl, as exemplified, but not limited by, —CH$_2$CH$_2$CH$_2$CH$_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched non-cyclic chain, or combinations thereof, including at least one carbon atom and at least one heteroatom (e.g., O, N, P, Si, or S), and wherein the nitrogen and sulfur atoms may optionally be oxidized, and the nitrogen heteroatom may optionally be quaternized. The heteroatom(s) (e.g., O, N, P, S, or Si) may be placed at any interior position of the heteroalkyl group or at the position at which the alkyl group is attached to the remainder of the molecule. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, —O—CH$_3$, —O—CH$_2$—CH$_3$, and —CN. Up to two or three heteroatoms may be consecutive, such as, for example, —CH$_2$—NH—OCH$_3$ and CH$_2$—O—Si(CH$_3$)$_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P).

Similarly, the term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, non-aromatic cyclic versions of "alkyl" and "heteroalkyl," respectively, wherein the carbons making up the ring or rings do not necessarily need to be bonded to a hydrogen due to all carbon valencies participating in bonds with non-hydrogen atoms. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, 3-hydroxy-cyclobut-3-enyl-1,2, dione, 1H-1,2,4-triazolyl-5(4H)-one, 4H-1,2,4-triazolyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively. A heterocycloalkyl moiety may include one ring heteroatom (e.g., O, N, S, Si, or P). A heterocycloalkyl moiety may include two optionally different ring heteroatoms (e.g., O, N, S, Si, or P). A heterocycloalkyl moiety may include three optionally different ring heteroatoms (e.g., O, N, S, Si, or P). A heterocycloalkyl moiety may include four optionally different ring heteroatoms (e.g., O, N, S, Si, or P). A heterocycloalkyl moiety may include five optionally different ring heteroatoms (e.g., O, N, S, Si, or P). A heterocycloalkyl moiety may include up to 8 optionally different ring heteroatoms (e.g., O, N, S, Si, or P).

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$) alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. Non-limiting examples of aryl and heteroaryl groups include pyridinyl, pyrimidinyl, thiophenyl, thienyl, furanyl, indolyl, benzoxadiazolyl, benzodioxolyl, benzodioxanyl, thianaphthanyl, pyrrolopyridinyl, indazolyl, quinolinyl, quinoxalinyl, pyridopyrazinyl, quinazolinonyl, benzoisoxazolyl, imidazopyridinyl, benzofuranyl, benzothienyl, benzothiophenyl, phenyl, naphthyl, biphenyl, pyrrolyl, pyrazolyl, imidazolyl, pyrazinyl, oxazolyl, isoxazolyl, thiazolyl, furylthienyl, pyridyl, pyrimidyl, benzothiazolyl, purinyl, benzimidazolyl, isoquinolyl, thiadiazolyl, oxadiazolyl, pyrrolyl, diazolyl, triazolyl, tetrazolyl, benzothiadiazolyl, isothiazolyl, pyrazolopyrimidinyl, pyrrolopyrimidinyl, benzotriazolyl, benzoxazolyl, or quinolyl. The examples above may be substituted or unsubstituted and divalent radicals of each heteroaryl example above are non-limiting examples of heteroarylene. A heteroaryl moiety may include one ring heteroatom (e.g., O, N, or S). A heteroaryl moiety may include two optionally different ring heteroatoms (e.g., O, N, or S). A heteroaryl moiety may include three optionally different ring heteroatoms (e.g., O, N, or S). A heteroaryl moiety may include four optionally different ring heteroatoms (e.g., O, N, or S). A heteroaryl moiety may include five optionally different ring heteroatoms (e.g., O, N, or S). An aryl moiety may have a single ring. An aryl moiety may have two optionally different rings. An aryl moiety may have three optionally different rings. An aryl moiety may have four optionally different rings. A heteroaryl moiety may have one ring. A heteroaryl moiety may have two optionally different rings. A heteroaryl moiety may have three optionally different rings. A heteroaryl moiety may have four optionally different rings. A heteroaryl moiety may have five optionally different rings.

A fused ring heterocyloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substitutents described herein.

The term "oxo," as used herein, means an oxygen that is double bonded to a carbon atom.

The term "alkylsulfonyl," as used herein, means a moiety having the formula —S($O_2$)—R', where R' is a substituted or unsubstituted alkyl group as defined above. R' may have a specified number of carbons (e.g., "$C_1$-$C_4$ alkylsulfonyl").

Each of the above terms (e.g., "alkyl," "heteroalkyl,", "cycloalkyl," "heterocycloalkyl", "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', —NR'R", —SR', -halogen, —SiR'R"R'", —OC(O)R', —C(O)R', —$CO_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', NR'NR"R'", —ONR'R", NR'C=(O)NR"NR'"R"", —CN, —$NO_2$, in a number ranging from zero to (2m'+1), where m' is the total number of carbon atoms in such radical. R, R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound of the invention includes more than one R group, for example, each of the R groups is independently selected as are each R', R", R'", and R"" group when more than one of these groups is present.

When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', -halogen, —SiR'R"R''', —OC(O)R', —C(O)R', —CONR'R", —OC(O)NR'R", —NR"C(O)R', —NR'—C(O)NR"R''', —NR"C(O)$_2$R', —NR—C(NR'R"R''')=NR'''', —NR—C(NR'R")=NR''', —S(O)R', —S(O)$_2$R', —S(O)$_2$NR'R", —NRSO$_2$R', NR'NR"R''', —ONR'R", NR'C=(O)NR"NR'''R'''', —CN, —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R''', and R'''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the invention includes more than one R group, for example, each of the R groups is independently selected as are each R', R", R''', and R'''' groups when more than one of these groups is present.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$), —B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$X'— (C"R"R''')$_d$—, where s and d are independently integers of from 0 to 3, and X' is —O—, —S—, —S(O)—, —S(O)$_2$—, or —S(O)$_2$NR'—. The substituents R, R', R", and R''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include, oxygen (O), nitrogen (N), sulfur (S), phosphorus (P), and silicon (Si).

A "substituent group," as used herein, means a group selected from the following moieties:

(A) oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, heteroaryl, substituted with at least one substituent selected from:

(i) oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, heteroaryl, substituted with at least one substituent selected from:

(a) oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, heteroaryl, substituted with at least one substituent selected from: oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_3$-C$_8$ cycloalkyl, each substituted or unsubstituted heterocycloalkyl is a substituted or unsubstituted 3 to 8 membered heterocycloalkyl, each substituted or unsubstituted aryl is a substituted or unsubstituted C$_6$-C$_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the compound is a chemical species set forth in the Examples section, figures, or tables below.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., *Journal of Pharmaceutical Science* 66:1-19 (1977)). Certain specific compounds of the present invention contain both basic and acidic functionalities that allow the compounds to be converted into either base or acid addition salts. Other pharmaceutically acceptable carriers known to those of skill in the art are suitable for the present invention. Salts tend to be more soluble in aqueous or other protonic solvents than are the corresponding free base forms. In other cases, the preparation may be a lyophilized powder in 1 mM-50 mM histidine, 0.1%-2% sucrose, 2%-7% mannitol at a pH range of 4.5 to 5.5, that is combined with buffer prior to use.

Thus, the compounds of the present invention may exist as salts, such as with pharmaceutically acceptable acids. The present invention includes such salts. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

Provided herein are agents (e.g. compounds, drugs, therapeutic agents) that may be in a prodrug form. Prodrugs of the compounds described herein are those compounds that readily undergo chemical changes under select physiological conditions to provide the final agents (e.g. compounds, drugs, therapeutic agents). Additionally, prodrugs can be converted to agents (e.g. compounds, drugs, therapeutic agents) by chemical or biochemical methods in an ex vivo environment. Prodrugs described herein include compounds that readily undergo chemical changes under select physiological conditions to provide agents (e.g. compounds, drugs, therapeutic agents) to a biological system (e.g. in a subject, in a cancer cell, in the extracellular space near a cancer cell).

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

As used herein, the term "salt" refers to acid or base salts of the compounds used in the methods of the present invention. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

Certain compounds of the present invention possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those which are known in the art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium ($^{3}$H), iodine-125 ($^{125}$I), or carbon-14 ($^{14}$C). All isotopic variations of the compounds of the present invention, whether radioactive or not, are encompassed within the scope of the present invention.

The symbol ⌇ denotes the point of attachment of a chemical moiety to the remainder of a molecule or chemical formula.

The terms "a" or "an," as used herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls. Moreover, where a moiety is substituted with an R substituent, the group may be referred to as "R-substituted." Where a moiety is R-substituted, the moiety is substituted with at least one R substituent and each R substituent is optionally different.

Descriptions of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The terms "treating" or "treatment" refers to any indicia of success in the treatment or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. For example, certain methods herein treat diseases associated with PCNA activity. Certain methods described herein may treat diseases associated with PCNA activity (e.g., cancer or neuroblastoma) by inhibiting PCNA activity. For example, certain methods herein treat cancer. For example certain methods herein treat cancer by decreasing a symptom of cancer. Symptoms of cancer would be known or may be determined by a person of ordinary skill in the art. The term "treating" and conjugations thereof, include prevention of an injury, pathology, condition, or disease.

An "effective amount" is an amount sufficient to accomplish a stated purpose (e.g. achieve the effect for which it is administered, treat a disease, reduce enzyme activity, increase enzyme activity, reduce protein function, reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug or prodrug is an amount of a drug or prodrug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

The term "associated" or "associated with" in the context of a substance or substance activity or function associated with a disease (e.g. cancer) means that the disease is caused by (in whole or in part), or a symptom of the disease is caused by (in whole or in part) the substance or substance activity or function. As used herein, what is described as being associated with a disease, if a causative agent, could be a target for treatment of the disease. For example, a disease associated with PCNA activity may be treated with an agent (e.g. compound as described herein) effective for decreasing the level of PCNA activity.

"Control" or "control experiment" or "standard control" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In embodiments, a control is the same experiment or treatment method in the absence of a compound (e.g., as described herein) used in the non-control experiment or treatment method being compared to the control.

"Contacting" is used in accordance with its plain ordinary meaning and refers to the process of allowing at least two distinct species (e.g. chemical compounds including biomolecules, or cells) to become sufficiently proximal to react, interact or physically touch. It should be appreciated, however, that the resulting reaction product can be produced directly from a reaction between the added reagents or from an intermediate from one or more of the added reagents which can be produced in the reaction mixture. The term "contacting" may include allowing two species to react, interact, or physically touch, wherein the two species may be a compound as described herein and a protein or enzyme. In some embodiments contacting includes allowing a compound described herein to interact with a protein (e.g., PCNA) or enzyme. In embodiments contacting includes allowing a compound described herein to interact with SEQ ID NO:2. In embodiments contacting includes allowing a compound described herein to interact with SEQ ID NO:3. In embodiments contacting includes allowing a compound described herein to interact with SEQ ID NO:4.

As defined herein, the term "inhibition", "inhibit", "inhibiting" and the like in reference to a protein-inhibitor (e.g. antagonist) interaction means negatively affecting (e.g. decreasing) the level of activity or function of the protein relative to the level of activity or function of the protein in the absence of the inhibitor. In some embodiments inhibition refers to reduction of a disease or symptoms of disease. Thus, inhibition may include, at least in part, partially or totally blocking stimulation, decreasing, preventing, or delaying activation, or inactivating, desensitizing, or down-regulating signal transduction or enzymatic activity or the amount of a protein.

As defined herein, the term "activation", "activate", "activating" and the like in reference to a protein-activator (e.g. agonist) interaction means positively affecting (e.g. increasing) the activity or function of the protein relative to the activity or function of the protein in the absence of the activator (e.g. compound described herein). Thus, activation may include, at least in part, partially or totally increasing stimulation, increasing or enabling activation, or activating, sensitizing, or up-regulating signal transduction or enzymatic activity or the amount of a protein decreased in a disease. Activation may include, at least in part, partially or totally increasing stimulation, increasing or enabling activation, or activating, sensitizing, or up-regulating signal transduction or enzymatic activity or the amount of a protein.

The term "modulator" refers to a composition that increases or decreases the level of a target molecule or the function of a target molecule. In embodiments, a modulator is an anti-cancer agent. In embodiments, a modulator is a PCNA antagonist. In embodiments, a modulator is a PCNA inhibitor.

"Anti-cancer agent" or "anti-cancer drug" is used in accordance with its plain ordinary meaning and refers to a composition (e.g. compound, drug, antagonist, inhibitor, modulator) having antineoplastic properties or the ability to inhibit the growth or proliferation of cells. In some embodiments, an anti-cancer agent is a chemotherapeutic. In some embodiments, an anti-cancer agent is an agent approved by the FDA or similar regulatory agency of a country other than the USA, for treating cancer. Examples of anti-cancer agents include, but are not limited to, anti-androgens (e.g., Casodex, Flutamide, MDV3100, or ARN-509), MEK (e.g. MEK1, MEK2, or MEK1 and MEK2) inhibitors (e.g. XL518, CI-1040, PD035901, selumetinib/AZD6244, GSK1120212/trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethylmelamine, thiotepa), alkyl sulfonates (e.g., busulfan), nitrosoureas (e.g., carmustine, lomusitne, semustine, streptozocin), triazenes (decarbazine)), anti-metabolites (e.g., 5-azathioprine, leucovorin, capecitabine, fludarabine, gemcitabine, pemetrexed, raltitrexed, folic acid analog (e.g., methotrexate), pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g. cisplatin, oxaliplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g. U0126, PD98059, PD184352, PD0325901, ARRY-142886, SB239063, SP600125, BAY 43-9006, wortmannin, or LY294002), mTOR inhibitors, antibodies (e.g., rituxan), 5-aza-2'-deoxycytidine, doxorubicin, vincristine, etoposide, gemcitabine, imatinib (Gleevec®), geldanamycin, 17-N-Allylamino-17-Demethoxygeldanamycin (17-AAG), bortezomib, trastuzumab, anastrozole; angiogenesis inhibitors; antiandrogen, antiestrogen; antisense oligonucleotides; apoptosis gene modulators; apoptosis regulators; arginine deaminase; BCR/ABL antagonists; beta lactam derivatives; bFGF inhibitor; bicalutamide; camptothecin derivatives; casein kinase inhibitors (ICOS); clomifene analogues; cytarabine dacliximab; dexamethasone; estrogen agonists; estrogen antagonists; etanidazole; etoposide phosphate; exemestane; fadrozole; finasteride; fludarabine; fluorodaunorunicin hydrochloride; gadolinium texaphyrin; gallium nitrate; gelatinase inhibitors; gemcitabine; glutathione inhibitors; hepsulfam; immunostimulant peptides; insulin-like growth factor-1 receptor inhibitor; interferon agonists; interferons; interleukins; letrozole; leukemia inhibiting factor; leukocyte alpha interferon; leuprolide+estrogen+progesterone; leuprorelin; matrilysin inhibitors; matrix metalloproteinase inhibitors; MIF inhibitor; mifepristone; mismatched double stranded RNA; monoclonal antibody; mycobacterial cell wall extract; nitric oxide modulators; oxaliplatin; panomifene; pentrozole; phosphatase inhibitors; plasminogen activator inhibitor; platinum complex; platinum compounds; prednisone; proteasome inhibitors; protein A-based immune modulator; protein kinase C inhibitor; protein tyrosine phosphatase inhibitors; purine nucleoside phosphorylase inhibitors; ras farnesyl protein transferase inhibitors; ras inhibitors; ras-GAP inhibitor; ribozymes; signal transduction inhibitors; signal transduction modulators; single chain antigen-binding protein; stem cell inhibitor; stem-cell division inhibitors; stromelysin inhibitors; synthetic glycosaminoglycans; tamoxifen methiodide; telomerase inhibitors; thyroid stimulating hormone; translation inhibitors; tyrosine kinase inhibitors; urokinase receptor antagonists; steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), immunostimulants (e.g., *Bacillus* Calmette-Gurin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-*pseudomonas* exotoxin conjugate, etc.), radioimmunotherapy (e.g., anti-CD20 monoclonal antibody conjugated to $^{111}$In, $^{90}$Y or $^{131}$I, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g. gefitinib (Iressa™), erlotinib (Tarceva™), cetuximab (Erbitux™), lapatinib (Tykerb™), panitumumab (Vectibix™), vandetanib (Caprelsa™), afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, pyrrolo benzodiazepines (e.g. tomaymycin), carboplatin, CC-1065 and CC-1065 analogs including amino-CBIs, nitrogen mustards (such as chlorambucil and melphalan), dolastatin and dolastatin analogs (including auristatins: eg. monomethyl auristatin E), anthracycline antibiotics (such as doxorubicin, daunorubicin, etc.), duocarmycins and duocarmycin analogs, enediynes (such as neocarzinostatin and calicheamicins), leptomycin derivaties, maytansinoids and maytansinoid analogs (e.g. mertansine), methotrexate, mitomycin C, taxoids, *vinca* alkaloids (such as vinblastine and vincristine), epothilones (e.g. epothilone B), camptothecin and its clinical analogs topotecan and irinotecan, or the like.

"Chemotherapeutic" or "chemotherapeutic agent" is used in accordance with its plain ordinary meaning and refers to a chemical composition or compound having antineoplastic properties or the ability to inhibit the growth or proliferation of cells.

"Patient" or "subject in need thereof" or "subject" refers to a living organism suffering from or prone to a disease or condition that can be treated by administration of a compound or pharmaceutical composition or by a method, as provided herein. Non-limiting examples include humans, other mammals, bovines, rats, mice, dogs, monkeys, goat, sheep, cows, deer, and other non-mammalian animals. In some embodiments, a patient is human. In some embodiments, a subject is human. In some embodiments, a subject is a human child (e.g., less than 18, 17, 16, 15, 14, 13, 12, 11, 10, 9, 8, 7, 6, 5, 4, 3, 2, or 1 years of age).

"Disease" or "condition" refer to a state of being or health status of a patient or subject capable of being treated with a compound, pharmaceutical composition, or method provided herein. In some embodiments, the disease is a disease having the symptom of cell hyperproliferation. In some embodiments, the disease is a disease having the symptom of an aberrant level of PCNA activity. In some embodiments, the disease is a cancer. In some further instances, "cancer" refers to human cancers and carcinomas, sarcomas, adenocarcinomas, lymphomas, leukemias, etc., including solid and lymphoid cancers, kidney, breast, lung, bladder, colon, ovarian, prostate, pancreas, stomach, brain, head and neck, skin, uterine, testicular, glioma, esophagus, and liver cancer, including hepatocarcinoma, lymphoma, including B-acute lymphoblastic lymphoma, non-Hodgkin's lymphomas (e.g., Burkitt's, Small Cell, and Large Cell lymphomas), Hodgkin's lymphoma, leukemia (including AML, ALL, and CML), or multiple myeloma. In embodiments, the disease is brain cancer. In embodiments, the disease is neuroblastoma. In embodiments, the disease is glioblastoma. In embodiments, the disease is a central nervous system (CNS) cancer. In embodiments, the disease is a sympathetic nervous system (SNS) cancer. In embodiments, the disease is an adrenal gland cancer. In embodiments, the disease is a cancer of a neuron in the neck, chest, abdomen, or pelvis. In embodiments, the disease is an esthesioneuroblastoma. In embodiments, the disease is a stage 1 neuroblastoma (e.g., localized tumor confined to an area near the origin). In embodiments, the disease is a stage 2A neuroblastoma (e.g., Unilateral tumor with incomplete gross resection and/or identifiable ipsilateral and contralateral lymph node negative for tumor). In embodiments, the disease is a stage 2B neuroblastoma (e.g., Unilateral tumor with complete or incomplete gross resection; with ipsilateral lymph node positive for tumor; identifiable contralateral lymph node negative for tumor). In embodiments, the disease is a stage 3 neuroblastoma (e.g., Tumor infiltrating across midline with or without regional lymph node involvement; or unilateral tumor with contralateral lymph node involvement; or midline tumor with bilateral lymph node involvement). In embodiments, the disease is a stage 4 neuroblastoma (e.g., Dissemination of tumor to distant lymph nodes, bone marrow, bone, liver, or other organs except as defined by Stage 4S). In embodiments, the disease is a stage 4S neuroblastoma (e.g., Age <1 year old with localized primary tumor as described in Stage 1 or Stage 2 above, with dissemination limited to liver, skin, or bone marrow (less than 10 percent of nucleated bone marrow cells are tumors). In embodiments, the disease is a stage L1 neuroblastoma (e.g., localized disease without image-defined risk factors) according to the International Neuroblastoma Risk Group (INRG) staging system. In embodiments, the disease is a stage L2 neuroblastoma (e.g., localized disease with image-defined risk factors) according to the International Neuroblastoma Risk Group (INRG) staging system. In embodiments, the disease is a stage M neuroblastoma (e.g., metastatic disease) according to the International Neuroblastoma Risk Group (INRG) staging system. In embodiments, the disease is a stage MS neuroblastoma (e.g., metastatic disease "special" where MS is equivalent to stage 4S as described above) according to the International Neuroblastoma Risk Group (INRG) staging system. In embodiments, the disease is a neuroblastoma risk stratification pre-treatment group, according to the International Neuroblastoma Risk Group (INRG) staging system, of very low. In embodiments, the disease is a neuroblastoma risk stratification pre-treatment group, according to the International Neuroblastoma Risk Group (INRG) staging system, of low. In embodiments, the disease is a neuroblastoma risk stratification pre-treatment group, according to the International Neuroblastoma Risk Group (INRG) staging system, of intermediate. In embodiments, the disease is a neuroblastoma risk stratification pre-treatment group, according to the International Neuroblastoma Risk Group (INRG) staging system, of high risk.

As used herein, the term "cancer" refers to all types of cancer, neoplasm or malignant tumors found in mammals (e.g. humans), including leukemia, carcinomas and sarcomas. Exemplary cancers that may be treated with a compound or method provided herein include cancer of the prostate, thyroid, endocrine system, brain, breast, cervix, colon, head & neck, liver, kidney, lung, non-small cell lung, melanoma, mesothelioma, ovary, sarcoma, stomach, uterus, Medulloblastoma, colorectal cancer, pancreatic cancer. Additional examples may include, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, or prostate cancer.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

The term "sarcoma" generally refers to a tumor which is made up of a substance like the embryonic connective tissue and is generally composed of closely packed cells embedded in a fibrillar or homogeneous substance. Sarcomas that may be treated with a compound or method provided herein include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" is taken to mean a tumor arising from the melanocytic system of the skin and other organs. Melanomas that may be treated with a compound or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas that may be treated with a compound or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma *cutaneum*, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma *mucosum*, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma *tuberosum*, tuberous carcinoma, verrucous carcinoma, or carcinoma *villosum*.

The term "signaling pathway" as used herein refers to a series of interactions between cellular and optionally extracellular components (e.g. proteins, nucleic acids, small molecules, ions, lipids) that conveys a change in one component to one or more other components, which in turn may convey a change to additional components, which is optionally propagated to other signaling pathway components.

The term "aberrant" as used herein refers to different from normal. When used to describe enzymatic activity, aberrant refers to activity that is greater or less than a normal control or the average of normal non-diseased control samples. Aberrant activity may refer to an amount of activity that results in a disease, wherein returning the aberrant activity to a normal or non-disease-associated amount (e.g. by administering a compound or using a method as described herein), results in reduction of the disease or one or more disease symptoms.

"Nucleic acid" or "oligonucleotide" or "polynucleotide" or grammatical equivalents used herein means at least two nucleotides covalently linked together. The term "nucleic acid" includes single-, double-, or multiple-stranded DNA, RNA and analogs (derivatives) thereof. Oligonucleotides are typically from about 5, 6, 7, 8, 9, 10, 12, 15, 25, 30, 40, 50 or more nucleotides in length, up to about 100 nucleotides in length. Nucleic acids and polynucleotides are a polymers of any length, including longer lengths, e.g., 200, 300, 500, 1000, 2000, 3000, 5000, 7000, 10,000, etc. Nucleic acids containing one or more carbocyclic sugars are also included within one definition of nucleic acids.

A particular nucleic acid sequence also encompasses "splice variants." Similarly, a particular protein encoded by a nucleic acid encompasses any protein encoded by a splice variant of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are near each other, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or higher identity over a specified region when compared and aligned for maximum correspondence over a comparison window or designated region) as measured using a BLAST or BLAST 2.0 sequence comparison algorithms with default parameters described below, or by manual alignment and visual inspection (see, e.g., NCBI web site or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 10 amino acids or 20 nucleotides in length, or more preferably over a region that is 10-50 amino acids or 20-50 nucleotides in length. As used herein, percent (%) amino acid sequence identity is defined as the percentage of amino acids in a candidate sequence that are identical to the amino acids in a reference sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

For sequence comparisons, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 10 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

The phrase "selectively (or specifically) hybridizes to" refers to the binding, duplexing, or hybridizing of a molecule only to a particular nucleotide sequence with a higher affinity, e.g., under more stringent conditions, than to other nucleotide sequences (e.g., total cellular or library DNA or RNA).

The phrase "stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous reference, e.g., and *Current Protocols in Molecular Biology*, ed. Ausubel, et al.

Twenty amino acids are commonly found in proteins. Those amino acids can be grouped into nine classes or groups based on the chemical properties of their side chains. Substitution of one amino acid residue for another within the same class or group is referred to herein as a "conservative" substitution. Conservative amino acid substitutions can frequently be made in a protein without significantly altering the conformation or function of the protein. Substitution of one amino acid residue for another from a different class or group is referred to herein as a "non-conservative" substitution. In contrast, non-conservative amino acid substitutions tend to modify conformation and function of a protein.

Example of Amino Acid Classification

Small/Aliphatic residues: Gly, Ala, Val, Leu, Ile
Cyclic Imino Acid: Pro
Hydroxyl-containing Residues: Ser, Thr
Acidic Residues: Asp, Glu
Amide Residues: Asn, Gln
Basic Residues: Lys, Arg
Imidazole Residue: His
Aromatic Residues: Phe, Tyr, Trp
Sulfur-containing Residues: Met, Cys In some embodiments, the conservative amino acid substitution comprises substituting any of glycine (G), alanine (A), isoleucine (I), valine (V), and leucine (L) for any other of these aliphatic amino acids; serine (S) for threonine (T) and vice versa; aspartic acid (D) for glutamic acid (E) and vice versa; glutamine (Q) for asparagine (N) and vice versa; lysine (K) for arginine (R) and vice versa; phenylalanine (F), tyrosine (Y) and tryptophan (W) for any other of these aromatic amino acids; and methionine (M) for cysteine (C) and vice versa. Other substitutions can also be considered conservative, depending on the environment of the particular amino acid and its role in the three-dimensional structure of the protein. For example, glycine (G) and alanine (A) can frequently be interchangeable, as can alanine (A) and valine (V). Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pKs of these two amino acid residues are not significant. Still other changes can be considered "conservative" in particular environments (see, e.g., BIOCHEMISTRY at pp. 13-15, 2nd ed. Lubert Stryer ed. (Stanford University); Henikoff et al., *Proc. Nat'l Acad. Sci. USA* (1992) 89:10915-10919; Lei et al., *J. Biol. Chem.* (1995) 270(20):11882-11886).

"Polypeptide," "peptide," and "protein" are used herein interchangeably and mean any peptide-linked chain of amino acids, regardless of length or post-translational modification. As noted below, the polypeptides described herein can be, e.g., wild-type proteins, biologically-active fragments of the wild-type proteins, or variants of the wild-type proteins or fragments. Variants, in accordance with the disclosure, can contain amino acid substitutions, deletions, or insertions. The substitutions can be conservative or non-conservative.

Following expression, the proteins can be isolated. The term "purified" or "isolated" as applied to any of the proteins described herein refers to a polypeptide that has been separated or purified from components (e.g., proteins or other naturally-occurring biological or organic molecules) which naturally accompany it, e.g., other proteins, lipids, and nucleic acid in a cell expressing the proteins. Typically, a polypeptide is purified when it constitutes at least 60 (e.g., at least 65, 70, 75, 80, 85, 90, 92, 95, 97, or 99) %, by weight, of the total protein in a sample.

An amino acid residue in a protein "corresponds" to a given residue when it occupies the same essential structural position within the protein as the given residue. For example, a selected residue in a selected protein corresponds to L126 to Y133 of human PCNA when the selected residue occupies the same essential spatial or other structural relationship as L126 to Y133 in human PCNA. In some embodiments, where a selected protein is aligned for maximum homology with the human PCNA protein, the position in the aligned selected protein aligning with L126 to Y133 is said to correspond to L126 to Y133. Instead of a primary sequence alignment, a three dimensional structural alignment can also be used, e.g., where the structure of the selected protein is aligned for maximum correspondence with the human PCNA protein and the overall structures compared. In this case, an amino acid that occupies the same essential position as L126 to Y133 in the structural model is said to correspond to the L126 to Y133 residues.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethylcellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "administering" means oral administration, administration as a suppository, topical contact, intravenous, parenteral, intraperitoneal, intramuscular, intralesional, intrathecal, intracranial, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies (e.g. anti-cancer agent). The compound of the invention can be administered alone or can be coadministered to the patient. Coadministration is meant to include simultaneous or sequential administration of the compound individually or in combination (more than one compound or agent). Thus, the preparations can also be combined, when desired, with other active substances (e.g. to reduce metabolic degradation, to increase degradation of a prodrug and release of the drug, detectable agent). The compositions of the present invention can be delivered by transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions of the present invention can also be delivered as microspheres for slow release in the body. For example, microspheres can be administered via intradermal injection of drug-containing microspheres, which slowly release subcutaneously (see Rao, *J. Biomater Sci. Polym.* Ed. 7:623-645, 1995; as biodegradable and injectable gel formulations (see, e.g., *Gao Pharm. Res.* 12:857-863, 1995); or, as microspheres for oral administration (see, e.g., Eyles, *J. Pharm. Pharmacol.* 49:669-674, 1997). In another embodiment, the formulations of the compositions of the present invention can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present invention into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989). The compositions of the present invention can also be delivered as nanoparticles.

Pharmaceutical compositions provided by the present invention include compositions wherein the active ingredient (e.g. compounds described herein, including embodiments or examples) is contained in a therapeutically effective amount, i.e., in an amount effective to achieve its intended purpose. The actual amount effective for a particular application will depend, inter alia, on the condition being treated. When administered in methods to treat a disease, such compositions will contain an amount of active ingredient effective to achieve the desired result, e.g., reducing, eliminating, or slowing the progression of disease symptoms (e.g. symptoms of cancer or aberrant PCNA activity). Determination of a therapeutically effective amount of a compound of the invention is well within the capabilities of those skilled in the art, especially in light of the detailed disclosure herein.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated (e.g. symptoms of cancer), kind of concurrent treatment, complications from the disease being treated or other health-related problems. Other therapeutic regimens or agents can be used in conjunction with the methods and compounds of Applicants' invention. Adjustment and manipulation of established dosages (e.g., frequency and duration) are well within the ability of those skilled in the art.

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present invention should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

The compounds described herein can be used in combination with one another, with other active agents known to be useful in treating cancer, or with adjunctive agents that may not be effective alone, but may contribute to the efficacy of the active agent.

In some embodiments, co-administration includes administering one active agent within 0.5, 1, 2, 4, 6, 8, 10, 12, 16, 20, or 24 hours of a second active agent. Co-administration includes administering two active agents simultaneously, approximately simultaneously (e.g., within about 1, 5, 10, 15, 20, or 30 minutes of each other), or sequentially in any order. In some embodiments, co-administration can be accomplished by co-formulation, i.e., preparing a single pharmaceutical composition including both active agents. In other embodiments, the active agents can be formulated separately. In another embodiment, the active and/or adjunctive agents may be linked or conjugated to one another. In some embodiments, the compounds described herein may be combined with treatments for cancer such as radiation or surgery.

As used herein, the term "about" means a range of values including the specified value, which a person of ordinary skill in the art would consider reasonably similar to the specified value. In embodiments, about means within a standard deviation using measurements generally acceptable in the art. In embodiments, about means a range extending to +/−10% of the specified value. In embodiments, about means the specified value.

The term "Proliferating cell nuclear antigen" or "PCNA" refers to an 29 kDa protein that self assembles into a protein complex consisting of 3 subunits of individual PCNA proteins. Together these joined PCNA molecules form a DNA clamp that acts as a processivity factor for DNA polymerase δ in eukaryotic cells. The term "PCNA" may refer to the nucleotide sequence or protein sequence of human PCNA (e.g., Entrez 5111, Uniprot P12004, RefSeq NM_002592 (SEQ ID NO:1), or RefSeq NP_002583 (SEQ ID NO:2)). The term "PCNA" includes both the wild-type form of the nucleotide sequences or proteins as well as any mutants thereof. In some embodiments, "PCNA" is wild-type PCNA. In some embodiments, "PCNA" is one or more mutant forms. The term "PCNA" XYZ refers to a nucleotide sequence or protein of a mutant PCNA wherein the Y numbered amino acid of PCNA that normally has an X amino acid in the wild-type, instead has a Z amino acid in the mutant. In embodiments, a PCNA is the human PCNA. In embodiments, the PCNA has the nucleotide sequence corresponding to reference number GI:33239449 (SEQ ID NO:1). In embodiments, the PCNA has the nucleotide sequence corresponding to RefSeq NM_002592.2 (SEQ ID NO:1). In embodiments, the PCNA has the protein sequence corresponding to reference number GI:4505641 (SEQ ID NO:2). In embodiments, the PCNA has the nucleotide sequence corresponding to RefSeq NP_002583.1 (SEQ ID NO:2). In embodiments, the PCNA has the following amino acid sequence:

```
                                          (SEQ ID NO: 2)
MFEARLVQGSILKKVLEALKDLINEACWDISSSGVNLQSMDSSHVSLVQL

TLRSEGFDTYRCDRNLAMGVNLTSMSKILKCAGNEDIITLRAEDNADTLA

LVFEAPNQEKVSDYEMKLMDLDVEQLGIPEQEYSCVVKMPSGEFARICRD

LSHIGDAVVISCAKDGVKFSASGELGNGNIKLSQTSNVDKEEEAVTIEMN

EPVQLTFALRYLNFFTKATPLSSTVTLSMSADVPLVVEYKIADMGHLKYY

LAPKIEDEEGS.
```

In embodiments, the PCNA is a mutant PCNA. In embodiments, the mutant PCNA is associated with a disease that is not associated with wild-type PCNA. In embodiments, the PCNA includes at least one amino acid mutation (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 mutations) compared to the sequence above. PCNA may be post-translationally modified. Modifications may include phosphorylation, methylation, methylesters of acidic amino acids, ribosylation, acetylation, glycosylation with a variety of sugars, lipidation with a variety of different lipids, poly(ADP) ribosylation, or other post-translational modifications known in the art. Differences in the extent and type of modification influences the levels (e.g., protein levels) of the ca- and nm-PCNA isoforms. In embodiments, a post-translational modification or plurality of post-translational modifications modify the inhibition of PCNA by a compound described herein (e.g., AOH1160, PCNA7) or the binding of a compound described herein (e.g., AOH1160, PCNA7) to PCNA, relative to PCNA without the post-translational modification(s).

The terms "cancer-associated Proliferating cell nuclear antigen" or "caPCNA" as used herein refer to an isoform of PCNA having an acidic isoelectric point (e.g., peptide including protonated amine and/or carboxyl groups, acidic isoelectric point compared to a non-cancer-associated PCNA, PCNA in non-cancerous cells, non-malignant PCNA, prevalent PCNA isoform in non-cancerous cells, or less acidic PCNA isoform in non-cancerous cells). In embodiments, the caPCNA protein includes methylated amino acids (e.g., glutamate, aspartic acid). In embodiments, the caPCNA protein is post-translationally modified with a methylester of an acidic amino acid. In embodiments, the methylesterification of the acidic amino acid residues on PCNA exhibit a $T_{1/2}$ of approximately 20 minutes at pH 8.5. In embodiments, caPCNA is post-translationally modified as described in F. Shen, et al. *J Cell Biochem.* 2011 March; 112(3): 756-760, which is incorporated by reference in its entirety for all purposes.

The terms "non-malignant Proliferating cell nuclear antigen" or "nmPCNA" as used herein refer to an isoform of PCNA having a basic isoelectric point (e.g., peptide including deprotonated amine and/or carboxyl groups, basic isoelectric point compared to a caPCNA, caPCNA in cancerous cells). In embodiments, nmPCNA is the prevalent PCNA isoform in non-cancerous cells.

B. Compounds

Provided herein, inter alia, are compositions of a compound, or a pharmaceutically acceptable salt thereof, having the formula:

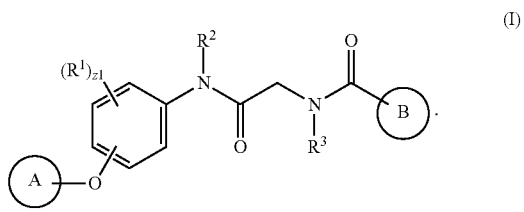

(I)

Ring A is a substituted or unsubstituted phenyl or a substituted or unsubstituted 5 to 6 membered heteroaryl. Ring B is a substituted or unsubstituted naphthyl, a substituted or unsubstituted quinolinyl, or a substituted or unsubstituted isoquinolinyl.

$R^1$ is independently hydrogen, halogen, —$CX^1_3$, —$CHX^1_2$, —$CH_2X^1$, —CN, —$SO_2Cl$, —$SO_nR^{10}$, —$SO_{v1}NR^7R^8$, —$NHNR^7R^8$, —$ONR^7R^8$, —NHC=(O)NHNR⁷R⁸, —NHC=(O)NR⁷R⁸, —N(O)$_{m1}$, —$NR^7R^8$, —C(O)R⁹, —C(O)—OR⁹, —C(O)NR⁷R⁸, —OR¹⁰, —NR⁷SO₂R¹⁰, —NR⁷C=(O)R⁹, —NR⁷C(O)—OR⁹, —NR⁷OR⁹, —OCX¹₃, —OCHX¹₂, —OCH₂X¹, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^1$ substituents may optionally be joined to form a substituted or unsubstituted cycloalkyl, substituted or unsubstituted heterocycloalkyl, substituted or unsubstituted aryl, or substituted or unsubstituted heteroaryl. In embodiments, $R^1$ is independently a halogen, —CX¹₃, —CHX¹₂, —CH₂X¹, —CN, —SO$_{n1}$R¹⁰, —SO$_{v1}$NR⁷R⁸, —NHNH₂, —ONR⁷R⁸, —NHC=(O)NHNH₂, —NHC=(O)NR⁷R⁸, —N(O)$_{m1}$, —NR⁷R⁸, —C(O)R⁹, —C(O)—OR⁹, —C(O)NR⁷R⁸, —OR¹⁰, —NR⁷SO₂R¹⁰, —NR⁷C=(O)R⁹, —NR⁷C(O)—OR⁹, —NR⁷OR⁹, —OCX¹₃, —OCHX¹₂, —OCH₂X¹, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^1$ substituents may optionally be joined to form a substituted or unsubstituted cycloalkyl, substituted or unsubstituted heterocycloalkyl, substituted or unsubstituted aryl, or substituted or unsubstituted heteroaryl. It is understood that when z1 is 0, then $R^1$ is hydrogen.

$R^2$ is independently hydrogen, halogen, —CX²₃, —CHX²₂, —CH₂X², —CN, —OH, —NH₂, —COOH, —CONH₂, —NO₂, —SH, —SO₃H, —SO₄H, —SO₂NH₂, —NHNH₂, —ONH₂, —NHC=(O)NHNH₂, —NHC=(O)NH₂, —NHSO₂H, —NHC=(O)H, —NHC(O)—OH, —NHOH, —OCX²³, —OCHX²², —OCH₂X², substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^3$ is independently hydrogen, halogen, —CX³₃, —CHX³₂, —CH₂X³, —CN, —OH, —NH₂, —COOH, —CONH₂, —NO₂, —SH, —SO₃H, —SO₄H, —SO₂NH₂, —NHNH₂, —ONH₂, —NHC=(O)NHNH₂, —NHC=(O)NH₂, —NHSO₂H, —NHC=(O)H, —NHC(O)—OH, —NHOH, —OCX$^{33}$, —OCHX$^{32}$, —OCH$_2$X$^3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

R$^7$, R$^8$, R$^9$, and R$^{10}$ are independently hydrogen, halogen, —CX$^A_3$, —CHX$^A_2$, —CH$_2$X$^A$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCX$^A_3$, —OCHX$^A_2$, —OCH$_2$X$^A$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^7$ and R$^8$ substituents bonded to the same nitrogen atom may optionally be joined to form a substituted or unsubstituted heterocycloalkyl or substituted or unsubstituted heteroaryl.

The symbol z1 is an integer from 0 to 4. The symbols m1 and v1 are independently an integer 1 or 2. The symbol n1 is an integer from 0 to 4. The symbols X$^1$, X$^2$, X$^3$, and X$^A$ are independently —Cl, —Br, —I, or —F.

In embodiments, the compound has the formula:

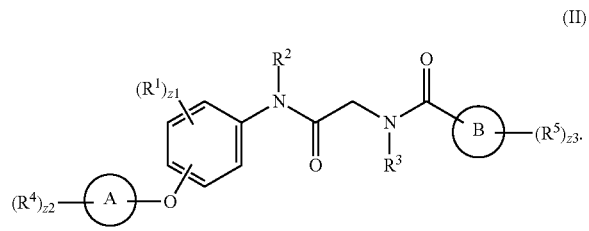

(II)

R$^1$, R$^2$, R$^3$, Ring A, Ring B, and z1 are as described herein, including in compounds of formula (I) and including in embodiments. In embodiments, Ring A is phenyl (substituted or unsubstituted with R$^4$) or 5 to 6 membered heteroaryl (substituted or unsubstituted with R$^4$) and Ring B is napththyl (substituted or unsubstituted with R$^5$), quinolinyl (substituted or unsubstituted with R$^5$), or isoquinolinyl (substituted or unsubstituted with R$^5$).

R$^4$ is independently halogen, —CX$^{43}$, —CHX$^{42}$, —CH$_2$X$^4$, —CN, —SO$_2$Cl, —SO$_{n4}$R$^{14}$, —SO$_{v4}$NR$^{11}$R$^{12}$, —NHNR$^{11}$R$^{12}$, —ONR$^{11}$R$^{12}$, —NHC=(O)NHNR$^{11}$R$^{12}$, —NHC=(O)NR$^{11}$R$^{12}$, —N(O)$_{m4}$, —NR$^{11}$R$^{12}$, —C(O)R$^{13}$, —C(O)—OR$^{13}$, —C(O)NR$^{11}$R$^{12}$, —OR$^{14}$, —NR$^{11}$SO$_2$R$^{14}$, —NR$^{11}$C=(O)R$^{13}$, —NR$^{11}$C(O)—OR$^{13}$, —NR$^{11}$OR$^{13}$, —OCX$^4_3$, —OCHX$^4_2$, —OCH$_2$X$^4$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent R$^4$ substituents may optionally be joined to form a substituted or unsubstituted cycloalkyl, substituted or unsubstituted heterocycloalkyl, substituted or unsubstituted aryl, or substituted or unsubstituted heteroaryl. In embodiments, R$^4$ is independently a halogen, —CX$^{43}$, —CHX$^4_2$, —CH$_2$X$^4$, —CN, —SO$_{n4}$R$^{14}$, —SO$_{v4}$NR$^{11}$R$^{12}$, —NHNR$^{11}$R$^{12}$, —ONR$^{11}$R$^{12}$, —NHC=(O)NHNR$^{11}$R$^{12}$, —NHC=(O)NR$^{11}$R$^{12}$, —N(O)$_{m4}$, —NR$^{11}$R$^{12}$, —C(O)R$^{13}$, —C(O)—OR$^{13}$, —C(O)NR$^{11}$R$^{12}$, —OR$^{14}$, —NR$^{11}$SO$_2$R$^{14}$, —NR$^{11}$C=(O)R$^{13}$, —NR$^{11}$C(O)—OR$^{13}$, —NR$^{11}$OR$^{13}$, —OCX$^4_3$, —OCHX$^4_2$, —OCH$_2$X$^4$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent R$^4$ substituents may optionally be joined to form a substituted or unsubstituted cycloalkyl, substituted or unsubstituted heterocycloalkyl, substituted or unsubstituted aryl, or substituted or unsubstituted heteroaryl. It is understood that when z2 is 0, then R$^4$ is hydrogen.

R$^5$ is independently halogen, —CX$^5_3$, —CHX$^5_2$, —CH$_2$X$^5$, —CN, —SO$_2$Cl, —SO$_{n5}$R$^{18}$, —SO$_{v5}$NR$^{15}$R$^{16}$, —NHNR$^{15}$R$^{16}$, —ONR$^{15}$R$^{16}$, —NHC=(O)NHNR$^{15}$R$^{16}$, —NHC=(O)NR$^{15}$R$^{16}$, —N(O)$_{m5}$, —NR$^{15}$R$^{16}$, —C(O)R$^{17}$, —C(O)—OR$^{17}$, —C(O)NR$^{15}$R$^{16}$, —OR$^{18}$, —NR$^{15}$SO$_2$R$^{18}$, —NR$^{15}$C=(O)R$^{17}$, —NR$^{15}$C(O)—OR$^{17}$, —NR$^{15}$OR$^{17}$, —OCX$^5_3$, —OCHX$^5_2$, —OCH$_2$X$^5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent R$^5$ substituents may optionally be joined to form a substituted or unsubstituted cycloalkyl, substituted or unsubstituted heterocycloalkyl, substituted or unsubstituted aryl, or substituted or unsubstituted heteroaryl. In embodiments, R$^5$ is independently a halogen, —CX$^5_3$, —CHX$^5_2$, —CH$_2$X$^5$, —CN, —SO$_{n5}$R$^{18}$, —SO$_{v5}$NR$^{15}$R$^{16}$, —NHNR$^{15}$R$^{16}$, —ONR$^{15}$R$^{16}$, —NHC=(O)NHNR$^{15}$R$^{16}$, —NHC=(O)NR$^{15}$R$^{16}$, —N(O)$_{m5}$, —NR$^{15}$R$^{16}$, —C(O)R$^{17}$, —C(O)—OR$^{17}$, —C(O)NR$^{15}$R$^{16}$, —OR$^{18}$, —NR$^{15}$SO$_2$R$^{18}$, —NR$^{15}$C=(O)R$^{17}$, —NR$^{15}$C(O)—OR$^{17}$, —NR$^{15}$OR$^{17}$, —OCX$^5_3$, —OCHX$^5_2$, —OCH$_2$X$^5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent R$^5$ substituents may optionally be joined to form a substituted or unsubstituted cycloalkyl, substituted or unsubstituted heterocycloalkyl, substituted or unsubstituted aryl, or substituted or unsubstituted heteroaryl. It is understood that when z3 is 0, then R$^5$ is hydrogen, R$^{11}$, R$^{12}$, R$^{13}$, and R$^{14}$ are independently hydrogen, halogen, —CX$^B_3$, —CHX$^B_2$, —CH$_2$X$^B$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCX$^B_3$, —OCHX$^B_2$, —OCH$_2$X$^B$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{11}$ and R$^{12}$ substituents bonded to the same nitrogen atom may optionally be joined to form a substituted or unsubstituted heterocycloalkyl or substituted or unsubstituted heteroaryl.

R$^{15}$, R$^{16}$, R$^{17}$, and R$^{18}$ are independently hydrogen, halogen, —CX$^C_3$, —CHX$^C_2$, —CH$_2$X$^C$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCX$^{C3}$, —OCHX$^{C2}$, —OCH$_2$X$^C$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{15}$ and R$^{16}$ substituents bonded to the same nitrogen atom may optionally be joined to form a substituted or unsubstituted heterocycloalkyl or substituted or unsubstituted heteroaryl.

The symbol z2 is an integer from 0 to 5. The symbol z3 is an integer from 0 to 7. The symbols m4, m5, v4 and v5 are independently an integer 1 or 2. The symbols n4 and n5 are independently an integer from 0 to 4. The symbols $X^4$, $X^5$, $X^B$, and $X^C$ are independently Cl, —Br, —I, or —F.

In embodiments, Ring A is substituted phenyl. In embodiments, Ring A is unsubstituted phenyl. In embodiments, Ring A is phenyl. In embodiments, Ring A is a substituted 5 to 6 membered heteroaryl. In embodiments, Ring A is an unsubstituted 5 to 6 membered heteroaryl. In embodiments, Ring A is a 5 to 6 membered heteroaryl. In embodiments, Ring A is a substituted thienyl. In embodiments, Ring A is an unsubstituted thienyl. In embodiments, Ring A is a thienyl. In embodiments, Ring A is a 2-thienyl. In embodiments, Ring A is a 3-thienyl. In embodiments, Ring A is a substituted pyridyl. In embodiments, Ring A is an unsubstituted pyridyl. In embodiments, Ring A is a pyridyl. In embodiments, Ring A is a 2-pyridyl. In embodiments, Ring A is a 3-pyridyl. In embodiments, Ring A is a 4-pyridyl. In embodiments, Ring A is unsubstituted pyrrolyl. In embodiments, Ring A is substituted pyrrolyl. In embodiments, Ring A is pyrrolyl. In embodiments, Ring A is unsubstituted furanyl. In embodiments, Ring A is substituted furanyl. In embodiments, Ring A is furanyl. In embodiments, Ring A is unsubstituted pyrazolyl. In embodiments, Ring A is substituted pyrazolyl. In embodiments, Ring A is pyrazolyl. In embodiments, Ring A is unsubstituted imidazolyl. In embodiments, Ring A is substituted imidazolyl. In embodiments, Ring A is imidazolyl. In embodiments, Ring A is unsubstituted oxazolyl. In embodiments, Ring A is substituted oxazolyl. In embodiments, Ring A is oxazolyl. In embodiments, Ring A is unsubstituted isoxazolyl. In embodiments, Ring A is substituted isoxazolyl. In embodiments, Ring A is isoxazolyl. In embodiments, Ring A is unsubstituted thiazolyl. In embodiments, Ring A is substituted thiazolyl. In embodiments, Ring A is thiazolyl. In embodiments, Ring A is unsubstituted triazolyl. In embodiments, Ring A is substituted triazolyl. In embodiments, Ring A is triazolyl. In embodiments, Ring B is a substituted naphthyl. In embodiments, Ring B is unsubstituted naphthyl. In embodiments, Ring B is a naphthyl. In embodiments, Ring B is a 1-naphthyl. In embodiments, Ring B is a 2-naphthyl. In embodiments, Ring B is a quinolinyl. In embodiments, Ring B is a substituted quinolinyl. In embodiments, Ring B is unsubstituted quinolinyl. In embodiments, Ring B is an isoquinolinyl. In embodiments, Ring B is a substituted isoquinolinyl. In embodiments, Ring B is unsubstituted isoquinolinyl. In embodiments, Ring B is a 1-isoquinolinyl. In embodiments, Ring B is a 3-isoquinolinyl. In embodiments, Ring B is a 4-isoquinolinyl.

In embodiments, $R^1$ is independently halogen, —$CF_3$, —$CHF_2$, —$OCF_3$, —$OCHF_2$, substituted or unsubstituted $C_1$-$C_8$ alkyl, substituted or unsubstituted 2 to 8 membered heteroalkyl, substituted or unsubstituted $C_3$-$C_8$ cycloalkyl, substituted or unsubstituted 3 to 8 membered heterocycloalkyl, substituted or unsubstituted $C_6$-$C_{10}$ aryl, or substituted or unsubstituted 5 to 10 membered heteroaryl. In embodiments, $R^1$ is independently halogen, —$CF_3$, —OH, —$NH_2$, —SH, substituted or unsubstituted $C_1$-$C_4$ alkyl, substituted or unsubstituted 2 to 4 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl. In embodiments, $R^1$ is independently halogen, —OH, —$NH_2$, —SH, unsubstituted $C_1$-$C_4$ alkyl, or unsubstituted 2 to 4 membered heteroalkyl. In embodiments, $R^1$ is independently halogen, —OH, unsubstituted methyl, or unsubstituted methoxy. In embodiments, $R^1$ is independently halogen. In embodiments, $R^1$ is independently —$CF_3$. In embodiments, $R^1$ is independently $CHF_2$. In embodiments, $R^1$ is independently —$CH_2F$. In embodiments, $R^1$ is independently —$OCF_3$. In embodiments, $R^1$ is independently —$OCHF_2$. In embodiments, $R^1$ is independently —$OCH_2F$. In embodiments, $R^1$ is independently substituted or unsubstituted $C_1$-$C_8$ alkyl. In embodiments, $R^1$ is independently substituted or unsubstituted 2 to 8 membered heteroalkyl. In embodiments, $R^1$ is independently substituted or unsubstituted $C_3$-$C_8$ cycloalkyl. In embodiments, $R^1$ is independently substituted or unsubstituted 3 to 8 membered heterocycloalkyl. In embodiments, $R^1$ is independently substituted or unsubstituted $C_6$-$C_{10}$ aryl. In embodiments, $R^1$ is independently substituted or unsubstituted 5 to 10 membered heteroaryl. In embodiments, $R^1$ is independently —OH. In embodiments, $R^1$ is independently —$NH_2$. In embodiments, $R^1$ is independently —SH. In embodiments, $R^1$ is independently substituted or unsubstituted $C_1$-$C_4$ alkyl. In embodiments, $R^1$ is independently substituted or unsubstituted 2 to 4 membered heteroalkyl. In embodiments, $R^1$ is independently substituted or unsubstituted $C_3$-$C_6$ cycloalkyl. In embodiments, $R^1$ is independently substituted or unsubstituted 3 to 6 membered heterocycloalkyl. In embodiments, $R^1$ is independently substituted or unsubstituted phenyl. In embodiments, $R^1$ is independently substituted or unsubstituted 5 to 6 membered heteroaryl.

In embodiments, $R^1$ is independently substituted $C_1$-$C_8$ alkyl. In embodiments, $R^1$ is independently substituted 2 to 8 membered heteroalkyl. In embodiments, $R^1$ is independently substituted $C_3$-$C_8$ cycloalkyl. In embodiments, $R^1$ is independently substituted 3 to 8 membered heterocycloalkyl. In embodiments, $R^1$ is independently substituted $C_6$-$C_{10}$ aryl. In embodiments, $R^1$ is independently substituted 5 to 10 membered heteroaryl. In embodiments, $R^1$ is independently substituted $C_1$-$C_4$ alkyl. In embodiments, $R^1$ is independently substituted to 4 membered heteroalkyl. In embodiments, $R^1$ is independently substituted $C_3$-$C_6$ cycloalkyl. In embodiments, $R^1$ is independently substituted 3 to 6 membered heterocycloalkyl. In embodiments, $R^1$ is independently substituted phenyl. In embodiments, $R^1$ is independently substituted 5 to 6 membered heteroaryl. In embodiments, $R^1$ is independently unsubstituted $C_1$-$C_8$ alkyl. In embodiments, $R^1$ is independently unsubstituted 2 to 8 membered heteroalkyl. In embodiments, $R^1$ is independently unsubstituted $C_3$-$C_8$ cycloalkyl. In embodiments, $R^1$ is independently unsubstituted 3 to 8 membered heterocycloalkyl. In embodiments, $R^1$ is independently unsubstituted $C_6$-$C_{10}$ aryl. In embodiments, $R^1$ is independently unsubstituted 5 to 10 membered heteroaryl. In embodiments, $R^1$ is independently unsubstituted $C_1$-$C_4$ alkyl. In embodiments, $R^1$ is independently unsubstituted 2 to 4 membered heteroalkyl. In embodiments, $R^1$ is independently unsubstituted $C_3$-$C_6$ cycloalkyl. In embodiments, $R^1$ is independently unsubstituted 3 to 6 membered heterocycloalkyl. In embodiments, $R^1$ is independently unsubstituted phenyl. In embodiments, $R^1$ is independently unsubstituted 5 to 6 membered heteroaryl. In embodiments, $R^1$ is independently unsubstituted methyl. In embodiments, $R^1$ is independently unsubstituted ethyl. In embodiments, $R^1$ is independently unsubstituted isopropyl. In embodiments, $R^1$ is independently unsubstituted tert-butyl. In embodiments, $R^1$ is independently unsubstituted methoxy. In embodiments, $R^1$ is independently unsubstituted ethoxy. In embodiments, $R^1$ is independently —F. In embodiments, $R^1$ is independently —Cl. In embodiments, $R^1$ is independently —Br. In embodiments, $R^1$ is independently —I. In embodiments, $R^1$ is independently hydrogen. In embodiments, $R^1$ is independently halogen, —$CF_3$, —$CHF_2$, —$CH_2F$, —$OCF_3$, —$OCHF_2$, —$OCH_2F$, —OH, —$NH_2$, —SH, unsubstituted $C_1$-$C_4$ alkyl, or unsubstituted 2 to 4 membered heteroalkyl.

In embodiments, z1 is 1. In embodiments, z1 is 0. In embodiments, z1 is 2. In embodiments, z1 is 3. In embodiments, z1 is 4.

In embodiments, $R^2$ is independently hydrogen, —$CX^2_3$, —$CHX^2_2$, —$CH_2X^2$, —CN, —C(O)H, —C(O)OH, —C(O)$NH_2$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl. In embodiments $R^2$ is independently hydrogen, unsubstituted methyl, unsubstituted ethyl, or unsubstituted isopropyl. In embodiments, $R^2$ is independently hydrogen. In embodiments, $R^2$ is independently unsubstituted methyl. In embodiments, $R^2$ is independently unsubstituted ethyl. In embodiments, $R^2$ is independently unsubstituted isopropyl. In embodiments, $R^2$ is independently unsubstituted tert-butyl.

In embodiments, $R^2$ is independently hydrogen, halogen, —$CX^2_3$, —$CHX^2_2$, —$CH_2X^2$, —CN, —COOH, —$CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^3$ is independently hydrogen, —$CX^2_3$, —$CHX^2_2$, —$CH_2X^2$, —CN, —C(O)H, —C(O)OH, —C(O)$NH_2$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl. In embodiments, $R^3$ is independently hydrogen, unsubstituted methyl, unsubstituted ethyl, or unsubstituted isopropyl. In embodiments, $R^3$ is independently hydrogen. In embodiments, $R^3$ is independently unsubstituted methyl. In embodiments, $R^3$ is independently unsubstituted ethyl. In embodiments, $R^3$ is independently unsubstituted isopropyl. In embodiments, $R^3$ is independently unsubstituted tert-butyl. In embodiments, $R^3$ is independently hydrogen, halogen, —$CX^3_3$, —$CHX^3_2$, —$CH_2X^3$, —CN, —COOH, —$CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^4$ is independently halogen, —$CF_3$, —$CHF_2$, —$CH_2F$, —CN, —OH, —$NH_2$, —COOH, —$CONH_2$, —$NO_2$, —SH, —$OCF_3$, —$OCHF_2$, —$OCH_2F$, substituted or unsubstituted $C_1$-$C_8$ alkyl, substituted or unsubstituted 2 to 8 membered heteroalkyl, substituted or unsubstituted $C_3$-$C_8$ cycloalkyl, substituted or unsubstituted 3 to 8 membered heterocycloalkyl, substituted or unsubstituted $C_6$-$C_{10}$ aryl, or substituted or unsubstituted 5 to 10 membered heteroaryl. In embodiments, $R^4$ is independently halogen, —$CF_3$, —OH, —$NH_2$, —SH, substituted or unsubstituted $C_1$-$C_4$ alkyl, substituted or unsubstituted 2 to 4 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl. In embodiments, $R^4$ is independently halogen, —OH, —$NH_2$, —SH, unsubstituted $C_1$-$C_4$ alkyl, or unsubstituted 2 to 4 membered heteroalkyl. In embodiments, $R^4$ is independently halogen, —OH, unsubstituted methyl, or unsubstituted methoxy. In embodiments, $R^4$ is independently halogen. In embodiments, $R^4$ is independently —OH. In embodiments, $R^4$ is independently unsubstituted methyl. In embodiments, $R^4$ is independently unsubstituted methoxy. In embodiments, $R^4$ is independently unsubstituted ethyl. In embodiments, $R^4$ is independently —F. In embodiments, $R^4$ is independently —Cl. In embodiments, $R^4$ is independently —Br. In embodiments, $R^4$ is independently —I. In embodiments, $R^4$ is independently —$CF_3$. In embodiments, $R^4$ is independently —$NH_2$. In embodiments, $R^4$ is independently —SH. In embodiments, $R^4$ is independently unsubstituted isopropyl. In embodiments, $R^4$ is independently unsubstituted tert-butyl. In embodiments, $R^4$ is independently unsubstituted ethoxy. In embodiments, $R^4$ is independently unsubstituted propoxy.

In embodiments, $R^4$ is independently a halogen. In embodiments, $R^4$ is independently —$CX^4_3$. In embodiments, $R^4$ is independently —$CHX^4_2$. In embodiments, $R^4$ is independently —$CH_2X^4$. In embodiments, $R^4$ is independently —CN. In embodiments, $R^4$ is independently —$SO_{n4}R^{14}$. In embodiments, $R^4$ is independently —$SR^{14}$. In embodiments, $R^4$ is independently —$SO_{v4}NR^{11}R^{12}$. In embodiments, $R^4$ is independently —$NHNR^{11}R^{12}$. In embodiments, $R^4$ is independently —$ONR^{11}R^{12}$. In embodiments, $R^4$ is independently —NHC=(O)$NHNR^{11}R^{12}$. In embodiments, $R^4$ is independently —NHC=(O)$NR^{11}R^{12}$. In embodiments, $R^4$ is independently —$N(O)_{m4}$. In embodiments, $R^4$ is independently —$NR^{11}R^{12}$. In embodiments, $R^4$ is independently —$C(O)R^{13}$. In embodiments, $R^4$ is independently —C(O)—$OR^{13}$. In embodiments, $R^4$ is independently —$C(O)NR^{11}R^{12}$. In embodiments, $R^4$ is independently —$OR^{14}$. In embodiments, $R^4$ is independently —$NR^{11}SO_2R^{14}$. In embodiments, $R^4$ is independently —$NR^{11}C=(O)R^{13}$. In embodiments, $R^4$ is independently —(O) $OR^{13}$. In embodiments, $R^4$ is independently —$NR^{11}OR^{13}$. In embodiments, $R^4$ is independently —$OCX^4_3$. In embodiments, $R^4$ is independently —$OCHX^4_2$. In embodiments, $R^4$ is independently —$OCH_2X^4$. In embodiments, $R^4$ is independently —$CF_3$. In embodiments, $R^4$ is independently —$CHF_2$. In embodiments, $R^4$ is independently —$CH_2F$. In embodiments, $R^4$ is independently —$SO_2CH_3$. In embodiments, $R^4$ is independently —$SO_2NH_2$. In embodiments, $R^4$ is independently —SH. In embodiments, $R^4$ is independently —$N(O)_2$. In embodiments, $R^4$ is independently —$NH_2$. In embodiments, $R^4$ is independently —$C(O)CH_3$. In embodiments, $R^4$ is independently —C(O)OH. In embodiments, $R^4$ is independently —$C(O)NH_2$. In embodiments, $R^4$ is independently —OH. In embodiments, $R^4$ is independently —$OCF_3$. In embodiments, $R^4$ is independently —$OCHF_2$. In embodiments, $R^4$ is independently —$OCH_2F$.

In embodiments, $R^4$ is independently halogen, —$CF_3$, —$CHF_2$, —$CH_2F$, —CN, —OH, —$NH_2$, —COOH, —$CONH_2$, —$NO_2$, —SH, —$OCF_3$, —$OCHF_2$, —$OCH_2F$, substituted or unsubstituted $C_1$-$C_8$ alkyl, substituted or unsubstituted 2 to 8 membered heteroalkyl, substituted or unsubstituted $C_3$-$C_8$ cycloalkyl, substituted or unsubstituted 3 to 8 membered heterocycloalkyl, substituted or unsubstituted $C_6$-$C_{10}$ aryl, or substituted or unsubstituted 5 to 10 membered heteroaryl. In embodiments, $R^4$ is independently halogen, —$CF_3$, —OH, —$NH_2$, —SH, substituted or unsubstituted $C_1$-$C_4$ alkyl, substituted or unsubstituted 2 to 4 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl. In embodiments, $R^4$ is independently halogen, —$CF_3$, —$CHF_2$, —$CH_2F$, —$OCF_3$, —$OCHF_2$, —$OCH_2F$, —OH, —$NH_2$, —SH, unsubstituted $C_1$-$C_4$ alkyl, or unsubstituted 2 to 4 membered heteroalkyl.

In embodiments, $R^4$ is independently substituted or unsubstituted alkyl. In embodiments, $R^4$ is independently substituted or unsubstituted heteroalkyl. In embodiments, $R^4$ is independently substituted or unsubstituted cycloalkyl. In embodiments, $R^4$ is independently substituted or unsubstituted heterocycloalkyl. In embodiments, $R^4$ is independently substituted or unsubstituted aryl. In embodiments, $R^4$ is independently substituted or unsubstituted heteroaryl. In embodiments, two adjacent $R^4$ substituents may optionally be joined to form a substituted or unsubstituted cycloalkyl. In embodiments, two adjacent $R^4$ substituents may optionally be joined to form a substituted or unsubstituted heterocycloalkyl. In embodiments, two adjacent $R^4$ substituents may optionally be joined to form a substituted or unsubstituted aryl. In embodiments, two adjacent $R^4$ substituents may optionally be joined to form a substituted or unsubstituted heteroaryl.

In embodiments, $R^4$ is independently substituted or unsubstituted alkyl (e.g. $C_1$-$C_8$ alkyl, $C_1$-$C_6$ alkyl, or $C_1$-$C_4$ alkyl), substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), substituted or unsubstituted cycloalkyl (e.g. $C_3$-$C_8$ cycloalkyl, $C_4$-$C_8$ cycloalkyl, or $C_5$-$C_6$ cycloalkyl), substituted or unsubstituted heterocycloalkyl (e.g. 3 to 8 membered heterocycloalkyl, 4 to 8 membered heterocycloalkyl, or 5 to 6 membered heterocycloalkyl), substituted or unsubstituted aryl (e.g. $C_6$-$C_{10}$ aryl or $C_6$ aryl), or substituted or unsubstituted heteroaryl (e.g. 5 to 10 membered heteroaryl, 5 to 9 membered heteroaryl, or 5 to 6 membered heteroaryl). In embodiments, $R^4$ is independently substituted alkyl (e.g. $C_1$-$C_8$ alkyl, $C_1$-$C_6$ alkyl, or $C_1$-$C_4$ alkyl), substituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), substituted cycloalkyl (e.g. $C_3$-$C_8$ cycloalkyl, $C_4$-$C_8$ cycloalkyl, or $C_5$-$C_6$ cycloalkyl), substituted heterocycloalkyl (e.g. 3 to 8 membered heterocycloalkyl, 4 to 8 membered heterocycloalkyl, or 5 to 6 membered heterocycloalkyl), substituted aryl (e.g. $C_6$-$C_{10}$ aryl or $C_6$ aryl), or substituted heteroaryl (e.g. 5 to 10 membered heteroaryl, 5 to 9 membered heteroaryl, or 5 to 6 membered heteroaryl). In embodiments, $R^4$ is independently unsubstituted alkyl (e.g. $C_1$-$C_8$ alkyl, $C_1$-$C_6$ alkyl, or $C_1$-$C_4$ alkyl), unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_8$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl or $C_6$ aryl), or unsubstituted heteroaryl (e.g. 5 to 10 membered heteroaryl, 5 to 9 membered heteroaryl, or 5 to 6 membered heteroaryl).

In embodiments, $R^{14}$ is independently hydrogen, —$CX^B_3$, —$CHX^B_2$, —$CH_2X^B$, —CN, —COOH, —$CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^{14}$ is independently hydrogen. In embodiments, $R^{14}$ is independently —$CX^B_3$. In embodiments, $R^{14}$ is independently —$CHX^B_2$. In embodiments, $R^{14}$ is independently $CH_2X^B$. In embodiments, $R^{14}$ is independently —CN. In embodiments, $R^{14}$ is independently —COOH. In embodiments, $R^{14}$ is independently —$CONH_2$. In embodiments, $R^{14}$ is independently substituted or unsubstituted alkyl. In embodiments, $R^{14}$ is independently substituted or unsubstituted heteroalkyl. In embodiments, $R^{14}$ is independently substituted or unsubstituted cycloalkyl. In embodiments, $R^{14}$ is independently substituted or unsubstituted heterocycloalkyl. In embodiments, $R^{14}$ is independently substituted or unsubstituted aryl. In embodiments, $R^{14}$ is independently substituted or unsubstituted heteroaryl. In embodiments, $R^{14}$ is independently substituted alkyl. In embodiments, $R^{14}$ is independently substituted heteroalkyl. In embodiments, $R^{14}$ is independently substituted cycloalkyl. In embodiments, $R^{14}$ is independently substituted heterocycloalkyl. In embodiments, $R^{14}$ is independently substituted aryl. In embodiments, $R^{14}$ is independently substituted heteroaryl. In embodiments, $R^{14}$ is independently unsubstituted alkyl. In embodiments, $R^{14}$ is independently unsubstituted heteroalkyl. In embodiments, $R^{14}$ is independently unsubstituted cycloalkyl. In embodiments, $R^{14}$ is independently unsubstituted heterocycloalkyl. In embodiments, $R^{14}$ is independently unsubstituted aryl. In embodiments, $R^{14}$ is independently unsubstituted heteroaryl. In embodiments, $R^{14}$ is independently substituted or unsubstituted $C_1$-$C_4$ alkyl. In embodiments, $R^{14}$ is independently substituted or unsubstituted 2 to 4 membered heteroalkyl. In embodiments, $R^{14}$ is independently substituted or unsubstituted $C_3$-$C_6$ cycloalkyl. In embodiments, $R^{14}$ is independently substituted or unsubstituted 3 to 6 membered heterocycloalkyl. In embodiments, $R^{14}$ is independently substituted or unsubstituted phenyl. In embodiments, $R^{14}$ is independently substituted or unsubstituted 5 to 6 membered heteroaryl. In embodiments, $R^{14}$ is independently substituted $C_1$-$C_4$ alkyl. In embodiments, $R^{14}$ is independently substituted 2 to 4 membered heteroalkyl. In embodiments, $R^{14}$ is independently substituted $C_3$-$C_6$ cycloalkyl. In embodiments, $R^{14}$ is independently substituted 3 to 6 membered heterocycloalkyl. In embodiments, $R^{14}$ is independently substituted phenyl. In embodiments, $R^{14}$ is independently substituted 5 to 6 membered heteroaryl. In embodiments, $R^{14}$ is independently unsubstituted $C_1$-$C_4$ alkyl. In embodiments, $R^{14}$ is independently unsubstituted 2 to 4 membered heteroalkyl. In embodiments, $R^{14}$ is independently unsubstituted $C_3$-$C_6$ cycloalkyl. In embodiments, $R^{14}$ is independently unsubstituted 3 to 6 membered heterocycloalkyl. In embodiments, $R^{14}$ is independently unsubstituted phenyl. In embodiments, $R^{14}$ is independently unsubstituted 5 to 6 membered heteroaryl. In embodiments, $R^{14}$ is hydrogen or unsubstituted methyl.

In embodiments, $R^{14}$ is substituted or unsubstituted pyrazolyl. In embodiments, $R^{14}$ is substituted or unsubstituted pyridyl. In embodiments, $R^{14}$ is substituted or unsubstituted imidazolyl. In embodiments, $R^{14}$ is substituted or unsubstituted oxazolyl. In embodiments, $R^{14}$ is substituted or unsubstituted isoxazolyl. In embodiments, $R^{14}$ is substituted or unsubstituted thiazolyl. In embodiments, $R^{14}$ is substituted or unsubstituted furanyl. In embodiments, $R^{14}$ is substituted or unsubstituted pyrrolyl. In embodiments, $R^{14}$ is substituted or unsubstituted thienyl.

In embodiments, $R^{14}$ is substituted pyrazolyl. In embodiments, $R^{14}$ is substituted pyridyl. In embodiments, $R^{14}$ is substituted imidazolyl. In embodiments, $R^{14}$ is substituted oxazolyl. In embodiments, $R^{14}$ is substituted isoxazolyl. In embodiments, $R^{14}$ is substituted thiazolyl. In embodiments, $R^{14}$ is substituted furanyl. In embodiments, $R^{14}$ is substituted pyrrolyl. In embodiments, $R^{14}$ is substituted thienyl. In embodiments, $R^{14}$ is unsubstituted pyrazolyl. In embodiments, $R^{14}$ is unsubstituted pyridyl. In embodiments, $R^{14}$ is unsubstituted imidazolyl. In embodiments, $R^{14}$ is unsubstituted oxazolyl. In embodiments, $R^{14}$ is unsubstituted isoxazolyl. In embodiments, $R^{14}$ is unsubstituted thiazolyl. In embodiments, $R^{14}$ is unsubstituted furanyl. In embodiments, $R^{14}$ is unsubstituted pyrrolyl. In embodiments, $R^{14}$ is unsubstituted thienyl.

In embodiments, $R^{14}$ is independently hydrogen or unsubstituted alkyl. In embodiments, $R^{14}$ is independently hydrogen or unsubstituted $C_1$-$C_6$ alkyl. In embodiments, $R^{14}$ is independently hydrogen or unsubstituted $C_1$-$C_5$ alkyl. In embodiments, $R^{14}$ is independently hydrogen or unsubstituted $C_1$-$C_4$ alkyl. In embodiments, $R^{14}$ is independently hydrogen or unsubstituted $C_1$-$C_3$ alkyl. In embodiments, $R^{14}$ is independently hydrogen or unsubstituted $C_1$-$C_2$ alkyl. In embodiments, $R^{14}$ is independently hydrogen or unsubstituted $C_2$-$C_6$ alkyl. In embodiments, $R^{14}$ is independently hydrogen or unsubstituted $C_2$-$C_5$ alkyl. In embodiments, $R^{14}$ is independently hydrogen or unsubstituted $C_2$-$C_4$ alkyl. In embodiments, $R^{14}$ is independently hydrogen or unsubstituted $C_2$-$C_3$ alkyl. In embodiments, $R^{14}$ is independently hydrogen or unsubstituted $C_3$-$C_6$ alkyl. In embodiments, $R^{14}$ is independently hydrogen or unsubstituted $C_4$-$C_6$ alkyl. In embodiments, $R^{14}$ is independently hydrogen or unsubstituted $C_5$-$C_6$ alkyl. In embodiments, $R^{14}$ is independently hydrogen. In embodiments, $R^{14}$ is independently unsubstituted alkyl. In embodiments, $R^{14}$ is independently unsubstituted $C_1$-$C_6$ alkyl. In embodiments, $R^{14}$ is independently unsubstituted $C_1$-$C_5$ alkyl. In embodiments, $R^{14}$ is independently unsubstituted $C_1$-$C_4$ alkyl. In embodiments, $R^{14}$ is independently unsubstituted $C_1$-$C_3$ alkyl. In embodiments, $R^{14}$ is independently unsubstituted $C_1$-$C_2$ alkyl. In embodiments, $R^{14}$ is independently unsubstituted $C_2$-$C_6$ alkyl. In embodiments, $R^{14}$ is independently unsubstituted $C_2$-$C_5$ alkyl. In embodiments, $R^{14}$ is independently unsubstituted $C_2$-$C_4$ alkyl. In embodiments, $R^{14}$ is independently unsubstituted $C_2$-$C_3$ alkyl. In embodiments, $R^{14}$ is independently unsubstituted $C_3$-$C_6$ alkyl. In embodiments, $R^{14}$ is independently unsubstituted $C_4$-$C_6$ alkyl. In embodiments, $R^{14}$ is independently unsubstituted $C_5$-$C_6$ alkyl. In embodiments, $R^{14}$ is independently —$CF_3$. In embodiments, $R^{14}$ is independently —$CHF_2$. In embodiments, $R^{14}$ is independently —$CH_2F$. In embodiments, $R^{14}$ is independently —$CCl_3$. In embodiments, $R^{14}$ is independently —$CHCl_2$. In embodiments, $R^{14}$ is independently —$CH_2Cl$. In embodiments, $R^{14}$ is independently —$CBr_3$. In embodiments, $R^{14}$ is independently —$CHBr_2$. In embodiments, $R^{14}$ is independently —$CH_2Br$. In embodiments, $R^{14}$ is independently —$CI_3$. In embodiments, $R^{14}$ is independently —$CHI_2$. In embodiments, $R^{14}$ is independently —$CH_2I$. In embodiments, $R^{14}$ is independently unsubstituted $C_1$-$C_4$ haloalkyl. In embodiments, $R^{14}$ is independently unsubstituted $C_1$-$C_3$ haloalkyl. In embodiments, $R^{14}$ is independently unsubstituted $C_1$-$C_2$ haloalkyl. In embodiments, $R^{14}$ is independently unsubstituted $C_2$-$C_6$ haloalkyl. In embodiments, $R^{14}$ is independently unsubstituted $C_2$-$C_5$ haloalkyl. In embodiments, $R^{14}$ is independently unsubstituted $C_2$-$C_4$ haloalkyl. In embodiments, $R^{14}$ is independently unsubstituted $C_2$-$C_3$ haloalkyl. In embodiments, $R^{14}$ is independently unsubstituted methyl. In embodiments, $R^{14}$ is independently unsubstituted ethyl. In embodiments, $R^{14}$ is independently unsubstituted propyl. In embodiments, $R^{14}$ is independently unsubstituted isopropyl. In embodiments, $R^{14}$ is independently unsubstituted butyl. In embodiments, $R^{14}$ is independently unsubstituted isobutyl. In embodiments, $R^{14}$ is independently unsubstituted tert-butyl.

In embodiments, z2 is 1. In embodiments, z2 is 0. In embodiments, z2 is 2. In embodiments, z2 is 3. In embodiments, z2 is 4. In embodiments, z2 is 5.

In embodiments, $R^5$ is independently halogen, —$CF_3$, —$CHF_2$, —$CH_2F$, —CN, —OH, —$NH_2$, —COOH, —$CONH_2$, —$NO_2$, —SH, —$OCF_3$, —$OCHF_2$, —$OCH_2F$, substituted or unsubstituted $C_1$-$C_8$ alkyl, substituted or unsubstituted 2 to 8 membered heteroalkyl, substituted or unsubstituted $C_3$-$C_8$ cycloalkyl, substituted or unsubstituted 3 to 8 membered heterocycloalkyl, substituted or unsubstituted $C_6$-$C_{10}$ aryl, or substituted or unsubstituted 5 to 10 membered heteroaryl. In embodiments, $R^5$ is independently halogen, —$CF_3$, —$CHF_2$, —$CH_2F$, —CN, —OH, —$NH_2$, —COOH, —$CONH_2$, —$NO_2$, —SH, —$OCF_3$, —$OCHF_2$, —$OCH_2F$, substituted or unsubstituted $C_1$-$C_8$ alkyl or substituted or unsubstituted 2 to 8 membered heteroalkyl.

In embodiments, $R^5$ is independently halogen, —$CF_3$, —OH, —$NH_2$, —SH, substituted or unsubstituted $C_1$-$C_4$ alkyl, substituted or unsubstituted 2 to 4 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl. In embodiments, $R^5$ is independently halogen, —OH, —$NH_2$, —SH, unsubstituted $C_1$-$C_4$ alkyl, or unsubstituted 2 to 4 membered heteroalkyl. In embodiments, $R^5$ is independently halogen, —OH, unsubstituted methyl, or unsubstituted methoxy. In embodiments, $R^5$ is independently halogen. In embodiments, $R^5$ is independently —OH. In embodiments, $R^5$ is independently unsubstituted methyl. In embodiments, $R^5$ is independently unsubstituted methoxy. In embodiments, $R^5$ is independently unsubstituted ethyl. In embodiments, $R^5$ is independently —F. In embodiments, $R^5$ is independently —Cl. In embodiments, $R^5$ is independently —Br. In embodiments, $R^5$ is independently —I. In embodiments, $R^5$ is independently —$CF_3$. In embodiments, $R^5$ is independently —$NH_2$. In embodiments, $R^5$ is independently —SH. In embodiments, $R^5$ is independently unsubstituted isopropyl. In embodiments, $R^5$ is independently unsubstituted tert-butyl. In embodiments, $R^5$ is independently unsubstituted ethoxy. In embodiments, $R^5$ is independently unsubstituted propoxy.

In embodiments, $R^5$ is independently substituted or unsubstituted alkyl (e.g. $C_1$-$C_8$ alkyl, $C_1$-$C_6$ alkyl, or $C_1$-$C_4$ alkyl), substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), substituted or unsubstituted cycloalkyl (e.g. $C_3$-$C_8$ cycloalkyl, $C_4$-$C_8$ cycloalkyl, or $C_5$-$C_6$ cycloalkyl), substituted or unsubstituted heterocycloalkyl (e.g. 3 to 8 membered heterocycloalkyl, 4 to 8 membered heterocycloalkyl, or 5 to 6 membered heterocycloalkyl), substituted or unsubstituted aryl (e.g. $C_6$-$C_{10}$ aryl or $C_6$ aryl), or substituted or unsubstituted heteroaryl (e.g. 5 to 10 membered heteroaryl, 5 to 9 membered heteroaryl, or 5 to 6 membered heteroaryl). In embodiments, $R^5$ is independently substituted alkyl (e.g. $C_1$-$C_8$ alkyl, $C_1$-$C_6$ alkyl, or $C_1$-$C_4$ alkyl), substituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), substituted cycloalkyl (e.g. $C_3$-$C_8$ cycloalkyl, $C_4$-$C_8$ cycloalkyl, or $C_5$-$C_6$ cycloalkyl), substituted heterocycloalkyl (e.g. 3 to 8 membered heterocycloalkyl, 4 to 8 membered heterocycloalkyl, or 5 to 6 membered heterocycloalkyl), substituted aryl (e.g. $C_6$-$C_{10}$ aryl or $C_6$ aryl), or substituted heteroaryl (e.g. 5 to 10 membered heteroaryl, 5 to 9 membered heteroaryl, or 5 to 6 membered heteroaryl). In embodiments, $R^5$ is independently unsubstituted alkyl (e.g. $C_1$-$C_8$ alkyl, $C_1$-$C_6$ alkyl, or $C_1$-$C_4$ alkyl), unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_8$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl or $C_6$ aryl), or unsubstituted heteroaryl (e.g. 5 to 10 membered heteroaryl, 5 to 9 membered heteroaryl, or 5 to 6 membered heteroaryl). In embodiments, $R^5$ is independently halogen, —$CF_3$, —$CHF_2$, —$CH_2F$, —$OCF_3$, —$OCHF_2$, —$OCH_2F$, —OH, —$NH_2$, —SH, unsubstituted $C_1$-$C_4$ alkyl, or unsubstituted 2 to 4 membered heteroalkyl. In embodiments, $R^5$ is unsubstituted $C_1$-$C_4$ alkyl, or unsubstituted 2 to 4 membered heteroalkyl. In embodiments, $R^5$ is unsubstituted $C_1$-$C_4$ alkyl. In embodiments, $R^5$ is unsubstituted 2 to 4 membered heteroalkyl.

In embodiments, $R^5$ is independently unsubstituted alkyl. In embodiments, $R^5$ is independently unsubstituted $C_1$-$C_6$ alkyl. In embodiments, $R^5$ is independently unsubstituted $C_1$-$C_5$ alkyl. In embodiments, $R^5$ is independently unsubstituted $C_1$-$C_4$ alkyl. In embodiments, $R^5$ is independently unsubstituted $C_1$-$C_3$ alkyl. In embodiments, $R^5$ is independently unsubstituted $C_1$-$C_2$ alkyl. In embodiments, $R^5$ is independently unsubstituted $C_2$-$C_6$ alkyl. In embodiments, $R^5$ is independently unsubstituted $C_2$-$C_5$ alkyl. In embodiments, $R^5$ is independently unsubstituted $C_2$-$C_4$ alkyl. In embodiments, $R^5$ is independently unsubstituted $C_2$-$C_3$ alkyl. In embodiments, $R^5$ is independently unsubstituted $C_3$-$C_6$ alkyl. In embodiments, $R^5$ is independently unsubstituted $C_4$-$C_6$ alkyl. In embodiments, $R^5$ is independently unsubstituted $C_5$-$C_6$ alkyl.

In embodiments, z3 is 1. In embodiments, z3 is 0. In embodiments, z3 is 2. In embodiments, z3 is 3. In embodiments, z3 is 4. In embodiments, z3 is 5. In embodiments, z3 is 6. In embodiments, z3 is 7.

In embodiments, $R^{11}$, $R^{12}$, $R^{13}$, or $R^{14}$ is independently hydrogen, —$CX^B_3$, —$CHX^B_2$, —$CH_2X^B$, —CN, —COOH, —$CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^{11}$, $R^{12}$, $R^{13}$, or $R^{14}$ is independently hydrogen. In embodiments, $R^{11}$, $R^{12}$, $R^{13}$, or $R^{14}$ is independently —$CX^B_3$. In embodiments, $R^{11}$, $R^{12}$, $R^{13}$, or $R^{14}$ is independently —$CHX^B_2$. In embodiments, $R^{11}$, $R^{12}$, $R^{13}$, or $R^{14}$ is independently —$CH_2X^B$. In embodiments, $R^{11}$, $R^{12}$, $R^{13}$, or $R^{14}$ is independently —CN. In embodiments, $R^{11}$, $R^{12}$, $R^{13}$, or $R^{14}$ is independently —COOH. In embodiments, $R^{11}$, $R^{12}$, $R^{13}$, or $R^{14}$ is independently —$CONH_2$. In embodiments, $R^{11}$, $R^{12}$, $R^{13}$, or $R^{14}$ is independently substituted or unsubstituted alkyl. In embodiments, $R^{11}$, $R^{12}$, $R^{13}$, or $R^{14}$ is independently substituted or unsubstituted heteroalkyl. In embodiments, $R^{11}$, $R^{12}$, $R^{13}$, or $R^{14}$ is independently substituted or unsubstituted cycloalkyl. In embodiments, $R^{11}$, $R^{12}$, $R^{13}$, or $R^{14}$ is independently substituted or unsubstituted heterocycloalkyl. In embodiments, $R^{11}$, $R^{12}$, $R^{13}$, or $R^{14}$ is independently substituted or unsubstituted aryl. In embodiments, $R^{11}$, $R^{12}$, $R^{13}$, or $R^{14}$ is independently substituted or unsubstituted heteroaryl. In embodiments, $R^{11}$, $R^{12}$, $R^{13}$, or $R^{14}$ is independently substituted heteroalkyl. In embodiments, $R^{11}$, $R^{12}$, $R^{13}$, or $R^{14}$ is independently substituted cycloalkyl. In embodiments, $R^{11}$, $R^{12}$, $R^{13}$, or $R^{14}$ is independently substituted heterocycloalkyl. In embodiments, $R^{11}$, $R^{12}$, $R^{13}$, or $R^{14}$ is independently substituted aryl. In embodiments, $R^{11}$, $R^{12}$, $R^{13}$, or $R^{14}$ is independently substituted heteroaryl. In embodiments, $R^{11}$, $R^{12}$, $R^{13}$, or $R^{14}$ is independently unsubstituted alkyl. In embodiments, $R^{11}$, $R^{12}$, $R^{13}$, or $R^{14}$ is independently unsubstituted heteroalkyl. In embodiments, $R^{11}$, $R^{12}$, $R^{13}$, or $R^{14}$ is independently unsubstituted cycloalkyl. In embodiments, $R^{11}$, $R^{12}$, $R^{13}$, or $R^{14}$ is independently unsubstituted heterocycloalkyl. In embodiments, $R^{11}$, $R^{12}$, $R^{13}$, or $R^{14}$ is independently unsubstituted aryl. In embodiments, $R^{11}$, $R^{12}$, $R^{13}$, or $R^{14}$ is independently unsubstituted heteroaryl. In embodiments, $R^{11}$, $R^{12}$, $R^{13}$, or $R^{14}$ is independently substituted or unsubstituted $C_1$-$C_4$ alkyl. In embodiments, $R^{11}$, $R^{12}$, $R^{13}$, or $R^{14}$ is independently substituted or unsubstituted 2 to 4 membered heteroalkyl. In embodiments, $R^{11}$, $R^{12}$, $R^{13}$, or $R^{14}$ is independently substituted or unsubstituted $C_3$-$C_6$ cycloalkyl. In embodiments, $R^{11}$, $R^{12}$, $R^{13}$, or $R^{14}$ is independently substituted or unsubstituted 3 to 6 membered heterocycloalkyl. In embodiments, $R^{11}$, $R^{12}$, $R^{13}$, or $R^{14}$ is independently substituted or unsubstituted phenyl. In embodiments, $R^{11}$, $R^{12}$, $R^{13}$, or $R^{14}$ is independently substituted or unsubstituted 5 to 6 membered heteroaryl. In embodiments, $R^{11}$, $R^{12}$, $R^{13}$, or $R^{14}$ is independently substituted $C_1$-$C_4$ alkyl. In embodiments, $R^{11}$, $R^{12}$, $R^{13}$, or $R^{14}$ is independently substituted 2 to 4 membered heteroalkyl. In embodiments, $R^{11}$, $R^{12}$, $R^{13}$, or $R^{14}$ is independently substituted $C_3$-$C_6$ cycloalkyl. In embodiments, $R^{11}$, $R^{12}$, $R^{13}$, or $R^{14}$ is independently substituted 3 to 6 membered heterocycloalkyl. In embodiments, $R^{11}$, $R^{12}$, $R^{13}$, or $R^{14}$ is independently substituted phenyl. In embodiments, $R^{11}$, $R^{12}$, $R^{13}$, or $R^{14}$ is independently substituted 5 to 6 membered heteroaryl. In embodiments, $R^{11}$, $R^{12}$, $R^{13}$, or $R^{14}$ is independently unsubstituted $C_1$-$C_4$ alkyl. In embodiments, $R^{11}$, $R^{12}$, $R^{13}$, or $R^{14}$ is independently unsubstituted 2 to 4 membered heteroalkyl. In embodiments, $R^{11}$, $R^{12}$, $R^{13}$, or $R^{14}$ is independently unsubstituted $C_3$-$C_6$ cycloalkyl. In embodiments, $R^{11}$, $R^{12}$, $R^{13}$, or $R^{14}$ is independently unsubstituted 3 to 6 membered heterocycloalkyl. In embodiments, $R^{11}$, $R^{12}$, $R^{13}$, or $R^{14}$ is independently unsubstituted phenyl. In embodiments, $R^{11}$, $R^{12}$, $R^{13}$, or $R^{14}$ is independently unsubstituted 5 to 6 membered heteroaryl.

In embodiments, $R^{11}$ and $R^{12}$ substituents bonded to the same nitrogen atom may optionally be joined to form a substituted or unsubstituted heterocycloalkyl. In embodiments, $R^{11}$ and $R^{12}$ substituents bonded to the same nitrogen atom may optionally be joined to form a substituted or unsubstituted heteroaryl. In embodiments, $R^{11}$ and $R^{12}$ substituents bonded to the same nitrogen atom may optionally be joined to form a substituted heterocycloalkyl. In embodiments, $R^{11}$ and $R^{12}$ substituents bonded to the same nitrogen atom may optionally be joined to form a substituted heteroaryl. In embodiments, $R^{11}$ and $R^{12}$ substituents bonded to the same nitrogen atom may optionally be joined to form an unsubstituted heterocycloalkyl. In embodiments, $R^{11}$ and $R^{12}$ substituents bonded to the same nitrogen atom may optionally be joined to form an unsubstituted heteroaryl. In embodiments, $R^{11}$ and $R^{12}$ substituents bonded to the same nitrogen atom may optionally be joined to form a substituted or unsubstituted 3 to 6 membered heterocycloalkyl. In embodiments, $R^{11}$ and $R^{12}$ substituents bonded to the same nitrogen atom may optionally be joined to form a substituted or unsubstituted 5 to 6 membered heteroaryl. In embodiments, $R^1$ and $R^{12}$ substituents bonded to the same nitrogen atom may optionally be joined to form a substituted 3 to 6 membered heterocycloalkyl. In embodiments, $R^{11}$ and $R^{12}$ substituents bonded to the same nitrogen atom may optionally be joined to form a substituted 5 to 6 membered heteroaryl. In embodiments, $R^{11}$ and $R^{12}$ substituents bonded to the same nitrogen atom may optionally be joined to form an unsubstituted 3 to 6 membered heterocycloalkyl. In embodiments, $R^{11}$ and $R^{12}$ substituents bonded to the same nitrogen atom may optionally be joined to form an unsubstituted 5 to 6 membered heteroaryl.

In embodiments, $R^{15}$, $R^{16}$, $R^{17}$, or $R^{18}$ is independently hydrogen, $-CX^C_3$, $-CHX^C_2$, $-CH_2X^C$, $-CN$, $-COOH$, $-CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^{15}$, $R^{16}$, $R^{17}$, or $R^{18}$ is independently hydrogen. In embodiments, $R^{15}$, $R^{16}$, $R^{17}$, or $R^{18}$ is independently $-CX^C_3$. In embodiments, $R^{15}$, $R^{16}$, $R^{17}$, or $R^{18}$ is independently $-CHX^{C2}$. In embodiments, $R^{15}$, $R^{16}$, $R^{17}$, or $R^{18}$ is independently $-CH_2X^C$. In embodiments, $R^{15}$, $R^{16}$, $R^{17}$, or $R^{18}$ is independently $-CN$. In embodiments, $R^{15}$, $R^{16}$, $R^{17}$, or $R^{18}$ is independently $-COOH$. In embodiments, $R^{15}$, $R^{16}$, $R^{17}$, or $R^{18}$ is independently $-CONH_2$. In embodiments, $R^{15}$, $R^{16}$, $R^{17}$, or $R^{18}$ is independently substituted or unsubstituted alkyl. In embodiments, $R^{15}$, $R^{16}$, $R^{17}$, or $R^8$ is independently substituted or unsubstituted heteroalkyl. In embodiments, $R^{15}$, $R^{16}$, $R^{17}$, or $R^{18}$ is independently substituted or unsubstituted cycloalkyl. In embodiments, $R^{15}$, $R^{16}$, $R^{17}$, or $R^8$ is independently substituted or unsubstituted heterocycloalkyl. In embodiments, $R^{15}$, $R^{16}$, $R^{17}$, or $R^{18}$ is independently substituted or unsubstituted aryl. In embodiments, $R^{15}$, $R^{16}$, $R^{17}$, or $R^{18}$ is independently substituted or unsubstituted heteroaryl. In embodiments, $R^{15}$, $R^{16}$, $R^{17}$, or $R^{18}$ is independently substituted alkyl. In embodiments, $R^{15}$, $R^{16}$, $R^{17}$, or $R^{18}$ is independently substituted heteroalkyl. In embodiments, $R^{15}$, $R^{16}$, $R^{17}$, or $R^8$ is independently substituted cycloalkyl. In embodiments, $R^{15}$, $R^{16}$, $R^{17}$, or $R^{18}$ is independently substituted heterocycloalkyl. In embodiments, $R^{15}$, $R^{16}$, $R^{17}$, or $R^{18}$ is independently substituted aryl. In embodiments, $R^{15}$, $R^{16}$, $R^{17}$, or $R^{18}$ is independently substituted heteroaryl. In embodiments, $R^{15}$, $R^{16}$, $R^{17}$, or $R^{18}$ is independently unsubstituted alkyl. In embodiments, $R^{15}$, $R^{16}$, $R^{17}$, or $R^{18}$ is independently unsubstituted heteroalkyl. In embodiments, $R^{15}$, $R^{16}$, $R^{17}$, or $R^{18}$ is independently unsubstituted cycloalkyl. In embodiments, $R^{15}$, $R^{16}$, $R^{17}$, or $R^{18}$ is independently unsubstituted heterocycloalkyl. In embodiments, $R^{15}$, $R^{16}$, $R^{17}$, or $R^{18}$ is independently unsubstituted aryl. In embodiments, $R^{15}$, $R^{16}$, $R^{17}$, or $R^{18}$ is independently unsubstituted heteroaryl. In embodiments, $R^{15}$, $R^{16}$, $R^{17}$, or $R^{18}$ is independently substituted or unsubstituted $C_1$-$C_4$ alkyl. In embodiments, $R^{15}$, $R^{16}$, $R^{17}$, or $R^8$ is independently substituted or unsubstituted 2 to 4 membered heteroalkyl. In embodiments, $R^{15}$, $R^{16}$, $R^{17}$, or $R^{18}$ is independently substituted or unsubstituted $C_3$-$C_6$ cycloalkyl. In embodiments, $R^{15}$, $R^{16}$, $R^{17}$, or $R^{18}$ is independently substituted or unsubstituted 3 to 6 membered heterocycloalkyl. In embodiments, $R^{15}$, $R^{16}$, $R^{17}$, or $R^{18}$ is independently substituted or unsubstituted phenyl. In embodiments, $R^{15}$, $R^{16}$, $R^{17}$, or $R^{18}$ is independently substituted or unsubstituted 5 to 6 membered heteroaryl. In embodiments, $R^{15}$, $R^{16}$, $R^{17}$, or $R^{18}$ is independently substituted $C_1$-$C_4$ alkyl. In embodiments, $R^{15}$, $R^{16}$, $R^{17}$, or $R^{18}$ is independently substituted 2 to 4 membered heteroalkyl. In embodiments, $R^{15}$, $R^{16}$, $R^{17}$, or $R^{18}$ is independently substituted $C_3$-$C_6$ cycloalkyl. In embodiments, $R^{15}$, $R^{16}$, $R^{17}$, or $R^{18}$ is independently substituted 3 to 6 membered heterocycloalkyl. In embodiments, $R^{15}$, $R^{16}$, $R^{17}$, or $R^{18}$ is independently substituted phenyl. In embodiments, $R^{15}$, $R^{16}$, $R^{17}$, or $R^{18}$ is independently substituted 5 to 6 membered heteroaryl. In embodiments, $R^{15}$, $R^{16}$, $R^{17}$, or $R^{18}$ is independently unsubstituted $C_1$-$C_4$ alkyl. In embodiments, $R^{15}$, $R^{16}$, $R^{17}$, or $R^{18}$ is independently unsubstituted 2 to 4 membered heteroalkyl. In embodiments, $R^{15}$, $R^{16}$, $R^{17}$, or $R^{18}$ is independently unsubstituted $C_3$-$C_6$ cycloalkyl. In embodiments, $R^{15}$, $R^{16}$, $R^{17}$, or $R^{18}$ is independently unsubstituted 3 to 6 membered heterocycloalkyl. In embodiments, $R^{15}$, $R^{16}$, $R^{17}$, or $R^{18}$ is independently unsubstituted phenyl. In embodiments, $R^{15}$, $R^{16}$, $R^{17}$, or $R^{18}$ is independently unsubstituted 5 to 6 membered heteroaryl.

In embodiments, $R^{15}$ and $R^{16}$ substituents bonded to the same nitrogen atom may optionally be joined to form a substituted or unsubstituted heterocycloalkyl. In embodiments, $R^{15}$ and $R^{16}$ substituents bonded to the same nitrogen atom may optionally be joined to form a substituted or unsubstituted heteroaryl. In embodiments, $R^{15}$ and $R^{16}$ substituents bonded to the same nitrogen atom may optionally be joined to form a substituted heterocycloalkyl. In embodiments, $R^{15}$ and $R^{16}$ substituents bonded to the same nitrogen atom may optionally be joined to form a substituted heteroaryl. In embodiments, $R^{15}$ and $R^{16}$ substituents bonded to the same nitrogen atom may optionally be joined to form an unsubstituted heterocycloalkyl. In embodiments, $R^{15}$ and $R^{16}$ substituents bonded to the same nitrogen atom may optionally be joined to form an unsubstituted heteroaryl. In embodiments, $R^{15}$ and $R^{16}$ substituents bonded to the same nitrogen atom may optionally be joined to form a substituted or unsubstituted 3 to 6 membered heterocycloalkyl. In embodiments, $R^{15}$ and $R^{16}$ substituents bonded to the same nitrogen atom may optionally be joined to form a substituted or unsubstituted 5 to 6 membered heteroaryl. In embodiments, $R^{15}$ and $R^{16}$ substituents bonded to the same nitrogen atom may optionally be joined to form a substituted 3 to 6 membered heterocycloalkyl. In embodiments, $R^{15}$ and $R^{16}$ substituents bonded to the same nitrogen atom may optionally be joined to form a substituted 5 to 6 membered heteroaryl. In embodiments, $R^{15}$ and $R^{16}$ substituents bonded to the same nitrogen atom may optionally be joined to form an unsubstituted 3 to 6 membered heterocycloalkyl. In embodiments, $R^{15}$ and $R^{16}$ substituents bonded to the same nitrogen atom may optionally be joined to form an unsubstituted 5 to 6 membered heteroaryl.

In embodiments, m1 is 1. In embodiments, m1 is 2. In embodiments, v1 is 1. In embodiments, v1 is 2. In embodiments, m4 is 1. In embodiments, m4 is 2. In embodiments, m5 is 1. In embodiments, m5 is 2. In embodiments, v4 is 1. In embodiments, v4 is 2. In embodiments, v5 is 1. In embodiments, v5 is 2. In embodiments, n1 is 0. In embodiments, n1 is 1. In embodiments, n1 is 2. In embodiments, n1 is 3. In embodiments, n1 is 4. In embodiments, n4 is 0. In embodiments, n4 is 1. In embodiments, n4 is 2. In embodiments, n4 is 3. In embodiments, n4 is 4. In embodiments, n5 is 0. In embodiments, n5 is 1. In embodiments, n5 is 2. In embodiments, n5 is 3. In embodiments, n5 is 4.

In embodiments, $X^1$ is independently $-Cl$. In embodiments, $X^1$ is independently $-Br$. In embodiments, $X^1$ is independently $-I$. In embodiments, $X^1$ is independently $-F$. In embodiments, $X^2$ is independently $-Cl$. In embodiments, $X^2$ is independently $-Br$. In embodiments, $X^2$ is independently $-I$. In embodiments, $X^2$ is independently $-F$. In embodiments, $X^3$ is independently $-Cl$. In embodiments, $X^3$ is independently $-Br$. In embodiments, $X^3$ is independently $-I$. In embodiments, $X^3$ is independently —F. In embodiments, $X^4$ is independently —Cl. In embodiments, $X^4$ is independently —Br. In embodiments, $X^4$ is independently —I. In embodiments, $X^4$ is independently —F. In embodiments, $X^5$ is independently —Cl. In embodiments, $X^5$ is independently —Br. In embodiments, $X^5$ is independently —I. In embodiments, $X^5$ is independently —F. In embodiments, $X^A$ is independently —Cl. In embodiments, $X^A$ is independently —Br. In embodiments, $X^A$ is independently —I. In embodiments, $X^A$ is independently —F. In embodiments, $X^B$ is independently —Cl. In embodiments, $X^B$ is independently —Br. In embodiments, $X^B$ is independently —I. In embodiments, $X^B$ is independently —F. In embodiments, $X^C$ is independently —Cl. In embodiments, $X^C$ is independently —Br. In embodiments, $X^C$ is independently —I. In embodiments, $X^C$ is independently —F.

In embodiments, the compound has the formula:

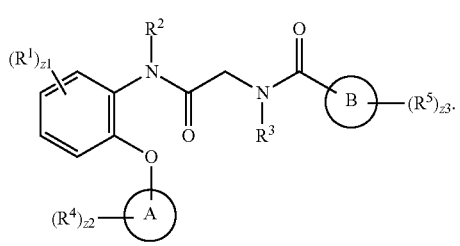

(III)

$R^1$, $R^2$, $R^3$, $R^4$, $R^5$, Ring A, Ring B, z1, z2, and z3 are as described herein, including in compounds of formula (I) and (II). In embodiments, z1 is 0. In embodiments, z2 is 0. In embodiments, z3 is 0. In embodiments, $R^2$ is hydrogen. In embodiments, $R^3$ is hydrogen.

In embodiments, the compound has the formula:

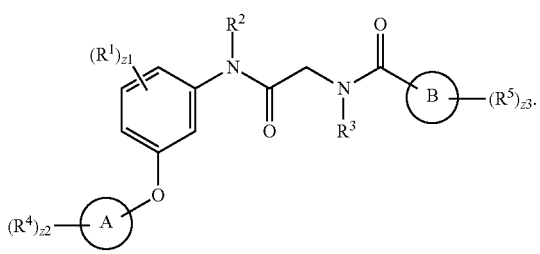

(IV)

$R^1$, $R^2$, $R^3$, $R^4$, $R^5$, Ring A, Ring B, z1, z2, and z3 are as described herein, including in compounds of formula (I) and (II).

In embodiments, the compound has the formula:

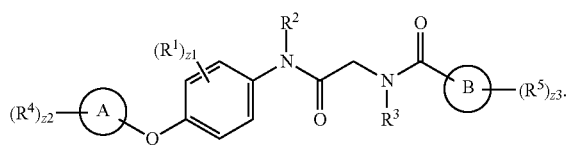

(V)

$R^1$, $R^2$, $R^3$, $R^4$, $R^5$, Ring A, Ring B, z1, z2, and z3 are as described herein, including in compounds of formula (I) and (II).

In embodiments, the compound has the formula:

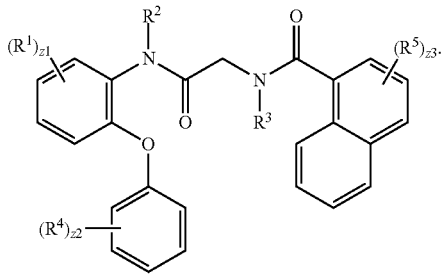

$R^1$, $R^2$, $R^3$, $R^4$, $R^5$, z1, z2, and z3 are as described herein, including in compounds of formula (I) to (V).

In embodiments, the compound has the formula:

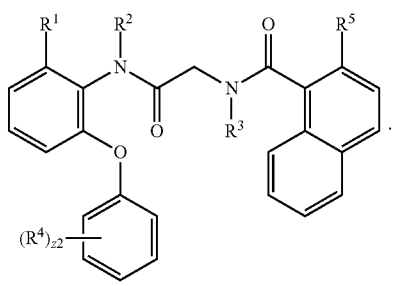

$R^1$, $R^2$, $R^3$, $R^4$, $R^5$, and z2 are as described herein, including in compounds of formula (I) to (V).

In embodiments, the compound has the formula:

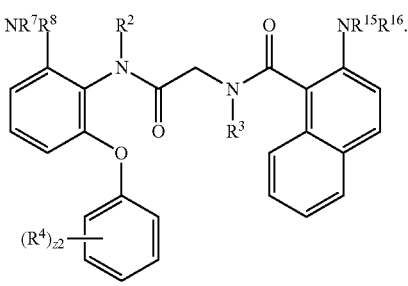

$R^2$, $R^3$, $R^4$, $R^7$, $R^8$, $R^{15}$, $R^{16}$, and z2 are as described herein, including in compounds of formula (I) to (V).

In embodiments, the compound has the formula:

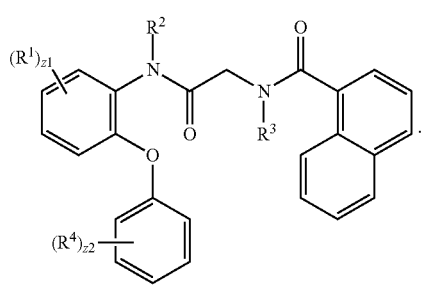

$R^1$, $R^2$, $R^3$, $R^4$, z1, and z2 are as described herein, including in compounds of formula (I) to (V).

In embodiments, the compound has the formula:

[Structure with R², R³, (R⁴)_{z2}]

R², R³, R⁴, and z2 are as described herein, including in compounds of formula (I) to (V).

In embodiments, the compound has the formula:

[Structure with R², R³, R⁴]

R³, and R⁴ are as described herein, including in compounds of formula (I) to (V).

In embodiments, the compound has the formula:

[Structure with R⁴]

R⁴ is as described herein, including in compounds of formula (I) to (V). In embodiments, R⁴ is independently —OR¹⁴. In embodiments, R⁴ is independently —SR¹⁴. In embodiments, R¹⁴ is independently hydrogen or unsubstituted alkyl. In embodiments, R¹⁴ is independently hydrogen or unsubstituted $C_1$-$C_6$ alkyl. In embodiments, R¹⁴ is independently hydrogen or unsubstituted $C_1$-$C_5$ alkyl. In embodiments, R¹⁴ is independently hydrogen or unsubstituted $C_1$-$C_4$ alkyl. In embodiments, R¹⁴ is independently hydrogen or unsubstituted $C_1$-$C_3$ alkyl. In embodiments, R¹⁴ is independently hydrogen or unsubstituted $C_1$-$C_2$ alkyl. In embodiments, R¹⁴ is independently hydrogen or unsubstituted $C_2$-$C_6$ alkyl. In embodiments, R¹⁴ is independently hydrogen or unsubstituted $C_2$-$C_5$ alkyl. In embodiments, R¹⁴ is independently hydrogen or unsubstituted $C_2$-$C_4$ alkyl. In embodiments, R¹⁴ is independently hydrogen or unsubstituted $C_2$-$C_3$ alkyl. In embodiments, R¹⁴ is independently hydrogen or unsubstituted $C_3$-$C_6$ alkyl. In embodiments, R¹⁴ is independently hydrogen or unsubstituted $C_4$-$C_6$ alkyl. In embodiments, R¹⁴ is independently hydrogen or unsubstituted $C_5$-$C_6$ alkyl. In embodiments, R¹⁴ is independently hydrogen. In embodiments, R¹⁴ is independently unsubstituted alkyl. In embodiments, R¹⁴ is independently unsubstituted $C_1$-$C_6$ alkyl. In embodiments, R¹⁴ is independently unsubstituted $C_1$-$C_5$ alkyl. In embodiments, R¹⁴ is independently unsubstituted $C_1$-$C_4$ alkyl. In embodiments, R¹⁴ is independently unsubstituted $C_1$-$C_3$ alkyl. In embodiments, R¹⁴ is independently unsubstituted $C_1$-$C_2$ alkyl. In embodiments, R¹⁴ is independently unsubstituted $C_2$-$C_6$ alkyl. In embodiments, R¹⁴ is independently unsubstituted $C_2$-$C_5$ alkyl. In embodiments, R¹⁴ is independently unsubstituted $C_2$-$C_4$ alkyl. In embodiments, R¹⁴ is independently unsubstituted $C_2$-$C_3$ alkyl. In embodiments, R¹⁴ is independently unsubstituted $C_3$-$C_6$ alkyl. In embodiments, R¹⁴ is independently unsubstituted $C_4$-$C_6$ alkyl. In embodiments, R¹⁴ is independently unsubstituted $C_5$-$C_6$ alkyl. In embodiments, R¹⁴ is independently unsubstituted methyl. In embodiments, R¹⁴ is independently unsubstituted ethyl. In embodiments, R¹⁴ is independently unsubstituted propyl. In embodiments, R¹⁴ is independently unsubstituted isopropyl. In embodiments, R¹⁴ is independently unsubstituted tert-butyl.

In embodiments, the compound has the formula:

[Structure with R⁴]

R⁴ is as described herein, including in compounds of formula (I) to (V). In embodiments, R⁴ is independently —OR¹⁴. In embodiments, R⁴ is independently —SR¹⁴. In embodiments, R¹⁴ is independently hydrogen or unsubstituted alkyl. In embodiments, R¹⁴ is independently hydrogen or unsubstituted $C_1$-$C_6$ alkyl. In embodiments, R¹⁴ is independently hydrogen or unsubstituted $C_1$-$C_5$ alkyl. In embodiments, R¹⁴ is independently hydrogen or unsubstituted $C_1$-$C_4$ alkyl. In embodiments, R¹⁴ is independently hydrogen or unsubstituted $C_1$-$C_3$ alkyl. In embodiments, R¹⁴ is independently hydrogen or unsubstituted $C_1$-$C_2$ alkyl. In embodiments, R¹⁴ is independently hydrogen or unsubstituted $C_2$-$C_6$ alkyl. In embodiments, R¹⁴ is independently hydrogen or unsubstituted $C_2$-$C_5$ alkyl. In embodiments, R¹⁴ is independently hydrogen or unsubstituted $C_2$-$C_4$ alkyl. In embodiments, R¹⁴ is independently hydrogen or unsubstituted $C_2$-$C_3$ alkyl. In embodiments, R¹⁴ is independently hydrogen or unsubstituted $C_3$-$C_6$ alkyl. In embodiments, R¹⁴ is independently hydrogen or unsubstituted $C_4$-$C_6$ alkyl. In embodiments, R¹⁴ is independently hydrogen or unsubstituted $C_5$-$C_6$ alkyl. In embodiments, R¹⁴ is independently hydrogen. In embodiments, R¹⁴ is independently unsubstituted alkyl. In embodiments, R¹⁴ is independently unsubstituted $C_1$-$C_6$ alkyl. In embodiments, R¹⁴ is independently unsubstituted $C_1$-$C_5$ alkyl. In embodiments, R¹⁴ is independently unsubstituted $C_1$-$C_4$ alkyl. In embodiments, R¹⁴ is independently unsubstituted $C_1$-$C_3$ alkyl. In embodiments, R¹⁴ is independently unsubstituted $C_1$-$C_2$ alkyl. In embodiments, R¹⁴ is independently unsubstituted $C_2$-$C_6$ alkyl. In embodiments, R¹⁴ is independently unsubstituted $C_2$-$C_5$ alkyl. In embodiments, $R^{14}$ is independently unsubstituted $C_2$-$C_4$ alkyl. In embodiments, $R^{14}$ is independently unsubstituted $C_2$-$C_3$ alkyl. In embodiments, $R^{14}$ is independently unsubstituted $C_3$-$C_6$ alkyl. In embodiments, $R^{14}$ is independently unsubstituted $C_4$-$C_6$ alkyl. In embodiments, $R^{14}$ is independently unsubstituted $C_5$-$C_6$ alkyl. In embodiments, $R^{14}$ is independently unsubstituted methyl. In embodiments, $R^{14}$ is independently unsubstituted ethyl. In embodiments, $R^{14}$ is independently unsubstituted propyl. In embodiments, $R^{14}$ is independently unsubstituted isopropyl. In embodiments, $R^{14}$ is independently unsubstituted tert-butyl.

In embodiments, the compound has the formula:

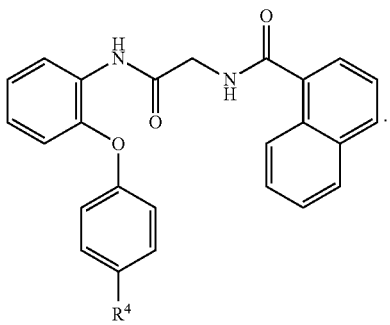

$R^4$ is as described herein, including in compounds of formula (I) to (V). In embodiments, $R^4$ is independently —$OR^{14}$. In embodiments, $R^4$ is independently —$SR^{14}$. In embodiments, $R^{14}$ is independently hydrogen or unsubstituted alkyl. In embodiments, $R^{14}$ is independently hydrogen or unsubstituted $C_1$-$C_6$ alkyl. In embodiments, $R^{14}$ is independently hydrogen or unsubstituted $C_1$-$C_5$ alkyl. In embodiments, $R^{14}$ is independently hydrogen or unsubstituted $C_1$-$C_4$ alkyl. In embodiments, $R^{14}$ is independently hydrogen or unsubstituted $C_1$-$C_3$ alkyl. In embodiments, $R^{14}$ is independently hydrogen or unsubstituted $C_1$-$C_2$ alkyl. In embodiments, $R^{14}$ is independently hydrogen or unsubstituted $C_2$-$C_6$ alkyl. In embodiments, $R^{14}$ is independently hydrogen or unsubstituted $C_2$-$C_5$ alkyl. In embodiments, $R^{14}$ is independently hydrogen or unsubstituted $C_2$-$C_4$ alkyl. In embodiments, $R^{14}$ is independently hydrogen or unsubstituted $C_2$-$C_3$ alkyl. In embodiments, $R^{14}$ is independently hydrogen or unsubstituted $C_3$-$C_6$ alkyl. In embodiments, $R^{14}$ is independently hydrogen or unsubstituted $C_4$-$C_6$ alkyl. In embodiments, $R^{14}$ is independently hydrogen or unsubstituted $C_5$-$C_6$ alkyl. In embodiments, $R^{14}$ is independently hydrogen. In embodiments, $R^{14}$ is independently unsubstituted alkyl. In embodiments, $R^{14}$ is independently unsubstituted $C_1$-$C_6$ alkyl. In embodiments, $R^{14}$ is independently unsubstituted $C_1$-$C_5$ alkyl. In embodiments, $R^{14}$ is independently unsubstituted $C_1$-$C_4$ alkyl. In embodiments, $R^{14}$ is independently unsubstituted $C_1$-$C_3$ alkyl. In embodiments, $R^{14}$ is independently unsubstituted $C_1$-$C_2$ alkyl. In embodiments, $R^{14}$ is independently unsubstituted $C_2$-$C_6$ alkyl. In embodiments, $R^{14}$ is independently unsubstituted $C_2$-$C_5$ alkyl. In embodiments, $R^{14}$ is independently unsubstituted $C_2$-$C_4$ alkyl. In embodiments, $R^{14}$ is independently unsubstituted $C_2$-$C_3$ alkyl. In embodiments, $R^{14}$ is independently unsubstituted $C_3$-$C_6$ alkyl. In embodiments, $R^{14}$ is independently unsubstituted $C_4$-$C_6$ alkyl. In embodiments, $R^{14}$ is independently unsubstituted $C_5$-$C_6$ alkyl. In embodiments, $R^{14}$ is independently unsubstituted methyl. In embodiments, $R^{14}$ is independently unsubstituted ethyl. In embodiments, $R^{14}$ is independently unsubstituted propyl. In embodiments, $R^{14}$ is independently unsubstituted isopropyl. In embodiments, $R^{14}$ is independently unsubstituted tert-butyl.

In embodiments, the compound has the formula:

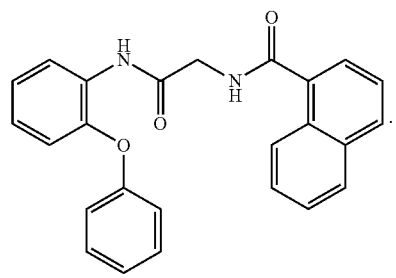 [SMILES: O=C(CNC(=O)c1cccc2ccccc12)Nc1ccccc1Oc1ccccc1]

In embodiments, the compound has the formula:

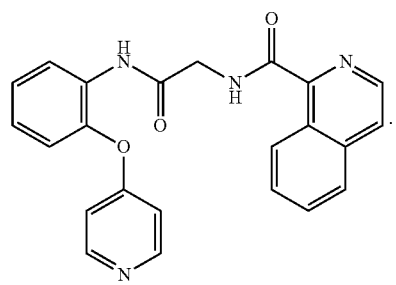 [SMILES: O=C(CNC(=O)c1nccc2ccccc12)Nc1ccccc1Oc1ccncc1]

In embodiments, the compound has the formula:

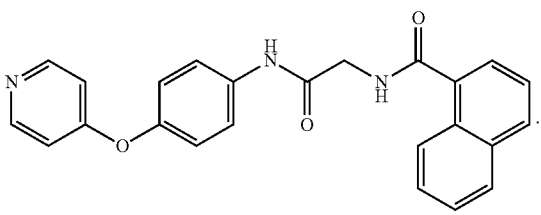 [SMILES: O=C(CNC(=O)c1cccc2ccccc12)Nc1ccc(Oc2ccncc2)cc1]

In embodiments, the compound has the formula:

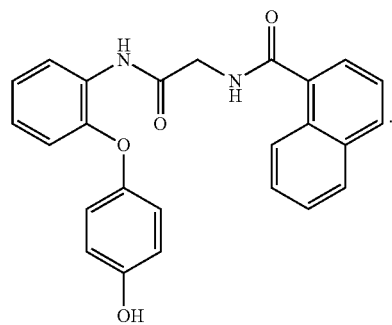 [SMILES: O=C(CNC(=O)c1cccc2ccccc12)Nc1ccccc1Oc1ccc(O)cc1]

In embodiments, the compound has the formula:

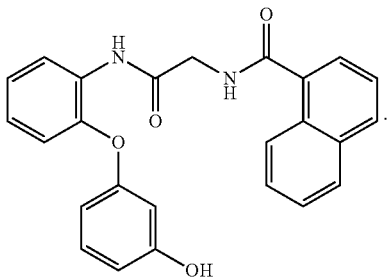 [SMILES: O=C(CNC(=O)c1cccc2ccccc12)Nc1ccccc1Oc1cccc(O)c1]

In embodiments, the compound has the formula:

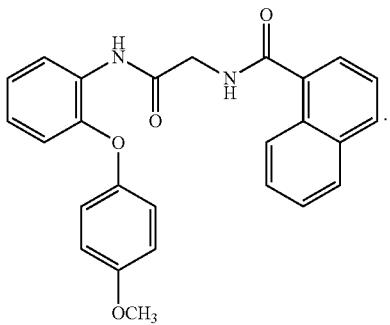 [SMILES: COc1ccc(Oc2ccccc2NC(=O)CNC(=O)c2cccc3ccccc23)cc1]

In embodiments, the compound has the formula:

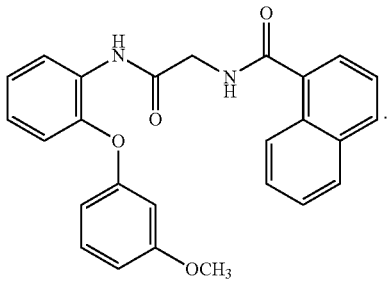 [SMILES: COc1cccc(Oc2ccccc2NC(=O)CNC(=O)c2cccc3ccccc23)c1]

In embodiments, $R^1$ is independently hydrogen, oxo, halogen, —$CX^1_3$, —$CHX^1_2$, —$OCH_2X^1$, —CN, —OH, —$NH_2$, —COOH, —$CONH_2$, —$NO_2$, —SH, —$SO_3H$, —$SO_4H$, —$SO_2NH_2$, —$NNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^1_3$, —$OCHX^1_2$, —$OCH_2X^1$, $R^{30}$-substituted or unsubstituted alkyl (e.g. $C_1$-$C_8$ alkyl, $C_1$-$C_6$ alkyl, or $C_1$-$C_4$ alkyl), $R^{30}$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^{30}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{30}$-substituted or unsubstituted heterocycloalkyl (e.g. 3 to 8 membered heterocycloalkyl, 4 to 8 membered heterocycloalkyl, or 5 to 6 membered heterocycloalkyl), $R^{30}$-substituted or unsubstituted aryl (e.g. $C_6$-$C_{10}$ aryl or $C_6$ aryl), or $R^{30}$-substituted or unsubstituted heteroaryl (e.g. 5 to 10 membered heteroaryl, 5 to 9 membered heteroaryl, or 5 to 6 membered heteroaryl). $X^1$ is halogen. In embodiments, $X^1$ is F. In embodiments, $R^1$ is independently halogen, —$CX^1_3$, —$CHX^1_2$, —$OCH_2X^1$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^1_3$, —$OCHX^1_2$, —$OCH_2X^1$, $R^{30}$-substituted or unsubstituted alkyl (e.g. $C_1$-$C_8$ alkyl, $C_1$-$C_6$ alkyl, or $C_1$-$C_4$ alkyl), $R^{30}$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^{30}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{30}$-substituted or unsubstituted heterocycloalkyl (e.g. 3 to 8 membered heterocycloalkyl, 4 to 8 membered heterocycloalkyl, or 5 to 6 membered heterocycloalkyl), $R^{30}$-substituted or unsubstituted aryl (e.g. $C_6$-$C_{10}$ aryl or $C_6$ aryl), or $R^{30}$-substituted or unsubstituted heteroaryl (e.g. 5 to 10 membered heteroaryl, 5 to 9 membered heteroaryl, or 5 to 6 membered heteroaryl).

$R^{30}$ is independently oxo, halogen, —$CX^{30}_3$, —$CHX^{30}_2$, —$CH_2X^{30}$, —$OCH_2X^{30}$, —$OCHX^{30}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —$NHSO_2H$, —NHC=(O)H, —NHC=(O)$NH_2$, —NHC(O)—OH, —NHOH, —$OCX^{30}_3$, $R^{31}$-substituted or unsubstituted alkyl (e.g. $C_1$-$C_8$ alkyl, $C_1$-$C_6$ alkyl, or $C_1$-$C_4$ alkyl), $R^{31}$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^{31}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{31}$-substituted or unsubstituted heterocycloalkyl (e.g. 3 to 8 membered heterocycloalkyl, 4 to 8 membered heterocycloalkyl, or 5 to 6 membered heterocycloalkyl), $R^{31}$-substituted or unsubstituted aryl (e.g. $C_6$-$C_{10}$ aryl or $C_6$ aryl), or $R^{31}$-substituted or unsubstituted heteroaryl (e.g. 5 to 10 membered heteroaryl, 5 to 9 membered heteroaryl, or 5 to 6 membered heteroaryl). $X^{30}$ is halogen. In embodiments, $X^{30}$ is F.

$R^{31}$ is independently oxo, halogen, —$CX^{31}_3$, —$CHX^{31}_2$, —$CH_2X^{31}$, —$OCH_2X^{31}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{31}_3$, —$OCHX^{31}_2$, $R^{32}$-substituted or unsubstituted alkyl (e.g. $C_1$-$C_8$ alkyl, $C_1$-$C_6$ alkyl, or $C_1$-$C_4$ alkyl), $R^{32}$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^{32}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{32}$-substituted or unsubstituted heterocycloalkyl (e.g. 3 to 8 membered heterocycloalkyl, 4 to 8 membered heterocycloalkyl, or 5 to 6 membered heterocycloalkyl), $R^{32}$-substituted or unsubstituted aryl (e.g. $C_6$-$C_{10}$ aryl or $C_6$ aryl), or $R^{32}$-substituted or unsubstituted heteroaryl (e.g. 5 to 10 membered heteroaryl, 5 to 9 membered heteroaryl, or 5 to 6 membered heteroaryl). $X^{31}$ is halogen. In embodiments, $X^{31}$ is F.

In embodiments, $R^2$ is independently hydrogen, oxo, halogen, —$CX^{23}_3$, —$CHX^{22}_2$, —$CH_2X^2$, —$OCH_2X^2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{23}_3$, —$OCHX^{22}_2$, $R^{33}$-substituted or unsubstituted alkyl (e.g. $C_1$-$C_8$ alkyl, $C_1$-$C_6$ alkyl, or $C_1$-$C_4$ alkyl), $R^{33}$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^{33}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{33}$-substituted or unsubstituted heterocycloalkyl (e.g. 3 to 8 membered heterocycloalkyl, 4 to 8 membered heterocycloalkyl, or 5 to 6 membered heterocycloalkyl), $R^{33}$-substituted or unsubstituted aryl (e.g. $C_6$-$C_{10}$ aryl or $C_6$ aryl), or $R^{33}$-substituted or unsubstituted heteroaryl (e.g. 5 to 10 membered heteroaryl, 5 to 9 membered heteroaryl, or 5 to 6 membered heteroaryl). $X^2$ is halogen. In embodiments, $X^2$ is F.

In embodiments, $R^2$ is independently halogen, —$CX^2_3$, —$CHX^2_2$, —$OCH_2X^2$, —$CH_2X^2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^2_3$, —$OCHX^2_2$, $R^{33}$-substituted or unsubstituted alkyl (e.g. $C_1$-$C_8$ alkyl, $C_1$-$C_6$ alkyl, or $C_1$-$C_4$ alkyl), $R^{33}$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^{33}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{33}$-substituted or unsubstituted heterocycloalkyl (e.g. 3 to 8 membered heterocycloalkyl, 4 to 8 membered heterocycloalkyl, or 5 to 6 membered heterocycloalkyl), $R^{33}$-substituted or unsubstituted aryl (e.g. $C_6$-$C_{10}$ aryl or $C_6$ aryl), or $R^{33}$-substituted or unsubstituted heteroaryl (e.g. 5 to 10 membered heteroaryl, 5 to 9 membered heteroaryl, or 5 to 6 membered heteroaryl). In embodiments, $R^2$ is hydrogen.

$R^{33}$ is independently oxo, halogen, —$CX^{33}_3$, —$CHX^{33}_2$, —$CHX^{33}_2$, —$OCH_2X^{33}$, —$OCHX^{33}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{33}_3$, —$OCHX^{33}_2$, $R^{34}$-substituted or unsubstituted alkyl (e.g. $C_1$-$C_8$ alkyl, $C_1$-$C_6$ alkyl, or $C_1$-$C_4$ alkyl), $R^{34}$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^{34}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{34}$-substituted or unsubstituted heterocycloalkyl (e.g. 3 to 8 membered heterocycloalkyl, 4 to 8 membered heterocycloalkyl, or 5 to 6 membered heterocycloalkyl), $R^{34}$-substituted or unsubstituted aryl (e.g. $C_6$-$C_{10}$ aryl or $C_6$ aryl), or $R^{34}$-substituted or unsubstituted heteroaryl (e.g. 5 to 10 membered heteroaryl, 5 to 9 membered heteroaryl, or 5 to 6 membered heteroaryl). $X^{33}$ is halogen. In embodiments, $X^{33}$ is F.

$R^{34}$ is independently oxo, halogen, —$CX^{34}_3$, —$CHX^{34}_2$, —$CH_2X^{34}_2$, —$OCH_2X^{34}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{34}_3$, —$OCHX^{34}_2$, $R^{35}$-substituted or unsubstituted alkyl (e.g. $C_1$-$C_8$ alkyl, $C_1$-$C_6$ alkyl, or $C_1$-$C_4$ alkyl), $R^{35}$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^{35}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{35}$-substituted or unsubstituted hetero-cycloalkyl (e.g. 3 to 8 membered heterocycloalkyl, 4 to 8 membered heterocycloalkyl, or 5 to 6 membered heterocycloalkyl), $R^{35}$-substituted or unsubstituted aryl (e.g. $C_6$-$C_{10}$ aryl or $C_6$ aryl), or $R^{35}$-substituted or unsubstituted heteroaryl (e.g. 5 to 10 membered heteroaryl, 5 to 9 membered heteroaryl, or 5 to 6 membered heteroaryl). $X^{34}$ is halogen. In embodiments, $X^{34}$ is F.

In embodiments, $R^3$ is independently hydrogen, oxo, halogen, —$CX^{33}_3$, —$CHX^{32}_2$, —$CH_2X^3$, —$OCH_2X^3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{33}_3$, —$OCHX^{32}_2$, $R^{36}$-substituted or unsubstituted alkyl (e.g. $C_1$-$C_8$ alkyl, $C_1$-$C_6$ alkyl, or $C_1$-$C_4$ alkyl), $R^{36}$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^{36}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{36}$-substituted or unsubstituted heterocycloalkyl (e.g. 3 to 8 membered heterocycloalkyl, 4 to 8 membered heterocycloalkyl, or 5 to 6 membered heterocycloalkyl), $R^{36}$-substituted or unsubstituted aryl (e.g. $C_6$-$C_{10}$ aryl or $C_6$ aryl), or $R^{36}$-substituted or unsubstituted heteroaryl (e.g. 5 to 10 membered heteroaryl, 5 to 9 membered heteroaryl, or 5 to 6 membered heteroaryl). $X^3$ is halogen. In embodiments, $X^3$ is F. In embodiments, $R^3$ is independently halogen, —$CX^{33}_3$, —$CHX^{32}_2$, —$CH_2X^3$, —$OCH_2X^3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{33}_3$, —$OCHX^{32}_2$, $R^{36}$-substituted or unsubstituted alkyl (e.g. $C_1$-$C_8$ alkyl, $C_1$-$C_6$ alkyl, or $C_1$-$C_4$ alkyl), $R^{36}$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^{36}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{36}$-substituted or unsubstituted heterocycloalkyl (e.g. 3 to 8 membered heterocycloalkyl, 4 to 8 membered heterocycloalkyl, or 5 to 6 membered heterocycloalkyl), $R^{36}$-substituted or unsubstituted aryl (e.g. $C_6$-$C_{10}$ aryl or $C_6$ aryl), or $R^{36}$-substituted or unsubstituted heteroaryl (e.g. 5 to 10 membered heteroaryl, 5 to 9 membered heteroaryl, or 5 to 6 membered heteroaryl). In embodiments, $R^3$ is hydrogen.

$R^{36}$ is independently oxo, halogen, —$CX^{36}_3$, —$CHX^{36}_2$, —$CH_2X^{36}$, —$OCH_2X^{36}$ —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{36}_3$, —$OCHX^{36}_2$, $R^{37}$-substituted or unsubstituted alkyl (e.g. $C_1$-$C_8$ alkyl, $C_1$-$C_6$ alkyl, or $C_1$-$C_4$ alkyl), $R^{37}$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^{37}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{37}$-substituted or unsubstituted heterocycloalkyl (e.g. 3 to 8 membered heterocycloalkyl, 4 to 8 membered heterocycloalkyl, or 5 to 6 membered heterocycloalkyl), $R^{37}$-substituted or unsubstituted aryl (e.g. $C_6$-$C_{10}$ aryl or $C_6$ aryl), or $R^{37}$-substituted or unsubstituted heteroaryl (e.g. 5 to 10 membered heteroaryl, 5 to 9 membered heteroaryl, or 5 to 6 membered heteroaryl). $X^{36}$ is halogen. In embodiments, $X^{36}$ is F.

$R^{37}$ is independently oxo, halogen, —$CX^{37}_3$, —$CHX^{37}_2$, —$CH_2X^{37}$, —$OCH_2X^{37}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{37}_3$, —$OCHX^{37}_2$, $R^{38}$-substituted or unsubstituted alkyl (e.g. $C_1$-$C_8$ alkyl, $C_1$-$C_6$ alkyl, or $C_1$-$C_4$ alkyl), $R^{38}$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^{38}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{38}$-substituted or unsubstituted heterocycloalkyl (e.g. 3 to 8 membered heterocycloalkyl, 4 to 8 membered heterocycloalkyl, or 5 to 6 membered heterocycloalkyl), $R^{38}$-substituted or unsubstituted aryl (e.g. $C_6$-$C_{10}$ aryl or $C_6$ aryl), or $R^{38}$-substituted or unsubstituted heteroaryl (e.g. 5 to 10 membered heteroaryl, 5 to 9 membered heteroaryl, or 5 to 6 membered heteroaryl). $X^{37}$ is halogen. In embodiments, $X^{37}$ is F.

In embodiments, $R^4$ is independently hydrogen, oxo, halogen, —$CX^{43}$, —$CHX^{42}$, —$CH_2X^4$, —$OCH_2X^4$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{43}$, —$OCHX^{42}$, $R^{39}$-substituted or unsubstituted alkyl (e.g. $C_1$-$C_8$ alkyl, $C_1$-$C_6$ alkyl, or $C_1$-$C_4$ alkyl), $R^{39}$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^{39}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{39}$-substituted or unsubstituted heterocycloalkyl (e.g. 3 to 8 membered heterocycloalkyl, 4 to 8 membered heterocycloalkyl, or 5 to 6 membered heterocycloalkyl), $R^{39}$-substituted or unsubstituted aryl (e.g. $C_6$-$C_{10}$ aryl or $C_6$ aryl), or $R^{39}$-substituted or unsubstituted heteroaryl (e.g. 5 to 10 membered heteroaryl, 5 to 9 membered heteroaryl, or 5 to 6 membered heteroaryl). $X^4$ is halogen. In embodiments, $X^4$ is F. In embodiments, $R^4$ is independently halogen, —$CX^{43}$, —$CHX^{42}$, —$CH_2X^4$, —$OCH_2X^4$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{43}$, —$OCHX^{42}$, $R^{39}$-substituted or unsubstituted alkyl (e.g. $C_1$-$C_8$ alkyl, $C_1$-$C_6$ alkyl, or $C_1$-$C_4$ alkyl), $R^{39}$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^{39}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{39}$-substituted or unsubstituted heterocycloalkyl (e.g. 3 to 8 membered heterocycloalkyl, 4 to 8 membered heterocycloalkyl, or 5 to 6 membered heterocycloalkyl), $R^{39}$-substituted or unsubstituted aryl (e.g. $C_6$-$C_{10}$ aryl or $C_6$ aryl), or $R^{39}$-substituted or unsubstituted heteroaryl (e.g. 5 to 10 membered heteroaryl, 5 to 9 membered heteroaryl, or 5 to 6 membered heteroaryl).

$R^{39}$ is independently oxo, halogen, —$CX^{39}_3$, —$CHX^{39}_2$, —$CH_2X^{39}$, —$OCH_2X^{39}$, —$OCHX^{39}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{39}_3$, —$OCHX^{39}_2$, $R^{40}$-substituted or unsubstituted alkyl (e.g. $C_1$-$C_8$ alkyl, $C_1$-$C_6$ alkyl, or $C_1$-$C_4$ alkyl), $R^{40}$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^{40}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{40}$-substituted or unsubstituted heterocycloalkyl (e.g. 3 to 8 membered heterocycloalkyl, 4 to 8 membered heterocycloalkyl, or 5 to 6 membered heterocycloalkyl), $R^{40}$-substituted or unsubstituted aryl (e.g. $C_6$-$C_{10}$ aryl or $C_6$ aryl), or $R^{40}$-substituted or unsubstituted heteroaryl (e.g. 5 to 10 membered heteroaryl, 5 to 9 membered heteroaryl, or 5 to 6 membered heteroaryl). $X^{39}$ is halogen. In embodiments, $X^{39}$ is F.

$R^{40}$ is independently oxo, halogen, —$CX^{40}_3$, —$CHX^{40}_2$, —$CH_2X^{40}$, —$OCH_2X^{40}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{40}_3$, —$OCHX^{40}_2$, $R^{41}$-substituted or unsubstituted alkyl (e.g. $C_1$-$C_8$ alkyl, $C_1$-$C_6$ alkyl, or $C_1$-$C_4$ alkyl), $R^{41}$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^{41}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{41}$-substituted or unsubstituted heterocycloalkyl (e.g. 3 to 8 membered heterocycloalkyl, 4 to 8 membered heterocycloalkyl, or 5 to 6 membered heterocycloalkyl), $R^{41}$-substituted or unsubstituted aryl (e.g. $C_6$-$C_{10}$ aryl or $C_6$ aryl), or $R^{41}$-substituted or unsubstituted heteroaryl (e.g. 5 to 10 membered heteroaryl, 5 to 9 membered heteroaryl, or 5 to 6 membered heteroaryl). $X^{40}$ is halogen. In embodiments, $X^{40}$ is F.

In embodiments, $R^5$ is independently hydrogen, oxo, halogen, —$CX^{53}$, —$CHX^{52}$, —$CH_2X^5$, —$OCH_2X^5$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{53}$, —$OCHX^{52}$, $R^{42}$-substituted or unsubstituted alkyl (e.g. $C_1$-$C_8$ alkyl, $C_1$-$C_6$ alkyl, or $C_1$-$C_4$ alkyl), $R^{42}$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^{42}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{42}$-substituted or unsubstituted heterocycloalkyl (e.g. 3 to 8 membered heterocycloalkyl, 4 to 8 membered heterocycloalkyl, or 5 to 6 membered heterocycloalkyl), $R^{42}$-substituted or unsubstituted aryl (e.g. $C_6$-$C_{10}$ aryl or $C_6$ aryl), or $R^{42}$-substituted or unsubstituted heteroaryl (e.g. 5 to 10 membered heteroaryl, 5 to 9 membered heteroaryl, or 5 to 6 membered heteroaryl). $X^5$ is halogen. In embodiments, $X^5$ is F. In embodiments, $R^5$ is independently halogen, —$CX^{53}$, —$CHX^{52}$, —$CH_2X^5$, —$OCH_2X^5$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{53}$, —$OCHX^{52}$, $R^{42}$-substituted or unsubstituted alkyl (e.g. $C_1$-$C_8$ alkyl, $C_1$-$C_6$ alkyl, or $C_1$-$C_4$ alkyl), $R^{42}$-substituted or unsubstituted heteroalkyl (e.g. 2 to 10 membered heteroalkyl, 2 to 8 membered heteroalkyl, 4 to 8 membered heteroalkyl, or 2 to 4 membered heteroalkyl), $R^{42}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{42}$-substituted or unsubstituted heterocycloalkyl (e.g. 3 to 8 membered heterocycloalkyl, 4 to 8 membered heterocycloalkyl, or 5 to 6 membered heterocycloalkyl), $R^{42}$-substituted or unsubstituted aryl (e.g. $C_6$-$C_{10}$ aryl or $C_6$ aryl), or $R^{42}$-substituted or unsubstituted heteroaryl (e.g. 5 to 10 membered heteroaryl, 5 to 9 membered heteroaryl, or 5 to 6 membered heteroaryl).

$R^{42}$ is independently oxo, halogen, —$CX^{42}{}_3$, —$CHX^{42}{}_2$, —$CH_2X^{42}$, —$OCH_2X^{42}$, —$OCHX^{42}{}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{42}{}_3$, —$OCHX^{42}{}_2$, $R^{43}$-substituted or unsubstituted alkyl (e.g. $C_1$-$C_8$ alkyl, $C_1$-$C_6$ alkyl, or $C_1$-$C_4$ alkyl), $R^{43}$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^{43}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{43}$-substituted or unsubstituted heterocycloalkyl (e.g. 3 to 8 membered heterocycloalkyl, 4 to 8 membered heterocycloalkyl, or 5 to 6 membered heterocycloalkyl), $R^{43}$-substituted or unsubstituted aryl (e.g. $C_6$-$C_{10}$ aryl or $C_6$ aryl), or $R^{43}$-substituted or unsubstituted heteroaryl (e.g. 5 to 10 membered heteroaryl, 5 to 9 membered heteroaryl, or 5 to 6 membered heteroaryl). $X^{42}$ is halogen. In embodiments, $X^{42}$ is F.

$R^{43}$ is independently oxo, halogen, —$CX^{43}{}_3$, —$CHX^{43}{}_2$, —$CH_2X^{43}$, —$OCH_2X^{43}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{43}{}_3$, —$OCHX^{43}{}_2$, $R^{44}$-substituted or unsubstituted alkyl (e.g. $C_1$-$C_8$ alkyl, $C_1$-$C_6$ alkyl, or $C_1$-$C_4$ alkyl), $R^{44}$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^{44}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{44}$-substituted or unsubstituted heterocycloalkyl (e.g. 3 to 8 membered heterocycloalkyl, 4 to 8 membered heterocycloalkyl, or 5 to 6 membered heterocycloalkyl), $R^{44}$-substituted or unsubstituted aryl (e.g. $C_6$-$C_{10}$ aryl or $C_6$ aryl), or $R^{44}$-substituted or unsubstituted heteroaryl (e.g. 5 to 10 membered heteroaryl, 5 to 9 membered heteroaryl, or 5 to 6 membered heteroaryl). $X^{43}$ is halogen. In embodiments, $X^{43}$ is F.

In embodiments, $R^7$ is independently hydrogen, oxo, halogen, —$CX^{73}$, —$CHX^{72}$, —$CH_2X^7$, —$OCH_2X^7$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{73}$, —$OCHX^{72}$, $R^{48}$-substituted or unsubstituted alkyl (e.g. $C_1$-$C_8$ alkyl, $C_1$-$C_6$ alkyl, or $C_1$-$C_4$ alkyl), $R^{48}$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^{48}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{48}$-substituted or unsubstituted heterocycloalkyl (e.g. 3 to 8 membered heterocycloalkyl, 4 to 8 membered heterocycloalkyl, or 5 to 6 membered heterocycloalkyl), $R^{48}$-substituted or unsubstituted aryl (e.g. $C_6$-$C_{10}$ aryl or $C_6$ aryl), or $R^{48}$-substituted or unsubstituted heteroaryl (e.g. 5 to 10 membered heteroaryl, 5 to 9 membered heteroaryl, or 5 to 6 membered heteroaryl). $X^7$ is halogen. In embodiments, $X^7$ is F. In embodiments, $R^7$ and $R^8$ substituents bonded to the same nitrogen atom may optionally be joined to form a $R^{48}$-substituted or unsubstituted heterocycloalkyl (e.g. 3 to 8 membered heterocycloalkyl, 4 to 8 membered heterocycloalkyl, or 5 to 6 membered heterocycloalkyl), or $R^{48}$-substituted or unsubstituted heteroaryl (e.g. 5 to 10 membered heteroaryl, 5 to 9 membered heteroaryl, or 5 to 6 membered heteroaryl).

In embodiments, $R^7$ is independently hydrogen or unsubstituted alkyl. In embodiments, $R^7$ is independently hydrogen or unsubstituted $C_1$-$C_6$ alkyl. In embodiments, $R^7$ is independently hydrogen or unsubstituted $C_1$-$C_5$ alkyl. In embodiments, $R^7$ is independently hydrogen or unsubstituted $C_1$-$C_4$ alkyl. In embodiments, $R^7$ is independently hydrogen or unsubstituted $C_1$-$C_3$ alkyl. In embodiments, $R^7$ is independently hydrogen or unsubstituted $C_1$-$C_2$ alkyl. In embodiments, $R^7$ is independently hydrogen or unsubstituted $C_2$-$C_6$ alkyl. In embodiments, $R^7$ is independently hydrogen or unsubstituted $C_2$-$C_5$ alkyl. In embodiments, $R^7$ is independently hydrogen or unsubstituted $C_2$-$C_4$ alkyl. In embodiments, $R^7$ is independently hydrogen or unsubstituted $C_2$-$C_3$ alkyl. In embodiments, $R^7$ is independently hydrogen or unsubstituted $C_3$-$C_6$ alkyl. In embodiments, $R^7$ is independently hydrogen or unsubstituted $C_4$-$C_6$ alkyl. In embodiments, $R^7$ is independently hydrogen or unsubstituted $C_5$-$C_6$ alkyl. In embodiments, $R^7$ is independently hydrogen. In embodiments, $R^7$ is independently unsubstituted alkyl. In embodiments, $R^7$ is independently unsubstituted $C_1$-$C_6$ alkyl. In embodiments, $R^7$ is independently unsubstituted $C_1$-$C_5$ alkyl. In embodiments, $R^7$ is independently unsubstituted $C_1$-$C_4$ alkyl. In embodiments, $R^7$ is independently unsubstituted $C_1$-$C_3$ alkyl. In embodiments, $R^7$ is independently unsubstituted $C_1$-$C_2$ alkyl. In embodiments, $R^7$ is independently unsubstituted $C_2$-$C_6$ alkyl. In embodiments, $R^7$ is independently unsubstituted $C_2$-$C_5$ alkyl. In embodiments, $R^7$ is independently unsubstituted $C_2$-$C_4$ alkyl. In embodiments, $R^7$ is independently unsubstituted $C_2$-$C_3$ alkyl. In embodiments, $R^7$ is independently unsubstituted $C_3$-$C_6$ alkyl. In embodiments, $R^7$ is independently unsubstituted $C_4$-$C_6$ alkyl. In embodiments, $R^7$ is independently unsubstituted $C_5$-$C_6$ alkyl. In embodiments, $R^7$ is hydrogen. In embodiments, $R^7$ is independently hydrogen, halogen, —$CX^{73}$, —$CHX^{72}$, —$CH_2X^7$, —CN, —COOH, —$CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^7$ and $R^8$ substituents bonded to the same nitrogen atom may optionally be joined to form a substituted or unsubstituted heterocycloalkyl or substituted or unsubstituted heteroaryl.

$R^{48}$ is independently oxo, halogen, —$CX^{48}{}_3$, —$CHX^{48}{}_2$, —$CH_2X^{48}$, —$OCH_2X^{48}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{48}{}_3$, —$OCHX^{48}{}_2$, $R^{49}$-substituted or unsubstituted alkyl (e.g. $C_1$-$C_8$ alkyl, $C_1$-$C_6$ alkyl, or $C_1$-$C_4$ alkyl), $R^{49}$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^{49}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{49}$-substituted or unsubstituted heterocycloalkyl (e.g. 3 to 8 membered heterocycloalkyl, 4 to 8 membered heterocycloalkyl, or 5 to 6 membered heterocycloalkyl), $R^{49}$-substituted or unsubstituted aryl (e.g. $C_6$-$C_{10}$ aryl or $C_6$ aryl), or $R^{49}$-substituted or unsubstituted heteroaryl (e.g. 5 to 10 membered heteroaryl, 5 to 9 membered heteroaryl, or 5 to 6 membered heteroaryl). $X^{48}$ is halogen. In embodiments, $X^{48}$ is F.

$R^{49}$ is independently oxo, halogen, $-CX^{49}_3$, $-CHX^{49}_2$, $-CH_2X^{49}$, $-OCH_2X^{49}$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{49}_3$, $-OCHX^{49}_2$, $R^{50}$-substituted or unsubstituted alkyl (e.g. $C_1$-$C_8$ alkyl, $C_1$-$C_6$ alkyl, or $C_1$-$C_4$ alkyl), $R^{50}$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^{50}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{50}$-substituted or unsubstituted heterocycloalkyl (e.g. 3 to 8 membered heterocycloalkyl, 4 to 8 membered heterocycloalkyl, or 5 to 6 membered heterocycloalkyl), $R^{50}$-substituted or unsubstituted aryl (e.g. $C_6$-$C_{10}$ aryl or $C_6$ aryl), or $R^{50}$-substituted or unsubstituted heteroaryl (e.g. 5 to 10 membered heteroaryl, 5 to 9 membered heteroaryl, or 5 to 6 membered heteroaryl). $X^{49}$ is halogen. In embodiments, $X^{49}$ is F.

In embodiments, $R^8$ is independently hydrogen, oxo, halogen, $-CX^{83}$, $-CHX^{82}$, $-CH_2X^8$, $-OCH_2X^8$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{83}$, $-OCHX^{82}$, $R^{51}$-substituted or unsubstituted alkyl (e.g. $C_1$-$C_8$ alkyl, $C_1$-$C_6$ alkyl, or $C_1$-$C_4$ alkyl), $R^{51}$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^{51}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{51}$-substituted or unsubstituted heterocycloalkyl (e.g. 3 to 8 membered heterocycloalkyl, 4 to 8 membered heterocycloalkyl, or 5 to 6 membered heterocycloalkyl), $R^{51}$-substituted or unsubstituted aryl (e.g. $C_6$-$C_{10}$ aryl or $C_6$ aryl), or $R^{51}$-substituted or unsubstituted heteroaryl (e.g. 5 to 10 membered heteroaryl, 5 to 9 membered heteroaryl, or 5 to 6 membered heteroaryl). $X^8$ is halogen. In embodiments, $X^8$ is F. In embodiments, $X^7$ is F. In embodiments, $R^7$ and $R^8$ substituents bonded to the same nitrogen atom may optionally be joined to form a $R^{s5}$-substituted or unsubstituted heterocycloalkyl (e.g. 3 to 8 membered heterocycloalkyl, 4 to 8 membered heterocycloalkyl, or 5 to 6 membered heterocycloalkyl) or $R^{51}$-substituted or unsubstituted heteroaryl (e.g. 5 to 10 membered heteroaryl, 5 to 9 membered heteroaryl, or 5 to 6 membered heteroaryl).

In embodiments, $R^8$ is independently hydrogen or unsubstituted alkyl. In embodiments, $R^8$ is independently hydrogen or unsubstituted $C_1$-$C_6$ alkyl. In embodiments, $R^8$ is independently hydrogen or unsubstituted $C_1$-$C_5$ alkyl. In embodiments, $R^8$ is independently hydrogen or unsubstituted $C_1$-$C_4$ alkyl. In embodiments, $R^8$ is independently hydrogen or unsubstituted $C_1$-$C_3$ alkyl. In embodiments, $R^8$ is independently hydrogen or unsubstituted $C_1$-$C_2$ alkyl. In embodiments, $R^8$ is independently hydrogen or unsubstituted $C_2$-$C_6$ alkyl. In embodiments, $R^8$ is independently hydrogen or unsubstituted $C_2$-$C_5$ alkyl. In embodiments, $R^8$ is independently hydrogen or unsubstituted $C_2$-$C_4$ alkyl. In embodiments, $R^8$ is independently hydrogen or unsubstituted $C_2$-$C_3$ alkyl. In embodiments, $R^8$ is independently hydrogen or unsubstituted $C_3$-$C_6$ alkyl. In embodiments, $R^8$ is independently hydrogen or unsubstituted $C_4$-$C_6$ alkyl. In embodiments, $R^8$ is independently hydrogen or unsubstituted $C_5$-$C_6$ alkyl. In embodiments, $R^8$ is independently hydrogen. In embodiments, $R^8$ is independently unsubstituted alkyl. In embodiments, $R^8$ is independently unsubstituted $C_1$-$C_6$ alkyl. In embodiments, $R^8$ is independently unsubstituted $C_1$-$C_5$ alkyl. In embodiments, $R^8$ is independently unsubstituted $C_1$-$C_4$ alkyl. In embodiments, $R^8$ is independently unsubstituted $C_1$-$C_3$ alkyl. In embodiments, $R^8$ is independently unsubstituted $C_1$-$C_2$ alkyl. In embodiments, $R^8$ is independently unsubstituted $C_2$-$C_6$ alkyl. In embodiments, $R^8$ is independently unsubstituted $C_2$-$C_5$ alkyl. In embodiments, $R^8$ is independently unsubstituted $C_2$-$C_4$ alkyl. In embodiments, $R^8$ is independently unsubstituted $C_2$-$C_3$ alkyl. In embodiments, $R^8$ is independently unsubstituted $C_3$-$C_6$ alkyl. In embodiments, $R^8$ is independently unsubstituted $C_4$-$C_6$ alkyl. In embodiments, $R^8$ is independently unsubstituted $C_5$-$C_6$ alkyl. In embodiments, $R^8$ is hydrogen. In embodiments, $R^8$ is independently hydrogen, halogen, $-CX^{83}$, $-CHX^{82}$, $-CH_2X^8$, $-CN$, $-COOH$, $-CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^{51}$ is independently oxo, halogen, $-CX^{51}_3$, $-CHX^{51}_2$, $-CH_2X^{51}$, $-OCH_2X^{51}$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{51}_3$, $-OCHX^{51}_2$, $R^{52}$-substituted or unsubstituted alkyl (e.g. $C_1$-$C_8$ alkyl, $C_1$-$C_6$ alkyl, or $C_1$-$C_4$ alkyl), $R^{52}$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^{52}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{52}$-substituted or unsubstituted heterocycloalkyl (e.g. 3 to 8 membered heterocycloalkyl, 4 to 8 membered heterocycloalkyl, or 5 to 6 membered heterocycloalkyl), $R^{52}$-substituted or unsubstituted aryl (e.g. $C_6$-$C_{10}$ aryl or $C_6$ aryl), or $R^{52}$-substituted or unsubstituted heteroaryl (e.g. 5 to 10 membered heteroaryl, 5 to 9 membered heteroaryl, or 5 to 6 membered heteroaryl). $X^{51}$ is halogen. In embodiments, $X^{51}$ is F.

$R^{52}$ is independently oxo, halogen, $-CX^{52}_3$, $-CHX^{52}_2$, $-CH_2X^{52}$, $-OCH_2X^{52}$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{52}_3$, $-OCHX^{52}_2$, $R^{53}$-substituted or unsubstituted alkyl (e.g. $C_1$-$C_8$ alkyl, $C_1$-$C_6$ alkyl, or $C_1$-$C_4$ alkyl), $R^{53}$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^{53}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{53}$-substituted or unsubstituted heterocycloalkyl (e.g. 3 to 8 membered heterocycloalkyl, 4 to 8 membered heterocycloalkyl, or 5 to 6 membered heterocycloalkyl), $R^{53}$-substituted or unsubstituted aryl (e.g. $C_6$-$C_{10}$ aryl or $C_6$ aryl), or $R^{53}$-substituted or unsubstituted heteroaryl (e.g. 5 to 10 membered heteroaryl, 5 to 9 membered heteroaryl, or 5 to 6 membered heteroaryl). $X^{52}$ is halogen. In embodiments, $X^{52}$ is F.

In embodiments, $R^9$ is independently hydrogen, oxo, halogen, $-CX^{93}$, $-CHX^{92}$, $-CH_2X^9$, $-OCH_2X^9$, $-CN$, $-OH$, $-NH_2$, $-COOH$, $-CONH_2$, $-NO_2$, $-SH$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{93}$, —$OCHX^{92}{}_2$, $R^{54}$-substituted or unsubstituted alkyl (e.g. $C_1$-$C_8$ alkyl, $C_1$-$C_6$ alkyl, or $C_1$-$C_4$ alkyl), $R^{54}$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^{54}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{54}$-substituted or unsubstituted heterocycloalkyl (e.g. 3 to 8 membered heterocycloalkyl, 4 to 8 membered heterocycloalkyl, or 5 to 6 membered heterocycloalkyl), $R^{54}$-substituted or unsubstituted aryl (e.g. $C_6$-$C_{10}$ aryl or $C_6$ aryl), or $R^{54}$-substituted or unsubstituted heteroaryl (e.g. 5 to 10 membered heteroaryl, 5 to 9 membered heteroaryl, or 5 to 6 membered heteroaryl). $X^9$ is halogen. In embodiments, $X^9$ is F. In embodiments, $R^9$ is hydrogen. In embodiments, $R^9$ is independently hydrogen, halogen, —$CX^{93}{}_3$, —$CHX^{92}{}_2$, —$CH_2X^9$, —CN, —COOH, —$CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^{54}$ is independently oxo, halogen, —$CX^{54}{}_3$, —$CHX^{54}{}_2$, —$CH_2X^{54}$, —$OCH_2X^{54}$, —$OCHX^{54}{}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{54}{}_3$, —$OCHX^{54}{}_2$, R-substituted or unsubstituted alkyl (e.g. $C_1$-$C_8$ alkyl, $C_1$-$C_6$ alkyl, or $C_1$-$C_4$ alkyl), $R^{55}$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^{55}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{55}$-substituted or unsubstituted heterocycloalkyl (e.g. 3 to 8 membered heterocycloalkyl, 4 to 8 membered heterocycloalkyl, or 5 to 6 membered heterocycloalkyl), $R^{55}$-substituted or unsubstituted aryl (e.g. $C_6$-$C_{10}$ aryl or $C_6$ aryl), or $R^{55}$-substituted or unsubstituted heteroaryl (e.g. 5 to 10 membered heteroaryl, 5 to 9 membered heteroaryl, or 5 to 6 membered heteroaryl). $X^{54}$ is halogen. In embodiments, $X^{54}$ is F.

$R^{55}$ is independently oxo, halogen, —$CX^{55}{}_3$, —$CHX^{55}{}_2$, —$CH_2X^{55}$, —$OCH_2X^{55}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{55}{}_3$, —$OCHX^{55}{}_2$, $R^{56}$-substituted or unsubstituted alkyl (e.g. $C_1$-$C_8$ alkyl, $C_1$-$C_6$ alkyl, or $C_1$-$C_4$ alkyl), $R^{56}$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^{56}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{56}$-substituted or unsubstituted heterocycloalkyl (e.g. 3 to 8 membered heterocycloalkyl, 4 to 8 membered heterocycloalkyl, or 5 to 6 membered heterocycloalkyl), $R^{56}$-substituted or unsubstituted aryl (e.g. $C_6$-$C_{10}$ aryl or $C_6$ aryl), or $R^{56}$-substituted or unsubstituted heteroaryl (e.g. 5 to 10 membered heteroaryl, 5 to 9 membered heteroaryl, or 5 to 6 membered heteroaryl). $X^{55}$ is halogen. In embodiments, $X^{55}$ is F.

In embodiments, $R^{10}$ is independently hydrogen, oxo, halogen, —$CX^{10}{}_3$, —$CHX^{10}{}_2$, —$CH_2X^{10}$, —$OCH_2X^{10}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{10}{}_3$, —$OCHX^{10}{}_2$, $R^{57}$-substituted or unsubstituted alkyl (e.g. $C_1$-$C_8$ alkyl, $C_1$-$C_6$ alkyl, or $C_1$-$C_4$ alkyl), $R^{57}$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^{57}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{57}$-substituted or unsubstituted heterocycloalkyl (e.g. 3 to 8 membered heterocycloalkyl, 4 to 8 membered heterocycloalkyl, or 5 to 6 membered heterocycloalkyl), $R^{57}$-substituted or unsubstituted aryl (e.g. $C_6$-$C_{10}$ aryl or $C_6$ aryl), or $R^{57}$-substituted or unsubstituted heteroaryl (e.g. 5 to 10 membered heteroaryl, 5 to 9 membered heteroaryl, or 5 to 6 membered heteroaryl). $X^{10}$ is halogen. In embodiments, $X^{10}$ is F. In embodiments, $R^{10}$ is hydrogen. In embodiments, $R^{10}$, is independently hydrogen, halogen, —$CX^{10}{}_3$, —$CHX^{10}{}_2$, —$CH_2X^{10}$, —CN, —COOH, —$CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^{57}$ is independently oxo, halogen, —$CX^{57}{}_3$, —$CHX^{57}{}_2$, —$CH_2X^{57}$, —$OCH_2X^{57}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{57}{}_3$, —$OCHX^{57}{}_2$, $R^{58}$-substituted or unsubstituted alkyl (e.g. $C_1$-$C_8$ alkyl, $C_1$-$C_6$ alkyl, or $C_1$-$C_4$ alkyl), $R^{58}$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^{58}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{58}$-substituted or unsubstituted heterocycloalkyl (e.g. 3 to 8 membered heterocycloalkyl, 4 to 8 membered heterocycloalkyl, or 5 to 6 membered heterocycloalkyl), $R^{58}$-substituted or unsubstituted aryl (e.g. $C_6$-$C_{10}$ aryl or $C_6$ aryl), or $R^{58}$-substituted or unsubstituted heteroaryl (e.g. 5 to 10 membered heteroaryl, 5 to 9 membered heteroaryl, or 5 to 6 membered heteroaryl). $X^{57}$ is halogen. In embodiments, $X^{57}$ is F.

$R^{58}$ is independently oxo, halogen, —$CX^{58}{}_3$, —$CHX^{58}{}_2$, —$CH_2X^{58}$, —$OCH_2X^{58}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{58}{}_3$, —$OCH_2X^{58}{}_2$, $R^{59}$-substituted or unsubstituted alkyl (e.g. $C_1$-$C_8$ alkyl, $C_1$-$C_6$ alkyl, or $C_1$-$C_4$ alkyl), $R^{59}$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^{59}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{59}$-substituted or unsubstituted heterocycloalkyl (e.g. 3 to 8 membered heterocycloalkyl, 4 to 8 membered heterocycloalkyl, or 5 to 6 membered heterocycloalkyl), $R^{59}$-substituted or unsubstituted aryl (e.g. $C_6$-$C_{10}$ aryl or $C_6$ aryl), or $R^{59}$-substituted or unsubstituted heteroaryl (e.g. 5 to 10 membered heteroaryl, 5 to 9 membered heteroaryl, or 5 to 6 membered heteroaryl). $X^{58}$ is halogen. In embodiments, $X^{58}$ is F.

In embodiments, $R^{11}$ is independently hydrogen, oxo, halogen, —$CX^{11}{}_3$, —$CHX^{11}{}_2$, —$CH_2X^{11}$, —$OCH_2X^1$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCX$^{11}$$_3$, —OCHX$^{11}$$_2$, R$^{60}$-substituted or unsubstituted alkyl (e.g. C$_1$-C$_8$ alkyl, C$_1$-C$_6$ alkyl, or C$_1$-C$_4$ alkyl), R$^{60}$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), R$^{60}$-substituted or unsubstituted cycloalkyl (e.g. C$_3$-C$_8$ cycloalkyl, C$_4$-C$_8$ cycloalkyl, or C$_5$-C$_6$ cycloalkyl), R$^{60}$-substituted or unsubstituted heterocycloalkyl (e.g. 3 to 8 membered heterocycloalkyl, 4 to 8 membered heterocycloalkyl, or 5 to 6 membered heterocycloalkyl), R$^{60}$-substituted or unsubstituted aryl (e.g. C$_6$-C$_{10}$ aryl or C$_6$ aryl), or R$^{60}$-substituted or unsubstituted heteroaryl (e.g. 5 to 10 membered heteroaryl, 5 to 9 membered heteroaryl, or 5 to 6 membered heteroaryl). X$^{11}$ is halogen. In embodiments, X$^{11}$ is F. In embodiments, R$^{11}$ and R$^{12}$ substituents bonded to the same nitrogen atom may optionally be joined to form a R$^{60}$-substituted or unsubstituted heterocycloalkyl (e.g. 3 to 8 membered heterocycloalkyl, 4 to 8 membered heterocycloalkyl, or 5 to 6 membered heterocycloalkyl) or R$^{60}$-substituted or unsubstituted heteroaryl (e.g. 5 to 10 membered heteroaryl, 5 to 9 membered heteroaryl, or 5 to 6 membered heteroaryl). In embodiments, R$^{11}$ is hydrogen. In embodiments, R$^{11}$ is independently hydrogen, halogen, —CX$^{11}$$_3$, —CHX$^{11}$$_2$, —CH$_2$X$^{11}$, —CN, —COOH, —CONH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

R$^{60}$ is independently oxo, halogen, —CX$^{60}$$_3$, —CHX$^{60}$$_2$, —CH$_2$X$^{60}$, —OCH$_2$X$^{60}$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCX$^{60}$$_3$, —OCH$_2$X$^{60}$$_2$, R$^{61}$-substituted or unsubstituted alkyl (e.g. C$_1$-C$_8$ alkyl, C$_1$-C$_6$ alkyl, or C$_1$-C$_4$ alkyl), R$^{61}$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), R$^{61}$-substituted or unsubstituted cycloalkyl (e.g. C$_3$-C$_8$ cycloalkyl, C$_4$-C$_8$ cycloalkyl, or C$_5$-C$_6$ cycloalkyl), R$^{61}$-substituted or unsubstituted heterocycloalkyl (e.g. 3 to 8 membered heterocycloalkyl, 4 to 8 membered heterocycloalkyl, or 5 to 6 membered heterocycloalkyl), R$^{61}$-substituted or unsubstituted aryl (e.g. C$_6$-C$_{10}$ aryl or C$_6$ aryl), or R$^{61}$-substituted or unsubstituted heteroaryl (e.g. 5 to 10 membered heteroaryl, 5 to 9 membered heteroaryl, or 5 to 6 membered heteroaryl). X$^{60}$ is halogen. In embodiments, X$^{60}$ is F.

R$^{61}$ is independently oxo, halogen, —CX$^{61}$$_3$, —CHX$^{61}$$_2$, —CH$_2$X$^{61}$, —OCH$_2$X$^{61}$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCX$^{61}$$_3$, —OCHX$^{61}$$_2$, R$^{62}$-substituted or unsubstituted alkyl (e.g. C$_1$-C$_8$ alkyl, C$_1$-C$_6$ alkyl, or C$_1$-C$_4$ alkyl), R$^{62}$-substituted or unsubstituted heteroalkyl (e.g. 2 to 10 membered heteroalkyl, 2 to 8 membered heteroalkyl, 4 to 8 membered heteroalkyl, or 2 to 4 membered heteroalkyl), R$^{62}$-substituted or unsubstituted cycloalkyl (e.g. C$_3$-C$_8$ cycloalkyl, C$_4$-C$_8$ cycloalkyl, or C$_5$-C$_6$ cycloalkyl), R$^{62}$-substituted or unsubstituted heterocycloalkyl (e.g. 3 to 8 membered heterocycloalkyl, 4 to 8 membered heterocycloalkyl, or 5 to 6 membered heterocycloalkyl), R$^{62}$-substituted or unsubstituted aryl (e.g. C$_6$-C$_{10}$ aryl or C$_6$ aryl), or R$^{62}$-substituted or unsubstituted heteroaryl (e.g. 5 to 10 membered heteroaryl, 5 to 9 membered heteroaryl, or 5 to 6 membered heteroaryl). X$^{61}$ is halogen. In embodiments, X$^{61}$ is F.

In embodiments, R$^{12}$ is independently hydrogen, oxo, halogen, —CX$^{12}$$_3$, —CHX$^{12}$$_2$, —CH$_2$X$^{12}$, —OCH$_2$X$^{12}$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCX$^{12}$$_3$, —OCHX$^{12}$$_2$, R$^{63}$-substituted or unsubstituted alkyl (e.g. C$_1$-C$_8$ alkyl, C$_1$-C$_6$ alkyl, or C$_1$-C$_4$ alkyl), R$^{63}$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), R$^{63}$-substituted or unsubstituted cycloalkyl (e.g. C$_3$-C$_8$ cycloalkyl, C$_4$-C$_8$ cycloalkyl, or C$_5$-C$_6$ cycloalkyl), R$^{63}$-substituted or unsubstituted heterocycloalkyl (e.g. 3 to 8 membered heterocycloalkyl, 4 to 8 membered heterocycloalkyl, or 5 to 6 membered heterocycloalkyl), R$^{63}$-substituted or unsubstituted aryl (e.g. C$_6$-C$_{10}$ aryl or C$_6$ aryl), or R$^{63}$-substituted or unsubstituted heteroaryl (e.g. 5 to 10 membered heteroaryl, 5 to 9 membered heteroaryl, or 5 to 6 membered heteroaryl). X$^{12}$ is halogen. In embodiments, X$^{12}$ is F. In embodiments, R$^{11}$ and R$^{12}$ substituents bonded to the same nitrogen atom may optionally be joined to form a R$^{63}$-substituted or unsubstituted heterocycloalkyl (e.g. 3 to 8 membered heterocycloalkyl, 4 to 8 membered heterocycloalkyl, or 5 to 6 membered heterocycloalkyl) or R$^{63}$-substituted or unsubstituted heteroaryl (e.g. 5 to 10 membered heteroaryl, 5 to 9 membered heteroaryl, or 5 to 6 membered heteroaryl). In embodiments, R$^{12}$ is hydrogen. In embodiments, R$^{12}$ is independently hydrogen, halogen, —CX$^{12}$$_3$, —CHX$^{12}$$_2$, —CH$_2$X$^{12}$, —CN, —COOH, —CONH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

R$^{63}$ is independently oxo, halogen, —CX$^{63}$$_3$, —CHX$^{63}$$_2$, —CH$_2$X$^{63}$, —OCH$_2$X$^{63}$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCX$^{63}$$_3$, —OCHX$^{63}$$_2$, R$^{64}$-substituted or unsubstituted alkyl (e.g. C$_1$-C$_8$ alkyl, C$_1$-C$_6$ alkyl, or C$_1$-C$_4$ alkyl), R$^{64}$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), R$^{64}$-substituted or unsubstituted cycloalkyl (e.g. C$_3$-C$_8$ cycloalkyl, C$_4$-C$_8$ cycloalkyl, or C$_5$-C$_6$ cycloalkyl), R$^{64}$-substituted or unsubstituted heterocycloalkyl (e.g. 3 to 8 membered heterocycloalkyl, 4 to 8 membered heterocycloalkyl, or 5 to 6 membered heterocycloalkyl), R$^{64}$-substituted or unsubstituted aryl (e.g. C$_6$-C$_{10}$ aryl or C$_6$ aryl), or R$^{64}$-substituted or unsubstituted heteroaryl (e.g. 5 to 10 membered heteroaryl, 5 to 9 membered heteroaryl, or 5 to 6 membered heteroaryl). X$^{63}$ is halogen. In embodiments, X$^{63}$ is F.

R$^{64}$ is independently oxo, halogen, —CX$^{64}$$_3$, —CHX$^{64}$$_2$, —CH$_2$X$^{64}$, —OCH$_2$X$^{64}$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCX$^{64}$$_3$, —OCHX$^{64}$2, R$^{65}$-substituted or unsubstituted alkyl (e.g. $C_1$-$C_8$ alkyl, $C_1$-$C_6$ alkyl, or $C_1$-$C_4$ alkyl), $R^{65}$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^{65}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{65}$-substituted or unsubstituted heterocycloalkyl (e.g. 3 to 8 membered heterocycloalkyl, 4 to 8 membered heterocycloalkyl, or 5 to 6 membered heterocycloalkyl), $R^{65}$-substituted or unsubstituted aryl (e.g. $C_6$-$C_{10}$ aryl or $C_6$ aryl), or $R^{65}$-substituted or unsubstituted heteroaryl (e.g. 5 to 10 membered heteroaryl, 5 to 9 membered heteroaryl, or 5 to 6 membered heteroaryl). $X^{64}$ is halogen. In embodiments, $X^{64}$ is F.

In embodiments, $R^{13}$ is independently hydrogen, oxo, halogen, —$CX^{13}_3$, —$CHX^{13}_2$, —$CH_2X^{13}$, —$OCH_2X^{13}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC$=$(O)NHNH_2$, —$NHC$=$(O)NH_2$, —$NHSO_2H$, —$NHC$=$(O)H$, —$NHC(O)$—OH, —NHOH, —$OCX^{13}_3$, —$OCHX^{13}_2$, $R^{66}$-substituted or unsubstituted alkyl (e.g. $C_1$-$C_8$ alkyl, $C_1$-$C_6$ alkyl, or $C_1$-$C_4$ alkyl), $R^{66}$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^{66}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{66}$-substituted or unsubstituted heterocycloalkyl (e.g. 3 to 8 membered heterocycloalkyl, 4 to 8 membered heterocycloalkyl, or 5 to 6 membered heterocycloalkyl), $R^{66}$-substituted or unsubstituted aryl (e.g. $C_6$-$C_{10}$ aryl or $C_6$ aryl), or $R^{66}$-substituted or unsubstituted heteroaryl (e.g. 5 to 10 membered heteroaryl, 5 to 9 membered heteroaryl, or 5 to 6 membered heteroaryl). $X^{13}$ is halogen. In embodiments, $X^{13}$ is F. In embodiments, $R^{13}$ is hydrogen. In embodiments, $R^{13}$ is independently hydrogen, halogen, —$CX^{13}_3$, —$CHX^{13}_2$, —$CH_2X^{13}$, —CN, —COOH, —$CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^{66}$ is independently oxo, halogen, —$CX^{66}_3$, —$CHX^{66}_2$, —$CH_2X^{66}$, —$OCH_2X^{66}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC$=$(O)NHNH_2$, —$NHC$=$(O)NH_2$, —$NHSO_2H$, —$NHC$=$(O)H$, —$NHC(O)$—OH, —NHOH, —$OCX^{66}_3$, —$OCHX^{66}_2$, $R^{67}$-substituted or unsubstituted alkyl (e.g. $C_1$-$C_8$ alkyl, $C_1$-$C_6$ alkyl, or $C_1$-$C_4$ alkyl), $R^{67}$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^{67}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{67}$-substituted or unsubstituted heterocycloalkyl (e.g. 3 to 8 membered heterocycloalkyl, 4 to 8 membered heterocycloalkyl, or 5 to 6 membered heterocycloalkyl), $R^{67}$-substituted or unsubstituted aryl (e.g. $C_6$-$C_{10}$ aryl or $C_6$ aryl), or $R^{67}$-substituted or unsubstituted heteroaryl (e.g. 5 to 10 membered heteroaryl, 5 to 9 membered heteroaryl, or 5 to 6 membered heteroaryl). $X^{66}$ is halogen. In embodiments, $X^{66}$ is F.

$R^{67}$ is independently oxo, halogen, —$CX^{67}_3$, —$CHX^{67}_2$, —$CH_2X^{67}$, —$OCH_2X^{67}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC$=$(O)NHNH_2$, —$NHC$=$(O)NH_2$, —$NHSO_2H$, —$NHC$=$(O)H$, —$NHC(O)$—OH, —NHOH, —$OCX^{67}_3$, —$OCHX^{67}_2$, $R^{68}$-substituted or unsubstituted alkyl (e.g. $C_1$-$C_8$ alkyl, $C_1$-$C_6$ alkyl, or $C_1$-$C_4$ alkyl), $R^{68}$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^{68}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{68}$-substituted or unsubstituted heterocycloalkyl (e.g. 3 to 8 membered heterocycloalkyl, 4 to 8 membered heterocycloalkyl, or 5 to 6 membered heterocycloalkyl), $R^{68}$-substituted or unsubstituted aryl (e.g. $C_6$-$C_{10}$ aryl or $C_6$ aryl), or $R^{68}$-substituted or unsubstituted heteroaryl (e.g. 5 to 10 membered heteroaryl, 5 to 9 membered heteroaryl, or 5 to 6 membered heteroaryl). $X^{67}$ is halogen. In embodiments, $X^{67}$ is F.

In embodiments, $R^{14}$ is independently hydrogen, oxo, halogen, —$CX^{14}_3$, —$CHX^{14}_2$, —$CH_2X^{14}$, —$OCH_2X^{14}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC$=$(O)NHNH_2$, —$NHC$=$(O)NH_2$, —$NHSO_2H$, —$NHC$=$(O)H$, —$NHC(O)$—OH, —NHOH, —$OCX^{14}_3$, —$OCHX^{14}_2$, $R^{69}$-substituted or unsubstituted alkyl (e.g. $C_1$-$C_8$ alkyl, $C_1$-$C_6$ alkyl, or $C_1$-$C_4$ alkyl), $R^{69}$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^{69}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{69}$-substituted or unsubstituted heterocycloalkyl (e.g. 3 to 8 membered heterocycloalkyl, 4 to 8 membered heterocycloalkyl, or 5 to 6 membered heterocycloalkyl), $R^{69}$-substituted or unsubstituted aryl (e.g. $C_6$-$C_{10}$ aryl or $C_6$ aryl), or $R^{69}$-substituted or unsubstituted heteroaryl (e.g. 5 to 10 membered heteroaryl, 5 to 9 membered heteroaryl, or 5 to 6 membered heteroaryl). $X^{14}$ is halogen. In embodiments, $X^{14}$ is F. In embodiments, $R^{14}$ is hydrogen. In embodiments, $R^{14}$ is independently hydrogen, halogen, —$CX^{14}_3$, —$CHX^{14}_2$, —$CH_2X^{14}$, —CN, —COOH, —$CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^{69}$ is independently oxo, halogen, —$CX^{69}_3$, —$CHX^{69}_2$, —$CH_2X^{69}$, —$OCH_2X^{69}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC$=$(O)NHNH_2$, —$NHC$=$(O)NH_2$, —$NHSO_2H$, —$NHC$=$(O)H$, —$NHC(O)$—OH, —NHOH, —$OCX^{69}_3$, —$OCHX^{69}_2$, $R^{70}$-substituted or unsubstituted alkyl (e.g. $C_1$-$C_8$ alkyl, $C_1$-$C_6$ alkyl, or $C_1$-$C_4$ alkyl), $R^{70}$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^{70}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{70}$-substituted or unsubstituted heterocycloalkyl (e.g. 3 to 8 membered heterocycloalkyl, 4 to 8 membered heterocycloalkyl, or 5 to 6 membered heterocycloalkyl), $R^{70}$-substituted or unsubstituted aryl (e.g. $C_6$-$C_{10}$ aryl or $C_6$ aryl), or $R^{70}$-substituted or unsubstituted heteroaryl (e.g. 5 to 10 membered heteroaryl, 5 to 9 membered heteroaryl, or 5 to 6 membered heteroaryl). $X^{69}$ is halogen. In embodiments, $X^{69}$ is F.

$R^{70}$ is independently oxo, halogen, —$CX^{70}_3$, —$CHX^{70}_2$, —$CH_2X^{70}$, —$OCH_2X^{70}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC$=$(O)NHNH_2$, —$NHC$=$(O)NH_2$, —$NHSO_2H$, —$NHC$=$(O)H$, —$NHC(O)$—OH, —NHOH, —$OCX^{70}_3$, —$OCHX^{70}_2$, $R^{71}$-substituted or unsubstituted alkyl (e.g. $C_1$-$C_8$ alkyl, $C_1$-$C_6$ alkyl, or $C_1$-$C_4$ alkyl), $R^{71}$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^{71}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{71}$-substituted or unsubstituted heterocycloalkyl (e.g. 3 to 8 membered heterocycloalkyl, 4 to 8 membered heterocycloalkyl, or 5 to 6 membered heterocycloalkyl), $R^{71}$-substituted or unsubstituted aryl (e.g. $C_6$-$C_{10}$ aryl or $C_6$ aryl), or $R^{71}$-substituted or unsubstituted heteroaryl (e.g. 5 to 10 membered heteroaryl, 5 to 9 membered heteroaryl, or 5 to 6 membered heteroaryl). $X^{70}$ is halogen. In embodiments, $X^{70}$ is F.

In embodiments, $R^{15}$ is independently hydrogen, oxo, halogen, —$CX^{15}_3$, —$CHX^{15}_2$, —$CH_2X^{15}$, —$OCH_2X^{15}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{15}_3$, —$OCHX^{15}_2$, $R^{72}$-substituted or unsubstituted alkyl (e.g. $C_1$-$C_8$ alkyl, $C_1$-$C_6$ alkyl, or $C_1$-$C_4$ alkyl), $R^{72}$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^{72}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{72}$-substituted or unsubstituted heterocycloalkyl (e.g. 3 to 8 membered heterocycloalkyl, 4 to 8 membered heterocycloalkyl, or 5 to 6 membered heterocycloalkyl), $R^{72}$-substituted or unsubstituted aryl (e.g. $C_6$-$C_{10}$ aryl or $C_6$ aryl), or $R^{72}$-substituted or unsubstituted heteroaryl (e.g. 5 to 10 membered heteroaryl, 5 to 9 membered heteroaryl, or 5 to 6 membered heteroaryl). $X^{15}$ is halogen. In embodiments, $X^{15}$ is F. In embodiments, $R^{15}$ and $R^{16}$ substituents bonded to the same nitrogen atom may optionally be joined to form a $R^{72}$-substituted or unsubstituted heterocycloalkyl (e.g. 3 to 8 membered heterocycloalkyl, 4 to 8 membered heterocycloalkyl, or 5 to 6 membered heterocycloalkyl) or $R^{72}$-substituted or unsubstituted heteroaryl (e.g. 5 to 10 membered heteroaryl, 5 to 9 membered heteroaryl, or 5 to 6 membered heteroaryl). In embodiments, $R^{15}$ is hydrogen. In embodiments, $R^{15}$ is independently hydrogen, halogen, —$CX^{15}_3$, —$CHX^{15}_2$, —$CH_2X^{15}$, —CN, —COOH, —$CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^{15}$ is independently hydrogen or unsubstituted alkyl. In embodiments, $R^{15}$ is independently hydrogen or unsubstituted $C_1$-$C_6$ alkyl. In embodiments, $R^{15}$ is independently hydrogen or unsubstituted $C_1$-$C_5$ alkyl. In embodiments, $R^{15}$ is independently hydrogen or unsubstituted $C_1$-$C_4$ alkyl. In embodiments, $R^{15}$ is independently hydrogen or unsubstituted $C_1$-$C_3$ alkyl. In embodiments, $R^{15}$ is independently hydrogen or unsubstituted $C_1$-$C_2$ alkyl. In embodiments, $R^{15}$ is independently hydrogen or unsubstituted $C_2$-$C_6$ alkyl. In embodiments, $R^{15}$ is independently hydrogen or unsubstituted $C_2$-$C_5$ alkyl. In embodiments, $R^{15}$ is independently hydrogen or unsubstituted $C_2$-$C_4$ alkyl. In embodiments, $R^{15}$ is independently hydrogen or unsubstituted $C_2$-$C_3$ alkyl. In embodiments, $R^{15}$ is independently hydrogen or unsubstituted $C_3$-$C_6$ alkyl. In embodiments, $R^{15}$ is independently hydrogen or unsubstituted $C_4$-$C_6$ alkyl. In embodiments, $R^{15}$ is independently hydrogen or unsubstituted $C_5$-$C_6$ alkyl. In embodiments, $R^{15}$ is independently hydrogen. In embodiments, $R^{15}$ is independently unsubstituted alkyl. In embodiments, $R^{15}$ is independently unsubstituted $C_1$-$C_6$ alkyl. In embodiments, $R^{15}$ is independently unsubstituted $C_1$-$C_5$ alkyl. In embodiments, $R^{15}$ is independently unsubstituted $C_1$-$C_4$ alkyl. In embodiments, $R^{15}$ is independently unsubstituted $C_1$-$C_3$ alkyl. In embodiments, $R^{15}$ is independently unsubstituted $C_1$-$C_2$ alkyl. In embodiments, $R^{15}$ is independently unsubstituted $C_2$-$C_6$ alkyl. In embodiments, $R^{15}$ is independently unsubstituted $C_2$-$C_5$ alkyl. In embodiments, $R^{15}$ is independently unsubstituted $C_2$-$C_4$ alkyl. In embodiments, $R^{15}$ is independently unsubstituted $C_2$-$C_3$ alkyl. In embodiments, $R^{15}$ is independently unsubstituted $C_3$-$C_6$ alkyl. In embodiments, $R^{15}$ is independently unsubstituted $C_4$-$C_6$ alkyl. In embodiments, $R^{15}$ is independently unsubstituted $C_5$-$C_6$ alkyl.

$R^{72}$ is independently oxo, halogen, —$CX^{72}_3$, —$CHX^{72}_2$, —$CH_2X^{72}$, —$OCH_2X^{72}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{72}_3$, —$OCHX^{72}_2$, $R^{73}$-substituted or unsubstituted alkyl (e.g. $C_1$-$C_8$ alkyl, $C_1$-$C_6$ alkyl, or $C_1$-$C_4$ alkyl), $R^{73}$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^{73}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{73}$-substituted or unsubstituted heterocycloalkyl (e.g. 3 to 8 membered heterocycloalkyl, 4 to 8 membered heterocycloalkyl, or 5 to 6 membered heterocycloalkyl), $R^{73}$-substituted or unsubstituted aryl (e.g. $C_6$-$C_{10}$ aryl or $C_6$ aryl), or $R^{73}$-substituted or unsubstituted heteroaryl (e.g. 5 to 10 membered heteroaryl, 5 to 9 membered heteroaryl, or 5 to 6 membered heteroaryl). $X^{72}$ is halogen. In embodiments, $X^{72}$ is F.

$R^{73}$ is independently oxo, halogen, —$CX^{73}_3$, —$CHX^{73}_2$, —$CH_2X^{73}$, —$OCH_2X^{73}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{73}_3$, —$OCHX^{73}_2$, $R^{74}$-substituted or unsubstituted alkyl (e.g. $C_1$-$C_8$ alkyl, $C_1$-$C_6$ alkyl, or $C_1$-$C_4$ alkyl), $R^{74}$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^{74}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{74}$-substituted or unsubstituted heterocycloalkyl (e.g. 3 to 8 membered heterocycloalkyl, 4 to 8 membered heterocycloalkyl, or 5 to 6 membered heterocycloalkyl), $R^{74}$-substituted or unsubstituted aryl (e.g. $C_6$-$C_{10}$ aryl or $C_6$ aryl), or $R^{74}$-substituted or unsubstituted heteroaryl (e.g. 5 to 10 membered heteroaryl, 5 to 9 membered heteroaryl, or 5 to 6 membered heteroaryl). $X^{73}$ is halogen. In embodiments, $X^{73}$ is F.

In embodiments, $R^{16}$ is independently hydrogen, oxo, halogen, —$CX^{16}_3$, —$CHX^{16}_2$, —$CH_2X^{16}$, —$OCH_2X^{16}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{16}_3$, —$OCHX^{16}_2$, $R^{75}$-substituted or unsubstituted alkyl (e.g. $C_1$-$C_8$ alkyl, $C_1$-$C_6$ alkyl, or $C_1$-$C_4$ alkyl), $R^{75}$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^{75}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{75}$-substituted or unsubstituted heterocycloalkyl (e.g. 3 to 8 membered heterocycloalkyl, 4 to 8 membered heterocycloalkyl, or 5 to 6 membered heterocycloalkyl), $R^{75}$-substituted or unsubstituted aryl (e.g. $C_6$-$C_{10}$ aryl or $C_6$ aryl), or $R^{75}$-substituted or unsubstituted heteroaryl (e.g. 5 to 10 membered heteroaryl, 5 to 9 membered heteroaryl, or 5 to 6 membered heteroaryl). $X^{16}$ is halogen. In embodiments, $X^{16}$ is F. In embodiments, $R^{15}$ and $R^{16}$ substituents bonded to the same nitrogen atom may optionally be joined to form a $R^{75}$-substituted or unsubstituted heterocycloalkyl (e.g. 3 to 8 membered heterocycloalkyl, 4 to 8 membered heterocycloalkyl, or 5 to 6 membered heterocycloalkyl) or $R^{75}$-substituted or unsubstituted heteroaryl (e.g. 5 to 10 membered heteroaryl, 5 to 9 membered heteroaryl, or 5 to 6 membered heteroaryl). In embodiments, $R^{16}$ is hydrogen. In embodiments, $R^{16}$ is independently hydrogen, halogen, —$CX^{16}_3$, —$CHX^{16}_2$, —$CH_2X^{16}$, —CN, —COOH, —$CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^{16}$ is independently hydrogen or unsubstituted alkyl. In embodiments, $R^{16}$ is independently hydrogen or unsubstituted $C_1$-$C_6$ alkyl. In embodiments, $R^{16}$ is independently hydrogen or unsubstituted $C_1$-$C_5$ alkyl. In embodiments, $R^{16}$ is independently hydrogen or unsubstituted $C_1$-$C_4$ alkyl. In embodiments, $R^{16}$ is independently hydrogen or unsubstituted $C_1$-$C_3$ alkyl. In embodiments, $R^{16}$ is independently hydrogen or unsubstituted $C_1$-$C_2$ alkyl. In embodiments, $R^{16}$ is independently hydrogen or unsubstituted $C_2$-$C_6$ alkyl. In embodiments, $R^{16}$ is independently hydrogen or unsubstituted $C_2$-$C_5$ alkyl. In embodiments, $R^{16}$ is independently hydrogen or unsubstituted $C_2$-$C_4$ alkyl. In embodiments, $R^{16}$ is independently hydrogen or unsubstituted $C_2$-$C_3$ alkyl. In embodiments, $R^{16}$ is independently hydrogen or unsubstituted $C_3$-$C_6$ alkyl. In embodiments, $R^{16}$ is independently hydrogen or unsubstituted $C_4$-$C_6$ alkyl. In embodiments, $R^{16}$ is independently hydrogen or unsubstituted $C_5$-$C_6$ alkyl. In embodiments, $R^{16}$ is independently hydrogen. In embodiments, $R^{16}$ is independently unsubstituted alkyl. In embodiments, $R^{16}$ is independently unsubstituted $C_1$-$C_6$ alkyl. In embodiments, $R^{16}$ is independently unsubstituted $C_1$-$C_5$ alkyl. In embodiments, $R^{16}$ is independently unsubstituted $C_1$-$C_4$ alkyl. In embodiments, $R^{16}$ is independently unsubstituted $C_1$-$C_3$ alkyl. In embodiments, $R^{16}$ is independently unsubstituted $C_1$-$C_2$ alkyl. In embodiments, $R^{16}$ is independently unsubstituted $C_2$-$C_6$ alkyl. In embodiments, $R^{16}$ is independently unsubstituted $C_2$-$C_5$ alkyl. In embodiments, $R^{16}$ is independently unsubstituted $C_2$-$C_4$ alkyl. In embodiments, $R^{16}$ is independently unsubstituted $C_2$-$C_3$ alkyl. In embodiments, $R^{16}$ is independently unsubstituted $C_3$-$C_6$ alkyl. In embodiments, $R^{16}$ is independently unsubstituted $C_4$-$C_6$ alkyl. In embodiments, $R^{16}$ is independently unsubstituted $C_5$-$C_6$ alkyl.

$R^{75}$ is independently oxo, halogen, —$CX^{75}_3$, —$CHX^{75}_2$, —$CH_2X^{75}$, —$OCH_2X^{75}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{75}_3$, —$OCHX^{75}_2$, $R^{76}$-substituted or unsubstituted alkyl (e.g. $C_1$-$C_8$ alkyl, $C_1$-$C_6$ alkyl, or $C_1$-$C_4$ alkyl), $R^{76}$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^{76}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{76}$-substituted or unsubstituted heterocycloalkyl (e.g. 3 to 8 membered heterocycloalkyl, 4 to 8 membered heterocycloalkyl, or 5 to 6 membered heterocycloalkyl), $R^{76}$-substituted or unsubstituted aryl (e.g. $C_6$-$C_{10}$ aryl or $C_6$ aryl), or $R^{76}$-substituted or unsubstituted heteroaryl (e.g. 5 to 10 membered heteroaryl, 5 to 9 membered heteroaryl, or 5 to 6 membered heteroaryl). $X^{75}$ is halogen. In embodiments, $X^{75}$ is F.

$R^{76}$ is independently oxo, halogen, —$CX^{76}_3$, —$CHX^{76}_2$, —$CH_2X^{76}$, —$OCH_2X^{76}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{76}_3$, —$OCHX^{76}_2$, $R^{77}$-substituted or unsubstituted alkyl (e.g. $C_1$-$C_8$ alkyl, $C_1$-$C_6$ alkyl, or $C_1$-$C_4$ alkyl), $R^{77}$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^{77}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{77}$-substituted or unsubstituted heterocycloalkyl (e.g. 3 to 8 membered heterocycloalkyl, 4 to 8 membered heterocycloalkyl, or 5 to 6 membered heterocycloalkyl), $R^{77}$-substituted or unsubstituted aryl (e.g. $C_6$-$C_{10}$ aryl or $C_6$ aryl), or $R^{77}$-substituted or unsubstituted heteroaryl (e.g. 5 to 10 membered heteroaryl, 5 to 9 membered heteroaryl, or 5 to 6 membered heteroaryl). $X^{76}$ is halogen. In embodiments, $X^{76}$ is F.

In embodiments, $R^{17}$ is independently hydrogen, oxo, halogen, —$CX^{17}_3$, —$CHX^{17}_2$, —$CH_2X^{17}$, —$OCH_2X^{17}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{17}_3$, —$OCHX^{17}_2$, $R^{78}$-substituted or unsubstituted alkyl (e.g. $C_1$-$C_8$ alkyl, $C_1$-$C_6$ alkyl, or $C_1$-$C_4$ alkyl), $R^{78}$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^{78}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{78}$-substituted or unsubstituted heterocycloalkyl (e.g. 3 to 8 membered heterocycloalkyl, 4 to 8 membered heterocycloalkyl, or 5 to 6 membered heterocycloalkyl), $R^{78}$-substituted or unsubstituted aryl (e.g. $C_6$-$C_{10}$ aryl or $C_6$ aryl), or $R^{78}$-substituted or unsubstituted heteroaryl (e.g. 5 to 10 membered heteroaryl, 5 to 9 membered heteroaryl, or 5 to 6 membered heteroaryl). $X^{17}$ is halogen. In embodiments, $X^{17}$ is F. In embodiments, $R^{17}$ is hydrogen. In embodiments, $R^{17}$ is independently hydrogen, halogen, —$CX^{17}_3$, —$CHX^{17}_2$, —$CH_2X^{17}$, —CN, —COOH, —$CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^{78}$ is independently oxo, halogen, —$CX^{78}_3$, —$CHX^{78}_2$, —$CH_2X^{78}$, —$OCH_2X^{78}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{78}_3$, —$OCHX^{78}_2$, $R^{79}$-substituted or unsubstituted alkyl (e.g. $C_1$-$C_8$ alkyl, $C_1$-$C_6$ alkyl, or $C_1$-$C_4$ alkyl), $R^{79}$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^{79}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{79}$-substituted or unsubstituted heterocycloalkyl (e.g. 3 to 8 membered heterocycloalkyl, 4 to 8 membered heterocycloalkyl, or 5 to 6 membered heterocycloalkyl), $R^{79}$-substituted or unsubstituted aryl (e.g. $C_6$-$C_{10}$ aryl or $C_6$ aryl), or $R^{79}$-substituted or unsubstituted heteroaryl (e.g. 5 to 10 membered heteroaryl, 5 to 9 membered heteroaryl, or 5 to 6 membered heteroaryl). $X^{78}$ is halogen. In embodiments, $X^{78}$ is F.

$R^{79}$ is independently oxo, halogen, $-CX^{79}_3$, $-CHX^{79}_2$, $-CH_2X^{79}$, $-OCH_2X^{79}$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{79}_3$, $-OCHX^{79}_2$, $R^{80}$-substituted or unsubstituted alkyl (e.g. $C_1$-$C_8$ alkyl, $C_1$-$C_6$ alkyl, or $C_1$-$C_4$ alkyl), $R^{80}$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^{80}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{80}$-substituted or unsubstituted heterocycloalkyl (e.g. 3 to 8 membered heterocycloalkyl, 4 to 8 membered heterocycloalkyl, or 5 to 6 membered heterocycloalkyl), $R^{80}$-substituted or unsubstituted aryl (e.g. $C_6$-$C_{10}$ aryl or $C_6$ aryl), or $R^{80}$-substituted or unsubstituted heteroaryl (e.g. 5 to 10 membered heteroaryl, 5 to 9 membered heteroaryl, or 5 to 6 membered heteroaryl). $X^{79}$ is halogen. In embodiments, $X^{79}$ is F.

In embodiments, $R^{18}$ is independently hydrogen, oxo, halogen, $-CX^{83}$, $-CHX^{18}_2$, $-CH_2X^{18}$, $-OCH_2X^{18}$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{83}$, $-OCHX^{18}_2$, $R^{81}$-substituted or unsubstituted alkyl (e.g. $C_1$-$C_5$ alkyl, $C_1$-$C_6$ alkyl, or $C_1$-$C_4$ alkyl), $R^{81}$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^{81}$-substituted or unsubstituted cycloalkyl (e.g. $C_3$-$C_5$ cycloalkyl, $C_4$-$C_5$ cycloalkyl, or $C_5$-$C_6$ cycloalkyl), $R^8$-substituted or unsubstituted heterocycloalkyl (e.g. 3 to 8 membered heterocycloalkyl, 4 to 8 membered heterocycloalkyl, or 5 to 6 membered heterocycloalkyl), $R^8$-substituted or unsubstituted aryl (e.g. $C_6$-$C_{10}$ aryl or $C_6$ aryl), or $R^{81}$-substituted or unsubstituted heteroaryl (e.g. 5 to 10 membered heteroaryl, 5 to 9 membered heteroaryl, or 5 to 6 membered heteroaryl). $X^{18}$ is halogen. In embodiments, $X^{18}$ is F. In embodiments, $R^{18}$ is hydrogen. In embodiments, $R^{18}$ is independently hydrogen, halogen, $-CX^{18}_3$, $-CHX^{18}_2$, $-CH_2X^{18}$, $-CN$, $-COOH$, $-CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^{81}$ is independently oxo, halogen, $-CX^{81}_3$, $-CHX^{81}_2$, $-CH_2X^{81}$, $-OCH_2X^{81}$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{81}_3$, $-OCHX^{81}_2$, $R^{82}$-substituted or unsubstituted alkyl (e.g. $C_1$-$C_5$ alkyl, $C_1$-$C_6$ alkyl, or $C_1$-$C_4$ alkyl), $R^{82}$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^{82}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{82}$-substituted or unsubstituted heterocycloalkyl (e.g. 3 to 8 membered heterocycloalkyl, 4 to 8 membered heterocycloalkyl, or 5 to 6 membered heterocycloalkyl), $R^{82}$-substituted or unsubstituted aryl (e.g. $C_6$-$C_{10}$ aryl or $C_6$ aryl), or $R^{82}$-substituted or unsubstituted heteroaryl (e.g. 5 to 10 membered heteroaryl, 5 to 9 membered heteroaryl, or 5 to 6 membered heteroaryl). $X^{81}$ is halogen. In embodiments, $X^{81}$ is F.

$R^{82}$ is independently oxo, halogen, $-CX^{82}_3$, $-CHX^{82}_2$, $-CH_2X^{82}$, $-OCH_2X^{82}$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{82}_3$, $-OCHX^{82}_2$, $R^{83}$-substituted or unsubstituted alkyl (e.g. $C_1$-$C_8$ alkyl, $C_1$-$C_6$ alkyl, or $C_1$-$C_4$ alkyl), $R^{83}$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^{83}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{83}$-substituted or unsubstituted heterocycloalkyl (e.g. 3 to 8 membered heterocycloalkyl, 4 to 8 membered heterocycloalkyl, or 5 to 6 membered heterocycloalkyl), $R^{83}$-substituted or unsubstituted aryl (e.g. $C_6$-$C_{10}$ aryl or $C_6$ aryl), or $R^{83}$-substituted or unsubstituted heteroaryl (e.g. 5 to 10 membered heteroaryl, 5 to 9 membered heteroaryl, or 5 to 6 membered heteroaryl). $X^{82}$ is halogen. In embodiments, $X^{82}$ is F.

$R^{32}$, $R^{35}$, $R^{38}$, $R^{41}$, $R^{44}$, $R^{50}$, $R^{53}$, $R^{56}$, $R^{59}$, $R^{62}$, $R^{65}$, $R^{68}$, $R^{71}$, $R^{74}$, $R^{77}$, $R^{80}$, and $R^{83}$ are independently hydrogen, oxo, halogen, $-CF_3$, $-CHF_2$, $-CH_2F$, $-OCH_2F$, $-OCF_3$, $-OCHF_2$, $-CCl_3$, $-CHCl_2$, $-CH_2Cl$, $-OCH_2Cl$, $-O\:CCl_3$, $-OCHCl_2$, $-CBr_3$, $-CHBr_2$, $-CH_2Br$, $-OCH_2Br$, $-OCBr_3$, $-OCHBr_2$, $-CI_3$, $-CHI_2$, $-CH_2I$, $-OCH_2I$, $-OCI_3$, $-OCHI_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, unsubstituted alkyl (e.g. $C_1$-$C_8$ alkyl, $C_1$-$C_6$ alkyl, or $C_1$-$C_4$ alkyl), unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_8$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl or $C_6$ aryl), or unsubstituted heteroaryl (e.g. 5 to 10 membered heteroaryl, 5 to 9 membered heteroaryl, or 5 to 6 membered heteroaryl). In embodiments, $R^{32}$, $R^{35}$, $R^{38}$, $R^{41}$, $R^{44}$, $R^{50}$, $R^{53}$, $R^{56}$, $R^{59}$, $R^{62}$, $R^{65}$, $R^{68}$, $R^{71}$, $R^{74}$, $R^{77}$, $R^{80}$, and $R^{83}$ are independently oxo, halogen, $-CF_3$, $-CHF_2$, $-CH_2F$, $-OCH_2F$, $-OCF_3$, $-OCHF_2$, $-CCl_3$, $-CHCl_2$, $-CH_2Cl$, $-OCH_2Cl$, $-O\:CCl_3$, $-OCHCl_2$, $-CBr_3$, $-CHBr_2$, $-CH_2Br$, $-OCH_2Br$, $-OCBr_3$, $-OCHBr_2$, $-CI_3$, $-CHI_2$, $-CH_2I$, $-OCH_2I$, $-OCI_3$, $-OCHI_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, unsubstituted alkyl (e.g. $C_1$-$C_8$ alkyl, $C_1$-$C_6$ alkyl, or $C_1$-$C_4$ alkyl), unsubstituted heteroalkyl (e.g. 2 to 10 membered heteroalkyl, 2 to 8 membered heteroalkyl, 4 to 8 membered heteroalkyl, or 2 to 4 membered heteroalkyl), unsubstituted cycloalkyl (e.g. $C_3$-$C_8$ cycloalkyl, $C_4$-$C_8$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl or $C_6$ aryl), or unsubstituted heteroaryl (e.g. 5 to 10 membered heteroaryl, 5 to 9 membered heteroaryl, or 5 to 6 membered heteroaryl).

In some embodiments, the compound is any one of the compounds described herein (e.g., in an aspect, embodiment, claim, figure, table, or example).

In some embodiments, a compound as described herein may include multiple instances of $R^1$, $R^4$, $R^5$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, and/or other variables. In such embodiments, each variable may optional be different and be appropriately labeled to distinguish each group for greater clarity. For example, where each $R^1$, $R^4$, $R^5$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, and/or $R^{19}$ is different, they may be referred to, for example, as $R^{1.1}$, $R^{1.2}$, $R^{1.3}$, $R^{1.4}$, $R^{1.5}$, $R^{4.1}$, $R^{4.2}$, $R^{4.3}$, $R^{4.4}$, $R^{4.5}$, $R^{5.1}$, $R^{5.2}$, $R^{5.3}$, $R^{5.4}$, $R^{5.5}$, $R^{5.6}$, $R^{5.7}$, $R^{7.1}$, $R^{7.2}$, $R^{7.3}$, $R^{7.4}$, $R^{7.5}$, $R^{7.6}$, $R^{7.7}$, $R^{7.8}$, $R^{7.9}$, $R^{7.10}$, $R^{7.11}$, $R^{7.12}$, $R^{7.13}$, $R^{7.14}$, $R^{7.15}$, $R^{7.16}$, $R^{7.17}$, $R^{7.18}$, $R^{7.19}$, $R^{7.20}$, $R^{7.21}$, $R^{7.22}$, $R^{7.23}$, $R^{7.24}$, $R^{7.25}$, $R^{7.26}$, $R^{7.27}$, $R^{7.28}$, $R^{7.29}$, $R^{7.30}$, $R^{7.31}$, $R^{7.32}$, $R^{7.33}$, $R^{7.34}$, $R^{7.35}$, $R^{7.36}$, $R^{7.37}$, $R^{7.38}$, $R^{7.39}$, $R^{7.40}$, $R^{7.41}$, $R^{7.42}$, $R^{8.1}$, $R^{8.2}$, $R^{83}$, $R^{84}$, $R^{85}$, $R^{8.6}$, $R^{87}$, $R^{88}$, $R^{8.9}$, $R^{8.10}$, $R^{8.11}$, $R^{8.12}$, $R^{8.13}$, $R^{8.14}$, $R^{8.15}$, $R^{8.16}$, $R^{8.17}$, $R^{8.18}$, $R^{8.19}$, $R^{8.20}$, $R^{8.21}$, $R^{8.22}$, $R^{8.23}$, $R^{8.24}$, $R^{8.25}$, $R^{8.26}$, $R^{8.27}$, $R^{8.28}$, $R^{8.29}$, $R^{8.30}$, $R^{8.31}$, $R^{8.32}$, $R^{8.33}$, $R^{8.34}$, $R^{8.35}$, $R^{8.36}$, $R^{8.37}$, $R^{8.38}$, $R^{8.39}$, $R^{8.40}$, $R^{8.41}$, $R^{8.42}$, $R^{9.1}$, $R^{9.2}$, $R^{9.3}$, $R^{9.4}$, $R^{9.5}$, $R^{9.6}$, $R^{9.7}$, $R^{9.8}$, $R^{9.9}$, $R^{9.10}$, $R^{9.11}$, $R^{9.12}$, $R^{9.13}$, $R^{9.14}$, $R^{9.15}$, $R^{9.16}$, $R^{9.17}$, $R^{9.18}$, $R^{9.19}$, $R^{9.20}$, $R^{9.21}$, $R^{9.22}$, $R^{9.23}$, $R^{9.24}$, $R^{9.25}$, $R^{9.26}$, $R^{9.27}$, $R^{9.28}$, $R^{9.29}$, $R^{9.30}$, $R^{9.31}$, $R^{9.32}$, $R^{9.33}$, $R^{9.34}$, $R^{9.35}$, $R^{9.36}$, $R^{9.37}$, $R^{9.38}$, $R^{9.39}$, $R^{9.40}$, $R^{9.41}$, $R^{9.42}$, $R^{10.1}$, $R^{10.2}$, $R^{10.3}$, $R^{10.4}$, $R^{10.5}$, $R^{10.6}$, $R^{10.7}$, $R^{10.8}$, $R^{10.9}$, $R^{10.10}$, $R^{10.11}$, $R^{10.12}$, $R^{10.13}$, $R^{10.14}$, $R^{10.15}$, $R^{10.16}$, $R^{10.17}$, $R^{10.18}$, $R^{10.19}$, $R^{10.20}$, $R^{10.21}$, $R^{10.22}$, $R^{10.23}$, $R^{10.24}$, $R^{10.25}$, $R^{10.26}$, $R^{10.27}$, $R^{10.28}$, $R^{10.29}$, $R^{10.30}$, $R^{10.31}$, $R^{10.32}$, $R^{10.33}$, $R^{10.34}$, $R^{10.35}$, $R^{10.36}$, $R^{10.37}$, $R^{10.38}$, $R^{10.39}$, $R^{10.40}$, $R^{10.41}$, $R^{10.42}$, $R^{11.1}$, $R^{11.2}$, $R^{11.3}$, $R^{11.4}$, $R^{11.5}$, $R^{11.6}$, $R^{11.7}$, $R^{11.8}$, $R^{11.9}$, $R^{11.10}$, $R^{11.11}$, $R^{11.12}$, $R^{11.13}$, $R^{11.14}$, $R^{11.15}$, $R^{11.16}$, $R^{11.17}$, $R^{11.18}$, $R^{11.19}$, $R^{11.20}$, $R^{11.21}$, $R^{11.22}$, $R^{11.23}$, $R^{11.24}$, $R^{11.25}$, $R^{11.26}$, $R^{11.27}$, $R^{11.28}$, $R^{11.29}$, $R^{11.30}$, $R^{11.31}$, $R^{11.32}$, $R^{11.33}$, $R^{11.34}$, $R^{11.35}$, $R^{11.36}$, $R^{11.37}$, $R^{11.38}$, $R^{11.39}$, $R^{11.40}$, $R^{11.41}$, $R^{11.42}$, $R^{12.1}$, $R^{12.2}$, $R^{12.3}$, $R^{12.4}$, $R^{12.5}$, $R^{12.6}$, $R^{12.7}$, $R^{12.8}$, $R^{12.9}$, $R^{12.10}$, $R^{12.11}$, $R^{12.12}$, $R^{12.13}$, $R^{12.14}$, $R^{12.15}$, $R^{12.16}$, $R^{12.17}$, $R^{12.18}$, $R^{12.19}$, $R^{12.20}$, $R^{12.21}$, $R^{12.22}$, $R^{12.23}$, $R^{12.24}$, $R^{12.25}$, $R^{12.26}$, $R^{12.27}$, $R^{12.28}$, $R^{12.29}$, $R^{12.30}$, $R^{12.31}$, $R^{12.32}$, $R^{12.33}$, $R^{12.34}$, $R^{12.35}$, $R^{12.36}$, $R^{12.37}$, $R^{12.38}$, $R^{12.39}$, $R^{12.40}$, $R^{12.41}$, $R^{12.42}$, $R^{13.1}$, $R^{13.2}$, $R^{13.3}$, $R^{13.4}$, $R^{13.5}$, $R^{13.6}$, $R^{13.7}$, $R^{13.8}$, $R^{13.9}$, $R^{13.10}$, $R^{13.11}$, $R^{13.12}$, $R^{13.13}$, $R^{13.14}$, $R^{13.15}$, $R^{13.16}$, $R^{13.17}$, $R^{13.18}$, $R^{13.19}$, $R^{13.20}$, $R^{13.21}$, $R^{13.22}$, $R^{13.23}$, $R^{13.24}$, $R^{13.25}$, $R^{13.26}$, $R^{13.27}$, $R^{13.28}$, $R^{13.29}$, $R^{13.30}$, $R^{13.31}$, $R^{13.32}$, $R^{13.33}$, $R^{13.34}$, $R^{13.35}$, $R^{13.36}$, $R^{13.37}$, $R^{13.38}$, $R^{13.39}$, $R^{13.40}$, $R^{13.41}$, $R^{13.42}$, $R^{14.1}$, $R^{14.2}$, $R^{14.3}$, $R^{14.4}$, $R^{14.5}$, $R^{14.6}$, $R^{14.7}$, $R^{14.8}$, $R^{14.9}$, $R^{14.10}$, $R^{14.11}$, $R^{14.12}$, $R^{14.13}$, $R^{14.14}$, $R^{14.15}$, $R^{14.16}$, $R^{14.17}$, $R^{14.18}$, $R^{14.19}$, $R^{14.20}$, $R^{14.21}$, $R^{14.22}$, $R^{14.23}$, $R^{14.24}$, $R^{14.25}$, $R^{14.26}$, $R^{14.27}$, $R^{14.28}$, $R^{14.29}$, $R^{14.30}$, $R^{14.31}$, $R^{14.32}$, $R^{14.33}$, $R^{14.34}$, $R^{14.35}$, $R^{14.36}$, $R^{14.37}$, $R^{14.38}$, $R^{14.39}$, $R^{14.40}$, $R^{14.41}$, $R^{14.42}$, $R^{15.1}$, $R^{15.2}$, $R^{15.3}$, $R^{15.4}$, $R^{15.5}$, $R^{15.6}$, $R^{15.7}$, $R^{15.8}$, $R^{15.9}$, $R^{15.10}$, $R^{15.11}$, $R^{15.12}$, $R^{15.13}$, $R^{15.14}$, $R^{15.15}$, $R^{15.16}$, $R^{15.17}$, $R^{15.18}$, $R^{15.19}$, $R^{15.20}$, $R^{15.21}$, $R^{15.22}$, $R^{15.23}$, $R^{15.24}$, $R^{15.25}$, $R^{15.26}$, $R^{15.27}$, $R^{15.28}$, $R^{15.29}$, $R^{15.30}$, $R^{15.31}$, $R^{15.32}$, $R^{15.33}$, $R^{15.34}$, $R^{15.35}$, $R^{15.36}$, $R^{15.37}$, $R^{15.38}$, $R^{15.39}$, $R^{15.40}$, $R^{15.41}$, $R^{15.42}$, $R^{16.1}$, $R^{16.2}$, $R^{16.3}$, $R^{16.4}$, $R^{16.5}$, $R^{16.6}$, $R^{16.7}$, $R^{16.8}$, $R^{16.9}$, $R^{16.10}$, $R^{16.11}$, $R^{16.12}$, $R^{16.13}$, $R^{16.14}$, $R^{16.15}$, $R^{16.16}$, $R^{16.17}$, $R^{16.18}$, $R^{16.19}$, $R^{16.20}$, $R^{16.21}$, $R^{16.22}$, $R^{16.23}$, $R^{16.24}$, $R^{16.25}$, $R^{16.26}$, $R^{16.27}$, $R^{16.28}$, $R^{16.29}$, $R^{16.30}$, $R^{16.31}$, $R^{16.32}$, $R^{16.33}$, $R^{16.34}$, $R^{16.35}$, $R^{16.36}$, $R^{16.37}$, $R^{16.38}$, $R^{16.39}$, $R^{16.40}$, $R^{16.41}$, $R^{16.42}$, $R^{17.1}$, $R^{17.2}$, $R^{17.3}$, $R^{17.4}$, $R^{17.5}$, $R^{17.6}$, $R^{17.7}$, $R^{17.8}$, $R^{17.9}$, $R^{17.10}$, $R^{17.11}$, $R^{17.12}$, $R^{17.13}$, $R^{17.14}$, $R^{17.15}$, $R^{17.16}$, $R^{17.17}$, $R^{17.18}$, $R^{17.19}$, $R^{17.20}$, $R^{17.21}$, $R^{17.22}$, $R^{17.23}$, $R^{17.24}$, $R^{17.25}$, $R^{17.26}$, $R^{17.27}$, $R^{17.28}$, $R^{17.29}$, $R^{17.30}$, $R^{17.31}$, $R^{17.32}$, $R^{17.33}$, $R^{17.34}$, $R^{17.35}$, $R^{17.36}$, $R^{17.37}$, $R^{17.38}$, $R^{17.39}$, $R^{17.40}$, $R^{17.41}$, $R^{17.42}$, $R^{18.1}$, $R^{18.2}$, $R^{18.3}$, $R^{18.4}$, $R^{18.5}$, $R^{18.6}$, $R^{18.7}$, $R^{18.8}$, $R^{18.9}$, $R^{18.10}$, $R^{18.11}$, $R^{18.12}$, $R^{18.13}$, $R^{18.14}$, $R^{18.15}$, $R^{18.16}$, $R^{18.17}$, $R^{18.18}$, $R^{18.19}$, $R^{18.20}$, $R^{18.21}$, $R^{18.22}$, $R^{18.23}$, $R^{18.24}$, $R^{18.25}$, $R^{18.26}$, $R^{18.27}$, $R^{18.28}$, $R^{18.29}$, $R^{18.30}$, $R^{18.31}$, $R^{18.32}$, $R^{18.33}$, $R^{18.34}$, $R^{18.35}$, $R^{18.36}$, $R^{18.37}$, $R^{18.38}$, $R^{18.39}$, $R^{18.40}$, $R^{18.41}$, $R^{18.42}$, respectively, wherein the definition of $R^1$ is assumed by $R^1$, $R^{1.2}$, $R^{1.3}$, $R^{1.4}$, $R^{1.5}$; $R^4$ is assumed by $R^{4.1}$, $R^{4.2}$, $R^{43}$, $R^{44}$, $R^{4.5}$; $R^5$ is assumed by $R^{5.1}$, $R^{5.2}$, $R^{5.3}$, $R^{5.4}$, $R^{5.5}$, $R^{5.6}$, $R^{5.7}$; $R^7$ is assumed by $R^{7.1}$, $R^{7.2}$, $R^{7.3}$, $R^{7.4}$, $R^{7.5}$, $R^{7.6}$, $R^{7.7}$, $R^{7.8}$, $R^{7.9}$, $R^{7.10}$, $R^{7.11}$, $R^{7.12}$, $R^{7.13}$, $R^{7.14}$, $R^{7.15}$, $R^{7.16}$, $R^{7.17}$, $R^{7.18}$, $R^{7.19}$, $R^{7.20}$, $R^{7.21}$, $R^{7.22}$, $R^{7.23}$, $R^{7.24}$, $R^{7.25}$, $R^{7.26}$, $R^{7.27}$, $R^{7.28}$, $R^{7.29}$, $R^{7.30}$, $R^{7.31}$, $R^{7.32}$, $R^{7.33}$, $R^{7.34}$, $R^{7.35}$, $R^{7.36}$, $R^{7.37}$, $R^{7.38}$, $R^{7.39}$, $R^{7.40}$, $R^{7.41}$, $R^{7.42}$; $R^8$ is assumed by $R^{8.1}$, $R^{8.2}$, $R^{83}$, $R^{8.4}$, $R^{8.5}$, $R^{8.6}$, $R^{8.7}$, $R^{8.8}$, $R^{8.9}$, $R^{8.10}$, $R^{8.11}$, $R^{8.12}$, $R^{8.13}$, $R^{8.14}$, $R^{8.15}$, $R^{8.16}$, $R^{8.17}$, $R^{8.18}$, $R^{8.19}$, $R^{8.20}$, $R^{8.21}$, $R^{8.22}$, $R^{8.23}$, $R^{8.24}$, $R^{8.25}$, $R^{8.26}$, $R^{8.27}$, $R^{8.28}$, $R^{8.29}$, $R^{8.30}$, $R^{8.31}$, $R^{8.32}$, $R^{8.33}$, $R^{8.34}$, $R^{8.35}$, $R^{8.36}$, $R^{8.37}$, $R^{8.38}$, $R^{8.39}$, $R^{8.40}$, $R^{8.41}$, $R^{8.42}$; $R^9$ is assumed by $R^{9.1}$, $R^{9.2}$, $R^{9.3}$, $R^{9.4}$, $R^{9.5}$, $R^{9.6}$, $R^{9.7}$, $R^{9.8}$, $R^{9.9}$, $R^{9.10}$, $R^{9.11}$, $R^{9.12}$, $R^{9.13}$, $R^{9.14}$, $R^{9.15}$, $R^{9.16}$, $R^{9.17}$, $R^{9.18}$, $R^{9.19}$, $R^{9.20}$, $R^{9.21}$, $R^{9.22}$, $R^{9.23}$, $R^{9.24}$, $R^{9.25}$, $R^{9.26}$, $R^{9.27}$, $R^{9.28}$, $R^{9.29}$, $R^{9.30}$, $R^{9.31}$, $R^{9.32}$, $R^{9.33}$, $R^{9.34}$, $R^{9.35}$, $R^{9.36}$, $R^{9.37}$, $R^{9.38}$, $R^{9.39}$, $R^{9.40}$, $R^{9.41}$, $R^{9.42}$; $R^{10}$ is assumed by $R^{1.1}$, $R^{10.2}$, $R^{10.3}$, $R^{10.4}$, $R^{10.5}$, $R^{10.6}$, $R^{10.7}$, $R^{10.8}$, $R^{10.9}$, $R^{10.10}$, $R^{10.11}$, $R^{10.12}$, $R^{10.13}$, $R^{10.14}$, $R^{10.15}$, $R^{10.16}$, $R^{10.17}$, $R^{10.18}$, $R^{10.19}$, $R^{10.20}$, $R^{10.21}$, $R^{10.22}$, $R^{10.23}$, $R^{10.24}$, $R^{10.25}$, $R^{10.26}$, $R^{10.27}$, $R^{10.28}$, $R^{10.29}$, $R^{10.30}$, $R^{10.31}$, $R^{10.32}$, $R^{10.33}$, $R^{10.34}$, $R^{10.35}$, $R^{10.36}$, $R^{10.37}$, $R^{10.38}$, $R^{10.39}$, $R^{10.40}$, $R^{10.41}$, $R^{10.42}$; $R^{11}$ is assumed by $R^{11.1}$, $R^{11.2}$, $R^{11.3}$, $R^{11.4}$, $R^{11.5}$, $R^{11.6}$, $R^{11.7}$, $R^{11.8}$, $R^{11.9}$, $R^{11.10}$, $R^{11.11}$, $R^{11.12}$, $R^{11.13}$, $R^{11.14}$, $R^{11.15}$, $R^{11.16}$, $R^{11.17}$, $R^{11.18}$, $R^{11.19}$, $R^{11.20}$, $R^{11.21}$, $R^{11.22}$, $R^{11.23}$, $R^{11.24}$, $R^{11.25}$, $R^{11.26}$, $R^{11.27}$, $R^{11.28}$, $R^{11.29}$, $R^{11.30}$, $R^{11.31}$, $R^{11.32}$, $R^{11.33}$, $R^{11.34}$, $R^{11.35}$, $R^{11.36}$, $R^{11.37}$, $R^{11.38}$, $R^{11.39}$, $R^{11.40}$, $R^{11.41}$, $R^{11.42}$; $R^{12}$ assumed by $R^{12.1}$, $R^{12.2}$, $R^{12.3}$, $R^{12.4}$, $R^{12.5}$, $R^{12.6}$, $R^{12.7}$, $R^{12.8}$, $R^{12.9}$, $R^{12.10}$, $R^{12.11}$, $R^{12.12}$, $R^{12.13}$, $R^{12.14}$, $R^{12.15}$, $R^{12.16}$, $R^{12.17}$, $R^{12.18}$, $R^{12.19}$, $R^{12.20}$, $R^{12.21}$, $R^{12.22}$, $R^{12.23}$, $R^{12.24}$, $R^{12.25}$, $R^{12.26}$, $R^{12.27}$, $R^{12.28}$, $R^{12.29}$, $R^{12.30}$, $R^{12.31}$, $R^{12.32}$, $R^{12.33}$, $R^{12.34}$, $R^{12.35}$, $R^{12.36}$, $R^{12.37}$, $R^{12.38}$, $R^{12.39}$, $R^{12.40}$, $R^{12.41}$, $R^{12.42}$; $R^{13}$ is assumed by $R^{13.1}$, $R^{13.2}$, $R^{13.3}$, $R^{13.4}$, $R^{13.5}$, $R^{13.6}$, $R^{13.7}$, $R^{13.8}$, $R^{13.9}$, $R^{13.10}$, $R^{13.11}$, $R^{13.12}$, $R^{13.13}$, $R^{13.14}$, $R^{13.15}$, $R^{13.16}$, $R^{13.17}$, $R^{13.18}$, $R^{13.19}$, $R^{13.20}$, $R^{13.21}$, $R^{13.22}$, $R^{13.23}$, $R^{13.24}$, $R^{13.25}$, $R^{13.26}$, $R^{13.27}$, $R^{13.28}$, $R^{13.29}$, $R^{13.30}$, $R^{13.31}$, $R^{13.32}$, $R^{13.33}$, $R^{13.34}$, $R^{13.35}$, $R^{13.36}$, $R^{13.37}$, $R^{13.38}$, $R^{13.39}$, $R^{13.40}$, $R^{13.41}$, $R^{13.42}$; $R^{14}$ is assumed by $R^{14.1}$, $R^{14.2}$, $R^{14.3}$, $R^{14.4}$, $R^{14.5}$, $R^{14.6}$, $R^{14.7}$, $R^{14.8}$, $R^{14.9}$, $R^{14.10}$, $R^{14.11}$, $R^{14.12}$, $R^{14.13}$, $R^{14.14}$, $R^{14.15}$, $R^{14.16}$, $R^{14.17}$, $R^{14.18}$, $R^{14.19}$, $R^{14.20}$, $R^{14.21}$, $R^{14.22}$, $R^{14.23}$, $R^{14.24}$, $R^{14.25}$, $R^{14.26}$, $R^{14.27}$, $R^{14.28}$, $R^{14.29}$, $R^{14.30}$, $R^{14.31}$, $R^{14.32}$, $R^{14.33}$, $R^{14.34}$, $R^{14.35}$, $R^{14.36}$, $R^{14.37}$, $R^{14.38}$, $R^{14.39}$, $R^{14.40}$, $R^{14.41}$, $R^{14.42}$; $R^{15}$ is assumed by $R^{15.1}$, $R^{15.2}$, $R^{15.3}$, $R^{15.4}$, $R^{15.5}$, $R^{15.6}$, $R^{15.7}$, $R^{15.8}$, $R^{15.9}$, $R^{15.10}$, $R^{15.11}$, $R^{15.12}$, $R^{15.13}$, $R^{15.14}$, $R^{15.15}$, $R^{15.16}$, $R^{15.17}$, $R^{15.18}$, $R^{15.19}$, $R^{15.20}$, $R^{15.21}$, $R^{15.22}$, $R^{15.23}$, $R^{15.24}$, $R^{15.25}$, $R^{15.26}$, $R^{15.27}$, $R^{15.28}$, $R^{15.29}$, $R^{15.30}$, $R^{15.31}$, $R^{15.32}$, $R^{15.33}$, $R^{15.34}$, $R^{15.35}$, $R^{15.36}$, $R^{15.37}$, $R^{15.38}$, $R^{15.39}$, $R^{15.40}$, $R^{15.41}$, $R^{15.42}$; $R^{16}$ is assumed by $R^{16.1}$, $R^{16.2}$, $R^{16.3}$, $R^{16.4}$, $R^{16.5}$, $R^{16.6}$, $R^{16.7}$, $R^{16.8}$, $R^{16.9}$, $R^{16.10}$, $R^{16.11}$, $R^{16.12}$, $R^{16.13}$, $R^{16.14}$, $R^{16.15}$, $R^{16.16}$, $R^{16.17}$, $R^{16.18}$, $R^{16.19}$, $R^{16.20}$, $R^{16.21}$, $R^{16.22}$, $R^{16.23}$, $R^{16.24}$, $R^{16.25}$, $R^{16.26}$, $R^{16.27}$, $R^{16.28}$, $R^{16.29}$, $R^{16.30}$, $R^{16.31}$, $R^{16.32}$, $R^{16.33}$, $R^{16.34}$, $R^{16.35}$, $R^{16.36}$, $R^{16.37}$, $R^{16.38}$, $R^{16.39}$, $R^{16.40}$, $R^{16.41}$, $R^{16.42}$; $R^{17}$ is assumed by $R^{17.1}$, $R^{17.2}$, $R^{17.3}$, $R^{17.4}$, $R^{17.5}$, $R^{17.6}$, $R^{17.7}$, $R^{17.8}$, $R^{17.9}$, $R^{17.10}$, $R^{17.11}$, $R^{17.12}$, $R^{17.13}$, $R^{17.14}$, $R^{17.15}$, $R^{17.16}$, $R^{17.17}$, $R^{17.18}$, $R^{17.19}$, $R^{17.20}$, $R^{17.21}$, $R^{17.22}$, $R^{17.23}$, $R^{17.24}$, $R^{17.25}$, $R^{17.26}$, $R^{17.27}$, $R^{17.28}$, $R^{17.29}$, $R^{17.30}$, $R^{17.31}$, $R^{17.32}$, $R^{17.33}$, $R^{17.34}$, $R^{17.35}$, $R^{17.36}$, $R^{17.37}$, $R^{17.38}$, $R^{17.39}$, $R^{17.40}$, $R^{17.41}$, $R^{17.42}$; and/or $R^{18}$ is assumed by $R^{18.1}$, $R^{18.2}$, $R^{18.3}$, $R^{18.4}$, $R^{18.5}$, $R^{18.6}$, $R^{18.7}$, $R^{18.8}$, $R^{18.9}$, $R^{18.10}$, $R^{18.11}$, $R^{18.12}$, $R^{18.13}$, $R^{18.14}$, $R^{18.15}$, $R^{18.16}$, $R^{18.17}$, $R^{18.18}$, $R^{18.19}$, $R^{18.20}$, $R^{18.21}$, $R^{18.22}$, $R^{18.23}$, $R^{18.24}$, $R^{18.25}$, $R^{18.26}$, $R^{18.27}$, $R^{18.28}$, $R^{18.29}$, $R^{18.30}$, $R^{18.31}$, $R^{18.32}$, $R^{18.33}$, $R^{18.34}$, $R^{18.35}$, $R^{18.36}$, $R^{18.37}$, $R^{18.38}$, $R^{18.39}$, $R^{18.40}$, $R^{18.41}$, $R^{18.42}$. The variables used within a definition of $R^1$, $R^4$, $R^5$, $R^7$, $R^6$, $R^9$, $R^{10}$, $R^{11}$, $R^{12}$, $R^{13}$, $R^{14}$, $R^{15}$, $R^{16}$, $R^{17}$, $R^{18}$, $R^{19}$, and/or other variables that appear at multiple instances and are different may similarly be appropriately labeled to distinguish each group for greater clarity. In some embodiments, the compound is a compound described herein (e.g., in an aspect, embodiment, example, claim, table, scheme, drawing, or figure).

In embodiments, the compound has the formula:

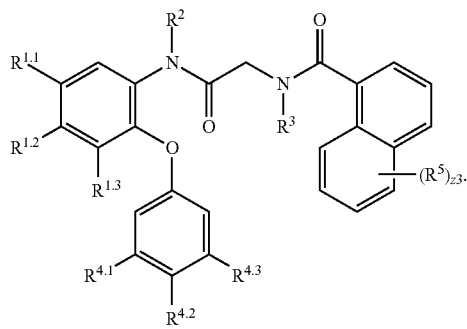

(VI)

$R^2$, $R^3$, $R^5$, and z3 are as described herein, including in compounds of formula (I) to (V). $R^{1.1}$, $R^{1.2}$, and $R^{1.3}$ are each independently a moiety of $R^1$ as described herein, including in embodiments. $R^{4.1}$, $R^{4.2}$, and $R^{4.3}$ are each independently a moiety of $R^4$ as described herein, including in embodiments. In embodiment, z3 is 0. In embodiments, one or more of $R^{1.1}$, $R^{1.2}$, $R^{1.3}$, $R^{4.1}$, $R^{4.2}$, $R^{4.3}$, $R^2$ and/or $R^3$ are hydrogen. In embodiments, $R^{1.1}$, $R^{1.2}$ and/or $R^{1.3}$ are hydrogen. In embodiments, $R^{4.1}$, $R^{4.2}$ and/or $R^{4.3}$ are hydrogen. In embodiments, $R^2$ is hydrogen. In embodiments, $R^3$ is hydrogen. In embodiments, $R^{4.1}$ is hydrogen, $R^{4.2}$ is —OH, and $R^{4.3}$ is hydrogen. In embodiments, $R^{4.1}$ is hydrogen, $R^{4.2}$ is hydrogen, and $R^{4.3}$ is —OH. In embodiments, $R^{4.1}$ is hydrogen, $R^{4.2}$ is unsubstituted methoxy, and $R^{4.3}$ is hydrogen. In embodiments, $R^{4.1}$ is hydrogen, $R^{4.2}$ is hydrogen, and $R^{4.3}$ is unsubstituted methoxy. It will be understood that $R^5$ is/are a floating substituent and may be positioned on either or both rings.

In embodiments, the compound has the formula:

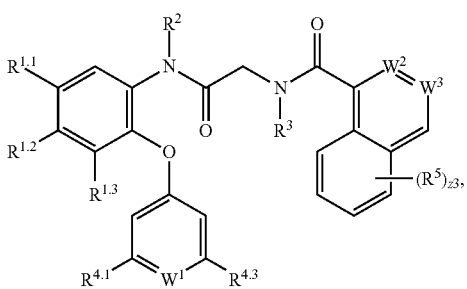

(VII)

$R^2$, $R^3$, $R^5$, and z3 are as described herein, including in compounds of formula (I) to (V). It will be understood that $R^5$ is/are a floating substituent and may be positioned on either or both rings. $R^{1.1}$, $R^{1.2}$, and $R^{1.3}$ are each independently a moiety of $R^1$ as described herein, including in embodiments. $R^{4.1}$ and $R^{4.3}$ are each independently a moiety of $R^4$ as described herein, including in embodiments.

$W^1$ is N or $C(R^{4.2})$. $W^2$ is N or $C(R^{5.1})$. $W^3$ is N or $C(R^{5.2})$. $R^{5.1}$ and $R^{5.2}$ are each independently a moiety of $R^5$ as described herein, including in embodiments. $R^{4.2}$ is independently a moiety of $R^4$ as described herein, including in embodiments. In embodiments, $W^1$ is N. In embodiments, $W^2$ is N. In embodiments, $W^3$ is N. In embodiments, $W^1$ is $C(R^{42})$. In embodiments, $W^2$ is $C(R^{51})$. In embodiments, $W^3$ is $C(R^{5.2})$. In embodiments, $W^1$ is CH. In embodiments, $W^2$ is CH. In embodiments, $W^3$ is CH.

In embodiments, the compound has the formula:

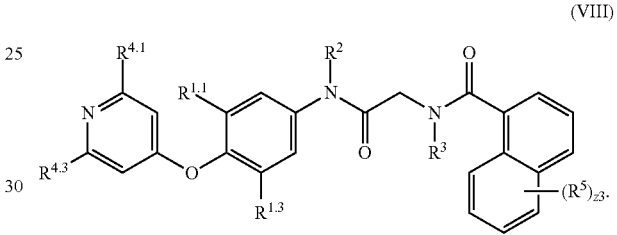

(VIII)

$R^2$, $R^3$, $R^5$, and z3 are as described herein, including in compounds of formula (I) to (V). It will be understood that $R^5$ is/are a floating substituent and may be positioned on either or both rings. $R^{1.1}$ and $R^{1.3}$ are each independently a moiety of $R^1$ as described herein, including in embodiments. $R^{4.1}$ and $R^{4.3}$ are each independently a moiety of $R^4$ as described herein, including in embodiments.

In embodiments, the compound has the formula:

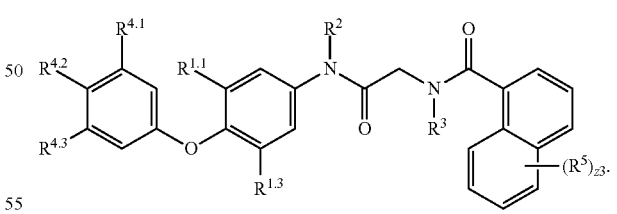

(IX)

$R^2$, $R^3$, $R^5$, and z3 are as described herein, including in compounds of formula (I) to (V). It will be understood that $R^5$ is/are a floating substituent and may be positioned on either or both rings. $R^{1.1}$ and $R^{1.3}$ are each independently a moiety of $R^1$ as described herein, including in embodiments. $R^{4.1}$, $R^{4.2}$, and $R^{4.3}$ are each independently a moiety of $R^4$ as described herein, including in embodiments.

In embodiments, the compound has the formula:

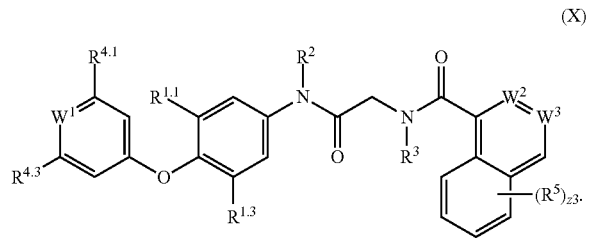

(X)

$R^2$, $R^3$, $R^5$, and z3 are as described herein, including in compounds of formula (I) to (V). It will be understood that $R^5$ is/are a floating substituent and may be positioned on either or both rings. $R^{1.1}$ and $R^{1.3}$ are each independently a moiety of $R^1$ as described herein, including in embodiments. $R^{4.1}$ and $R^{4.3}$ are each independently a moiety of $R^4$ as described herein, including in embodiments.

$W^1$ is N or $C(R^{4.2})$. $W^2$ is N or $C(R^{5.1})$. $W^3$ is N or $C(R^{5.2})$. $R^{5.1}$ and $R^{5.2}$ are each independently a moiety of $R^5$ as described herein, including in embodiments. $R^{4.2}$ is independently a moiety of $R^4$ as described herein, including in embodiments. In embodiments, $W^1$ is N. In embodiments, $W^2$ is N. In embodiments, $W^3$ is N. In embodiments, $W^1$ is $C(R^{42})$. In embodiments, $W^2$ is $C(R^{5.1})$. In embodiments, $W^3$ is $C(R^{5.2})$. In embodiments, $W^1$ is CH. In embodiments, $W^2$ is CH. In embodiments, $W^3$ is CH.

In embodiments of the compounds of formula (VI) to (X), $R^2$ is hydrogen. In embodiments of the compounds of formula (VI) to (X), $R^3$ is hydrogen. In embodiments of the compounds of formula (VI) to (X), $R^2$ and $R^3$ are hydrogen.

In embodiments, $R^{11}$ is independently halogen. In embodiments, $R^{1.1}$ is independently —$CF_3$. In embodiments, $R^{1.1}$ is independently —$CHF_2$. In embodiments, $R^{1.1}$ is independently —$CH_2F$. In embodiments, $R^{1.1}$ is independently —$OCF_3$. In embodiments, $R^{1.1}$ is independently —$OCHF_2$. In embodiments, $R^{1.1}$ is independently —$OCH_2F$. In embodiments, $R^{1.1}$ is independently —OH. In embodiments, $R^{1.1}$ is independently —$NH_2$. In embodiments, $R^{1.1}$ is independently —SH. In embodiments, $R^{1.1}$ is independently substituted or unsubstituted $C_1$-$C_4$ alkyl. In embodiments, $R^{1.1}$ is independently substituted or unsubstituted 2 to 4 membered heteroalkyl. In embodiments, $R^{1.1}$ is independently substituted or unsubstituted $C_3$-$C_6$ cycloalkyl. In embodiments, $R^{1.1}$ is independently substituted or unsubstituted 3 to 6 membered heterocycloalkyl. In embodiments, $R^{1.1}$ is independently substituted or unsubstituted phenyl. In embodiments, $R^{1.1}$ is independently substituted or unsubstituted 5 to 6 membered heteroaryl. In embodiments, $R^{1.1}$ is independently substituted $C_1$-$C_4$ alkyl. In embodiments, $R^{1.1}$ is independently substituted to 4 membered heteroalkyl. In embodiments, $R^{1.1}$ is independently substituted $C_3$-$C_6$ cycloalkyl. In embodiments, $R^{1.1}$ is independently substituted 3 to 6 membered heterocycloalkyl. In embodiments, $R^{1.1}$ is independently substituted phenyl. In embodiments, $R^{1.1}$ is independently substituted 5 to 6 membered heteroaryl. In embodiments, $R^{1.1}$ is independently unsubstituted $C_1$-$C_4$ alkyl. In embodiments, $R^{1.1}$ is independently unsubstituted 2 to 4 membered heteroalkyl. In embodiments, $R^{1.1}$ is independently unsubstituted $C_3$-$C_6$ cycloalkyl. In embodiments, $R^{1.1}$ is independently unsubstituted 3 to 6 membered heterocycloalkyl. In embodiments, $R^{1.1}$ is independently unsubstituted phenyl. In embodiments, $R^{1.1}$ is independently unsubstituted 5 to 6 membered heteroaryl. In embodiments, $R^{1.1}$ is independently unsubstituted methyl. In embodiments, $R^{11}$ is independently unsubstituted ethyl. In embodiments, $R^{11}$ is independently unsubstituted isopropyl. In embodiments, $R^{11}$ is independently unsubstituted tert-butyl. In embodiments, $R^{11}$ is independently unsubstituted methoxy. In embodiments, $R^{11}$ is independently unsubstituted ethoxy. In embodiments, $R^{11}$ is independently —F. In embodiments, $R^{11}$ is independently —Cl. In embodiments, $R^{11}$ is independently —Br. In embodiments, $R^{11}$ is independently —I. In embodiments, $R^{11}$ is independently hydrogen.

In embodiments, $R^{1.2}$ is independently halogen. In embodiments, $R^{1.2}$ is independently —$CF_3$. In embodiments, $R^{1.2}$ is independently —$CHF_2$. In embodiments, $R^{1.2}$ is independently —$CH_2F$. In embodiments, $R^{1.2}$ is independently —$OCF_3$. In embodiments, $R^{1.2}$ is independently —$OCHF_2$. In embodiments, $R^{1.2}$ is independently —$OCH_2F$. In embodiments, $R^{1.2}$ is independently —OH. In embodiments, $R^{1.2}$ is independently —$NH_2$. In embodiments, $R^{1.2}$ is independently —SH. In embodiments, $R^{1.2}$ is independently substituted or unsubstituted $C_1$-$C_4$ alkyl. In embodiments, $R^{1.2}$ is independently substituted or unsubstituted 2 to 4 membered heteroalkyl. In embodiments, $R^{1.2}$ is independently substituted or unsubstituted $C_3$-$C_6$ cycloalkyl. In embodiments, $R^{1.2}$ is independently substituted or unsubstituted 3 to 6 membered heterocycloalkyl. In embodiments, $R^{1.2}$ is independently substituted or unsubstituted phenyl. In embodiments, $R^{1.2}$ is independently substituted or unsubstituted 5 to 6 membered heteroaryl. In embodiments, $R^{1.2}$ is independently substituted $C_1$-$C_4$ alkyl. In embodiments, $R^{1.2}$ is independently substituted to 4 membered heteroalkyl. In embodiments, $R^{1.2}$ is independently substituted $C_3$-$C_6$ cycloalkyl. In embodiments, $R^{1.2}$ is independently substituted 3 to 6 membered heterocycloalkyl. In embodiments, $R^{1.2}$ is independently substituted phenyl. In embodiments, $R^{1.2}$ is independently substituted 5 to 6 membered heteroaryl. In embodiments, $R^{1.2}$ is independently unsubstituted $C_1$-$C_4$ alkyl. In embodiments, $R^{1.2}$ is independently unsubstituted 2 to 4 membered heteroalkyl. In embodiments, $R^{1.2}$ is independently unsubstituted $C_3$-$C_6$ cycloalkyl. In embodiments, $R^{1.2}$ is independently unsubstituted 3 to 6 membered heterocycloalkyl. In embodiments, $R^{1.2}$ is independently unsubstituted phenyl. In embodiments, $R^{1.2}$ is independently unsubstituted 5 to 6 membered heteroaryl. In embodiments, $R^{1.2}$ is independently unsubstituted methyl. In embodiments, $R^{1.2}$ is independently unsubstituted ethyl. In embodiments, $R^{1.2}$ is independently unsubstituted isopropyl. In embodiments, $R^{1.2}$ is independently unsubstituted tert-butyl. In embodiments, $R^{1.2}$ is independently unsubstituted methoxy. In embodiments, $R^{1.2}$ is independently unsubstituted ethoxy. In embodiments, $R^{1.2}$ is independently —F. In embodiments, $R^{1.2}$ is independently —Cl. In embodiments, $R^{1.2}$ is independently —Br. In embodiments, $R^{1.2}$ is independently —I. In embodiments, $R^{1.2}$ is independently hydrogen.

In embodiments, $R^{1.3}$ is independently halogen. In embodiments, $R^{1.3}$ is independently —$CF_3$. In embodiments, $R^{13}$ is independently —$CHF_2$. In embodiments, $R^{1.3}$ is independently —$CH_2F$. In embodiments, $R^{1.3}$ is independently —$OCF_3$. In embodiments, $R^{1.3}$ is independently —$OCHF_2$. In embodiments, $R^{1.3}$ is independently —$OCH_2F$. In embodiments, $R^{1.3}$ is independently —OH. In embodiments, $R^{1.3}$ is independently —$NH_2$. In embodiments, $R^{1.3}$ is independently —SH. In embodiments, $R^{1.3}$ is independently substituted or unsubstituted $C_1$-$C_4$ alkyl. In embodiments, $R^{1.3}$ is independently substituted or unsubstituted 2 to 4 membered heteroalkyl. In embodiments, $R^{1.3}$ is independently substituted or unsubstituted $C_3$-$C_6$ cycloalkyl.

In embodiments, $R^{1.3}$ is independently substituted or unsubstituted 3 to 6 membered heterocycloalkyl. In embodiments, $R^{1.3}$ is independently substituted or unsubstituted phenyl. In embodiments, $R^{1.3}$ is independently substituted or unsubstituted 5 to 6 membered heteroaryl. In embodiments, $R^{1.3}$ is independently substituted $C_1$-$C_4$ alkyl. In embodiments, $R^{1.3}$ is independently substituted to 4 membered heteroalkyl. In embodiments, $R^{1.3}$ is independently substituted $C_3$-$C_6$ cycloalkyl. In embodiments, $R^{1.3}$ is independently substituted 3 to 6 membered heterocycloalkyl. In embodiments, $R^{1.3}$ is independently substituted phenyl. In embodiments, $R^{1.3}$ is independently substituted 5 to 6 membered heteroaryl. In embodiments, $R^{1.3}$ is independently unsubstituted $C_1$-$C_4$ alkyl. In embodiments, $R^{1.3}$ is independently unsubstituted 2 to 4 membered heteroalkyl. In embodiments, $R^{1.3}$ is independently unsubstituted $C_3$-$C_6$ cycloalkyl. In embodiments, $R^{1.3}$ is independently unsubstituted 3 to 6 membered heterocycloalkyl. In embodiments, $R^{1.3}$ is independently unsubstituted phenyl. In embodiments, $R^{1.3}$ is independently unsubstituted 5 to 6 membered heteroaryl. In embodiments, $R^{1.3}$ is independently unsubstituted methyl. In embodiments, $R^{1.3}$ is independently unsubstituted ethyl. In embodiments, $R^{1.3}$ is independently unsubstituted isopropyl. In embodiments, $R^{1.3}$ is independently unsubstituted tert-butyl. In embodiments, $R^{1.3}$ is independently unsubstituted methoxy. In embodiments, $R^{1.3}$ is independently unsubstituted ethoxy. In embodiments, $R^{1.3}$ is independently —F. In embodiments, $R^{1.3}$ is independently —Cl. In embodiments, $R^{1.3}$ is independently —Br. In embodiments, $R^{1.3}$ is independently —I. In embodiments, $R^{1.3}$ is independently hydrogen.

In embodiments, $R^{1.4}$ is independently halogen. In embodiments, $R^{1.4}$ is independently —$CF_3$. In embodiments, $R^{1.4}$ is independently —$CHF_2$. In embodiments, $R^{1.4}$ is independently —$CH_2F$. In embodiments, $R^{1.4}$ is independently —$OCF_3$. In embodiments, $R^{1.4}$ is independently —$OCHF_2$. In embodiments, $R^{1.4}$ is independently —$OCH_2F$. In embodiments, $R^{1.4}$ is independently —OH. In embodiments, $R^{1.4}$ is independently —$NH_2$. In embodiments, $R^{1.4}$ is independently —SH. In embodiments, $R^{1.4}$ is independently substituted or unsubstituted $C_1$-$C_4$ alkyl. In embodiments, $R^{1.4}$ is independently substituted or unsubstituted 2 to 4 membered heteroalkyl. In embodiments, $R^{1.4}$ is independently substituted or unsubstituted $C_3$-$C_6$ cycloalkyl. In embodiments, $R^{1.4}$ is independently substituted or unsubstituted 3 to 6 membered heterocycloalkyl. In embodiments, $R^{1.4}$ is independently substituted or unsubstituted phenyl. In embodiments, $R^{1.4}$ is independently substituted or unsubstituted 5 to 6 membered heteroaryl. In embodiments, $R^{1.4}$ is independently substituted $C_1$-$C_4$ alkyl. In embodiments, $R^{1.4}$ is independently substituted to 4 membered heteroalkyl. In embodiments, $R^{1.4}$ is independently substituted $C_3$-$C_6$ cycloalkyl. In embodiments, $R^{1.4}$ is independently substituted 3 to 6 membered heterocycloalkyl. In embodiments, $R^{1.4}$ is independently substituted phenyl. In embodiments, $R^{1.4}$ is independently substituted 5 to 6 membered heteroaryl. In embodiments, $R^{1.4}$ is independently unsubstituted $C_1$-$C_4$ alkyl. In embodiments, $R^{1.4}$ is independently unsubstituted 2 to 4 membered heteroalkyl. In embodiments, $R^{1.4}$ is independently unsubstituted $C_3$-$C_6$ cycloalkyl. In embodiments, $R^{1.4}$ is independently unsubstituted 3 to 6 membered heterocycloalkyl. In embodiments, $R^{1.4}$ is independently unsubstituted phenyl. In embodiments, $R^{1.4}$ is independently unsubstituted 5 to 6 membered heteroaryl. In embodiments, $R^{1.4}$ is independently unsubstituted methyl. In embodiments, $R^{1.4}$ is independently unsubstituted ethyl. In embodiments, $R^{1.4}$ is independently unsubstituted isopropyl. In embodiments, $R^{1.4}$ is independently unsubstituted tert-butyl. In embodiments, $R^{1.4}$ is independently unsubstituted methoxy. In embodiments, $R^{1.4}$ is independently unsubstituted ethoxy. In embodiments, $R^{1.4}$ is independently —F. In embodiments, $R^{1.4}$ is independently —Cl. In embodiments, $R^{1.4}$ is independently —Br. In embodiments, $R^{1.4}$ is independently —I. In embodiments, $R^{1.4}$ is independently hydrogen.

In embodiments, $R^{4.1}$ is independently halogen, —$CF_3$, —OH, —$NH_2$, —SH, substituted or unsubstituted $C_1$-$C_4$ alkyl, substituted or unsubstituted 2 to 4 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl. In embodiments, $R^{4.1}$ is independently halogen, —OH, —$NH_2$, —SH, unsubstituted $C_1$-$C_4$ alkyl, or unsubstituted 2 to 4 membered heteroalkyl. In embodiments, $R^{4.1}$ is independently halogen, —OH, unsubstituted methyl, or unsubstituted methoxy. In embodiments, $R^{4.1}$ is independently halogen. In embodiments, $R^{4.1}$ is independently —OH. In embodiments, $R^{4.1}$ is independently unsubstituted methyl. In embodiments, $R^{4.1}$ is independently unsubstituted methoxy. In embodiments, $R^{4.1}$ is independently unsubstituted ethyl. In embodiments, $R^{4.1}$ is independently —F. In embodiments, $R^{4.1}$ is independently —Cl. In embodiments, $R^{4.1}$ is independently —Br. In embodiments, $R^{4.1}$ is independently —I. In embodiments, $R^{4.1}$ is independently —$CF_3$. In embodiments, $R^{4.1}$ is independently —$NH_2$. In embodiments, $R^{4.1}$ is independently —SH. In embodiments, $R^{4.1}$ is independently hydrogen. In embodiments, $R^{4.1}$ is independently unsubstituted isopropyl. In embodiments, $R^{4.1}$ is independently unsubstituted ethoxy. In embodiments, $R^{4.1}$ is independently unsubstituted tert-butyl. In embodiments, $R^{4.1}$ is independently unsubstituted propoxy.

In embodiments, $R^{4.2}$ is independently halogen, —$CF_3$, —OH, —$NH_2$, —SH, substituted or unsubstituted $C_1$-$C_4$ alkyl, substituted or unsubstituted 2 to 4 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl. In embodiments, $R^{4.2}$ is independently halogen, —OH, —$NH_2$, —SH, unsubstituted $C_1$-$C_4$ alkyl, or unsubstituted 2 to 4 membered heteroalkyl. In embodiments, $R^{4.2}$ is independently halogen, —OH, unsubstituted methyl, or unsubstituted methoxy. In embodiments, $R^{4.2}$ is independently halogen. In embodiments, $R^{4.2}$ is independently —OH. In embodiments, $R^{4.2}$ is independently unsubstituted methyl. In embodiments, $R^{4.2}$ is independently unsubstituted methoxy. In embodiments, $R^{4.2}$ is independently unsubstituted ethoxy. In embodiments, $R^{4.2}$ is independently unsubstituted ethyl. In embodiments, $R^{4.2}$ is independently —F. In embodiments, $R^{4.2}$ is independently —Cl. In embodiments, $R^{4.2}$ is independently —Br. In embodiments, $R^{4.2}$ is independently —I. In embodiments, $R^{4.2}$ is independently —$CF_3$. In embodiments, $R^{4.2}$ is independently —$NH_2$. In embodiments, $R^{4.2}$ is independently —SH. In embodiments, $R^{4.2}$ is independently hydrogen. In embodiments, $R^{4.2}$ is independently unsubstituted isopropyl. In embodiments, $R^{4.2}$ is independently unsubstituted ethoxy. In embodiments, $R^{4.2}$ is independently unsubstituted tert-butyl. In embodiments, $R^{4.2}$ is independently unsubstituted propoxy.

In embodiments, $R^{4.3}$ is independently halogen, —$CF_3$, —OH, —$NH_2$, —SH, substituted or unsubstituted $C_1$-$C_4$ alkyl, substituted or unsubstituted 2 to 4 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl. In embodiments, $R^{4.3}$ is independently halogen, —OH, —NH$_2$, —SH, unsubstituted C$_1$-C$_4$ alkyl, or unsubstituted 2 to 4 membered heteroalkyl. In embodiments, $R^{4.3}$ is independently halogen, —OH, unsubstituted methyl, or unsubstituted methoxy. In embodiments, $R^{4.3}$ is independently halogen. In embodiments, $R^{4.3}$ is independently —OH. In embodiments, $R^{4.3}$ is independently unsubstituted methyl. In embodiments, $R^{4.3}$ is independently unsubstituted methoxy. In embodiments, $R^{4.3}$ is independently unsubstituted ethyl. In embodiments, $R^{4.3}$ is independently —F. In embodiments, $R^{4.3}$ is independently —Cl. In embodiments, $R^{4.3}$ is independently —Br. In embodiments, $R^{4.3}$ is independently —I. In embodiments, $R^{4.3}$ is independently —CF$_3$. In embodiments, $R^{4.3}$ is independently —NH$_2$. In embodiments, $R^{4.3}$ is independently —SH. In embodiments, $R^{4.3}$ is independently hydrogen. In embodiments, $R^{4.3}$ is independently unsubstituted isopropyl. In embodiments, $R^{4.3}$ is independently unsubstituted ethoxy. In embodiments, $R^{4.3}$ is independently unsubstituted tert-butyl. In embodiments, $R^{4.3}$ is independently unsubstituted propoxy.

In embodiments, $R^{4.4}$ is independently halogen, —CF$_3$, —OH, —NH$_2$, —SH, substituted or unsubstituted C$_1$-C$_4$ alkyl, substituted or unsubstituted 2 to 4 membered heteroalkyl, substituted or unsubstituted C$_3$-C$_6$ cycloalkyl, substituted or unsubstituted 3 to 6 membered heterocycloalkyl, substituted or unsubstituted phenyl, or substituted or unsubstituted 5 to 6 membered heteroaryl. In embodiments, $R^{4.4}$ is independently halogen, —OH, —NH$_2$, —SH, unsubstituted C$_1$-C$_4$ alkyl, or unsubstituted 2 to 4 membered heteroalkyl. In embodiments, $R^{4.4}$ is independently halogen, —OH, unsubstituted methyl, or unsubstituted methoxy. In embodiments, $R^{4.4}$ is independently halogen. In embodiments, $R^{4.4}$ is independently —OH. In embodiments, $R^{4.4}$ is independently unsubstituted methyl. In embodiments, $R^{4.4}$ is independently unsubstituted methoxy. In embodiments, $R^{4.4}$ is independently unsubstituted ethyl. In embodiments, $R^{4.4}$ is independently —F. In embodiments, $R^{4.4}$ is independently —Cl. In embodiments, $R^{4.4}$ is independently —Br. In embodiments, $R^{4.4}$ is independently —I. In embodiments, $R^{4.4}$ is independently —CF$_3$. In embodiments, $R^{4.4}$ is independently —NH$_2$. In embodiments, $R^{4.4}$ is independently —SH. In embodiments, $R^{4.4}$ is independently hydrogen. In embodiments, $R^{4.4}$ is independently unsubstituted isopropyl. In embodiments, $R^{4.4}$ is independently unsubstituted ethoxy. In embodiments, $R^{4.4}$ is independently unsubstituted tert-butyl. In embodiments, $R^{4.4}$ is independently unsubstituted propoxy.

In embodiments, $R^{4.5}$ is independently halogen, —CF$_3$, —OH, —NH$_2$, —SH, substituted or unsubstituted C$_1$-C$_4$ alkyl, substituted or unsubstituted 2 to 4 membered heteroalkyl, substituted or unsubstituted C$_3$-C$_6$ cycloalkyl, substituted or unsubstituted 3 to 6 membered heterocycloalkyl, substituted or unsubstituted phenyl, or substituted or unsubstituted 5 to 6 membered heteroaryl. In embodiments, $R^{4.5}$ is independently halogen, —OH, —NH$_2$, —SH, unsubstituted C$_1$-C$_4$ alkyl, or unsubstituted 2 to 4 membered heteroalkyl. In embodiments, $R^{4.5}$ is independently halogen, —OH, unsubstituted methyl, or unsubstituted methoxy. In embodiments, $R^{4.5}$ is independently halogen. In embodiments, $R^{4.5}$ is independently —OH. In embodiments, $R^{4.5}$ is independently unsubstituted methyl. In embodiments, $R^{4.5}$ is independently unsubstituted methoxy. In embodiments, $R^{4.5}$ is independently unsubstituted ethyl. In embodiments, $R^{4.5}$ is independently —F. In embodiments, $R^{4.5}$ is independently —Cl. In embodiments, $R^{4.5}$ is independently —Br. In embodiments, $R^{4.5}$ is independently —I. In embodiments, $R^{4.5}$ is independently —CF$_3$. In embodiments, $R^{4.5}$ is independently —NH$_2$. In embodiments, $R^{4.5}$ is independently —SH. In embodiments, $R^{4.5}$ is independently hydrogen. In embodiments, $R^{4.5}$ is independently unsubstituted isopropyl. In embodiments, $R^{4.5}$ is independently unsubstituted ethoxy. In embodiments, $R^{4.5}$ is independently unsubstituted tert-butyl. In embodiments, $R^{4.5}$ is independently unsubstituted propoxy.

In embodiments, $R^{5.1}$ is independently halogen, —CF$_3$, —OH, —NH$_2$, —SH, substituted or unsubstituted C$_1$-C$_4$ alkyl, substituted or unsubstituted 2 to 4 membered heteroalkyl, substituted or unsubstituted C$_3$-C$_6$ cycloalkyl, substituted or unsubstituted 3 to 6 membered heterocycloalkyl, substituted or unsubstituted phenyl, or substituted or unsubstituted 5 to 6 membered heteroaryl. In embodiments, $R^{51}$ is independently halogen, —OH, —NH$_2$, —SH, unsubstituted C$_1$-C$_4$ alkyl, or unsubstituted 2 to 4 membered heteroalkyl. In embodiments, $R^{5.1}$ is independently halogen, —OH, unsubstituted methyl, or unsubstituted methoxy. In embodiments, $R^{5.1}$ is independently halogen. In embodiments, $R^{5.1}$ is independently —OH. In embodiments, $R^{5.1}$ is independently unsubstituted methyl. In embodiments, $R^{5.1}$ is independently unsubstituted methoxy. In embodiments, $R^{5.1}$ is independently unsubstituted ethyl. In embodiments, $R^{5.1}$ is independently —F. In embodiments, $R^{5.1}$ is independently —Cl. In embodiments, $R^{5.1}$ is independently —Br. In embodiments, $R^{5.1}$ is independently —I. In embodiments, $R^{5.1}$ is independently —CF$_3$. In embodiments, $R^{5.1}$ is independently —NH$_2$. In embodiments, $R^{5.1}$ is independently —SH. In embodiments, $R^{5.1}$ is independently hydrogen. In embodiments, $R^{5.1}$ is independently unsubstituted isopropyl. In embodiments, $R^{5.1}$ is independently unsubstituted ethoxy. In embodiments, $R^{5.1}$ is independently unsubstituted tert-butyl. In embodiments, $R^{5.1}$ is independently unsubstituted propoxy.

In embodiments, $R^{5.2}$ is independently halogen, —CF$_3$, —OH, —NH$_2$, —SH, substituted or unsubstituted C$_1$-C$_4$ alkyl, substituted or unsubstituted 2 to 4 membered heteroalkyl, substituted or unsubstituted C$_3$-C$_6$ cycloalkyl, substituted or unsubstituted 3 to 6 membered heterocycloalkyl, substituted or unsubstituted phenyl, or substituted or unsubstituted 5 to 6 membered heteroaryl. In embodiments, $R^{5.2}$ is independently halogen, —OH, —NH$_2$, —SH, unsubstituted C$_1$-C$_4$ alkyl, or unsubstituted 2 to 4 membered heteroalkyl. In embodiments, $R^{5.2}$ is independently halogen, —OH, unsubstituted methyl, or unsubstituted methoxy. In embodiments, $R^{5.2}$ is independently halogen. In embodiments, $R^{5.2}$ is independently —OH. In embodiments, $R^{5.2}$ is independently unsubstituted methyl. In embodiments, $R^{5.2}$ is independently unsubstituted methoxy. In embodiments, $R^{5.2}$ is independently unsubstituted ethyl. In embodiments, $R^{5.2}$ is independently —F. In embodiments, $R^{5.2}$ is independently —Cl. In embodiments, $R^{5.2}$ is independently —Br. In embodiments, $R^{5.2}$ is independently —I. In embodiments, $R^{5.2}$ is independently —CF$_3$. In embodiments, $R^{5.2}$ is independently —NH$_2$. In embodiments, $R^{5.2}$ is independently —SH. In embodiments, $R^{5.2}$ is independently hydrogen. In embodiments, $R^{5.2}$ is independently unsubstituted isopropyl. In embodiments, $R^{5.2}$ is independently unsubstituted ethoxy. In embodiments, $R^{5.2}$ is independently unsubstituted tert-butyl. In embodiments, $R^{5.2}$ is independently unsubstituted propoxy.

In embodiments, $W^1$ is N. In embodiments, $W^1$ is C($R^{4.2}$). In embodiments, $W^2$ is N. In embodiments, $W^2$ is C($R^{5.1}$). In embodiments, $W^3$ is N. In embodiments, $W^3$ is $C(R^{5.2})$. In embodiments, $W^1$ is $C(H)$. In embodiments, $W^2$ is $C(H)$. In embodiments, $W^3$ is $C(H)$.

In embodiments, $R^{1.1}$ and $R^{1.3}$ are —I. In embodiments, $R^{1.1}$ and $R^{1.3}$ are —F. In embodiments, $R^{1.1}$ and $R^{1.3}$ are —Br. In embodiments, $R^{1.1}$ and $R^{1.3}$ are —Cl. In embodiments, $R^{1.1}$ and $R^{1.3}$ are unsubstituted methyl. In embodiments, $R^{1.1}$ and $R^{1.3}$ are —$CF_3$. In embodiments, $R^{1.1}$ and $R^{1.3}$ are —$NH_2$. In embodiments, $R^{1.1}$ and $R^{1.3}$ are —OH. In embodiments, $R^{1.1}$ and $R^{1.3}$ are unsubstituted methoxy. In embodiments, $R^{1.1}$ and $R^{1.3}$ are halogen. In embodiments, $R^{1.1}$ and $R^{1.3}$ are unsubstituted $C_1$-$C_4$ alkyl. In embodiments, $R^{1.1}$ and $R^{1.3}$ are substituted $C_1$-$C_4$ alkyl. In embodiments, $R^{1.1}$ and $R^{1.3}$ are halogen substituted $C_1$-$C_4$ alkyl. In embodiments, $R^{1.1}$ and $R^{1.3}$ are unsubstituted $C_1$-$C_2$ alkyl. In embodiments, $R^{1.1}$ and $R^{1.3}$ are substituted $C_1$-$C_2$ alkyl. In embodiments, $R^{1.1}$ and $R^{1.3}$ are halogen substituted $C_1$-$C_2$ alkyl.

In embodiments, $R^{4.1}$ and $R^{4.3}$ are —I. In embodiments, $R^{4.1}$ and $R^{4.3}$ are —F. In embodiments, $R^{4.1}$ and $R^{4.3}$ are —Br. In embodiments, $R^{4.1}$ and $R^{4.3}$ are —Cl. In embodiments, $R^{4.1}$ and $R^{4.3}$ are unsubstituted methyl. In embodiments, $R^{4.1}$ and $R^{4.3}$ are —$CF_3$. In embodiments, $R^{4.1}$ and $R^{4.3}$ are —$NH_2$. In embodiments, $R^{4.1}$ and $R^{4.3}$ are —OH. In embodiments, $R^{4.1}$ and $R^{4.3}$ are unsubstituted methoxy. In embodiments, $R^{4.1}$ and $R^{4.3}$ are halogen. In embodiments, $R^{4.1}$ and $R^{43}$ are unsubstituted $C_1$-$C_4$ alkyl. In embodiments, $R^{4.1}$ and $R^{4.3}$ are substituted $C_1$-$C_4$ alkyl. In embodiments, $R^{4.1}$ and $R^{4.3}$ are halogen substituted $C_1$-$C_4$ alkyl. In embodiments, $R^{4.1}$ and $R^{4.3}$ are unsubstituted $C_1$-$C_2$ alkyl. In embodiments, $R^{4.1}$ and $R^{4.3}$ are substituted $C_1$-$C_2$ alkyl. In embodiments, $R^{4.1}$ and $R^{4.3}$ are halogen substituted $C_1$-$C_2$ alkyl.

In embodiments, the compound has the formula:

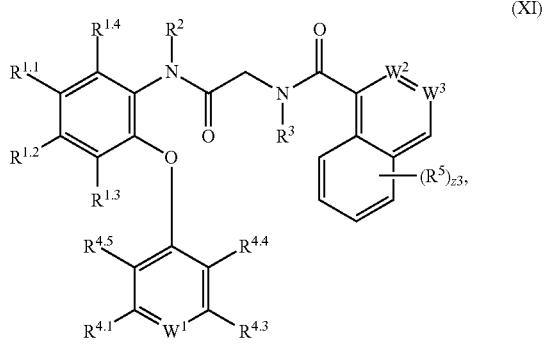

(XI)

$R^2$, $R^3$, $R^5$, and z3 are as described herein, including in compounds of formula (I) to (V). $R^{1.1}$, $R^{1.2}$, $R^{1.3}$, and $R^{1.4}$ are each independently a moiety of $R^1$ as described herein, including in embodiments. In embodiments, $R^{1.1}$, $R^{1.2}$, $R^{1.3}$, and/or $R^{1.4}$ are hydrogen. In embodiments, $R^{4.1}$, $R^{4.2}$, $R^{43}$, $R^{44}$, and/or $R^{45}$ are hydrogen. In embodiments, $R^2$ is hydrogen. In embodiments, $R^3$ is hydrogen. In embodiments $R^{11}$ is halogen. In embodiments $R^{1.2}$ is halogen. In embodiments $R^{1.3}$ is halogen. In embodiments $R^{1.4}$ is halogen. In embodiments $R^{11}$ is —Cl. In embodiments $R^{1.2}$ is —Cl. In embodiments $R^{1.3}$ is —Cl. In embodiments $R^{1.4}$ is —Cl. In embodiments $R^{1.1}$ is —F. In embodiments $R^{1.2}$ is —F. In embodiments $R^{1.3}$ is —F. In embodiments $R^{1.4}$ is —F. In embodiments $R^{1.2}$, $R^{1.3}$, and $R^{1.4}$ are hydrogen and $R^{11}$ is halogen. In embodiments $R^{1.1}$, $R^{1.3}$, and $R^{1.4}$ are hydrogen and $R^{1.2}$ is halogen. In embodiments $R^{1.2}$, $R^{1.1}$, and $R^{1.4}$ are hydrogen and $R^{1.3}$ is halogen. In embodiments $R^{1.2}$, $R^{1.3}$, and $R^{1.1}$ are hydrogen and $R^{1.4}$ is halogen. In embodiments $R^{1.2}$, $R^{1.3}$, and $R^{1.4}$ are hydrogen and $R^{1.1}$ is —Cl. In embodiments $R^{1.1}$, $R^{1.3}$, and $R^{1.4}$ are hydrogen and $R^{1.2}$ is —Cl. In embodiments $R^{1.2}$, $R^{1.1}$, and $R^{1.4}$ are hydrogen and $R^{1.3}$ is —Cl. In embodiments $R^{1.2}$, $R^{1.3}$, and $R^{1.1}$ are hydrogen and $R^{1.4}$ is —Cl. In embodiments $R^{1.2}$, $R^{1.3}$, and $R^{1.4}$ are hydrogen and $R^{1.1}$ is —F. In embodiments $R^{1.1}$, $R^{1.3}$, and $R^{1.4}$ are hydrogen and $R^{1.2}$ is —F. In embodiments $R^{1.2}$, $R^{1.1}$, and $R^{1.4}$ are hydrogen and $R^{1.3}$ is —F. In embodiments $R^{1.2}$, $R^{1.3}$, and $R^{1.1}$ are hydrogen and $R^{1.4}$ is —F. $W^1$ is N or $C(R^{4.2})$. $W^2$ is N or $C(R^{5.1})$. $W^3$ is N or $C(R^{5.2})$. In embodiments, $W^1$ is N. In embodiments, $W^2$ is N. In embodiments, $W^3$ is N. In embodiments, $W^1$ is $C(R^{4.2})$. In embodiments, $W^2$ is $C(R^{5.1})$. In embodiments, $W^3$ is $C(R^{52})$. In embodiments, $W^1$ is CH. In embodiments, $W^2$ is CH. In embodiments, $W^3$ is CH. $R^{5.1}$ and $R^{5.2}$ are each independently a moiety of $R^5$ as described herein, including in embodiments. In embodiment, z3 is 0. $R^{4.1}$, $R^{4.2}$, $R^{4.3}$, $R^{4.4}$, and $R^{4.5}$ are each independently a moiety of $R^4$ as described herein, including in embodiments. In embodiments, $R^{4.1}$ is unsubstituted methoxy. In embodiments, $R^{4.2}$ is unsubstituted methoxy. In embodiments, $R^{4.3}$ is unsubstituted methoxy. In embodiments, $R^{4.4}$ is unsubstituted methoxy. In embodiments, $R^{4.5}$ is unsubstituted methoxy. In embodiments, $R^{4.2}$, $R^{4.3}$, $R^{4.4}$, and $R^{4.5}$ are hydrogen and $R^{4.1}$ is unsubstituted methoxy. In embodiments, $R^{4.1}$, $R^{4.3}$, $R^{4.4}$, and $R^{4.5}$ are hydrogen and $R^{4.2}$ is unsubstituted methoxy. In embodiments, $R^{4.2}$, $R^{4.1}$, $R^{4.4}$, and $R^{4.5}$ are hydrogen and $R^{4.3}$ is unsubstituted methoxy. In embodiments, $R^{4.2}$, $R^{4.3}$, $R^{4.1}$, and $R^{4.5}$ are hydrogen and $R^{4.4}$ is unsubstituted methoxy. In embodiments, $R^{4.2}$, $R^{4.3}$, $R^{4.4}$, and $R^{4.1}$ are hydrogen and $R^{4.5}$ is unsubstituted methoxy. In embodiments, $R^{4.1}$ is unsubstituted ethoxy. In embodiments, $R^{4.2}$ is unsubstituted ethoxy. In embodiments, $R^{4.3}$ is unsubstituted ethoxy. In embodiments, $R^{4.4}$ is unsubstituted ethoxy. In embodiments, $R^{4.5}$ is unsubstituted ethoxy. In embodiments, $R^{4.2}$, $R^{4.3}$, $R^{4.4}$, and $R^{4.5}$ are hydrogen and $R^{4.1}$ is unsubstituted ethoxy. In embodiments, $R^{4.1}$, $R^{4.3}$, $R^{4.4}$, and $R^{4.5}$ are hydrogen and $R^{4.2}$ is unsubstituted ethoxy. In embodiments, $R^{4.2}$, $R^{4.}$, $R^{4.4}$, and $R^{4.5}$ are hydrogen and $R^{4.3}$ is unsubstituted ethoxy. In embodiments, $R^{4.2}$, $R^{4.3}$, $R^{4.}$, and $R^{4.5}$ are hydrogen and $R^{4.4}$ is unsubstituted ethoxy. In embodiments, $R^{4.2}$, $R^{4.3}$, $R^{4.4}$, and $R^{4.5}$ are hydrogen and $R^{4.5}$ is unsubstituted ethoxy. In embodiments, $R^{4.1}$ is —OH. In embodiments $R^{4.2}$ is —OH. In embodiments, $R^{4.3}$ is —OH. In embodiments, $R^{4.4}$ is —OH. In embodiments, $R^{4.5}$ is —OH. In embodiments, $R^{4.2}$, $R^{4.3}$, $R^{4.4}$, and $R^{4.5}$ are hydrogen and $R^{4.1}$ is —OH. In embodiments, $R^{4.1}$, $R^{4.3}$, $R^{4.4}$, and $R^{4.5}$ are hydrogen and $R^{4.2}$ is —OH. In embodiments, $R^{4.2}$, $R^{4.1}$, $R^{4.4}$, and $R^{4.5}$ are hydrogen and $R^{4.3}$ is —OH. In embodiments, $R^{4.2}$, $R^{4.3}$, $R^{4.1}$, and $R^{4.5}$ are hydrogen and $R^{4.4}$ is —OH. In embodiments, $R^{4.2}$, $R^{4.3}$, $R^{4.4}$, and $R^{4.1}$ are hydrogen and $R^{4.5}$ is —OH. In embodiments, $R^{4.1}$ is halogen. In embodiments, $R^{4.2}$ is halogen. In embodiments, $R^{4.3}$ is halogen. In embodiments, $R^{4.4}$ is halogen. In embodiments, $R^{4.5}$ is halogen. In embodiments, $R^{4.2}$, $R^{4.3}$, $R^{4.4}$, and $R^{4.5}$ are hydrogen and $R^{4.1}$ is halogen. In embodiments, $R^{4.1}$, $R^{4.3}$, $R^{4.4}$, and $R^{4.5}$ are hydrogen and $R^{4.2}$ is halogen. In embodiments, $R^{4.2}$, $R^{4.1}$, $R^{4.4}$, and $R^{4.5}$ are hydrogen and $R^{4.3}$ is halogen. In embodiments, $R^{4.2}$, $R^{4.3}$, $R^{4.1}$, and $R^{4.5}$ are hydrogen and $R^{4.4}$ is halogen. In embodiments, $R^{4.2}$, $R^{4.3}$, $R^{4.4}$, and $R^{4.1}$ are hydrogen and $R^{4.5}$ is halogen. In embodiments, $R^{4.1}$ is unsubstituted methyl. In embodiments, $R^{4.2}$ is unsubstituted methyl. In embodiments, $R^{4.3}$ is unsubstituted methyl. In embodiments, $R^{4.4}$ is unsubstituted methyl. In embodiments, $R^{4.5}$ is unsubstituted methyl. In embodiments, $R^{4.2}$, $R^{4.3}$, $R^{4.4}$, and $R^{4.5}$ are hydrogen and $R^{4.1}$ is unsubstituted methyl. In embodiments, $R^{4.1}$, $R^{4.3}$, $R^{4.4}$, and $R^{4.5}$ are hydrogen and $R^{4.2}$ is unsubstituted methyl. In embodiments, $R^{4.2}$, $R^{4.1}$, $R^{4.4}$, and $R^{4.5}$ are hydrogen and $R^{4.3}$ is unsubstituted methyl. In embodiments, $R^{4.2}$, $R^{4.3}$, $R^{4.1}$, and $R^{4.5}$ are hydrogen and $R^{4.4}$ is unsubstituted methyl. In embodiments, $R^{4.2}$, $R^{4.3}$, $R^{4.4}$, and $R^{4.1}$ are hydrogen and $R^{4.5}$ is unsubstituted methyl. In embodiments, one or more of $R^{1.1}$, $R^{1.2}$, $R^{1.3}$, $R^{1.4}$, $R^{4.1}$, $R^{4.2}$, $R^{4.3}$, $R^{4.4}$, $R^{4.5}$, $R^2$ and/or $R^3$ are hydrogen. It will be understood that $R^5$ is/are a floating substituent and may be positioned on either or both rings.

In embodiments, the compound has the formula:

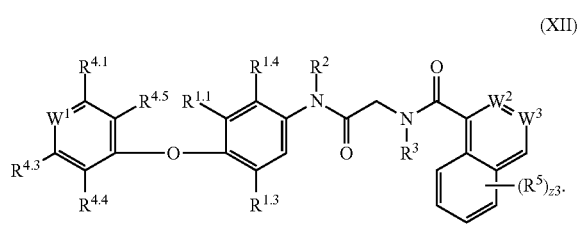

(XII)

$R^{1.1}$, $R^{1.3}$, $R^{1.4}$, $R^2$, $R^3$, $R^{4.1}$, $R^{4.3}$, $R^{4.4}$, $R^{4.5}$, R, $W^1$, $W^2$, $W^3$, and z3 are as described herein, including in compounds of formula (I) to (XI). It will be understood that $R^5$ is/are a floating substituent and may be positioned on either or both rings. $R^{1.1}$, $R^{1.3}$, and $R^{1.4}$ are each independently a moiety of $R^1$ as described herein, including in embodiments. $R^{4.1}$, $R^{4.3}$, $R^{4.4}$, and $R^{4.5}$ are each independently a moiety of $R^4$ as described herein, including in embodiments. In embodiments, $R^{1.1}$, $R^{1.3}$, and/or $R^{1.4}$ are hydrogen. In embodiments, $R^{4.1}$, $R^{4.2}$, $R^{4.3}$, $R^{4.4}$, and/or $R^{4.5}$ are hydrogen. In embodiments, $R^2$ is hydrogen. In embodiments, $R^3$ is hydrogen. In embodiments $R^{1.1}$ is halogen. In embodiments $R^{1.3}$ is halogen. In embodiments $R^{1.4}$ is halogen. In embodiments $R^{1.1}$ is —Cl. In embodiments $R^{1.3}$ is —Cl. In embodiments $R^{1.4}$ is —Cl. In embodiments $R^{1.1}$ is —F. In embodiments $R^{1.3}$ is —F. In embodiments $R^{1.4}$ is —F. In embodiments $R^{1.3}$ and $R^{1.4}$ are hydrogen and $R^{1.1}$ is halogen. In embodiments $R^{1.1}$ and $R^{14}$ are hydrogen and $R^{13}$ is halogen. In embodiments $R^{1.3}$ and $R^{1.1}$ are hydrogen and $R^{1.4}$ is halogen. In embodiments $R^{1.3}$ and $R^{1.4}$ are hydrogen and $R^{1.1}$ is —Cl. In embodiments $R^{1.1}$ and $R^{1.4}$ are hydrogen and $R^{1.3}$ is —Cl. In embodiments $R^{1.3}$ and $R^{1.1}$ are hydrogen and $R^{1.4}$ is —Cl. In embodiments $R^{1.3}$ and $R^{1.4}$ are hydrogen and $R^{1.1}$ is —F. In embodiments $R^{1.1}$ and $R^{1.4}$ are hydrogen and $R^{1.3}$ is —F. In embodiments $R^{1.3}$ and $R^{1.1}$ are hydrogen and $R^{1.4}$ is —F. $W^1$ is N or $C(R^{4.2})$. $W^2$ is N or $C(R^{5.1})$ $W^3$ is N or $C(R^{5.2})$. In embodiments, $W^1$ is N. In embodiments, $W^2$ is N. In embodiments, $W^3$ is N. In embodiments, $W^1$ is $C(R^{4.2})$. In embodiments, $W^2$ is $C(R^{5.1})$. In embodiments, $W^3$ is $C(R^{5.2})$. In embodiments, $W^1$ is CH. In embodiments, $W^2$ is CH. In embodiments, $W^3$ is CH. $R^{5.1}$ and $R^{5.2}$ are each independently a moiety of $R^5$ as described herein, including in embodiments. In embodiment, z3 is 0. $R^{4.1}$, $R^{4.2}$, $R^{4.3}$, $R^{4.4}$, and $R^{4.5}$ are each independently a moiety of $R^4$ as described herein, including in embodiments. In embodiments, $R^{4.1}$ is unsubstituted methoxy. In embodiments, $R^{4.2}$ is unsubstituted methoxy. In embodiments, $R^{4.3}$ is unsubstituted methoxy. In embodiments, $R^{4.4}$ is unsubstituted methoxy. In embodiments, $R^{4.5}$ is unsubstituted methoxy. In embodiments, $R^{4.2}$, $R^{4.3}$, $R^{4.4}$, and $R^{4.5}$ are hydrogen and $R^{4.1}$ is unsubstituted methoxy. In embodiments, $R^{4.1}$, $R^{4.3}$, $R^{4.4}$, and $R^{4.5}$ are hydrogen and $R^{4.2}$ is unsubstituted methoxy. In embodiments, $R^{4.2}$, $R^{4.1}$, $R^{4.4}$, and $R^{4.5}$ are hydrogen and $R^{4.3}$ is unsubstituted methoxy. In embodiments, $R^{4.2}$, $R^{4.3}$, $R^{4.1}$, and $R^{4.5}$ are hydrogen and $R^{4.4}$ is unsubstituted methoxy. In embodiments, $R^{4.2}$, $R^{4.3}$, $R^{4.4}$, and $R^{4.1}$ are hydrogen and $R^{4.5}$ is unsubstituted methoxy. In embodiments, $R^{4.1}$ is unsubstituted ethoxy. In embodiments, $R^{4.2}$ is unsubstituted ethoxy. In embodiments, $R^{4.3}$ is unsubstituted ethoxy. In embodiments, $R^{4.4}$ is unsubstituted ethoxy. In embodiments, $R^{4.5}$ is unsubstituted ethoxy. In embodiments, $R^{4.2}$, $R^{4.3}$, $R^{4.4}$, and $R^{4.5}$ are hydrogen and $R^{4.1}$ is unsubstituted ethoxy. In embodiments, $R^{4.1}$, $R^{4.3}$, $R^{4.4}$, and $R^{4.5}$ are hydrogen and $R^{4.2}$ is unsubstituted ethoxy. In embodiments, $R^{4.2}$, $R^{4.1}$, $R^{4.4}$, and $R^{4.5}$ are hydrogen and $R^{4.3}$ is unsubstituted ethoxy. In embodiments, $R^{4.2}$, $R^{4.3}$, $R^{4.1}$, and $R^{4.5}$ are hydrogen and $R^{4.4}$ is unsubstituted ethoxy. In embodiments, $R^{4.2}$, $R^{4.3}$, $R^{4.4}$, and $R^{4.1}$ are hydrogen and $R^{4.5}$ is unsubstituted ethoxy. In embodiments, $R^{4.1}$ is —OH. In embodiments $R^{4.2}$ is —OH. In embodiments, $R^{4.3}$ is —OH. In embodiments, $R^{4.4}$ is —OH. In embodiments, $R^{4.5}$ is —OH. In embodiments, $R^{4.2}$, $R^{4.3}$, $R^{4.4}$, and $R^{4.5}$ are hydrogen and $R^{4.1}$ is —OH. In embodiments, $R^{4.1}$, $R^{4.3}$, $R^{4.4}$, and $R^{4.5}$ are hydrogen and $R^{4.2}$ is —OH. In embodiments, $R^{4.2}$, $R^{4.1}$, $R^{4.4}$, and $R^{4.5}$ are hydrogen and $R^{4.3}$ is —OH. In embodiments, $R^{4.2}$, $R^{4.3}$, $R^{4.1}$, and $R^{4.5}$ are hydrogen and $R^{4.4}$ is —OH. In embodiments, $R^{4.2}$, $R^{4.3}$, $R^{4.4}$, and $R^{4.1}$ are hydrogen and $R^{4.5}$ is —OH. In embodiments, $R^{4.1}$ is halogen. In embodiments, $R^{4.2}$ is halogen. In embodiments, $R^{4.3}$ is halogen. In embodiments, $R^{4.4}$ is halogen. In embodiments, $R^{4.5}$ is halogen. In embodiments, $R^{4.2}$, $R^{4.3}$, $R^{4.4}$, and $R^{4.5}$ are hydrogen and $R^{4.1}$ is halogen. In embodiments, $R^{4.1}$, $R^{4.3}$, $R^{4.4}$, and $R^{4.5}$ are hydrogen and $R^{4.2}$ is halogen. In embodiments, $R^{4.2}$, $R^{4.1}$, $R^{4.4}$, and $R^{4.5}$ are hydrogen and $R^{4.3}$ is halogen. In embodiments, $R^{4.2}$, $R^{4.3}$, $R^{4.1}$, and $R^{4.5}$ are hydrogen and $R^{4.4}$ is halogen. In embodiments, $R^{4.2}$, $R^{4.3}$, $R^{4.4}$, and $R^{4.1}$ are hydrogen and $R^{4.5}$ is halogen. In embodiments, $R^{4.1}$ is unsubstituted methyl. In embodiments, $R^{4.2}$ is unsubstituted methyl. In embodiments, $R^{4.3}$ is unsubstituted methyl. In embodiments, $R^{4.4}$ is unsubstituted methyl. In embodiments, $R^{4.5}$ is unsubstituted methyl. In embodiments, $R^{4.2}$, $R^{4.3}$, $R^{4.4}$, and $R^{4.5}$ are hydrogen and $R^{4.1}$ is unsubstituted methyl. In embodiments, $R^4$, $R^{4.3}$, $R^{4.4}$, and $R^{4.5}$ are hydrogen and $R^{4.2}$ is unsubstituted methyl. In embodiments, $R^{4.2}$, $R^{4.1}$, $R^{4.4}$, and $R^{4.5}$ are hydrogen and $R^{4.3}$ is unsubstituted methyl. In embodiments, $R^{4.2}$, $R^{4.3}$, $R^{4.1}$, and $R^{4.5}$ are hydrogen and $R^{4.4}$ is unsubstituted methyl. In embodiments, $R^{4.2}$, $R^{4.3}$, $R^{4.4}$, and $R^{4.1}$ are hydrogen and $R^{4.5}$ is unsubstituted methyl. In embodiments, one or more of $R^{1.1}$, $R^{1.3}$, $R^{14}$, $R^{4.1}$, $R^{4.2}$, $R^{4.3}$, $R^{4.4}$, $R^{4.5}$, $R^2$ and/or $R^3$ are hydrogen. It will be understood that $R^5$ is/are a floating substituent and may be positioned on either or both rings.

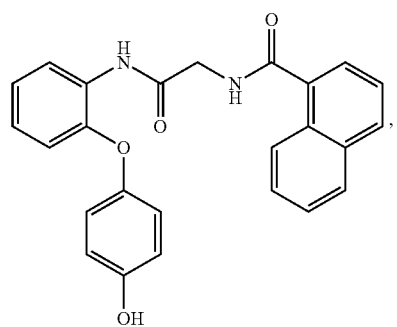

-continued
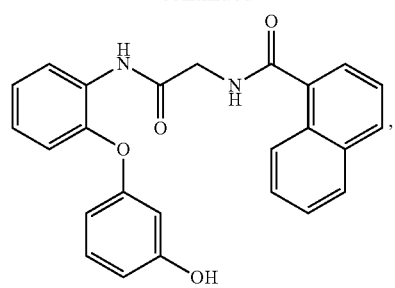,
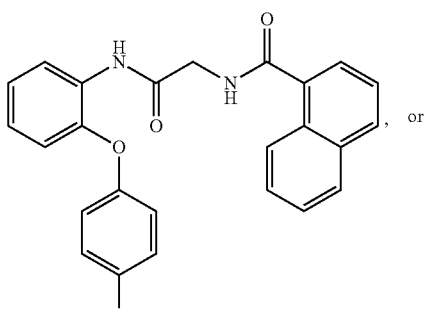, or
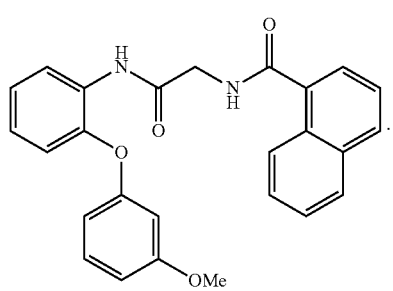.
In embodiments, the compound has the formula:
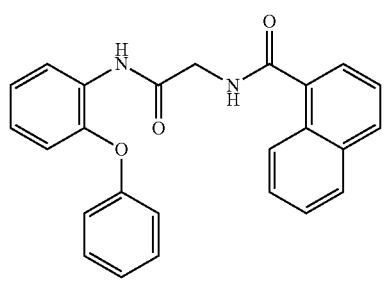 [SMILES: O=C(CNC(=O)c1cccc2ccccc12)Nc1ccccc1Oc1ccccc1]
In embodiments, the compound has the formula:
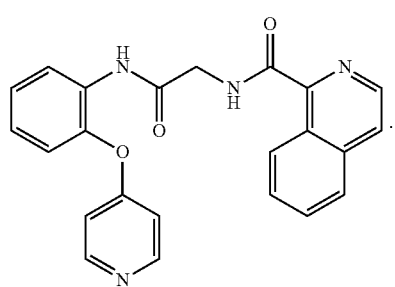 [SMILES: O=C(CNC(=O)c1nccc2ccccc12)Nc1ccccc1Oc1ccncc1]
In embodiments the compound has the formula:
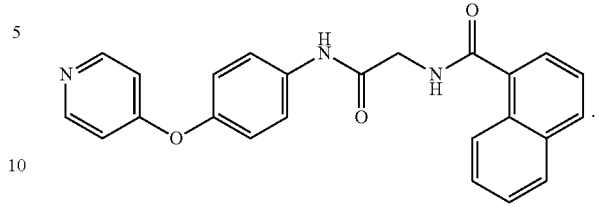
TABLE 1
Examples of compounds of formula (I), (II), (III), (IV) and (V) are shown in the table below:
| Compound ID | Structures |
|---|---|
| AOH1160 | 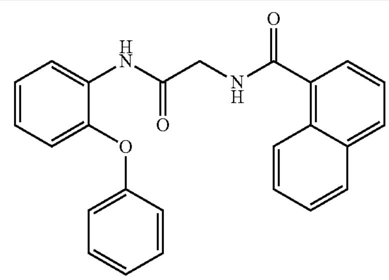 [SMILES: O=C(CNC(=O)c1cccc2ccccc12)Nc1ccccc1Oc1ccccc1] |
| PCNA1 | 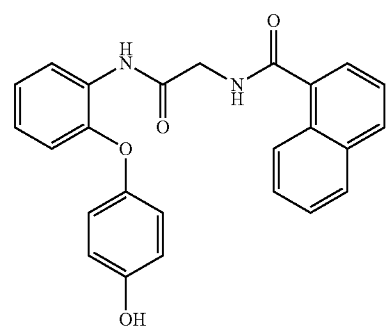 [SMILES: O=C(CNC(=O)c1cccc2ccccc12)Nc1ccccc1Oc1ccc(O)cc1] |
| PCNA2 | 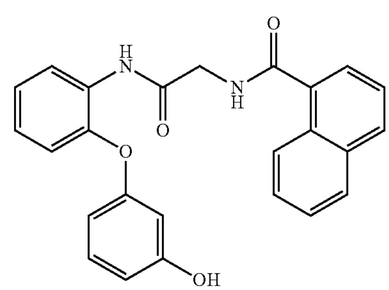 [SMILES: O=C(CNC(=O)c1cccc2ccccc12)Nc1ccccc1Oc1cccc(O)c1] |
| PCNA3 | 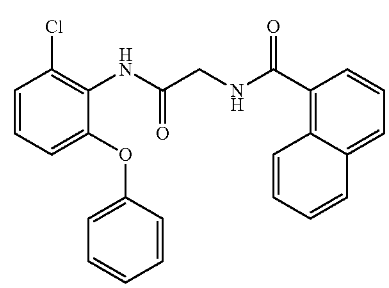 [SMILES: O=C(CNC(=O)c1cccc2ccccc12)Nc1c(Cl)cccc1Oc1ccccc1] |

TABLE 1-continued

Examples of compounds of formula (I), (II), (III), (IV) and (V) are shown in the table below:

| Compound ID | Structures |
|---|---|
| PCNA3A | 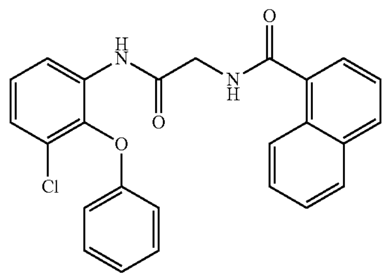 [SMILES: O=C(CNC(=O)c1cccc2ccccc12)Nc1cccc(Cl)c1Oc1ccccc1] |
| PCNA4 | 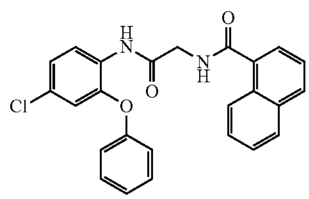 [SMILES: O=C(CNC(=O)c1cccc2ccccc12)Nc1ccc(Cl)cc1Oc1ccccc1] |
| PCNA6 | 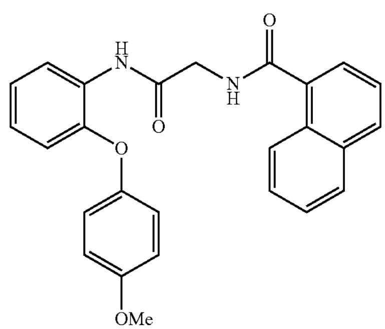 [SMILES: COc1ccc(Oc2ccccc2NC(=O)CNC(=O)c2cccc3ccccc23)cc1] |
| PCNA7/AOH1996 | 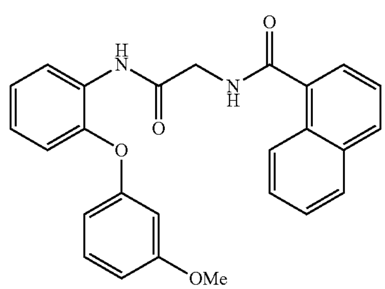 [SMILES: COc1cccc(Oc2ccccc2NC(=O)CNC(=O)c2cccc3ccccc23)c1] |
| #1161 | 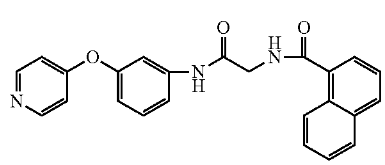 [SMILES: O=C(CNC(=O)c1cccc2ccccc12)Nc1cccc(Oc2ccncc2)c1] |
| #1162 | 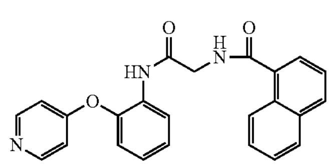 [SMILES: O=C(CNC(=O)c1cccc2ccccc12)Nc1ccccc1Oc1ccncc1] |
| #1165 | 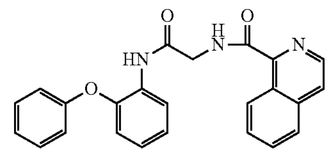 [SMILES: O=C(CNC(=O)c1nccc2ccccc12)Nc1ccccc1Oc1ccccc1] |
| #1166 | 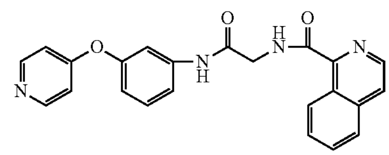 [SMILES: O=C(CNC(=O)c1nccc2ccccc12)Nc1cccc(Oc2ccncc2)c1] |
| #1167 | 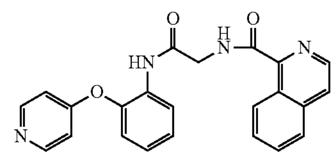 [SMILES: O=C(CNC(=O)c1nccc2ccccc12)Nc1ccccc1Oc1ccncc1] |
| #1175 | 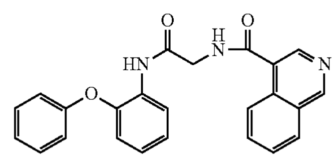 [SMILES: O=C(CNC(=O)c1cncc2ccccc12)Nc1ccccc1Oc1ccccc1] |
| #1176 | 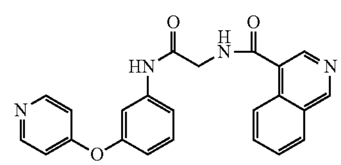 [SMILES: O=C(CNC(=O)c1cncc2ccccc12)Nc1cccc(Oc2ccncc2)c1] |
| #1177 | 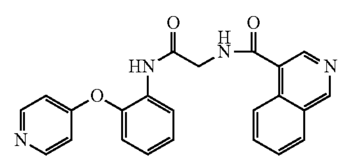 [SMILES: O=C(CNC(=O)c1cncc2ccccc12)Nc1ccccc1Oc1ccncc1] |
| #1178 | 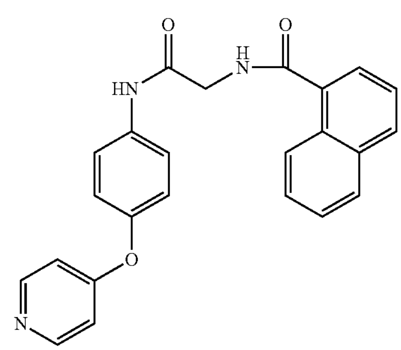 [SMILES: O=C(CNC(=O)c1cccc2ccccc12)Nc1ccc(Oc2ccncc2)cc1] |

TABLE 1-continued

Examples of compounds of formula (I), (II), (III), (IV) and (V) are shown in the table below:

| Compound ID | Structures |
|---|---|
| AOH1179 | 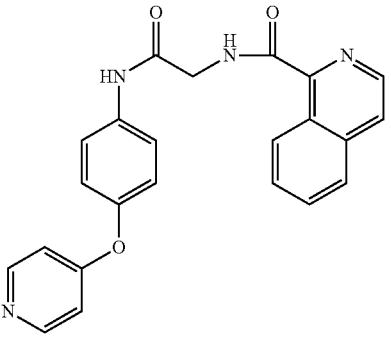 [SMILES: O=C(CNC(=O)c1nccc2ccccc12)Nc1ccc(Oc2ccncc2)cc1] |
| AOH1180 | 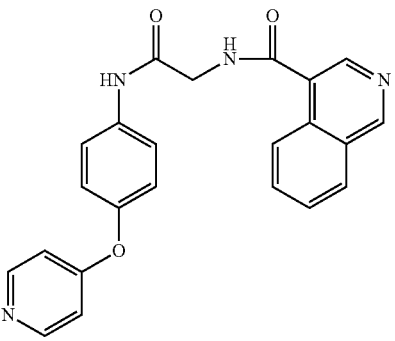 [SMILES: O=C(CNC(=O)c1cncc2ccccc12)Nc1ccc(Oc2ccncc2)cc1] |

In embodiments, the compound binds the interdomain connecting loop of PCNA (e.g., the loop including the amino acids corresponding to human PCNA M121 to Y133). In embodiments, the compound binds to an amino acid in the sequence corresponding to human PCNA M121 to Y133. In embodiments, the compound binds an amino acid in the sequence corresponding to human PCNA L126 to Y133. In embodiments, the compound binds to a plurality of amino acids in the sequence corresponding to human PCNA M121 to Y133. In embodiments, the compound binds a plurality of amino acids in the sequence corresponding to human PCNA L126 to Y133. In embodiments, the compound binds to an amino acid in human PCNA M121 to Y133. In embodiments, the compound binds an amino acid in human PCNA L126 to Y133. In embodiments, the compound binds to a plurality of amino acids in human PCNA M121 to Y133. In embodiments, the compound binds a plurality of amino acids in human PCNA L126 to Y133. In embodiments, the compound binds an amino acid corresponding to human PCNA L126. In embodiments, the compound binds an amino acid corresponding to human PCNA G127. In embodiments, the compound binds an amino acid corresponding to human PCNA I128. In embodiments, the compound binds an amino acid corresponding to human PCNA P129. In embodiments, the compound binds an amino acid corresponding to human PCNA E130. In embodiments, the compound binds an amino acid corresponding to human PCNA Q131. In embodiments, the compound binds an amino acid corresponding to human PCNA E132. In embodiments, the compound binds an amino acid corresponding to human PCNA Y133. In embodiments, the compound binds an amino acid corresponding to human PCNA D41. In embodiments, the compound binds an amino acid corresponding to human PCNA S42. In embodiments, the compound binds an amino acid corresponding to human PCNA S43. In embodiments, the compound binds an amino acid corresponding to human PCNA H44. In embodiments, the compound binds an amino acid corresponding to human PCNA V45. In embodiments, the compound binds an amino acid corresponding to human PCNA P234. In embodiments, the compound binds to human PCNA L126. In embodiments, the compound binds to human PCNA G127. In embodiments, the compound binds to human PCNA I128. In embodiments, the compound binds to human PCNA P129. In embodiments, the compound binds to human PCNA E130. In embodiments, the compound binds to human PCNA Q131. In embodiments, the compound binds to human PCNA E132. In embodiments, the compound binds to human PCNA Y133. In embodiments, the compound binds to human PCNA D41. In embodiments, the compound binds to human PCNA S42. In embodiments, the compound binds to human PCNA S43. In embodiments, the compound binds to human PCNA H44. In embodiments, the compound binds to human PCNA V45. In embodiments, the compound binds to human PCNA P234. In embodiments, the compound competes with T3 for binding to PCNA. In embodiments, the compound competes with p21 (CDKN1A) for binding to PCNA. In embodiments, the compound competes with DNA polymerase δ for binding to PCNA. In embodiments, the compound competes with flap endonuclease 1 (FEN1) for binding to PCNA. In embodiments, the compound inhibits T3 binding to PCNA. In embodiments, the compound inhibits p21 (CDKN1A) binding to PCNA. In embodiments, the compound inhibits DNA polymerase δ binding to PCNA. In embodiments, the compound inhibits flap endonuclease 1 (FEN1) binding to PCNA. In embodiments, the compound inhibits PIP-box containing protein (e.g., PIP box includes eight amino acid sequence of QXX-(hydrophobic amino acid)-XX-(acidic amino acid)-(acidic amino acid), X is independently any amino acid) binding to PCNA. In embodiments, the compound inhibits DNA replication. In embodiments, the compound reduces DNA replication (e.g., relative to the absence of the compound, or relative to control). In embodiments, the compound inhibits DNA repair. In embodiments, the compound reduces DNA repair (e.g., relative to the absence of the compound, or relative to control). In embodiments, the compound inhibits cell (e.g., cancer cell) growth. In embodiments, the compound reduces cell (e.g., cancer cell) growth (e.g., relative to the absence of the compound, or relative to control). In embodiments, the compound inhibits cell (e.g., cancer cell) proliferation. In embodiments, the compound reduces cell (e.g., cancer cell) proliferation (e.g., relative to the absence of the compound, or relative to control). In embodiments, the compound inhibits cell survival. In embodiments, the compound reduces cell survival (e.g., relative to the absence of the compound, or relative to control). In embodiments, the compound binds the acidic form of PCNA (e.g., caPCNA, form having an acidic isoelectric point). In embodiments, the compound does not bind the basic form of PCNA (e.g., nmPCNA, form having an apparent basic isoelectric point). In embodiments, the compound binds the acidic form of PCNA (e.g., caPCNA, form having an acidic isoelectric point) more strongly than the basic form of PCNA (e.g., nmPCNA, form having an apparent basic isoelectric point) (e.g., about 1.1, 1.2, 1.3, 1.4, 1.5, 1.6, 1.7, 1.8, 1.9, 2, 3, 4, 5, 6, 7, 8, 9, 10, 20, 30, 40, 50, 60, 70, 80, 90, 100, 200, 300, 400, 500, 600, 700, 800, 900, 1000, 10000, or 100000-fold). In embodiments, the compound inhibits homologous recombination. In embodiments, the compound reduces homologous recombination (e.g., relative to the absence of the compound or relative to control). In embodiments, the compound induces cell cycle arrest. In embodiments, the compound increases cell cycle arrest. In embodiments, the compound slows tumor growth. In embodiments, the compound reduces tumor growth. In embodiments, the compound induces apoptosis. In embodiments, the compound induces apoptosis of cancer cells. In embodiments, the compound induces apoptosis of cancer cells to a greater degree than healthy cells of the same cell type (e.g., about 1.1, 1.2, 1.3, 1.4, 1.5, 1.6, 1.7, 1.8, 1.9, 2, 3, 4, 5, 6, 7, 8, 9, 10, 20, 30, 40, 50, 60, 70, 80, 90, 100, 200, 300, 400, 500, 600, 700, 800, 900, 1000, 10000, or 100000-fold more). In embodiments, the compound induces apoptosis of cancer cells to a greater degree than healthy cells of the same cell type (e.g., 1.1, 1.2, 1.3, 1.4, 1.5, 1.6, 1.7, 1.8, 1.9, 2, 3, 4, 5, 6, 7, 8, 9, 10, 20, 30, 40, 50, 60, 70, 80, 90, 100, 200, 300, 400, 500, 600, 700, 800, 900, 1000, 10000, or 100000-fold more). In embodiments, the compound induces cell death of cancer cells at a lower compound concentration than for healthy cells (e.g., at an IC50 at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, 2000, 3000, 4000, 5000, 6000, 7000, 8000, 9000, or 10000-fold lower). In embodiments, the compound increases S phase arrest. In embodiments, the compound increases G2 phase arrest. In embodiments, the compound increases the level of double strand breaks. In embodiments, the compound inhibits DNA repair (e.g., relative to the absence of the compound or relative to control). In embodiments, the compound does not reduce non-homologous end joining. In embodiments, the compound does not inhibit non-homologous end joining. In embodiments, the compound does not activate thyroid receptor. In embodiments, the compound increases caspase-3 activity. In embodiments, the compound increases caspase-9 activity.

In embodiments, the compound binds to a PCNA protein that is post-translationally modified with a stronger affinity than to the same PCNA protein that is not post-translationally modified. In embodiments, the compound binds to a PCNA protein that is not post-translationally modified with a stronger affinity than to the same PCNA protein that is post-translationally modified. In embodiments, the compound binds with a stronger affinity to a PCNA protein that is post-translationally modified with a lipid than to the same PCNA protein that is not post-translationally modified with the lipid. In embodiments, the compound binds with a stronger affinity to a PCNA protein that is not post-translationally modified with a lipid than to the same PCNA protein that is post-translationally modified with the lipid. In embodiments, the compound binds with a stronger affinity to a PCNA protein that is post-translationally modified with a sugar than to the same PCNA protein that is not post-translationally modified with the sugar. In embodiments, the compound binds with a stronger affinity to a PCNA protein that is not post-translationally modified with a sugar than to the same PCNA protein that is post-translationally modified with the sugar. In embodiments, the compound binds with a stronger affinity to a PCNA protein that is post-translationally modified with an amino acid than to the same PCNA protein that is not post-translationally modified with the amino acid. In embodiments, the compound binds with a stronger affinity to a PCNA protein that is not post-translationally modified with an amino acid than to the same PCNA protein that is post-translationally modified with the amino acid. In embodiments, the compound binds with a stronger affinity to a PCNA protein that is post-translationally modified with a nucleobase than to the same PCNA protein that is not post-translationally modified with the nucleobase. In embodiments, the compound binds with a stronger affinity to a PCNA protein that is not post-translationally modified with a nucleobase than to the same PCNA protein that is post-translationally modified with the nucleobase. In embodiments, the compound binds with a stronger affinity to a PCNA protein that is post-translationally modified with a phosphate than to the same PCNA protein that is not post-translationally modified with the phosphate. In embodiments, the compound binds with a stronger affinity to a PCNA protein that is not post-translationally modified with a phosphate than to the same PCNA protein that is post-translationally modified with the phosphate. In embodiments, the compound binds with a stronger affinity to a PCNA protein that is post-translationally modified with a acetyl than to the same PCNA protein that is not post-translationally modified with the acetyl. In embodiments, the compound binds with a stronger affinity to a PCNA protein that is not post-translationally modified with a acetyl than to the same PCNA protein that is post-translationally modified with the acetyl. In embodiments, the compound binds with a stronger affinity to a PCNA protein that is phosphorylated than to the same PCNA protein that is not phosphorylated. In embodiments, the compound binds with a stronger affinity to a PCNA protein that is not phosphorylated than to the same PCNA protein that is phosphorylated. In embodiments, the compound binds with a stronger affinity to a PCNA protein that is alkylated (e.g., methylated) than to the same PCNA protein that is not alkylated (e.g., methylated). In embodiments, the compound binds with a stronger affinity to a PCNA protein that is not alkylated (e.g., methylated) than to the same PCNA protein that is alkylated (e.g., methylated). In embodiments, the compound binds with a stronger affinity to a PCNA protein that is ribosylated than to the same PCNA protein that is not ribosylated. In embodiments, the compound binds with a stronger affinity to a PCNA protein that is not ribosylated than to the same PCNA protein that is ribosylated. In embodiments, the compound binds with a stronger affinity to a PCNA protein that is acetylated than to the same PCNA protein that is not acetylated. In embodiments, the compound binds with a stronger affinity to a PCNA protein that is not acetylated than to the same PCNA protein that is acetylated. In embodiments, the compound binds with a stronger affinity to a PCNA protein that is glycosylated than to the same PCNA protein that is not glycosylated. In embodiments, the compound binds with a stronger affinity to a PCNA protein that is not glycosylated than to the same PCNA protein that is glycosylated. In embodiments, the compound binds with a stronger affinity to a PCNA protein that is lipidated than to the same PCNA protein that is not lipidated. In embodiments, the compound binds with a stronger affinity to a PCNA protein that is not lipidated than to the same PCNA protein that is lipidated. In embodiments, the compound binds with a stronger affinity to a PCNA protein that is poly(ADP) ribosylated than to the same PCNA protein that is not poly(ADP) ribosylated. In embodiments, the compound binds with a stronger affinity to a PCNA protein that is not poly(ADP) ribosylated than to the same PCNA protein that is poly(ADP) ribosylated. In embodiments, the compound binds with a stronger affinity to a PCNA protein that is post-translationally modified with a methylester of an acidic amino acid than to the same PCNA protein that is not post-translationally modified with the methylester of an acidic amino acid. In embodiments, the compound binds with a stronger affinity to a PCNA protein that is not post-translationally modified with a methylester of an acidic amino acid than to the same PCNA protein that is post-translationally modified with the methylester of an acidic amino acid. In embodiments, the post-translational modification is on an amino acid in the sequence corresponding to human PCNA M121 to Y133. In embodiments, the post-translational modification is on an amino acid in the sequence corresponding to human PCNA L126 to Y133. In embodiments, an increase or decrease (e.g., in binding or activity or level of protein or function, as described herein above) associated with a compound described herein, is in comparison to a control (e.g., identical experiment or conditions except for the absence of the compound described herein).

In embodiments, the compound (e.g., described herein) has a half-life of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 20, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 hours. In embodiments, the compound (e.g., described herein) has a half-life of about 1, 2, 3, 4, 5, 6, 7, 8, 9, 10, 11, 12, 13, 14, 15, 16, 17, 18, 19, 20, 21, 2, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 20, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 hours. In embodiments, the compound (e.g., described herein) has a half-life of 1, 2, 3, 4, 5, 6, 7, 8, 9, 10, 11, 12, 13, 14, 15, 16, 17, 18, 19, 20, 21, 2, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 20, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 hours. In embodiments, the half-life is a plasma half-life. In embodiments, the half-life is a tissue half-life. In embodiments, the half-life is the half-life in a cell. In embodiments, the half-life is a blood half-life.

In embodiments, a compound is a compound described herein, including in an aspect, embodiment, table, figure, example, scheme, or claim.

C. Pharmaceutical Compositions

In another aspect is provided a pharmaceutical composition including a pharmaceutically acceptable excipient and a compound, or pharmaceutically acceptable salt thereof, as described herein, including embodiments.

Pharmaceutical compositions provided by the present invention include compositions wherein the active ingredient (e.g., compound described herein) is contained in a therapeutically effective amount, i.e., in an amount effective to achieve its intended purpose. The actual amount effective for a particular application will depend, inter alia, on the condition being treated. When administered in methods to treat a disease, such compositions will contain an amount of active ingredient effective to achieve the desired result, e.g., inhibiting cell proliferation. Determination of a therapeutically effective amount of a compound of the invention is well within the capabilities of those skilled in the art, especially in light of the detailed disclosure herein. In embodiments, the pharmaceutical composition may include a second agent. In embodiments, the second agent is an anti-cancer agent. In embodiments, the second agent is a chemotherapeutic agent. In embodiments, the second agent is included in a therapeutically effective amount. In embodiments, the second agent is an agent for treating brain cancer. In embodiments, the second agent is an agent for treating neuroblastoma. In embodiments, the second agent is an agent for treating glioblastoma. In embodiments, the second agent is an agent for treating a central nervous system (CNS) cancer. In embodiments, the second agent is an agent for treating a sympathetic nervous system (SNS) cancer. In embodiments, the second agent is an agent for treating an adrenal gland cancer. In embodiments, the second agent is an agent for treating a cancer of a neuron in the neck, chest, abdomen, or pelvis. In embodiments, the second agent is an agent for treating esthesioneuroblastoma. In embodiments, the second agent includes stem cells (e.g., bone marrow or hematopietic stem cells). In embodiments, the second agent is 13-cis-retinoic acid. In embodiments, the second agent is GM-CSF. In embodiments, the second agent is IL-2. In embodiments, the second agent is a platinum-based compound (e.g., anti-cancer agent). In embodiments, the second agent is cisplatin. In embodiments, the second agent is carboplatin. In embodiments, the second agent is oxaloplatin. In embodiments, the second agent is a DNA damaging agent or cytotoxic agent in routine clinical use for treating cancer. In embodiments, the second agent is an alkylating agent. In embodiments, the second agent is cyclophosphamide. In embodiments, the second agent is ifosfamide. In embodiments, the second agent is melphalan. In embodiments, the second agent is topoisomerase II inhibitor. In embodiments, the second agent is etoposide. In embodiments, the second agent is an anthracycline antibiotic. In embodiments, the second agent is doxorubicin. In embodiments, the second agent is a *vinca* alkaloid. In embodiments, the second agent is vincristine. In embodiments, the second agent is topotecan. In embodiments, the second agent is irinotecan.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances, which may also act as diluents, flavoring agents, binders, preservatives, tablet disintegrating agents, or an encapsulating material.

In powders, the carrier is a finely divided solid in a mixture with the finely divided active component (e.g. a compound provided herein). In tablets, the active component is mixed with the carrier having the necessary binding properties in suitable proportions and compacted in the shape and size desired. The powders and tablets preferably contain from 5% to 70% of the active compound.

Suitable solid excipients include, but are not limited to, magnesium carbonate; magnesium stearate; talc; pectin; dextrin; starch; tragacanth; a low melting wax; cocoa butter; carbohydrates; sugars including, but not limited to, lactose, sucrose, mannitol, or sorbitol, starch from corn, wheat, rice, potato, or other plants; cellulose such as methyl cellulose, hydroxypropylmethyl-cellulose, or sodium carboxymethyl-cellulose; and gums including arabic and tragacanth; as well as proteins including, but not limited to, gelatin and collagen. If desired, disintegrating or solubilizing agents may be added, such as the cross-linked polyvinyl pyrrolidone, agar, alginic acid, or a salt thereof, such as sodium alginate.

Dragees cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage). Pharmaceutical preparations of the invention can also be used orally using, for example, push-fit capsules made of gelatin, as well as soft, sealed capsules made of gelatin and a coating such as glycerol or sorbitol.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

When parenteral application is needed or desired, particularly suitable admixtures for the compounds of the invention are injectable, sterile solutions, preferably oily or aqueous solutions, as well as suspensions, emulsions, or implants, including suppositories. In particular, carriers for parenteral administration include aqueous solutions of dextrose, saline, pure water, ethanol, glycerol, propylene glycol, peanut oil, sesame oil, polyoxyethylene-block polymers, and the like. Ampules are convenient unit dosages. The compounds of the invention can also be incorporated into liposomes or administered via transdermal pumps or patches. Pharmaceutical admixtures suitable for use in the present invention are well-known to those of skill in the art and are described, for example, in Pharmaceutical Sciences (17th Ed., Mack Pub. Co., Easton, Pa.) and WO 96/05309, the teachings of both of which are hereby incorporated by reference.

Aqueous solutions suitable for oral use can be prepared by dissolving the active component (e.g. compounds described herein, including embodiments, examples, compounds of Table 1) in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Also included are solid form preparations that are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

Oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, *J. Pharmacol. Exp. Ther.* 281:93-102, 1997. The pharmaceutical formulations of the invention can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

The compounds of the invention can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation).

In embodiments, the pharmaceutical composition further includes an anti-cancer agent. In embodiments, the anti-cancer agent is a platinum-based compound. In embodiments, the anti-cancer agent is cisplatin. In embodiments, the anti-cancer agent is oxaloplatin. In embodiments, the anti-cancer agent is carboplatin. In embodiments, the pharmaceutical composition includes a compound as described herein and a second agent, for example an anti-cancer agent (e.g., cisplatin, oxaloplatin, or carboplatin). In embodiments, the pharmaceutical composition further includes 13-cis-retinoid acid.

The compounds of the present invention can be prepared and administered in a wide variety of oral, parenteral and topical dosage forms. Oral preparations include tablets, pills, powder, dragees, capsules, liquids, lozenges, cachets, gels, syrups, slurries, suspensions, etc., suitable for ingestion by the patient. The compounds of the present invention can also be administered by injection, that is, intravenously, intramuscularly, intracutaneously, subcutaneously, intraduodenally, or intraperitoneally. Also, the compounds described herein can be administered by inhalation, for example, intranasally. Additionally, the compounds of the present invention can be administered transdermally. It is also envisioned that multiple routes of administration (e.g., intramuscular, oral, transdermal) can be used to administer the compounds of the invention. Accordingly, the present invention also provides pharmaceutical compositions comprising a pharmaceutically acceptable excipient and one or more compounds of the invention.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 10000 mg, more typically 1.0 mg to 1000 mg, most typically 10 mg to 500 mg, according to the particular application and the potency of the active component. The quantity of active compound may also be defined as mg/kg, ranging from about 0.1 mg/kg to 500 mg/kg. For example, the active compound can be administered in an amount of 30 mg/kg. The composition can, if desired, also contain other compatible therapeutic agents.

Some compounds may have limited solubility in water and therefore may require a surfactant or other appropriate co-solvent in the composition. Such co-solvents include: Polysorbate 20, 60 and 80; Pluronic F-68, F-84 and P-103; cyclodextrin; polyoxyl 35 castor oil; or other agents known to those skilled in the art. Such co-solvents are typically employed at a level between about 0.01% and about 2% by weight.

Viscosity greater than that of simple aqueous solutions may be desirable to decrease variability in dispensing the formulations, to decrease physical separation of components of a suspension or emulsion of formulation and/or otherwise to improve the formulation. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose, chondroitin sulfate and salts thereof, hyaluronic acid and salts thereof, combinations of the foregoing, and other agents known to those skilled in the art. Such agents are typically employed at a level between about 0.01% and about 2% by weight. Determination of acceptable amounts of any of the above adjuvants is readily ascertained by one skilled in the art.

The ratio between toxicity and therapeutic effect for a particular compound is its therapeutic index and can be expressed as the ratio between $LD_{50}$ (the amount of compound lethal in 50% of the population) and $ED_{50}$ (the amount of compound effective in 50% of the population). Compounds that exhibit high therapeutic indices are preferred. Therapeutic index data obtained from cell culture assays and/or animal studies can be used in formulating a range of dosages for use in humans. The dosage of such compounds preferably lies within a range of plasma concentrations that include the $ED_{50}$ with little or no toxicity. The dosage may vary within this range depending upon the dosage form employed and the route of administration utilized. See, e.g. Fingl et al., In: THE PHARMACOLOGICAL BASIS OF THERAPEUTICS, Ch. 1, p. 1, 1975. The exact formulation, route of administration and dosage can be chosen by the individual physician in view of the patient's condition and the particular method in which the compound is used.

D. Methods of Treatment

In an aspect is provided, a method of treating cancer, wherein the method includes administering a compound described herein to a subject in need thereof. In embodiments, the method includes administering a therapeutically effective amount of the compound. In embodiments, the cancer is associated with an increased level of caPCNA compared to a control (e.g., non-malignant cells). In embodiments, the cancer includes cancer cells. In embodiments, the cancer cells are associated with an increased level of caPCNA compared to a control (e.g., non-malignant cells). In embodiments, the ratio of caPCNA:nmPCNA is increased compared to a control. In embodiments, the cancer expresses caPCNA. In embodiments, the cancer expresses an increased level caPCNA as compared to a control (e.g., benign cells).

In embodiments, the cancer cells associated with an increased level of caPCNA is cervical cancer, colon cancer, thyroid cancer, gastric cancer, ovarian cancer, breast cancer, lung cancer, uterine cancer, or Ductal carcinoma in situ (DCIS).

The compounds described herein are useful, inter alia, in methods of treating cancer. Such methods include administering to a subject in need thereof an effective amount of a compound described herein, including embodiments and pharmaceutically acceptable salts thereof. In embodiments, the compound is chosen from a table disclosed herein (e.g., Table 1, Table 3). In embodiments, the compound is chosen from Table 1. In embodiments, the compound is chosen from Table 3.

In embodiments, the cancer is neuroblastoma. In embodiments, the cancer is metastatic cancer. In embodiments, the cancer is breast cancer. In embodiments, the cancer is triple negative breast cancer. In embodiments, the cancer is metastatic breast cancer. In embodiments, the cancer is brain cancer. In embodiments, the cancer is glioblastoma. In embodiments, the cancer is astrocytoma. In embodiments, the cancer is glioma. In embodiments, the cancer is pancreatic cancer. In embodiments, the cancer is lympohoma. In embodiments, the cancer is chronic lymphoid leukemia (CLL). In embodiments, the cancer is non-Hodgkin's lymphoma. In embodiments, the cancer is skin cancer. In embodiments, the cancer is squamous cell carcinoma. In embodiments, the cancer is T lymphotrophic leukemia. In embodiments, the cancer is melanoma. In embodiments, the cancer is malignant melanoma. In embodiments, the cancer is lung cancer. In embodiments, the cancer is non-small cell lung cancer. In embodiments, the cancer is colon cancer. In embodiments, the cancer is prostate cancer. In embodiments, the cancer is ovarian cancer. In embodiments, the cancer is leukemia. In embodiments, the cancer is kidney cancer. In embodiments, the cancer may be prostate, thyroid, endocrine system, brain, breast, cervix, colon, head & neck, liver, kidney, lung, non-small cell lung, melanoma, mesothelioma, ovary, sarcoma, stomach, uterus, Medulloblastoma, colorectal cancer, pancreatic cancer. Additional examples may include, but are not limited to Hodgkin's Disease, Non-Hodgkin's Lymphoma, multiple myeloma, neuroblastoma, glioma, glioblastoma multiforme, ovarian cancer, neuroblstoma, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, or prostate cancer. In embodiments, the cancer is leukemia, myeloma, non-small cell lung cancer, colon cancer, central nervous system cancer, melanoma, ovarian cancer, renal cancer, prostate cancer, or breast cancer. In embodiments, the cancer is triple negative breast cancer. In embodiments, the cancer is a central nervous system (CNS) cancer. In embodiments, the cancer is a sympathetic nervous system (SNS) cancer. In embodiments, the cancer is an adrenal gland cancer. In embodiments, the cancer is a cancer of a neuron in the neck, chest, abdomen, or pelvis. In embodiments, the cancer is an esthesioneuroblastoma. In embodiments, the cancer is a stage 1 neuroblastoma (e.g., localized tumor confined to an area near the origin). In embodiments, the cancer is a a stage 2A neuroblastoma (e.g., Unilateral tumor with incomplete gross resection and/or identifiable ipsilateral and contralateral lymph node negative for tumor). In embodiments, the cancer is a a stage 2B neuroblastoma (e.g., Unilateral tumor with complete or incomplete gross resection; with ipsilateral lymph node positive for tumor; identifiable contralateral lymph node negative for tumor). In embodiments, the cancer is a a stage 3 neuroblastoma (e.g., Tumor infiltrating across midline with or without regional lymph node involvement; or unilateral tumor with contralateral lymph node involvement; or midline tumor with bilateral lymph node involvement). In embodiments, the cancer is a a stage 4 neuroblastoma (e.g., Dissemination of tumor to distant lymph nodes, bone marrow, bone, liver, or other organs except as defined by Stage 4S). In embodiments, the cancer is a a stage 4S neuroblastoma (e.g., Age <1 year old with localized primary tumor as described in Stage 1 or Stage 2 above, with dissemination limited to liver, skin, or bone marrow (less than 10 percent of nucleated bone marrow cells are tumors). In embodiments, the cancer is a stage L1 neuroblastoma (e.g., localized cancer without image-defined risk factors) according to the International Neuroblastoma Risk Group (INRG) staging system. In embodiments, the cancer is a stage L2 neuroblastoma (e.g., localized cancer with image-defined risk factors) according to the International Neuroblastoma Risk Group (INRG) staging system. In embodiments, the cancer is a stage M neuroblastoma (e.g., metastatic cancer) according to the International Neuroblastoma Risk Group (INRG) staging system. In embodiments, the cancer is a stage MS neuroblastoma (e.g., metastatic cancer "special" where MS is equivalent to stage 4S as described above) according to the International Neuroblastoma Risk Group (INRG) staging system. In embodiments, the cancer is a neuroblastoma risk stratification pre-treatment group, according to the International Neuroblastoma Risk Group (INRG) staging system, of very low. In embodiments, the cancer is a neuroblastoma risk stratification pre-treatment group, according to the International Neuroblastoma Risk Group (INRG) staging system, of low. In embodiments, the cancer is a neuroblastoma risk stratification pre-treatment group, according to the International Neuroblastoma Risk Group (INRG) staging system, of intermediate. In embodiments, the cancer is a neuroblastoma risk stratification pre-treatment group, according to the International Neuroblastoma Risk Group (INRG) staging system, of high risk.

In embodiments, the cancer is cervical cancer, colon cancer, thyroid cancer, gastric cancer, ovarian cancer, breast cancer, lung cancer, uterine cancer, or Ductal carcinoma in situ (DCIS). In embodiments, the cancer is cervical cancer. In embodiments, the cancer is colon cancer. In embodiments, the cancer is thyroid cancer. In embodiments, the cancer is gastric cancer. In embodiments, the cancer is ovarian cancer. In embodiments, the cancer is breast cancer. In embodiments, the cancer is lung cancer. In embodiments, the cancer is uterine cancer. In embodiments, the cancer is Ductal carcinoma in situ (DCIS).

In embodiments, the cancer is esophageal adenocarcinoma. In embodiments, the cancer is stage 0 esophageal cancer. In embodiments, the cancer is stage I esophageal cancer. In embodiments, the cancer is stage IA esophageal cancer. In embodiments, the cancer is stage IB esophageal cancer. In embodiments, the cancer is stage IIA esophageal cancer. In embodiments, the cancer is stage IIB esophageal cancer. In embodiments, the cancer is stage IIIA esophageal cancer. In embodiments, the cancer is stage IIIB esophageal cancer. In embodiments, the cancer is stage IIIC esophageal cancer. In embodiments, the cancer is stage IV esophageal cancer. In embodiments, the cancer is stage I esophageal adenocarcinoma. In embodiments, the cancer is colorectal cancer. In embodiments, the cancer is prostate cancer (e.g., prostatic adenocarcinoma). In embodiments, the cancer is high-grade prostatic intraepithelial neoplasia (PIN). In embodiments, the cancer is associated with Barrett's esophagus. In embodiments, the cancer is associated with Barrett's esophagus without epithelial dysplasia. In embodiments, the cancer is associated with Barrett's esophagus with low grade epithelial dysplasia. In embodiments, the cancer is associated with Barrett's esophagus with high-grade epithelial dysplasia. In embodiments, the cancer is oesophagogastric junctional adenocarcinoma. In embodiments, the cancer is described in Hammoud et al (Z. T. Hammoud, et al. Journal of Thoracic & Cardiovascular Surgery 2006; 133(1):82-87); Wang X., et al. Prostate. 2011 May 15; 71(7):748-54; or Shen F., et al. J Cell Biochem. 2011 March; 112(3):756-60, which are incorporated by reference in their entirety for all purposes.

In embodiments, the compounds described herein are useful for methods of treating neuroblastoma. In embodiments, the compounds described herein are useful for methods of treating leukemia, non-small cell lung cancer, colon cancer, central nervous system cancer, melanoma, ovarian cancer, renal cancer, prostate cancer, or breast cancer.

Compounds described herein also inhibit cell proliferation in neuroblastoma cancer (e.g., cancer characterized by the cell line BE(2)-C, SK-N-BE(2), SK-N-SH, SH-SY5Y, IMR-32, SK-N-AS, SK-N-MC, MC-IXC, SHP-77, SK-N-FI, SK-N-DZ, CHP-212, BE(2)-M17, SK-N-FI, K-PN-DW, LA-N-2, LA-N-1, or LAN5). Compounds described herein also inhibit cell proliferation in neuroblastoma cancer cell lines. For example, these neuroblastoma cancer cell lines include BE(2)-C, SK-N-BE(2), SK-N-SH, SH-SY5Y, IMR-32, SK-N-AS, SK-N-MC, MC-IXC, SHP-77, SK-N-FI, SK-N-DZ, CHP-212, BE(2)-M17, SK-N-FI, K-PN-DW, LA-N-2, LA-N-1, and LAN5.

In embodiments, the cancer is a cancer identified in Table 6. Compounds described herein also inhibit cell proliferation in breast cancer (e.g., cancer characterized by the cell line BT-549, HS 578T, MCF7, MDA-MB-231/ATCC, MDA-MB-468, or T-47D). Compounds described herein also inhibit cell proliferation in central nervous system cancer (e.g., cancer characterized by the cell line SF-268, SF-295, SF-539, SNB-19, SNB-75, or U251). Compounds described herein also inhibit cell proliferation in colon cancer (e.g., cancer characterized by the cell line COLO 208, HCC-2998, HCT-116, HCT-15, HT29, KM12, or SW-620). Compounds described herein also inhibit cell proliferation in leukemia or myeloma (e.g., cancer characterized by the cell line CCRF-CEM, HL-60(TB), K-562, MOLT-4, RPMI-8226, or SR). Compounds described herein also inhibit cell proliferation in melanoma (e.g., cancer characterized by the cell line the LOX IMVI, MALME-3M, M14, MDA-MB-435, SK-MEL-2, SK-MEL-28, SK-MEL-5, UACC-257, or UACC-62). Compounds described herein also inhibit cell proliferation in Non-Small Cell Lung cancer (e.g., cancer characterized by the cell line A549/ATCC, EKVX, HOP-62, HOP-92, NCI-H226, NCI-H23, NCI-H322M, NCI-H460, or NCI-H522). Compounds described herein also inhibit cell proliferation in ovarian cancer (e.g., cancer characterized by the cell line IGROV1, NCI/ADR-RES, OVCAR-3, OVCAR-4, OVCAR-5, OVCAR-8, or SK-OV-3). Compounds described herein also inhibit cell proliferation in prostate cancer (e.g., cancer characterized by the cell line DU-145 or PC-3). Compounds described herein also inhibit cell proliferation in renal cancer (e.g., cancer characterized by the cell line 786-0, A498, ACHN, CAKI-1, RXF 393, SN12C, TK-10, or UO-31).

In embodiments, the cancer is a cancer identified in Table 6. Compounds described herein also inhibit cell proliferation in breast cancer cell lines. For example, these breast cancer cell lines include BT-549, HS 578T, MCF7, MDA-MB-231/ATCC, MDA-MB-468, and T-47D. Compounds described herein also inhibit cell proliferation in central nervous system cancer cell lines. For example, these central nervous system cancer cell lines include SF-268, SF-295, SF-539, SNB-19, SNB-75, and U251. Compounds described herein also inhibit cell proliferation in colon cancer cell lines. For example, these colon cancer cell lines include COLO 208, HCC-2998, HCT-116, HCT-15, HT29, KM12, and SW-620. Compounds described herein also inhibit cell proliferation in leukemia or myeloma cell lines. For example, these leukemia or myeloma cell lines include CCRF-CEM, HL-60(TB), K-562, MOLT-4, RPMI-8226, and SR. Compounds described herein also inhibit cell proliferation in melanoma cell lines. For example, these melanoma cell lines include LOX IMVI, MALME-3M, M14, MDA-MB-435, SK-MEL-2, SK-MEL-28, SK-MEL-5, UACC-257, and UACC-62. Compounds described herein also inhibit cell proliferation in Non-Small Cell Lung cancer cell lines. For example, these Non-Small Cell Lung cancer cell lines include A549/ATCC, EKVX, HOP-62, HOP-92, NCI-H226, NCI-H23, NCI-H322M, NCI-H460, and NCI-H522. Compounds described herein also inhibit cell proliferation in ovarian cancer cell lines. For example, these ovarian cancer cell lines include IGROV1, NCI/ADR-RES, OVCAR-3, OVCAR-4, OVCAR-5, OVCAR-8, and SK-OV-3. Compounds described herein also inhibit cell proliferation in prostate cancer cell lines. For example, these prostate cancer cell lines include DU-145 and PC-3. Compounds described herein also inhibit cell proliferation in renal cancer cell lines. For example, these renal cancer cell lines include 786-0, A498, ACHN, CAKI-1, RXF 393, SN12C, TK-10, and UO-31.

In another aspect a compound described herein is provided, including embodiments (e.g. compound of formula (I), (II), (III), (IV), or (V), or any embodiment thereof; or in an example, table, figure, or claim), for use as a medicament.

In another aspect is provided, a method of treating a disease associated with PCNA activity, wherein the method includes administering a compound described herein to a subject in need thereof. In embodiments, the method includes administering a therapeutically effective amount of the compound. In embodiments the disease is Barrett's esophagus.

In embodiments, the method includes administering a second agent (e.g., therapeutic agent). In embodiments, the second agent is an anti-cancer agent. In embodiments, the anti-cancer agent is a platinum-based compound. In embodiments, the anti-cancer agent is cisplatin. In embodiments, the anti-cancer agent is oxaloplatin. In embodiments, the anti-cancer agent is carboplatin. In embodiments, the anti-cancer agent is a DNA damaging agent or cytotoxic agent in routine clinical use for treating cancer. In embodiments, the method includes administration of high-dose chemotherapy. In embodiments, the method includes stem cell transplantation (HDCT/autoSCT). In embodiments, the method includes administration of 13-cis-retinoid acid. In embodiments, the method includes administration of immunotherapy. In embodiments, the method includes administration of radiation. In embodiments, the second agent is a chemotherapeutic agent. In embodiments, the second agent is included in a therapeutically effective amount. In embodiments, the second agent is an agent for treating brain cancer. In embodiments, the second agent is an agent for treating neuroblastoma. In embodiments, the second agent is an agent for treating glioblastoma. In embodiments, the second agent is an agent for treating a central nervous system (CNS) cancer. In embodiments, the second agent is an agent for treating a sympathetic nervous system (SNS) cancer. In embodiments, the second agent is an agent for treating an adrenal gland cancer. In embodiments, the second agent is an agent for treating a cancer of a neuron in the neck, chest, abdomen, or pelvis. In embodiments, the second agent is an agent for treating esthesioneuroblastoma. In embodiments, the second agent includes stem cells (e.g., bone marrow or hematopietic stem cells). In embodiments, the second agent is 13-cis-retinoic acid. In embodiments, the second agent is GM-CSF. In embodiments, the second agent is IL-2. In embodiments, the second agent is a platinum-based compound (e.g., anti-cancer agent). In embodiments, the second agent is cisplatin. In embodiments, the second agent is carboplatin. In embodiments, the second agent is oxaloplatin. In embodiments, the second agent is a DNA damaging agent or cytotoxic agent in routine clinical use for treating cancer. In embodiments, the second agent is an alkylating agent. In embodiments, the second agent is cyclophosphamide. In embodiments, the second agent is ifosfamide. In embodiments, the second agent is melphalan. In embodiments, the second agent is topoisomerase II inhibitor. In embodiments, the second agent is etoposide. In embodiments, the second agent is an anthracycline antibiotic. In embodiments, the second agent is doxorubicin. In embodiments, the second agent is a *vinca* alkaloid. In embodiments, the second agent is vincristine. In embodiments, the second agent is topotecan. In embodiments, the second agent is irinotecan.

In embodiments, the disease is cancer (e.g., a cancer described herein, including neuroblastoma). In embodiments, the disease is systemic lupus erythematosus (SLE). In embodiments, the disease is mycosis fungoides.

E. Methods of Inhibiting PCNA

In another aspect is provided, a method of inhibiting PCNA activity, wherein the method includes contacting PCNA with an effective amount of a compound described herein. In embodiments contacting includes allowing a compound described herein to interact with a protein of SEQ ID NO:2. In embodiments contacting includes allowing a compound described herein to interact with a protein of SEQ ID NO:3. In embodiments contacting includes allowing a compound described herein to interact with a protein of SEQ ID NO:4.

The compounds described herein are useful, inter alia, in methods of inhibiting PCNA activity in a subject in need thereof, including administering to the subject an effective amount of a compound as described herein, or a pharmaceutically acceptable salt thereof.

In embodiments, the PCNA is a human PCNA.

In embodiments, modulation of PCNA activity results in modulation of DNA replication, DNA repair, and the cell cycle. For example, inhibition of PCNA function induces cell cycle arrest resulting in apoptosis of cancer cells, i.e. neuroblastoma cells.

In another aspect, compounds described herein are useful, inter alia, in a method of treating a disease associated with PCNA activity in a patient in need of such treatment, said method comprising administering a therapeutically effective amount of a compound described herein, or a pharmaceutically acceptable salt thereof.

EMBODIMENTS

Embodiment 1

A compound having the formula:

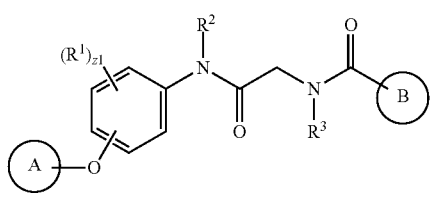

(I)

wherein

Ring A is substituted or unsubstituted phenyl or substituted or unsubstituted 5 to 6 membered heteroaryl;

Ring B is substituted or unsubstituted naphthyl, substituted or unsubstituted quinolinyl, or substituted or unsubstituted isoquinolinyl;

$R^1$ is independently a halogen, $-CX^1_3$, $-CHX^1_2$, $-CH_2X^1$, $-CN$, $-SO_2Cl$, $-SO_{n1}R^{10}$, $-SO_{v1}NR^7R^8$, $-NHNH_2$, $-ONR^7R^8$, $-NHC=(O)$ $NHNH_2$, $-NHC=(O)NR^7R^8$, $-N(O)_{m1}$, $-NR^7R^8$, $-C(O)R^9$, $-C(O)-OR^9$, $-C(O)NR^7R^8$, $-OR^{10}$, $-NR^7SO_2R^{10}$, $-NR^7C=(O)R^9$, $-NR^7C(O)-OR^9$, $-NR^7OR^9$, $-OCX^1_3$, $-OCHX^1_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^1$ substituents may optionally be joined to form a substituted or unsubstituted cycloalkyl, substituted or unsubstituted heterocycloalkyl, substituted or unsubstituted aryl, or substituted or unsubstituted heteroaryl;

$R^2$ is independently hydrogen, halogen, $-CX^2_3$, $-CHX^2_2$, $-CH_2X^2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)$ $NHNH_2$, $-NHC=(O)$ $NH_2$, $-NHSO_2H$, $-NHC=(O)H$, $-NHC(O)-OH$, $-NHOH$, $-OCX^2_3$, $-OCHX^2_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^3$ is independently hydrogen, halogen, $-CX^3_3$, $-CHX^3_2$, $-CH_2X^3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)$ $NHNH_2$, $-NHC=(O)$ $NH_2$, $-NHSO_2H$, $-NHC=(O)H$, $-NHC(O)-OH$, $-NHOH$, $-OCX^3_3$, $-OCHX^3_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^7$, $R^8$, $R^9$, and $R^{10}$ are independently hydrogen, halogen, $-CX^A_3$, $-CHX^A_2$, $-CH_2X^A$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)$ $NH_2$, $-NHSO_2H$, $-NHC=(O)H$, $-NHC(O)-OH$, $-NHOH$, $-OCX^A_3$, $-OCHX^A_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and $R^8$ substituents bonded to the same nitrogen atom may optionally be joined to form a substituted or unsubstituted heterocycloalkyl or substituted or unsubstituted heteroaryl;

z1 is independently an integer from 0 to 4;

m1 and v1 are independently 1 or 2;

n1 is independently an integer from 0 to 4;

$X^1$, $X^2$, $X^3$, and $X^A$ are independently $-Cl$, $-Br$, $-I$, or $-F$.

Embodiment 2

The compound of embodiment 1, having the formula:

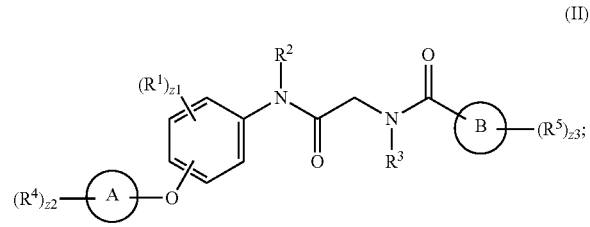

(II)

wherein $R^4$ is independently a halogen, $-CX^4_3$, $-CHX^4_2$, $-CH_2X^4$, $-CN$, $-SO_2Cl$, $-SO_{n4}R^{14}$, —SO$_{v4}$NR$^{11}$R$^{12}$, —NHNH$_2$, —ONR$^{11}$R$^{12}$, —NHC=(O)NHNH$_2$, —NHC=(O)NR$^{11}$R$^{12}$, -N(O)$_{m4}$, —NR$^{11}$R$^{12}$, —C(O)—OR$^{13}$, —C(O)NR$^{11}$R$^{12}$, —OR$^{13}$, —C(O)NR$^{11}$R$^{12}$, —OR$^{14}$, —NR$^{11}$SO$_2$R$^{14}$, —NR$^{11}$C=(O)R$^{13}$, NR$^{11}$OR$^{13}$, —NR$^{11}$OR$^{13}$, —OCX$^4_2$, —OCHX$^4_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent R$^4$ substituents may optionally be joined to form a substituted or unsubstituted cycloalkyl, substituted or unsubstituted heterocycloalkyl, substituted or unsubstituted aryl, or substituted or unsubstituted heteroaryl;

R$^5$ is independently a halogen, —CX$^5_3$, —CHX$^5_2$, —CH$_2$X$^5$, —CN, —SO$_2$Cl, —SO$_{n5}$R$^{18}$, —SO$_{v5}$NR$^{15}$R$^{16}$, —NHNH$_2$, —ONR$^{15}$R$^{16}$, —NHC=(O)NHNH$_2$, —NHC=(O)NR$^{15}$R$^{16}$, —N(O)$_{m5}$, —NR$^{15}$R$^{16}$, —C(O)—OR$^{17}$, —C(O)NR$^{15}$R$^{16}$, —OR$^{18}$, —NR$^{15}$SO$_2$R$^{18}$, —NR$^{15}$C=(O)R$^{17}$, —NR$^{15}$C(O)—OR$^{17}$, —NR$^{15}$OR$^{17}$, —OCX$^5_3$, —OCHX$^5_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent R$^5$ substituents may optionally be joined to form a substituted or unsubstituted cycloalkyl, substituted or unsubstituted heterocycloalkyl, substituted or unsubstituted aryl, or substituted or unsubstituted heteroaryl;

R$^{11}$, R$^{12}$, R$^{13}$, and R$^{14}$ are independently hydrogen, halogen, —CX$^B_3$, —CHX$^B_2$, —CH$_2$X$^B$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCX$^B_3$, —OCHX$^B_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and R$^{12}$ substituents bonded to the same nitrogen atom may optionally be joined to form a substituted or unsubstituted heterocycloalkyl or substituted or unsubstituted heteroaryl;

R$^{15}$, R$^{16}$, R$^{17}$, and R$^{18}$ are independently hydrogen, halogen, —CX$^C_3$, —CHX$^C_2$, —CH$_2$X$^C$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCX$^C_3$, —OCHX$^C_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{15}$ and R$^{16}$ substituents bonded to the same nitrogen atom may optionally be joined to form a substituted or unsubstituted heterocycloalkyl or substituted or unsubstituted heteroaryl;

z2 is independently an integer from 0 to 5;
z3 is independently an integer from 0 to 7;
m5, m5, v4 and v5 are independently 1 or 2;
n4 and n5 are independently an integer from 0 to 4;
X$^4$, X$^5$, X$^B$, and X$^C$ are independently —Cl, —Br, —I, or —F Embodiment 3

The compound of one of embodiments 1 to 2, having the formula:

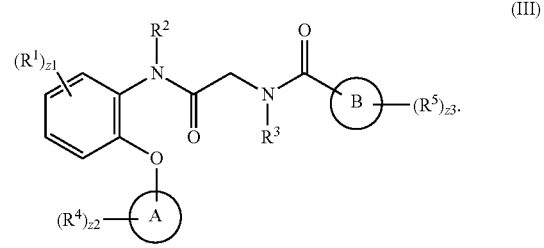

(III)

Embodiment 4

The compound of one of embodiments 1 to 2, having the formula:

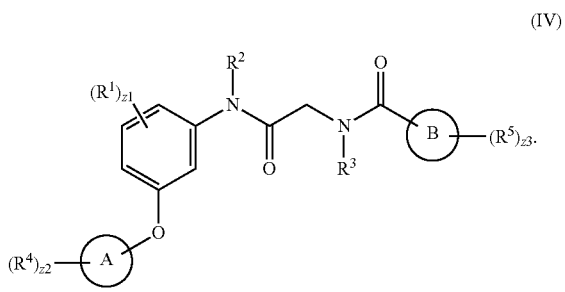

(IV)

Embodiment 5

The compound of one of embodiments 1 to 2, having the formula:

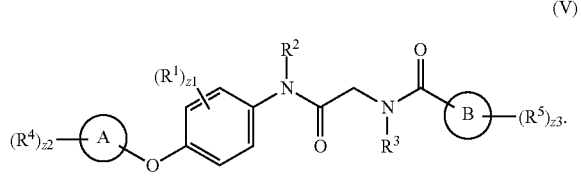

(V)

Embodiment 6

The compound of one of embodiments 1 to 5, wherein Ring A is phenyl.

Embodiment 7

The compound of one of embodiments 1 to 5, wherein Ring A is a 5 to 6 membered heteroaryl.

Embodiment 8

The compound of one of embodiments 1 to 5, wherein Ring A is a thienyl.

Embodiment 9

The compound of one of embodiments 1 to 5, wherein Ring A is a 2-thienyl.

Embodiment 10

The compound of one of embodiments 1 to 5, wherein Ring A is a 3-thienyl.

Embodiment 11

The compound of one of embodiments 1 to 5, wherein Ring A is a pyridyl.

Embodiment 12

The compound of one of embodiments 1 to 5, wherein Ring A is a 2-pyridyl.

Embodiment 13

The compound of one of embodiments 1 to 5, wherein Ring A is a 3-pyridyl.

Embodiment 14

The compound of one of embodiments 1 to 5, wherein Ring A is a 4-pyridyl.

Embodiment 15

The compound of one of embodiments 1 to 14, wherein Ring B is a naphthyl.

Embodiment 16

The compound of one of embodiments 1 to 14, wherein Ring B is a 1-naphthyl.

Embodiment 17

The compound of one of embodiments 1 to 14, wherein Ring B is a 2-naphthyl.

Embodiment 18

The compound of one of embodiments 1 to 14, wherein Ring B is a quinolinyl.

Embodiment 19

The compound of one of embodiments 1 to 14, wherein Ring B is a isoquinolinyl.

Embodiment 20

The compound of one of embodiments 1 to 14, wherein Ring B is a 1-isoquinolinyl.

Embodiment 21

The compound of one of embodiments 1 to 14, wherein Ring B is a 3-isoquinolinyl.

Embodiment 22

The compound of one of embodiments 1 to 14, wherein Ring B is a 4-isoquinolinyl.

Embodiment 23

The compound of one of embodiments 1 to 22, wherein $R^1$ is independently halogen, —$CF_3$, —$CHF_2$, —$CH_2F$, —CN, —OH, —$NH_2$, —COOH, —$CONH_2$, —$NO_2$, —SH, —$OCF_3$, —$OCHF_2$, substituted or unsubstituted $C_1$-$C_8$ alkyl, substituted or unsubstituted 2 to 8 membered heteroalkyl, substituted or unsubstituted $C_3$-$C_8$ cycloalkyl, substituted or unsubstituted 3 to 8 membered heterocycloalkyl, substituted or unsubstituted $C_6$-$C_{10}$ aryl, or substituted or unsubstituted 5 to 10 membered heteroaryl.

Embodiment 24

The compound of one of embodiments 1 to 22, wherein $R^1$ is independently halogen, —$CF_3$, —OH, —$NH_2$, —SH, substituted or unsubstituted $C_1$-$C_4$ alkyl, substituted or unsubstituted 2 to 4 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl.

Embodiment 25

The compound of one of embodiments 1 to 22, wherein $R^1$ is independently halogen, —OH, —$NH_2$, —SH, unsubstituted $C_1$-$C_4$ alkyl, or unsubstituted 2 to 4 membered heteroalkyl.

Embodiment 26

The compound of one of embodiments 1 to 22, wherein $R^1$ is independently halogen, —OH, unsubstituted methyl, or unsubstituted methoxy.

Embodiment 27

The compound of one of embodiments 1 to 26, wherein z1 is 1.

Embodiment 28

The compound of one of embodiments 1 to 26, wherein z1 is 0.

Embodiment 29

The compound of one of embodiments 1 to 28, wherein $R^4$ is independently halogen, —$CF_3$, —$CHF_2$, —$CH_2F$, —CN, —OH, —$NH_2$, —COOH, —$CONH_2$, —$NO_2$, —SH, —$OCF_3$, —$OCHF_2$, substituted or unsubstituted $C_1$-$C_8$ alkyl, substituted or unsubstituted 2 to 8 membered heteroalkyl, substituted or unsubstituted $C_3$-$C_8$ cycloalkyl, substituted or unsubstituted 3 to 8 membered heterocycloalkyl, substituted or unsubstituted $C_6$-$C_{10}$ aryl, or substituted or unsubstituted 5 to 10 membered heteroaryl.

Embodiment 30

The compound of one of embodiments 1 to 28, wherein $R^4$ is independently halogen, —$CF_3$, —OH, —$NH_2$, —SH, substituted or unsubstituted $C_1$-$C_4$ alkyl, substituted or unsubstituted 2 to 4 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl.

Embodiment 31

The compound of one of embodiments 1 to 28, wherein $R^4$ is independently halogen, —OH, —NH$_2$, —SH, unsubstituted $C_1$-$C_4$ alkyl, or unsubstituted 2 to 4 membered heteroalkyl.

Embodiment 32

The compound of one of embodiments 1 to 28, wherein $R^4$ is independently halogen, —OH, unsubstituted methyl, or unsubstituted methoxy.

Embodiment 33

The compound of one of embodiments 1 to 32, wherein z2 is 1.

Embodiment 34

The compound of one of embodiments 1 to 32, wherein z2 is 0.

Embodiment 35

The compound of one of embodiments 1 to 34, wherein $R^5$ is independently halogen, —CF$_3$, —CHF$_2$, —CH$_2$F, —CN, —OH, —NH$_2$, —COOH, —CONH$_2$, —NO$_2$, —SH, —OCF$_3$, —OCHF$_2$, substituted or unsubstituted $C_1$-$C_8$ alkyl, substituted or unsubstituted 2 to 8 membered heteroalkyl, substituted or unsubstituted $C_3$-$C_8$ cycloalkyl, substituted or unsubstituted 3 to 8 membered heterocycloalkyl, substituted or unsubstituted $C_6$-$C_{10}$ aryl, or substituted or unsubstituted 5 to 10 membered heteroaryl.

Embodiment 36

The compound of one of embodiments 1 to 34, wherein $R^5$ is independently halogen, —CF$_3$, —OH, —NH$_2$, —SH, substituted or unsubstituted $C_1$-$C_4$ alkyl, substituted or unsubstituted 2 to 4 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl.

Embodiment 37

The compound of one of embodiments 1 to 34, wherein $R^5$ is independently halogen, —OH, —NH$_2$, —SH, unsubstituted $C_1$-$C_4$ alkyl, or unsubstituted 2 to 4 membered heteroalkyl.

Embodiment 38

The compound of one of embodiments 1 to 34, wherein $R^5$ is independently halogen, —OH, unsubstituted methyl, or unsubstituted methoxy.

Embodiment 39

The compound of one of embodiments 1 to 38, wherein z3 is 1.

Embodiment 40

The compound of one of embodiments 1 to 38, wherein z3 is 0.

Embodiment 41

The compound of one of embodiments 1 to 40, wherein $R^2$ is independently hydrogen, —CX$^2_3$, —CHX$^2_2$, —CH$_2$X$^2$, —CN, —C(O)H, —C(O)OH, —C(O)NH$_2$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl.

Embodiment 42

The compound of one of embodiments 1 to 40, wherein $R^2$ is independently hydrogen, unsubstituted methyl, unsubstituted ethyl, or unsubstituted isopropyl.

Embodiment 43

The compound of one of embodiments 1 to 40, wherein $R^2$ is independently hydrogen.

Embodiment 44

The compound of one of embodiments 1 to 43, wherein $R^3$ is independently hydrogen, —CX$^2_3$, —CHX$^2_2$, —CH$_2$X$^2$, —CN, —C(O)H, —C(O)OH, —C(O)NH$_2$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl.

Embodiment 45

The compound of one of embodiments 1 to 43, wherein $R^3$ is independently hydrogen, unsubstituted methyl, unsubstituted ethyl, or unsubstituted isopropyl.

Embodiment 46

The compound of one of embodiments 1 to 43, wherein $R^3$ is independently hydrogen.

Embodiment 47

The compound of embodiment 1, having the formula:

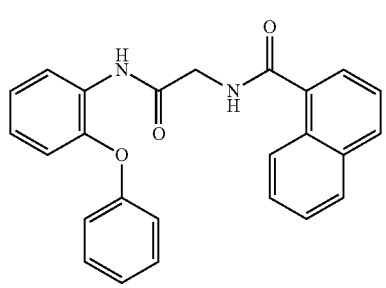 [SMILES: O=C(CNC(=O)c1cccc2ccccc12)Nc1ccccc1Oc1ccccc1]

Embodiment 48

The compound of embodiment 1, having the formula:

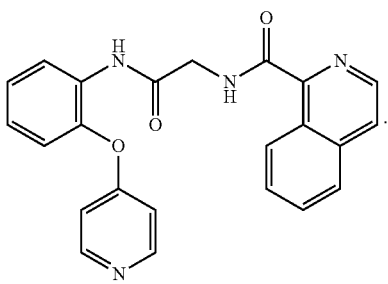 [SMILES: O=C(CNC(=O)c1nccc2ccccc12)Nc1ccccc1Oc1ccncc1]

Embodiment 49

The compound of embodiment 1, having the formula:

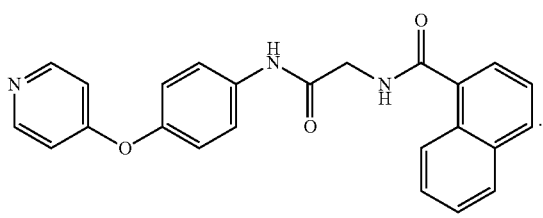 [SMILES: O=C(CNC(=O)c1cccc2ccccc12)Nc1ccc(Oc2ccncc2)cc1]

Embodiment 50

A pharmaceutical composition comprising a compound of one of embodiments 1 to 49 or a pharmaceutically acceptable salt thereof, and a pharmaceutically acceptable excipient.

Embodiment 51

The pharmaceutical composition of embodiment 50, further comprising an anti-cancer agent.

Embodiment 52

The pharmaceutical composition of embodiment 51, wherein the anti-cancer agent is a platinum-based compound.

Embodiment 53

The pharmaceutical composition of embodiment 51, wherein the anti-cancer agent is a cisplatin.

Embodiment 54

A method of treating a disease associated with PCNA activity in a patient in need of such treatment, said method comprising administering a therapeutically effective amount of a compound of one of embodiments 1 to 49, or a pharmaceutically acceptable salt thereof.

Embodiment 55

A method of treating cancer in a patient in need of such treatment, said method comprising administering a therapeutically effective amount of a compound of one of embodiments 1 to 49, or a pharmaceutically acceptable salt thereof.

Embodiment 56

The method of embodiment 55, wherein said cancer is neuroblastoma.

Embodiment 57

A method of inhibiting PCNA activity, said method comprising contacting PCNA with an effective amount of a compound of one of embodiments 1 to 49, or a pharmaceutically acceptable salt thereof.

Embodiments contemplated herein include the following.

Embodiment 1A

A compound having the formula:

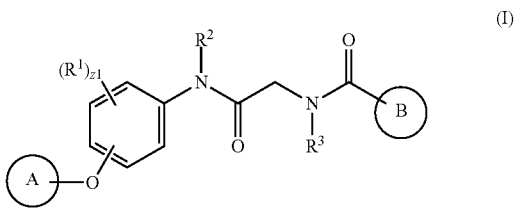

(I)

wherein Ring A is substituted or unsubstituted phenyl or substituted or unsubstituted 5 to 6 membered heteroaryl; Ring B is substituted or unsubstituted naphthyl, substituted or unsubstituted quinolinyl, or substituted or unsubstituted isoquinolinyl; $R^1$ is independently a halogen, $-CX^1_3$, $-CHX^1_2$, $-CH_2X^1$, $-CN$, $-SO_2Cl$, $-SO_{n1}R^{10}$, $-SO_{v1}NR^7R^8$, $-NHNH_2$, $-ONR^7R^8$, $-NHC=(O)NHNH_2$, $-NHC=(O)NR^7R^8$, $-N(O)_{m1}$, $-NR^7R^8$, $-C(O)R^9$, $-C(O)-OR^9$, $-C(O)NR^7R^8$, $-OR^{10}$, $-NR^7SO_2R^{10}$, $-NR^7C=(O)R^9$, $-NR^7C(O)-OR^9$, $-NR^7OR^9$, $-OCX^1_3$, $-OCHX^1_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^1$ substituents may optionally be joined to form a substituted or unsubstituted cycloalkyl, substituted or unsubstituted heterocycloalkyl, substituted or unsubstituted aryl, or substituted or unsubstituted heteroaryl; $R^2$ is independently hydrogen, halogen, $-CX^2_3$, $-CHX^2_2$, $-CH_2X^2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)$ $NH_2$, $-NHSO_2H$, $-NHC=(O)H$, $-NHC(O)-OH$, $-NHOH$, $-OCX^2_3$, $-OCHX^2_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^3$ is independently hydrogen, halogen, $-CX^3_3$, $-CHX^3_2$, $-CH_2X^3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)$ $NH_2$, $-NHSO_2H$, $-NHC=(O)H$, $-NHC(O)-OH$, $-NHOH$, $-OCX^3_3$, $-OCHX^3_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^7$, $R^8$, $R^9$, and $R^{10}$ are independently hydrogen, halogen, $-CX^A_3$, $-CHX^A_2$, $-CH_2X^A$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^A_3$, $-OCHX^A_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^7$ and $R^8$ substituents bonded to the same nitrogen atom may optionally be joined to form a substituted or unsubstituted heterocycloalkyl or substituted or unsubstituted heteroaryl; z1 is independently an integer from 0 to 4; m1 and v1 are independently 1 or 2; n1 is independently an integer from 0 to 4; $X^1$, $X^2$, $X^3$, and $X^4$ are independently $-Cl$, $-Br$, $-I$, or $-F$.

Embodiment 2A

The compound of embodiment 1A, having the formula:

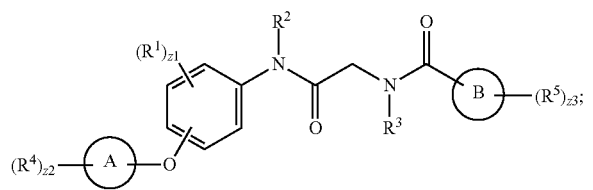

(II)

Wherein $R^4$ is independently a halogen, $-CX^4_3$, $-CHX^4_2$, $-CH_2X^4$, $-CN$, $-SO_2Cl$, $-SO_{n4}R^{14}$, $-SO_{v4}NR^{11}R^{12}$, $-NHNH_2$, $-ONR^{11}R^{12}$, $-NHC=(O)NHNH_2$, $-NHC=(O)NR^{11}R^{12}$, $-N(O)_{m4}$, $-NR^{11}R^{12}$, $-C(O)-OR^{13}$, $-C(O)NR^{11}R^{12}$, $-OR^{14}$, $-NR^{11}SO_2R^{14}$, $-NR^{11}C=(O)R^{13}$, $-NR^{11}C(O)-OR^{13}$, $-NR^{11}OR^{13}$, $-OCX^4_3$, $-OCHX^4_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^4$ substituents may optionally be joined to form a substituted or unsubstituted cycloalkyl, substituted or unsubstituted heterocycloalkyl, substituted or unsubstituted aryl, or substituted or unsubstituted heteroaryl; $R^5$ is independently a halogen, $-CX^5_3$, $-CHX^5_2$, $-CH_2X^5$, $-CN$, $-SO_2Cl$, $-SO_{n5}R^{18}$, $-SO_{v5}NR^{15}R^{16}$, $-NHNH_2$, $-ONR^{15}R^{16}$, $-NHC=(O)NHNH_2$, $-NHC=(O)NR^{15}R^{16}$, $-N(O)_{m5}$, $-NR^{15}R^{16}$, $-C(O)R^{17}$, $-C(O)-OR^{17}$, $-C(O)NR^{15}R^{16}$, $-OR^{18}$, $-NR^{15}SO_2R^{18}$, $-NR^{15}C=(O)R^{17}$, $-NR^{15}C(O)-OR^{17}$, $-NR^{15}OR^{17}$, $-OCX^5_3$, $-OCHX^5_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^5$ substituents may optionally be joined to form a substituted or unsubstituted cycloalkyl, substituted or unsubstituted heterocycloalkyl, substituted or unsubstituted aryl, or substituted or unsubstituted heteroaryl; $R^{11}$, $R^{12}$, $R^{13}$ and $R^{14}$ are independently hydrogen, halogen, $-CX^B_3$, $-CHX^B_2$, $-CH_2X^B$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^B_3$, $-OCHX^B_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{11}$ and $R^{12}$ substituents bonded to the same nitrogen atom may optionally be joined to form a substituted or unsubstituted heterocycloalkyl or substituted or unsubstituted heteroaryl; $R^{15}$, $R^{16}$, $R^{17}$, and $R^{18}$ are independently hydrogen, halogen, $-CX^C_3$, $-CHX^C_2$, $-CH_2X^C$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $ONH_2$, $-NHC=(O)NHNH_2$, $-NHC=(O)NH_2$, $-NHSO_2H$, $-NHC=(O)H$, $-NHC(O)-OH$, $-NHOH$, $-OCX^C_3$, $-OCHX^C_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{15}$ and $R^{16}$ substituents bonded to the same nitrogen atom may optionally be joined to form a substituted or unsubstituted heterocycloalkyl or substituted or unsubstituted heteroaryl; z2 is independently an integer from 0 to 5; z3 is independently an integer from 0 to 7; m4, m5, v4 and v5 are independently 1 or 2; n4 and n5 are independently an integer from 0 to 4; $X^4$, $X^5$, $X^B$, and $X^C$ are independently $-Cl$, $-Br$, $-I$, or $-F$.

Embodiment 3A

The compound of one of embodiments 1A to 2A, having the formula:

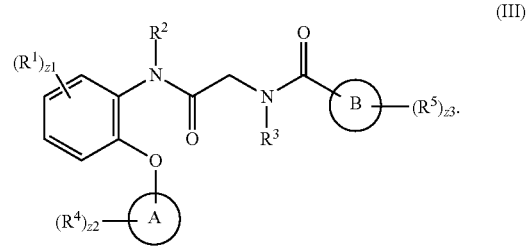

(III)

Embodiment 4A

The compound of one of embodiments 1A to 2A, having the formula:

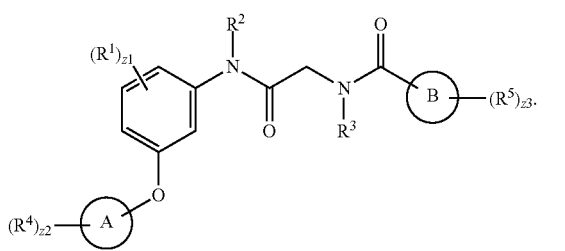

(IV)

Embodiment 5A

The compound of one of embodiments 1A to 2A, having the formula:

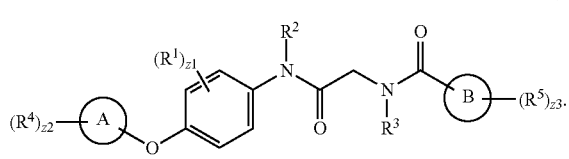

(V)

Embodiment 6A

The compound of one of embodiments 1A to 5A, wherein $R^1$ is independently halogen, —$CF_3$, —$CHF_2$, —$CH_2F$, —CN, —OH, —$NH_2$, —COOH, —$CONH_2$, —$NO_2$, —SH, —$OCF_3$, —$OCHF_2$, substituted or unsubstituted $C_1$-$C_8$ alkyl, substituted or unsubstituted 2 to 8 membered heteroalkyl, substituted or unsubstituted $C_3$-$C_8$ cycloalkyl, substituted or unsubstituted 3 to 8 membered heterocycloalkyl, substituted or unsubstituted $C_6$-$C_{10}$ aryl, or substituted or unsubstituted 5 to 10 membered heteroaryl.

Embodiment 7A

The compound of one of embodiments 1A to 5A, wherein $R^1$ is independently halogen, —$CF_3$, —OH, —$NH_2$, —SH, substituted or unsubstituted $C_1$-$C_4$ alkyl, substituted or unsubstituted 2 to 4 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl.

Embodiment 8A

The compound of one of embodiments 1A to 5A, wherein $R^1$ is independently halogen, —OH, —$NH_2$, —SH, unsubstituted $C_1$-$C_4$ alkyl, or unsubstituted 2 to 4 membered heteroalkyl.

Embodiment 9A

The compound of one of embodiments 1A to 5A, wherein $R^1$ is independently halogen, —OH, unsubstituted methyl, or unsubstituted methoxy.

Embodiment 10A

The compound of one of embodiments 1A to 9A, wherein z1 is 1.

Embodiment 11A

The compound of one of embodiments 1A to 9A, wherein z1 is 0.

Embodiment 12A

The compound of one of embodiments 1A to 11A, wherein $R^4$ is independently halogen, —$CF_3$, —$CHF_2$, —$CH_2F$, —CN, —OH, —$NH_2$, —COOH, —$CONH_2$, —$NO_2$, —SH, —$OCF_3$, —$OCHF_2$, substituted or unsubstituted $C_1$-$C_8$ alkyl, substituted or unsubstituted 2 to 8 membered heteroalkyl, substituted or unsubstituted $C_3$-$C_8$ cycloalkyl, substituted or unsubstituted 3 to 8 membered heterocycloalkyl, substituted or unsubstituted $C_6$-$C_{10}$ aryl, or substituted or unsubstituted 5 to 10 membered heteroaryl.

Embodiment 13A

The compound of one of embodiments 1A to 11A, wherein $R^4$ is independently halogen, —$CF_3$, —OH, —$NH_2$, —SH, substituted or unsubstituted $C_1$-$C_4$ alkyl, substituted or unsubstituted 2 to 4 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl.

Embodiment 14A

The compound of one of embodiments 1A to 11A, wherein $R^4$ is independently halogen, —OH, —$NH_2$, —SH, unsubstituted $C_1$-$C_4$ alkyl, or unsubstituted 2 to 4 membered heteroalkyl.

Embodiment 15A

The compound of one of embodiments 1A to 11A, wherein $R^4$ is independently halogen, —OH, unsubstituted methyl, or unsubstituted methoxy.

Embodiment 16A

The compound of one of embodiments 1A to 11A, wherein $R^4$ is independently —$OR^{14}$.

Embodiment 17A

The compound of embodiment 16A, wherein $R^{14}$ is hydrogen or substituted or unsubstituted alkyl.

Embodiment 18A

The compound of embodiment 16A, wherein $R^{14}$ is hydrogen or unsubstituted alkyl.

Embodiment 19A

The compound of embodiment 16A, wherein $R^{14}$ is hydrogen or unsubstituted $C_1$-$C_5$ alkyl.

Embodiment 20A

The compound of embodiment 16A, wherein $R^{14}$ is hydrogen or unsubstituted $C_1$-$C_3$ alkyl.

Embodiment 21A

The compound of embodiment 16A, wherein $R^{14}$ is hydrogen or methyl.

Embodiment 22A

The compound of one of embodiments 1A to 21A, wherein z2 is 1.

Embodiment 23A

The compound of one of embodiments 1A to 21A, wherein z2 is 0.

Embodiment 24A

The compound of one of embodiments 1A to 23A, wherein $R^5$ is independently halogen, —$CF_3$, —$CHF_2$, —$CH_2F$, —CN, —OH, —$NH_2$, —COOH, —$CONH_2$, —$NO_2$, —SH, —$OCF_3$, —$OCHF_2$, substituted or unsubstituted $C_1$-$C_8$ alkyl, substituted or unsubstituted 2 to 8 membered heteroalkyl, substituted or unsubstituted $C_3$-$C_8$ cycloalkyl, substituted or unsubstituted 3 to 8 membered heterocycloalkyl, substituted or unsubstituted $C_6$-$C_{10}$ aryl, or substituted or unsubstituted 5 to 10 membered heteroaryl.

Embodiment 25A

The compound of one of embodiments 1A to 23A, wherein $R^5$ is independently halogen, —$CF_3$, —OH, —$NH_2$, —SH, substituted or unsubstituted $C_1$-$C_1$ alkyl, substituted or unsubstituted 2 to 4 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl.

Embodiment 26A

The compound of one of embodiments 1A to 23A, wherein $R^5$ is independently halogen, —OH, —$NH_2$, —SH, unsubstituted $C_1$-$C_4$ alkyl, or unsubstituted 2 to 4 membered heteroalkyl.

Embodiment 27A

The compound of one of embodiments 1A to 23A, wherein $R^5$ is independently halogen, —OH, unsubstituted methyl, or unsubstituted methoxy.

Embodiment 28A

The compound of one of embodiments 1A to 27A, wherein z3 is 1.

Embodiment 29A

The compound of one of embodiments 1A to 27A, wherein z3 is 0.

Embodiment 30A

The compound of one of embodiments 1A to 29A, wherein $R^2$ is hydrogen, —$CX^2_3$, —$CHX^2_2$, —$CH_2X^2$, —CN, —C(O)H, —C(O)OH, —C(O)$NH_2$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl.

Embodiment 31A

The compound of one of embodiments 1A to 29A, wherein $R^2$ is hydrogen, unsubstituted methyl, unsubstituted ethyl, or unsubstituted isopropyl.

Embodiment 32A

The compound of one of embodiments 1A to 29A, wherein $R^2$ is hydrogen.

Embodiment 33A

The compound of one of embodiments 1A to 32A, wherein $R^3$ is hydrogen, —$CX^2_3$, —$CHX^2_2$, —$CH_2X^2$, —CN, —C(O)H, —C(O)OH, —C(O)$NH_2$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl.

Embodiment 34A

The compound of one of embodiments 1A to 32A, wherein $R^3$ is hydrogen, unsubstituted methyl, unsubstituted ethyl, or unsubstituted isopropyl.

Embodiment 35A

The compound of one of embodiments 1A to 32A, wherein $R^3$ is hydrogen.

Embodiment 36A

The compound of one of embodiments 1A to 35A, wherein Ring A is phenyl.

Embodiment 37A

The compound of one of embodiments 1A to 35A, wherein Ring A is a 5 to 6 membered heteroaryl.

Embodiment 38A

The compound of one of embodiments 1A to 35A, wherein Ring A is a thienyl.

Embodiment 39A

The compound of one of embodiments 1A to 35A, wherein Ring A is a 2-thienyl.

Embodiment 40A

The compound of one of embodiments 1A to 35A, wherein Ring A is a 3-thienyl.

Embodiment 41A

The compound of one of embodiments 1A to 35A, wherein Ring A is a pyridyl.

Embodiment 42A

The compound of one of embodiments 1A to 35A, wherein Ring A is a 2-pyridyl.

Embodiment 43A

The compound of one of embodiments 1A to 35A, wherein Ring A is a 3-pyridyl.

Embodiment 44A

The compound of one of embodiments 1A to 35A, wherein Ring A is a 4-pyridyl.

Embodiment 45A

The compound of one of embodiments 1A to 44A, wherein Ring B is a naphthyl.

Embodiment 46A

The compound of one of embodiments 1A to 44A, wherein Ring B is a 1-naphthyl.

Embodiment 47A

The compound of one of embodiments 1A to 44A, wherein Ring B is a 2-naphthyl.

Embodiment 48A

The compound of one of embodiments 1A to 44A, wherein Ring B is a quinolinyl.

Embodiment 49A

The compound of one of embodiments 1A to 44A, wherein Ring B is a isoquinolinyl.

Embodiment 50A

The compound of one of embodiments 1A to 44A, wherein Ring B is a 1-isoquinolinyl.

Embodiment 51A

The compound of one of embodiments 1A to 44A, wherein Ring B is a 3-isoquinolinyl.

Embodiment 52A

The compound of one of embodiments 1A to 44A, wherein Ring B is a 4-isoquinolinyl.

Embodiment 53A

The compound of one of embodiments 1A to 35A, having the formula:

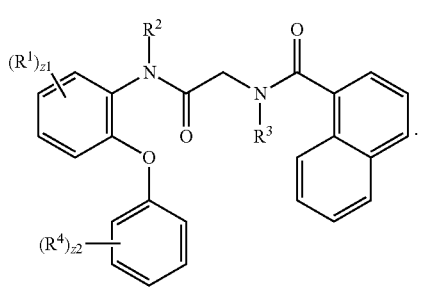

Embodiment 54A

The compound of one of embodiments 1A to 35A, having the formula:

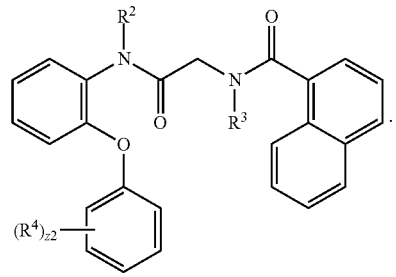

Embodiment 55A

The compound of one of embodiments 1A to 35A, having the formula:

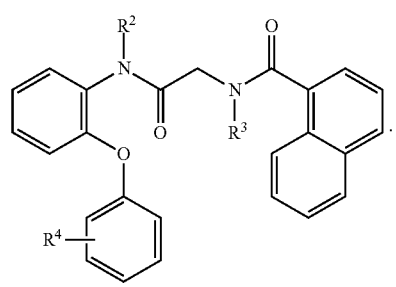

Embodiment 56A

The compound of one of embodiments 1A to 23A, having the formula:

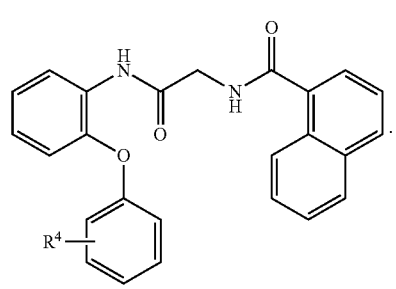

Embodiment 57A

The compound of one of embodiments 1A to 23A, having the formula:

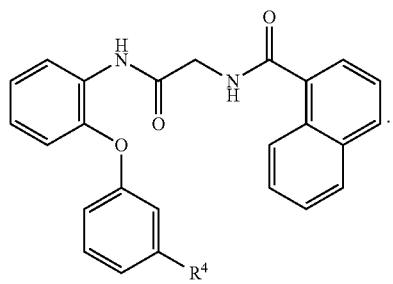

Embodiment 58A

The compound of one of embodiments 1A to 23A, having the formula:

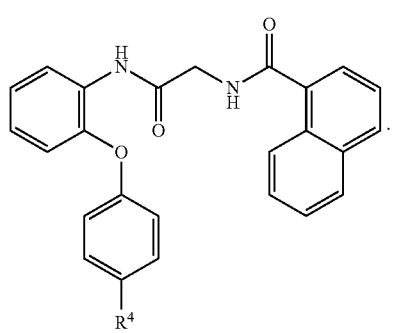

Embodiment 59A

The compound of embodiment 1A, having the formula:

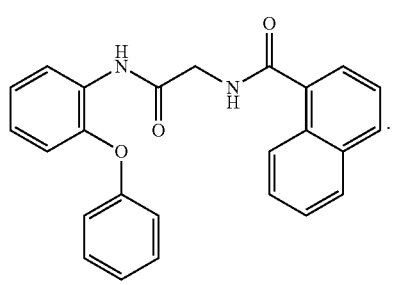 [SMILES: O=C(CNC(=O)c1cccc2ccccc12)Nc1ccccc1Oc1ccccc1]

Embodiment 60A

The compound of embodiment 1A, having the formula:

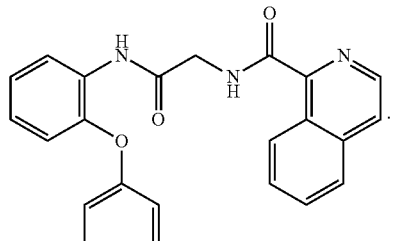

Embodiment 61A

The compound of embodiment 1A, having the formula:

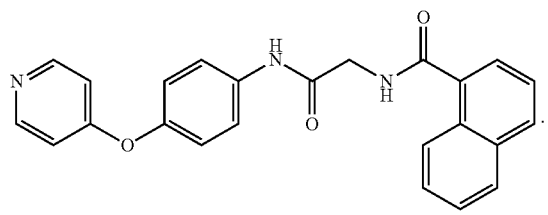 [SMILES: O=C(CNC(=O)c1cccc2ccccc12)Nc1ccc(Oc2ccncc2)cc1]

Embodiment 62A

The compound of embodiment 1A, having the formula:

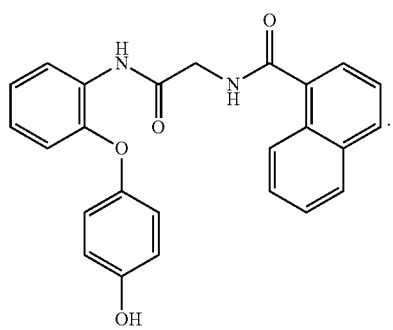 [SMILES: O=C(CNC(=O)c1cccc2ccccc12)Nc1ccccc1Oc1ccc(O)cc1]

Embodiment 63A

The compound of embodiment 1A, having the formula:

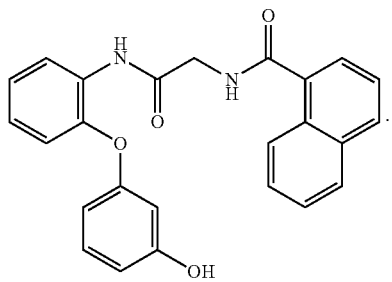 [SMILES: O=C(CNC(=O)c1cccc2ccccc12)Nc1ccccc1Oc1cccc(O)c1]

Embodiment 64A

The compound of embodiment 1A, having the formula:

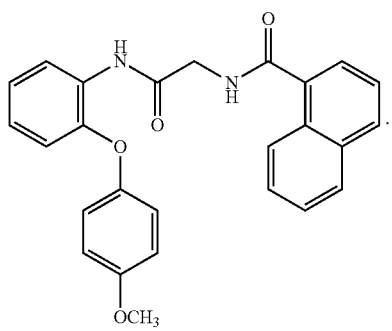 [SMILES: COc1ccc(Oc2ccccc2NC(=O)CNC(=O)c2cccc3ccccc23)cc1]

Embodiment 65A

The compound of embodiment 1A, having the formula:

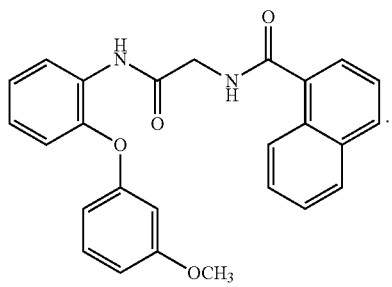 [SMILES: COc1cccc(Oc2ccccc2NC(=O)CNC(=O)c2cccc3ccccc23)c1]

Embodiment 66A

A pharmaceutical composition comprising a compound of one of embodiments 1A to 65A or a pharmaceutically acceptable salt thereof, and a pharmaceutically acceptable excipient.

Embodiment 67A

The pharmaceutical composition of embodiment 66A, further comprising an anti-cancer agent.

Embodiment 68A

The pharmaceutical composition of embodiment 67A, wherein the anti-cancer agent is a platinum-based compound.

Embodiment 69A

The pharmaceutical composition of embodiment 67A, wherein the anti-cancer agent is a cisplatin.

Embodiment 70A

A method of treating a disease associated with PCNA activity in a patient in need of such treatment, said method comprising administering a therapeutically effective amount of a compound of one of embodiments 1A to 65A, or a pharmaceutically acceptable salt thereof.

Embodiment 71A

A method of treating cancer in a patient in need of such treatment, said method comprising administering a therapeutically effective amount of a compound of one of embodiments 1A to 65A, or a pharmaceutically acceptable salt thereof.

Embodiment 72A

The method of embodiment 71A, wherein said cancer is brain cancer.

Embodiment 73A

The method of embodiment 71A, wherein said cancer is neuroblastoma.

Embodiment 74A

A method of inhibiting PCNA activity, said method comprising contacting PCNA with an effective amount of a compound of one of embodiments 1A to 65A, or a pharmaceutically acceptable salt thereof.

Additional Embodiments

Embodiment 1W

A compound having the formula:

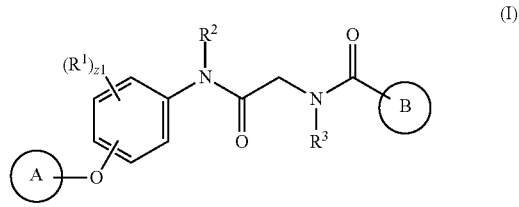

wherein
Ring A is substituted or unsubstituted phenyl or substituted or unsubstituted 5 to 6 membered heteroaryl;
Ring B is substituted or unsubstituted naphthyl, substituted or unsubstituted quinolinyl, or substituted or unsubstituted isoquinolinyl;

$R^1$ is independently a halogen, $-CX^1_3$, $-CHX^1_2$, $-CH_2X^1$, $-CN$, $-SO_{n1}R^{10}$, $-SO_{v1}NR^7R^8$, $-NHNH_2$, $-ONR^7R^8$, $-NHC=(O)NHNH_2$, $-NHC=(O)NR^7R^8$, $-N(O)_{m1}$, $-NR^7R^8$, $-C(O)R^9$, $-C(O)-OR^9$, $-C(O)NR^7R^8$, $-NR^7SO_2R^{10}$, $-NR^7C=(O)R^9$, $-NR^7C(O)-OR^9$, $-NR^7OR^9$, $-OCX^1_3$, $-OCHX^1_2$, $-OCH_2X^1$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^1$ substituents may optionally be joined to form a substituted or unsubstituted cycloalkyl, substituted or unsubstituted heterocycloalkyl, substituted or unsubstituted aryl, or substituted or unsubstituted heteroaryl;

$R^2$ is independently hydrogen, halogen, $-CX^2_3$, $-CHX^2_2$, $-CH_2X^2$, $-CN$, $-COOH$, $-CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^3$ is independently hydrogen, halogen, $-CX^3_3$, $-CHX^3_2$, $-CH_2X^3$, $-CN$, $-COOH$, $-CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^7$, $R^8$, $R^9$, and $R^{10}$ are independently hydrogen, halogen, $-CX^A_3$, $-CHX^A_2$, $-CH_2X^A$, $-CN$, $-COOH$, $-CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and $R^8$ substituents bonded to the same nitrogen atom may optionally be joined to form a substituted or unsubstituted heterocycloalkyl or substituted or unsubstituted heteroaryl;

z1 is independently an integer from 0 to 4;

m1 and v1 are independently 1 or 2;

n1 is independently an integer from 0 to 4;

$X^1$, $X^2$, $X^3$, and $X^A$ are independently $-Cl$, $-Br$, $-I$, or $-F$.

Embodiment 2W

The compound of embodiment 1W, having the formula:

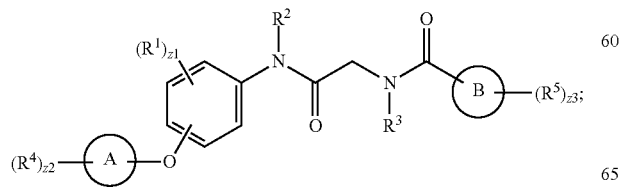

(II)

wherein $R^4$ is independently a halogen, $-CX^4_3$, $-CHX^4_2$, $-CH_2X^4$, $-CN$, $-SO_{n4}R^{14}$, $-SO_{v4}NR^{11}R^{12}$, $-NHNH_2$, $-ONR^{11}R^{12}$, $-NHC=(O)NHNH_2$, $-NHC=(O)NR^{11}R^{12}$, $-N(O)_{m4}$, $-NR^{11}R^{12}$, $-C(O)-OR^{13}$, $-OR^{14}$, $-NR^{11}SO_2R^{14}$, $-NR^{11}C=(O)R^{13}$, $-NR^{11}C(O)-OR^{13}$, $-NR^{11}OR^{13}$, $-OCX^4_3$, $-OCHX^4_2$, $-OCH_2X^4$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^4$ substituents may optionally be joined to form a substituted or unsubstituted cycloalkyl, substituted or unsubstituted heterocycloalkyl, substituted or unsubstituted aryl, or substituted or unsubstituted heteroaryl;

$R^5$ is independently a halogen, $-CX^5_3$, $-CHX^5_2$, $-CH_2X^5$, $-CN$, $-SO_{n5}R^{18}$, $-SO_{v5}NR^{15}R^{16}$, $-NHNH_2$, $-ONR^{15}R^{16}$, $-NHC=(O)NHNH_2$, $-NHC=(O)NR^{15}R^{16}$, $-N(O)_{m5}$, $-NR^{15}R^{16}$, $-C(O)R^{17}$, $-C(O)-OR^{17}$, $-C(O)NR^{15}R^{16}$, $-OR^{18}$, $-NR^{15}SO_2R^{18}$, $-NR^{15}C=(O)R^{17}$, $-NR^{15}C=(O)R^{17}$, $-NR^{15}OR^{17}$, $-OCX^5_3$, $-OCHX^5_2$, $-OCH_2X^5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^5$ substituents may optionally be joined to form a substituted or unsubstituted cycloalkyl, substituted or unsubstituted heterocycloalkyl, substituted or unsubstituted aryl, or substituted or unsubstituted heteroaryl;

$R^{11}$, $R^{12}$, $R^{13}$, and $R^{14}$ are independently hydrogen, halogen, $-CX^B_3$, $-CHX^B_2$, $-CH_2X^B$, $-CN$, $-COOH$, $-CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{11}$ and $R^{12}$ substituents bonded to the same nitrogen atom may optionally be joined to form a substituted or unsubstituted heterocycloalkyl or substituted or unsubstituted heteroaryl;

$R^{15}$, $R^{16}$, $R^{17}$ and $R^{18}$ are independently hydrogen, halogen, $-CX^C_3$, $-CHX^C_2$, $-CH_2X^C$, $-CN$, $-COOH$, $-CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{15}$ and $R^{16}$ substituents bonded to the same nitrogen atom may optionally be joined to form a substituted or unsubstituted heterocycloalkyl or substituted or unsubstituted heteroaryl;

z2 is independently an integer from 0 to 5;

z3 is independently an integer from 0 to 7;

m4, m5, v4 and v5 are independently 1 or 2;

n4 and n5 are independently an integer from 0 to 4;

$X^4$, $X^5$, $X^B$, and $X^C$ are independently $-Cl$, $-Br$, $-I$, or $-F$.

Embodiment 3W

The compound of one of embodiments 1W to 2W, having the formula:

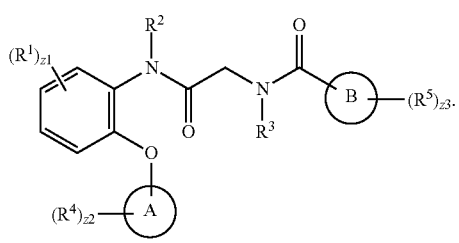

(III)

Embodiment 4W

The compound of one of embodiments 1W to 2W, having the formula:

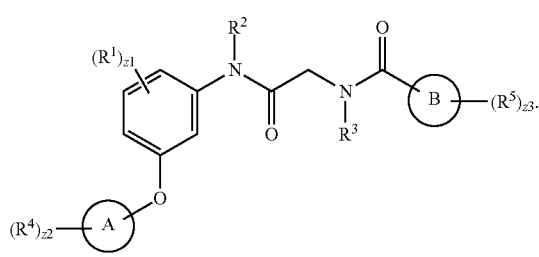

(IV)

Embodiment 5W

The compound of one of embodiments 1W to 2W, having the formula:

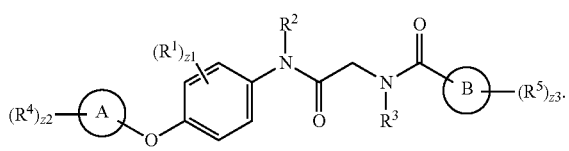

(V)

Embodiment 6W

The compound of one of embodiments 1W to 5W, wherein $R^1$ is independently halogen, —$CF_3$, —$CHF_2$, —$CH_2F$, —CN, —OH, —$NH_2$, —COOH, —$CONH_2$, —$NO_2$, —SH, —$OCF_3$, —$OCHF_2$, —$OCH_2F$, substituted or unsubstituted $C_1$-$C_8$ alkyl, substituted or unsubstituted 2 to 8 membered heteroalkyl, substituted or unsubstituted $C_3$-$C_8$ cycloalkyl, substituted or unsubstituted 3 to 8 membered heterocycloalkyl, substituted or unsubstituted $C_6$-$C_{10}$ aryl, or substituted or unsubstituted 5 to 10 membered heteroaryl.

Embodiment 7W

The compound of one of embodiments 1W to 5W, wherein $R^1$ is independently halogen, —$CF_3$, —OH, —$NH_2$, —SH, substituted or unsubstituted $C_1$-$C_4$ alkyl, substituted or unsubstituted 2 to 4 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl.

Embodiment 8W

The compound of one of embodiments 1W to 5W, wherein $R^1$ is independently halogen, —$CF_3$, —$CHF_2$, —$CH_2F$, —$OCF_3$, —$OCHF_2$, —$OCH_2F$, —OH, —$NH_2$, —SH, unsubstituted $C_1$-$C_4$ alkyl, or unsubstituted 2 to 4 membered heteroalkyl.

Embodiment 9W

The compound of one of embodiments 1W to 5W, wherein $R^1$ is independently halogen, —OH, —$CF_3$, —$CHF_2$, —$CH_2F$, —$OCF_3$, —$OCHF_2$, —$OCH_2F$, unsubstituted methyl, or unsubstituted methoxy.

Embodiment 10W

The compound of one of embodiments 1W to 9W, wherein z1 is 1.

Embodiment 11W

The compound of one of embodiments 1W to 9W, wherein z1 is 0.

Embodiment 12W

The compound of one of embodiments 1W to 11W, wherein $R^4$ is independently halogen, —$CF_3$, —$CHF_2$, —$CH_2F$, —CN, —OH, —$NH_2$, —COOH, —$CONH_2$, —$NO_2$, —SH, —$OCF_3$, —$OCHF_2$, —$OCH_2F$, substituted or unsubstituted $C_1$-$C_8$ alkyl, substituted or unsubstituted 2 to 8 membered heteroalkyl, substituted or unsubstituted $C_3$-$C_8$ cycloalkyl, substituted or unsubstituted 3 to 8 membered heterocycloalkyl, substituted or unsubstituted $C_6$-$C_{10}$ aryl, or substituted or unsubstituted 5 to 10 membered heteroaryl.

Embodiment 13W

The compound of one of embodiments 1W to 11W, wherein $R^4$ is independently halogen, —$CF_3$, —OH, —$NH_2$, —SH, substituted or unsubstituted $C_1$-$C_4$ alkyl, substituted or unsubstituted 2 to 4 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl.

Embodiment 14W

The compound of one of embodiments 1W to 11W, wherein $R^4$ is independently halogen, —$CF_3$, —$CHF_2$, —$CH_2F$, —$OCF_3$, —$OCHF_2$, —$OCH_2F$, —OH, —$NH_2$, —SH, unsubstituted $C_1$-$C_4$ alkyl, or unsubstituted 2 to 4 membered heteroalkyl.

Embodiment 15W

The compound of one of embodiments 1W to 11W, wherein $R^4$ is independently halogen, —$CF_3$, —$CHF_2$, —CH$_2$F, —OCF$_3$, —OCHF$_2$, —OCH$_2$F, —OH, unsubstituted methyl, or unsubstituted methoxy.

Embodiment 16W

The compound of one of embodiments 1W to 11W, wherein R$^4$ is independently —OR$^{14}$.

Embodiment 17W

The compound of embodiment 16W, wherein R$^{14}$ is hydrogen or substituted or unsubstituted alkyl.

Embodiment 18W

The compound of embodiment 16W, wherein R$^{14}$ is hydrogen or unsubstituted alkyl.

Embodiment 19W

The compound of embodiment 16W, wherein R$^{14}$ is hydrogen or unsubstituted C$_1$-C$_5$ alkyl.

Embodiment 20W

The compound of embodiment 16W, wherein R$^{14}$ is hydrogen or unsubstituted C$_1$-C$_3$ alkyl.

Embodiment 21W

The compound of embodiment 16W, wherein R$^{14}$ is hydrogen or unsubstituted methyl.

Embodiment 22W

The compound of embodiment 16W, wherein R$^{14}$ is unsubstituted methyl.

Embodiment 23W

The compound of one of embodiments 1W to 22W, wherein z2 is 1.

Embodiment 24W

The compound of one of embodiments 1W to 22W, wherein z2 is 0.

Embodiment 25W

The compound of one of embodiments 1W to 24W, wherein R$^5$ is independently halogen, —CF$_3$, —CHF$_2$, —CH$_2$F, —CN, —OH, —NH$_2$, —COOH, —CONH$_2$, —NO$_2$, —SH, —OCF$_3$, —OCHF$_2$, —OCH$_2$F, substituted or unsubstituted C$_1$-C$_8$ alkyl, substituted or unsubstituted 2 to 8 membered heteroalkyl, substituted or unsubstituted C$_3$-C$_8$ cycloalkyl, substituted or unsubstituted 3 to 8 membered heterocycloalkyl, substituted or unsubstituted C$_6$-C$_{10}$ aryl, or substituted or unsubstituted 5 to 10 membered heteroaryl.

Embodiment 26W

The compound of one of embodiments 1W to 24W, wherein R$^5$ is independently halogen, —CF$_3$, —OH, —NH$_2$, —SH, substituted or unsubstituted C$_1$-C$_4$ alkyl, substituted or unsubstituted 2 to 4 membered heteroalkyl, substituted or unsubstituted C$_3$-C$_6$ cycloalkyl, substituted or unsubstituted 3 to 6 membered heterocycloalkyl, substituted or unsubstituted phenyl, or substituted or unsubstituted 5 to 6 membered heteroaryl.

Embodiment 27

The compound of one of embodiments 1W to 24W, wherein R$^5$ is independently halogen, —CF$_3$, —CHF$_2$, —CH$_2$F, —OCF$_3$, —OCHF$_2$, —OCH$_2$F, —OH, —NH$_2$, —SH, unsubstituted C$_1$-C$_4$ alkyl, or unsubstituted 2 to 4 membered heteroalkyl.

Embodiment 28W

The compound of one of embodiments 1W to 24W, wherein R$^5$ is independently halogen, —CF$_3$, —CHF$_2$, —CH$_2$F, —OCF$_3$, —OCHF$_2$, —OCH$_2$F, —OH, unsubstituted methyl, or unsubstituted methoxy.

Embodiment 29W

The compound of one of embodiments 1W to 28W, wherein z3 is 1.

Embodiment 30W

The compound of one of embodiments 1W to 28W, wherein z3 is 0.

Embodiment 31W

The compound of one of embodiments 1W to 30W, wherein R$^2$ is hydrogen, —CX$^2_3$, —CHX$^2_2$, —CH$_2$X$^2$, —CN, —C(O)H, —C(O)OH, —C(O)NH$_2$, substituted or unsubstituted C$_1$-C$_6$ alkyl, substituted or unsubstituted 2 to 6 membered heteroalkyl, substituted or unsubstituted C$_3$-C$_6$ cycloalkyl, substituted or unsubstituted 3 to 6 membered heterocycloalkyl, substituted or unsubstituted phenyl, or substituted or unsubstituted 5 to 6 membered heteroaryl.

Embodiment 32W

The compound of one of embodiments 1W to 30W, wherein R$^2$ is hydrogen, unsubstituted methyl, unsubstituted ethyl, or unsubstituted isopropyl.

Embodiment 33W

The compound of one of embodiments 1W to 30W, wherein R$^2$ is hydrogen.

Embodiment 34W

The compound of one of embodiments 1W to 33W, wherein R$^3$ is hydrogen, —CX$^3_3$, —CHX$^3_2$, —CH$_2$X$^3$, —CN, —C(O)H, —C(O)OH, —C(O)NH$_2$, substituted or unsubstituted C$_1$-C$_6$ alkyl, substituted or unsubstituted 2 to 6 membered heteroalkyl, substituted or unsubstituted C$_3$-C$_6$ cycloalkyl, substituted or unsubstituted 3 to 6 membered heterocycloalkyl, substituted or unsubstituted phenyl, or substituted or unsubstituted 5 to 6 membered heteroaryl.

Embodiment 35W

The compound of one of embodiments 1W to 33W, wherein R$^3$ is hydrogen, unsubstituted methyl, unsubstituted ethyl, or unsubstituted isopropyl.

Embodiment 36W

The compound of one of embodiments 1W to 33W, wherein $R^3$ is hydrogen.

Embodiment 37W

The compound embodiment 1W, wherein Ring A is a substituted or unsubstituted phenyl.

Embodiment 38W

The compound of one of embodiments 2W to 36W, wherein Ring A is phenyl.

Embodiment 39W

The compound embodiment 1W, wherein Ring A is a substituted or unsubstituted 5 to 6 membered heteroaryl.

Embodiment 40W

The compound of one of embodiments 2W to 36W, wherein Ring A is a 5 to 6 membered heteroaryl.

Embodiment 41W

The compound embodiment 1W, wherein Ring A is a substituted or unsubstituted thienyl.

Embodiment 42W

The compound of one of embodiments 2W to 36W, wherein Ring A is a thienyl.

Embodiment 43W

The compound embodiment 1W, wherein Ring A is a substituted or unsubstituted 2-thienyl.

Embodiment 44W

The compound of one of embodiments 2W to 36W, wherein Ring A is a 2-thienyl.

Embodiment 45W

The compound embodiment 1W, wherein Ring A is a substituted or unsubstituted 3-thienyl.

Embodiment 46W

The compound of one of embodiments 2W to 36W, wherein Ring A is a 3-thienyl.

Embodiment 47W

The compound embodiment 1, wherein Ring A is a substituted or unsubstituted pyridyl.

Embodiment 48W

The compound of one of embodiments 2W to 36W, wherein Ring A is a pyridyl.

Embodiment 49W

The compound embodiment 1W, wherein Ring A is a substituted or unsubstituted 2-pyridyl.

Embodiment 50W

The compound of one of embodiments 2W to 36W, wherein Ring A is a 2-pyridyl.

Embodiment 51W

The compound embodiment 1W, wherein Ring A is a substituted or unsubstituted 3-pyridyl.

Embodiment 52W

The compound of one of embodiments 2W to 36W, wherein Ring A is a 3-pyridyl.

Embodiment 53W

The compound embodiment 1W, wherein Ring A is a substituted or unsubstituted 4-pyridyl.

Embodiment 54W

The compound of one of embodiments 2W to 36W, wherein Ring A is a 4-pyridyl.

Embodiment 55W

The compound of embodiment 1W, wherein Ring B is a substituted or unsubstituted naphthyl.

Embodiment 56W

The compound of one of embodiments 2W to 54W, wherein Ring B is a naphthyl.

Embodiment 57W

The compound of embodiment 1W, wherein Ring B is a substituted or unsubstituted 1-naphthyl.

Embodiment 58W

The compound of one of embodiments 2W to 54W, wherein Ring B is a 1-naphthyl.

Embodiment 59W

The compound of embodiment 1W, wherein Ring B is a substituted or unsubstituted 2-naphthyl.

Embodiment 60W

The compound of one of embodiments 2W to 54W, wherein Ring B is a 2-naphthyl.

Embodiment 61W

The compound of embodiment 1W, wherein Ring B is a substituted or unsubstituted quinolinyl.

Embodiment 62W

The compound of one of embodiments 2W to 54W, wherein Ring B is a quinolinyl.

Embodiment 63W

The compound of embodiment 1W, wherein Ring B is a substituted or unsubstituted isoquinolinyl.

Embodiment 64W

The compound of one of embodiments 2W to 54W, wherein Ring B is a isoquinolinyl.

Embodiment 65W

The compound of embodiment 1W, wherein Ring B is a substituted or unsubstituted 1-isoquinolinyl.

Embodiment 66W

The compound of one of embodiments 2W to 54W, wherein Ring B is a 1-isoquinolinyl.

Embodiment 67W

The compound of embodiment 1W, wherein Ring B is a substituted or unsubstituted 3-isoquinolinyl.

Embodiment 68W

The compound of one of embodiments 2W to 54W, wherein Ring B is a 3-isoquinolinyl.

Embodiment 69W

The compound of embodiment 1W, wherein Ring B is a substituted or unsubstituted 4-isoquinolinyl.

Embodiment 70W

The compound of one of embodiments 2W to 54W, wherein Ring B is a 4-isoquinolinyl.

Embodiment 71W

The compound of one of embodiments 1W to 36W, having the formula:

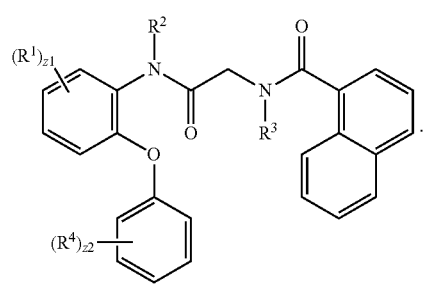

Embodiment 72W

The compound of one of embodiments 1W to 36W, having the formula:

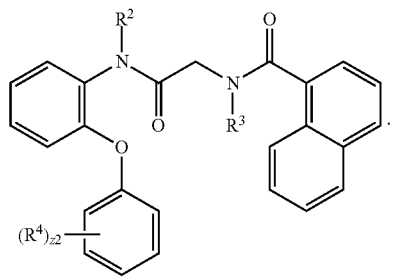

Embodiment 73W

The compound of one of embodiments 1W to 36W, having the formula:

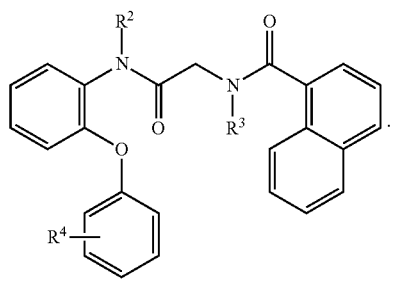

Embodiment 74W

The compound of one of embodiments 1W to 24W, having the formula:

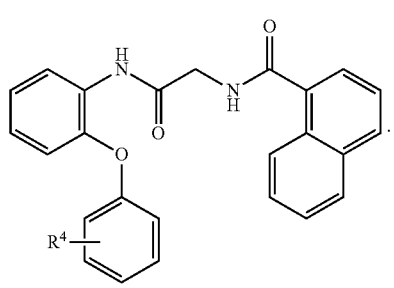

Embodiment 75W

The compound of one of embodiments 1W to 24W, having the formula:

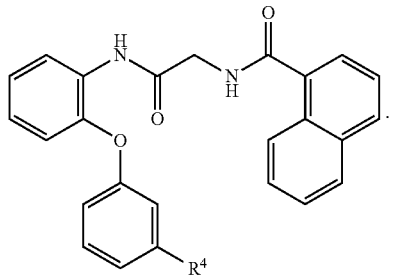

Embodiment 76W

The compound of one of embodiments 1W to 24W, having the formula:

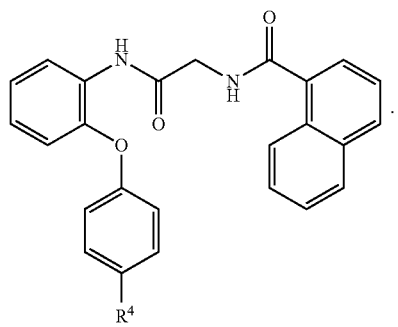

Embodiment 77W

The compound of embodiment 1W, having the formula:

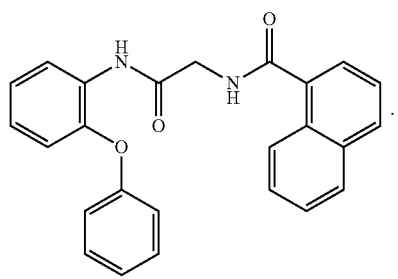 [SMILES: O=C(CNC(=O)c1cccc2ccccc12)Nc1ccccc1Oc1ccccc1]

Embodiment 78W

The compound of embodiment 1W, having the formula:

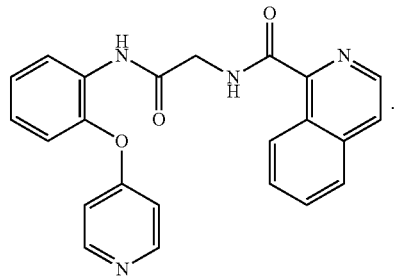 [SMILES: O=C(CNC(=O)c1nccc2ccccc12)Nc1ccccc1Oc1ccncc1]

Embodiment 79W

The compound of embodiment 1W, having the formula:

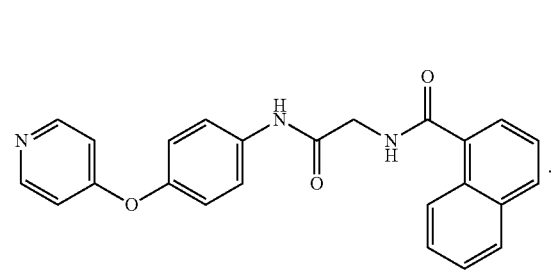 [SMILES: O=C(CNC(=O)c1cccc2ccccc12)Nc1ccc(Oc2ccncc2)cc1]

Embodiment 80W

The compound of embodiment 1W, having the formula:

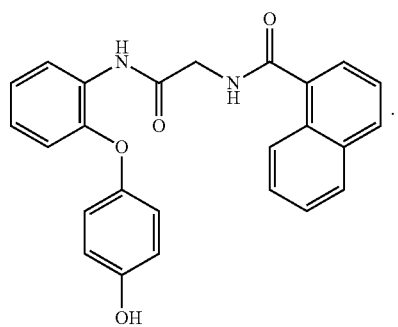 [SMILES: O=C(CNC(=O)c1cccc2ccccc12)Nc1ccccc1Oc1ccc(O)cc1]

Embodiment 81W

The compound of embodiment 1W, having the formula:

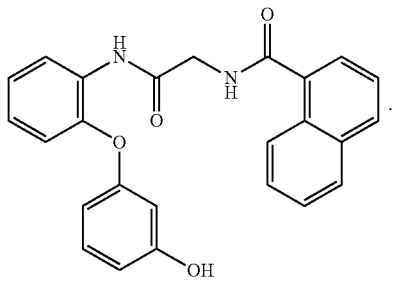 [SMILES: O=C(CNC(=O)c1cccc2ccccc12)Nc1ccccc1Oc1cccc(O)c1]

Embodiment 82W

The compound of embodiment 1W, having the formula:

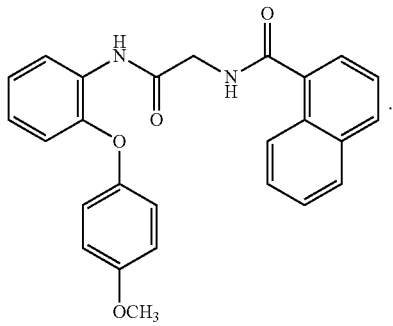 [SMILES: COc1ccc(Oc2ccccc2NC(=O)CNC(=O)c2cccc3ccccc23)cc1]

Embodiment 83W

The compound of embodiment 1W, having the formula:

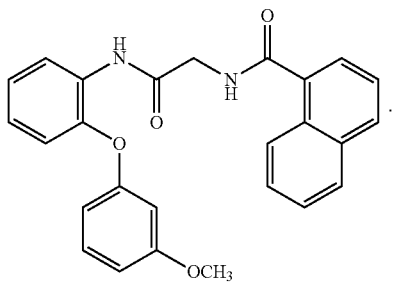 [SMILES: COc1cccc(Oc2ccccc2NC(=O)CNC(=O)c2cccc3ccccc23)c1]

Embodiment 84W

A pharmaceutical composition comprising a compound of one of embodiments 1W to 83W or a pharmaceutically acceptable salt thereof, and a pharmaceutically acceptable excipient.

Embodiment 85W

The pharmaceutical composition of embodiment 84W, further comprising an anti-cancer agent.

Embodiment 86W

The pharmaceutical composition of embodiment 85W, wherein the anti-cancer agent is a platinum-based compound.

Embodiment 87W

The pharmaceutical composition of embodiment 85W, wherein the anti-cancer agent is a cisplatin.

Embodiment 88W

A method of treating a disease associated with PCNA activity in a patient in need of such treatment, said method comprising administering a therapeutically effective amount of a compound of one of embodiments 1W to 83W, or a pharmaceutically acceptable salt thereof.

Embodiment 89W

A method of treating cancer in a patient in need of such treatment, said method comprising administering a therapeutically effective amount of a compound of one of embodiments 1W to 83W, or a pharmaceutically acceptable salt thereof.

Embodiment 90W

The method of embodiment 89W, wherein said cancer is leukemia, lung cancer, colon cancer, a central nervous system cancer, melanoma, ovarian cancer, renal cancer, prostate cancer, or breast cancer.

Embodiment 91W

The method of embodiment 89W, wherein said cancer is non-small cell lung cancer.

Embodiment 92W

The method of embodiment 89W, wherein said cancer is triple negative breast cancer.

Embodiment 93W

The method of embodiment 89W, wherein said cancer is a central nervous system cancer.

Embodiment 94W

The method of embodiment 89W, wherein said cancer is brain cancer.

Embodiment 95W

The method of embodiment 89W, wherein said cancer is neuroblastoma.

Embodiment 96W

A method of inhibiting PCNA activity, said method comprising contacting PCNA with an effective amount of a compound of one of embodiments 1W to 83W, or a pharmaceutically acceptable salt thereof.

Embodiment 97W

The method of embodiment 96W, wherein said contacting includes contacting a protein of SEQ ID NO:2 with an effective amount of a compound of one of embodiments 1W to 83W, or a pharmaceutically acceptable salt thereof.

Embodiment 98W

The method of embodiment 96W, wherein said contacting includes contacting a protein of SEQ ID NO:3 with an effective amount of a compound of one of embodiments 1W to 83W, or a pharmaceutically acceptable salt thereof.

Embodiment 99W

The method of embodiment 96W, wherein said contacting includes contacting a protein of SEQ ID NO:4 with an effective amount of a compound of one of embodiments 1W to 83W, or a pharmaceutically acceptable salt thereof.

F. Examples

A challenge of developing an anti-cancer therapy for any type of cancer has always been the ability to selectively destroy cancer cells, while sparing normal tissue. Most early chemotherapeutic or radiotherapeutic agents target DNA structures or mitotic spindles. Although they kill cancer cells effectively, these drugs cause significant side-effects. In case of treating childhood cancers such as NB, these drugs may give rise to secondary malignancy as well [4]. Following the pioneering and successful example of Gleevec [29], several therapeutic agents targeting specific oncogenic signaling components have reached the clinic over the past 15 years [30-35]. Whereas these target-based therapies in general cause less severe side-effects than early chemotherapeutic agents, drugs that target individual oncogenes often succumb to the development of resistance [36-38] by cancer cells through mutations at the target genes, alterations in the expression of the target, or by activation of alternative survival pathways. One way to preempt these types of the drug resistance inherent to the adaptive and heterogeneous nature of cancers is to target hub proteins (proteins that influence multiple pathways (e.g., signaling pathways) instead of only a single pathway) which influence the activity of broad cellular machineries, such as, but not limited to, the DNA replication/repair apparatus, which are necessary for the growth and survival of all cancer cells without causing unacceptable side-effects in non-malignant cells. Identification of cancer specific features of essential hub proteins and cellular machineries may be advantageous.

For example, proliferating cell nuclear antigen (PCNA), which is found in all eukaryotic cells as an evolutionally conserved protein, is widely used as a tumor progression marker [7-9] along with Ki67 and has been identified to play an essential role in regulating DNA synthesis and repair as well as its role in cancer cell growth and survival [10]. Therefore, it represents an attractive molecular target to develop broad-spectrum anti-cancer agents [11]. A major interaction site in PCNA is the interdomain connecting loop that spans from amino acid M121 to Y133 (SEQ ID NO:3) [12]. This loop is recognized by many PIP-box proteins including p21 (CDKN1A) [13], DNA polymerase δ (Pol 6) [14], and flap endonuclease 1 (FEN1) [15]. Using 2D-PAGE, we previously reported that normal cells and tissues express an isoform of PCNA with a basic isoelectric point (referred to as nmPCNA) [16]. In contrast, cancer cells express both the basic and, to a much higher level, a unique acidic isoform of PCNA (caPCNA) that is not significantly expressed in non-malignant cells [16]. The isoelectric point differences between the two isoforms results from changes in the malignant cells to post-translationally modify the PCNA polypeptide [17], and is not due to an mRNA splice variant or mutation within the PCNA gene. The caPCNA-specific antigenic site was mapped to contain a small eight amino acid peptide region (L126 Y133 (SEQ ID NO:4) within the interconnector domain of PCNA [16]. Interestingly, the L126-Y133 region is only accessible to immunohistochemistry staining by both a polyclonal and a monoclonal antibody specific to this region in tumor cells [16], suggesting that this region is structurally altered and becomes more accessible for protein-protein interaction in tumor cells, which predominantly express the caPCNA isoform. Using a cell permeable peptide harboring this eight amino acid sequence to block PCNA interactions, NB cells were selectively killed [18]. Consistent with the tumor-associated expression pattern of caPCNA [16], the peptide doesn't cause significant toxicity to non-malignant cells, including human neural crest stem cells [18].

In summary, there is a significant medical need for new therapies to improve the treatment outcomes of this aggressive cancer. In addition, new molecular targets such as PCNA also need to be further evaluated to determine their use as therapeutic targets for cancer treatment.

The alteration in structure and accessibility in the L126 Y133 region of caPCNA offers a structural basis for developing small molecules that specifically target caPCNA and are therefore selectively toxic to cancer cells. To translate these biological and structural insights into drug discovery, a virtual screen for compounds that target the binding pocket delineated by residues L126 and Y133 in PCNA was performed. Reported herein is the identification of a small molecule compound, which selectively kills NB cells at a low micromolar concentration and the development of AOH1160, which has a significantly improved potency and therapeutic window over prior compounds. Mechanistically, AOH1160 competes with T3, a known PCNA ligand [19], for binding to PCNA. It interferes with DNA replication and blocks homologous recombination (HR) mediated DNA repair, leading to cell cycle arrest, accumulation of unrepaired DNA damages, and enhanced sensitivity to cisplatin treatment. Therapeutically, AOH1160 is orally available to animals and suppresses tumor growth without causing significant weight loss in mice. In summary, our study demonstrated the feasibility of targeting PCNA, which is central to broad cellular processes and indispensible to the growth and survival of all cancer cells, without causing unacceptable toxicity. The favorable pharmacologic and therapeutic properties of AOH1160 demonstrate the potential of this compound as a novel therapeutic agent for treating NB.

Example 1. Identification of PCNA Inhibitors by Computer Modeling

Figure 1B:
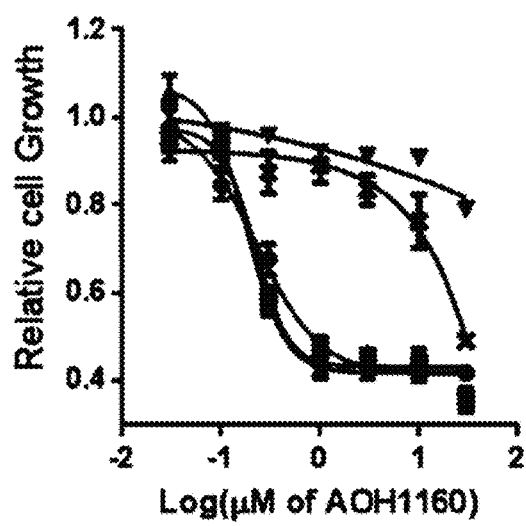
Figure 1C:
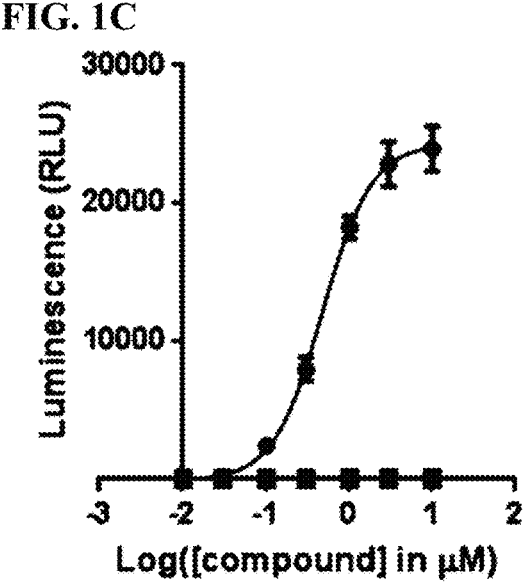
Figure 1D:
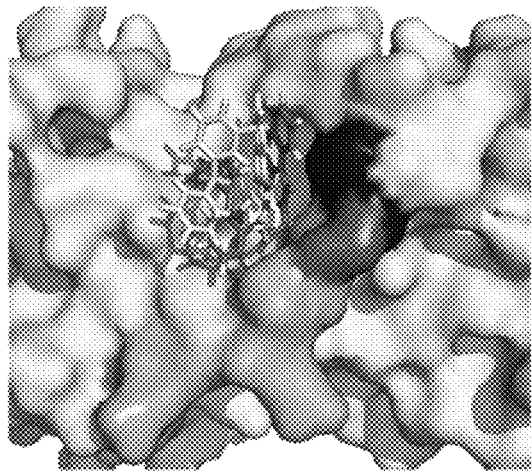

The virtual screen is based on the known crystal structures of the PCNA/FEN1 complex that are available from the RCSB protein database and focuses on the binding pocket in PCNA delineated by residues between L126 and Y133 of PCNA (see FIG. 1D). Chemical databases available at the Albany Molecular Research Institute (AMRI, Albany, N.Y.) were screened. The databases contain 300,000 chemical compounds available directly from AMRI in at least 2 mg quantities and more than 6.5 million additional compounds available from external vendors. For more than 3 million drug-like compounds in the databases, multiple conformations were pre-computed and a combination of substructure and pharmacophore searches using tools in the MOE software (Chemical Computing Group, Montreal, Canada, MOE v2008.05) was performed. The initial virtual screen yielded more than 8,000 hits. These hits were further analyzed by molecular docking studies using the computer program, Glide (Schrödinger, LLC, New York, N.Y., Impact v 50207) [20] and 57 compounds were selected for acquisition and experimental testing.

Development of a computer model for compound optimization. A computer model for compound optimization was initially built by the All-Around-Docking (AAD) methodology, which allows a small molecule to search the whole surface of the target protein for the binding site that has the lowest docking score by utilizing Schordinger Glide [20]. The model was further refined by 50 ns metadynamics simulation and minimized the initial docking pose by the NAMD software [21].

Example 2. Plasmids and Cell Lines

The human NB cell lines, SK-N-DZ, SK-N—BE(2)c, SK-N-AS, and LAN-5 obtained from the American Type Culture Collection (Rockville, Md.), were cultured in DMEM with 10% fetal bovine serum (FBS), 100 units/ml penicillin, and 100 µg/ml streptomycin in the presence of 5% $CO_2$ at 37° C. Human PBMCs from a healthy donor were purchased from Sanguine BioSciences (Valencia, Calif.) and grown in RPMI1640 with 10% FBS, 100 units/ml penicillin, 100 µg/ml streptomycin, and 10 ng/ml IL-2 in the presence of 5% $CO_2$ at 37° C. Human embryonic progenitor cell line 7SM0032 was acquired from Millipore (Billerica, Mass.) and grown in the hEPM-1 Media Kit purchased from the same company. The plasmid pCBASce expresses the rare cutting I-SceI meganuclease [22]. The U20S-derived cell lines, DR-GFP and EJ5-GFP, each contain a stably transfected reporter gene for DSB repair mediated by HR and end joining (EJ), respectively [23]. These cell lines were cultured in DMEM medium with 10% FBS at 37° C. in the presence of 5% $CO_2$.

Example 3. Cell Growth and Terminal Deoxynucleotidyl Transferasemediated dUTP Nick End Labeling (TUNEL) Assays To measure the effect of the compounds on cell growth, cells were seeded at $3 \times 10^4$/ml into a 96-well plate. Once attached, cells were treated with various concentrations of AOH1160 for 72 h. Cell growth was measured by the CellTitor-Glo assay (Promega, Madison, Wis.) according to the manufacturer's instructions. To measure apoptosis, cells were seeded at $1 \times 10^5$/ml onto a chamber slide. Once attached, cells were treated with the 500 nM AOH1160 for 24 h. Cells were fixed and analyzed by a TUNEL assay using the TMR red in situ cell death detection kit (Roche Diagnostics, Indianapolis, Ind.).

Example 4. Cell Cycle Analysis

Cells were seeded at $1 \times 10^5$/ml in a 6-well plate. Once attached overnight, cells were treated with or without AOH1160 for 6 or 24 h. After being fixed in 60% ethanol and stained with propidium iodide (PI), cells were analyzed by flow cytometry to determine the cellular PI fluorescence intensity. The flow cytometry data were analyzed by the FlowJo program to model various cell populations.

Example 5. DSB Repair Assays

DR-GFP and EJ5-GFP cell lines were seeded at $2.5 \times 10^4$ cells/cm² in a 12-well plate. Once attached overnight, cells were transfected with the pCBASce plasmid that expresses I-SceI by Lipofectamine 2000 (Invitrogen). After incubation for 3 h, the media containing transfection complexes was aspirated and replaced with fresh media containing AOH1160. The HR and EJ-mediated DSB repair, indicated by the restoration of a functional GFP gene in the respective cell lines, were quantified by measuring the relative abundance of GFP-positive cells by flow cytometry 3 days after transfection.

Example 6. Saturation Transfer Difference (STD) Nuclear Magnetic Resonance (NMR)

Recombinant human PCNA was purified and exchanged to $D_2O$-based phosphate buffered saline (PBS), pH 7.2. T3 purchased from Sigma (Saint Louis, Mo.) and AOH1160 synthesized in house were dissolved in D6-DMSO and stored at −20° C. freezer. The STD NMR experiments were carried out in the presence of 1 µM PCNA, 20 µM Deuterated-DTT, 0.02% NaN3, and 2% D6-DMSO with T3 and/or AOH1160. The reference spectra were acquired under the same condition without PCNA. 5 uM DSS was used as an internal reference to determine the reported ligand concentration in solution. All NMR experiments were carried out at 25° C. on 600 MHz Bruker Avance equipped with 5 mm triple resonance cryogenic probe. STD (Saturation Transfer Difference) NMR spectra were acquired with transients ranging from 2560 to 32000, spectral width 8012 Hz with 24 k data points. The recycle delay was 2.8s. Selective saturation was composed of 50 gauss shaped pulses at a field strength of 86 Hz, and the duration of each pulse is 50 ms with a 500 µs delay between pulses. The spin lock filter used to suppress protein signal was optimized to 60 ms at field strength of 5 kHz. The frequency for protein saturation was optimized to be 0.9 ppm; the ligand signals were not disturbed with the employed selective saturation condition at this frequency. The reference spectrum was acquired with saturation irradiated at −30 ppm. To eliminate potential artifacts, the saturation and reference experiments were acquired in an interleaved manner, and the finished experiments were separated into two 1D data for analysis. The peak integration was carried out with Bruker Topspin software. The STD effect was described using equation (IRef ISTD)/IRef, in which the IRef is the peak intensity from the reference experiment, and the ISTD is the peak intensity from the on-resonance saturation experiment.

Example 7. Human Thyroid Hormone Receptor Beta (TRβ) Reporter Assay

Reporter cells constitutively expressing human TRβ and containing a luciferase reporter gene functionally linked to a TRP-responsive promoter were purchased from Indigo Biosciences (State College, Pa.). Cells were treated by various concentration of T3 or AOH1160 for 24 hours. The effect of each compound on TRβ activity was examined by measuring the luciferase reporter gene expression according to the manufacturer's instruction.

Example 8. Clonogenic Assay

Three hundred human SK-N-DZ NB cells were seeded onto a 60-mm tissue culture dish. Once attached overnight, cells were treated with or without various concentrations of cisplatin in the presence or absence of 500 nM of AOH1160 for 18 h. Cells were washed twice with growth medium and were cultured in fresh medium for 3 weeks to allow surviving cells to form colonies. The medium was changed every 3 days throughout the experiment. The colonies formed under each treatment conditions were counted after being stained with 0.5% crystal violet.

Example 9. Western Blot

Cells were dissolved into the Laemmli sample buffer on the plate. The whole cell extracts were sonicated, and the proteins in the lysate were resolved using a 4-12% SDS polyacrylamide gel, and the resolved proteins were blotted onto a nitrocellulose membrane. Antibodies specific to H2A.X, cleaved caspase-3, full-length caspase-3, or cleaved caspase-9 were purchased from Cell Signaling Technology (Danvers, Mass.). The anti-γH2A.X antibody was purchased from Millipore. The membrane was blocked with 5% nonfat dry milk and incubated individually with each of these antibodies dissolved in the blocking buffer. After incubation with peroxidase-conjugated secondary antibodies, the protein of interest was detected using an ECL kit purchased from Thermo Fisher Scientific (Waltham, Mass.).

Example 10. In Vivo Tumor Model

All experiments involving live animals were carried out in strict accordance with the recommendations in the Guide for the Care and Use of Laboratory Animals of the National Institutes of Health. The protocol (#11034) was reviewed and approved by the City of Hope Institutional Animal Care and Use Committee. Nude mice 6-8 weeks of age were purchased from the Jackson Laboratory (Bar Harbor, Me.). SK-N-BE(2)c cells were harvested and washed twice in PBS. Cells were suspended in Matrigel (BD Biosciences) at $5 \times 10^7$/ml. 0.1 ml of suspended cells was subcutaneously injected into the right flank of each of 40 nude mice. A dosing solution of 5 mg/ml AOH1160 was preparing by dissolving an appropriate amount of AOH1160 in a dosing vehicle of 1% carboxymethyl cellulose and 0.5% Tween 80. Mice were randomly grouped into two groups with 20 mice in each group. The mice were treated with 30 mg/kg AOH1160 or vehicle twice a day by gavages throughout the entire experiment starting one day after tumor cell injection. Mice were monitored twice weekly for any sign of side effects. The weight of the animals was measured as an indicator of compound toxicity. At the end of the experiment, tumors were isolated from sacrificed mice and their masses were measured.

Example 11. Identification and Characterization of Compounds

To identify small molecule compounds that target the PCNA and FEN1 interface, we started with known crystal structures of the PCNA/FEN1 complex that are available from the RCSB protein database. To improve the likelihood of identifying novel small molecules that specifically target caPCNA, we focused our virtual screen on the binding pocket in PCNA delineated by residues L126 and Y133 and screened databases consisting of more than 6.8 million chemical structures available at the AMRI. A set of 57 compounds identified by the virtual screen was acquired and further tested in a cell viability assay. A compound (AOH39) was selected for further development due to its anti-cancer activity and selectivity. The compound is toxic to multiple NB cell lines with $IC_{50}$ ranging from 1.3 to 2.8 µM. It's much less toxic to non-malignant cells including human peripheral blood mononuclear cells (PBMC) and human neural crest stem cells (7SM0032) with $IC_{50}$ of 15.4 µM and about 100 µM on these cells respectively, indicating that this compound selectively inhibits the growth of NB cancer cells.

To explore possible mechanisms for the compound anti-tumor activity, we performed cell cycle analysis and found that the compound treatment caused cell cycle arrest at the S and G2 phases, suggesting an interference of DNA replication and repair. As early as 24 hours after treatment, cells start to die through apoptosis as indicated by the rise of a sub-G1 cell population. The S and G2 arrest by treatment coincides with enhanced intracellular γH2A.X levels, indicating an accumulation of double stranded DNA breaks (DSB). DSB's, if not resolved in time, are lethal to cells. Cells deal with double-stranded DNA breaks mainly through EJ-mediated DNA repair pathways in G1 phase and HR-mediated pathways during S and G2 phases [24, 25]. Reporter cell lines have been established to monitor each of these DNA repair pathways [23]. These cells lines each contain a GFP reporter cassette disrupted by an insertion of recognition site(s) for the endonuclease I-SceI. Introduction of exogenous I-SceI creates DSB(s) within the reporters. Each reporter is designed such that repair of the I-SceI-induced DSB(s) by a specific pathway can result in restoration of the GFP cassette: HR for DR-GFP and EJ for EJ5-GFP. The relative abundance of GFP-positive cells determined by flow cytometry, therefore, reflects the efficiency of the respective DSB repair pathways in these reporter cell lines. Using these characterized reporter cell lines, we observed that treatment inhibited HR-mediated DNA repair, without exerting any statistically significant effect on EJ. Collectively, these results suggest that the compound interferes with DNA synthesis and HR-mediated DNA repair, causing accumulation of DNA damage and S and G2 cell cycle arrest.

Example 12. AOH1160 is Surprisingly Improved Over the Prior Compound

To improve the anti-tumor potency of the compound while preserving its favorable selectivity, a series of compounds were synthesized and tested. One compound (AOH1160) (FIG. 1A) is significantly more potent than the prior compound in killing NB cells with $IC_{50}$s ranging 0.18 µM to 0.22 µM (FIG. 1B). Furthermore, AOH1160 is less toxic to non-malignant PBMC and 7SM0032 cells than AOH39. The combined improvements in potency and selectivity lead to a significant improvement in the therapeutic window (FIG. 1B). AOH1160 was tested in a broad range of non-malignant cells, including human primary mammary epithelial and small airway epithelial cells, and no significant toxicity was found in these cells up to a concentration of 10 µM. Although AOH1160 shares certain sub-structural similarity with T3 and T2AA, both known PCNA ligands with significant thyroid hormone (TR) activities [19], AOH1160 did not show any thyroid hormone activity in a TR reporter assay (FIG. 1C).

In addition numerous analogs related to AOH1160 were screened in numerous neuroblastoma cell lines for anti-cancer activity (Table 2). AOH1160 was screened for anti-cancer activity in additional cancer cell lines besides neuroblastoma (Table 3).

To gain further structural insight into the binding of AOH1160 to PCNA, an in-house computer program based on the All-Around-Docking (AAD) methodology [20] was employed to model the best binding site and the binding pose of AOH1160. In contrast to the virtual screen strategy that focused on the binding pocket delineated by L126 and Y133, the AAD approach allows a small molecule to search the whole surface of the target protein for the binding site that has the lowest docking score. The AAD docking method was validated by modeling the binding of T3, a known PCNA inhibitor [19], to PCNA. The T3 model pose predicted by the program is only 0.47 Å in root mean square deviation (RMSD) from what's indicated by the crystallographic study of the T3/PCNA complex (PDB: 3vkx), indicating that the calculation fits well with crystallographic results. Using this program, it was found that AOH1160 binds to the same binding pocket as T3 does on PCNA (FIG. 1D). The model also indicated that the binding affinity of AOH1160 and AOH39 to PCNA are −5.54 kcal/mol and −4.62 kcal/mol respectively, indicating approximately a 5-fold enhancement in binding affinity of AOH1160 to PCNA over that of AOH39. The calculated difference in PCNA binding affinity agrees well with the 6-7 fold increase in compound potency observed in cell viability assays (FIG. 1B).

Figure 1E:
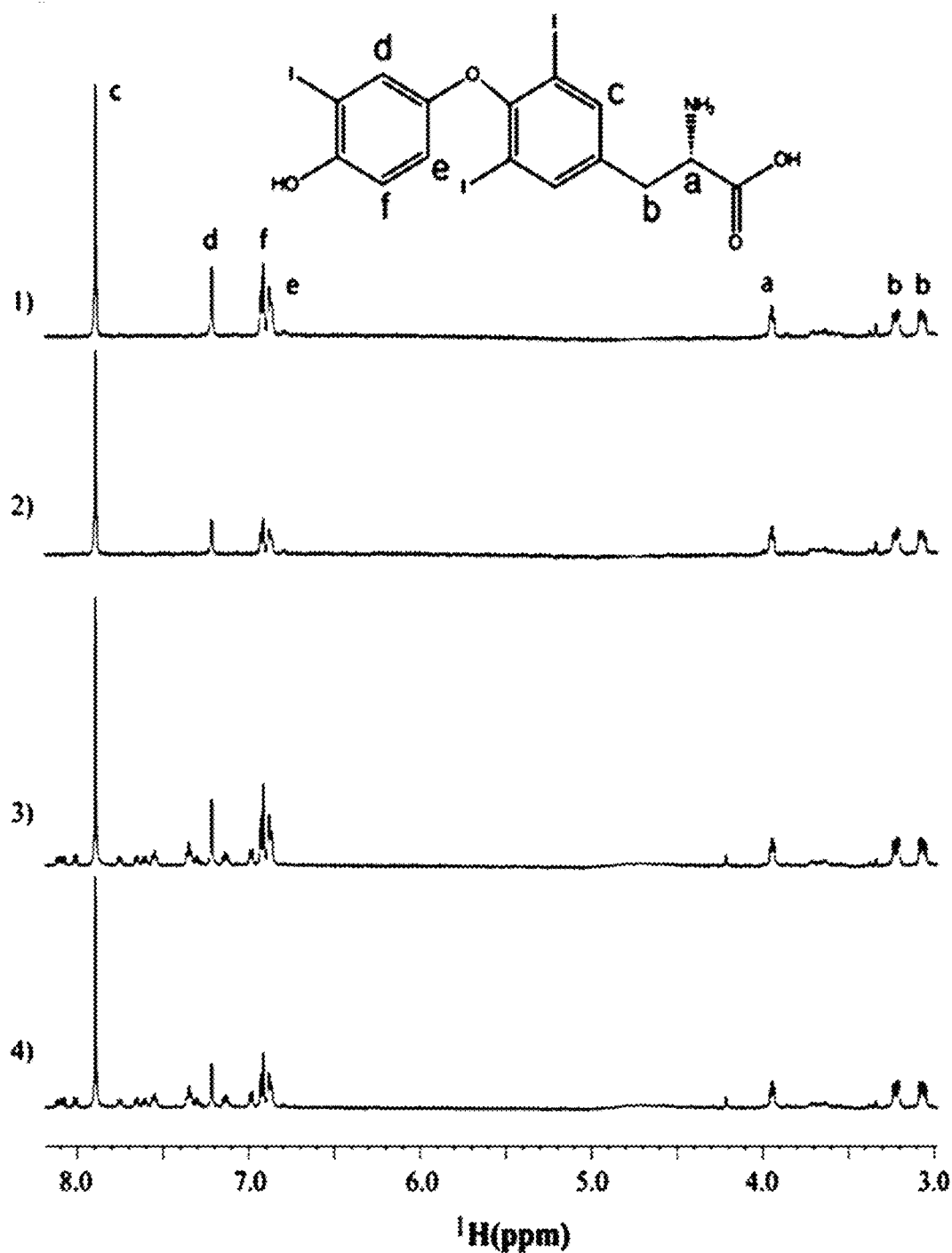

To verify whether AOH1160 competes with T3 in binding to PCNA, the interaction of both compounds with PCNA was analyzed by a Saturation Transfer Difference (STD) NMR experiment [26]. STD NMR is a technique to detect binding of small ligands to large proteins by observing the resulted suppression of NMR signals of the small ligands. The STD NMR experiment of T3 revealed that binding of T3 to PCNA results in a more dramatic signal reduction at protons d, e, and f than at protons a and b (FIG. 1E, spectrum 1 and 2), indicating that the aromatic ring containing protons d, e and f of T3 forms more intimate contact with PCNA than the rest of T3. This structural pose is consistent with the crystal structure of T3 in complex with PCNA (PDB: 3VKX). AOH1160 significantly reduced the STD of T3, as indicated by less reduction of protons d, e, and f signals in the presence of AOH1160 than in its absence (FIG. 1E, spectrum 4 and 2), indicating that AOH1160 competes with T3 for binding to PCNA. The ability of 3.2 µM AOH1160 to effectively compete with 29 µM T3 is consistent with the fact that AOH1160 is a much more potent compound than T3 in a cell viability assay ([19] and FIG. 1B).

Figure 2A:
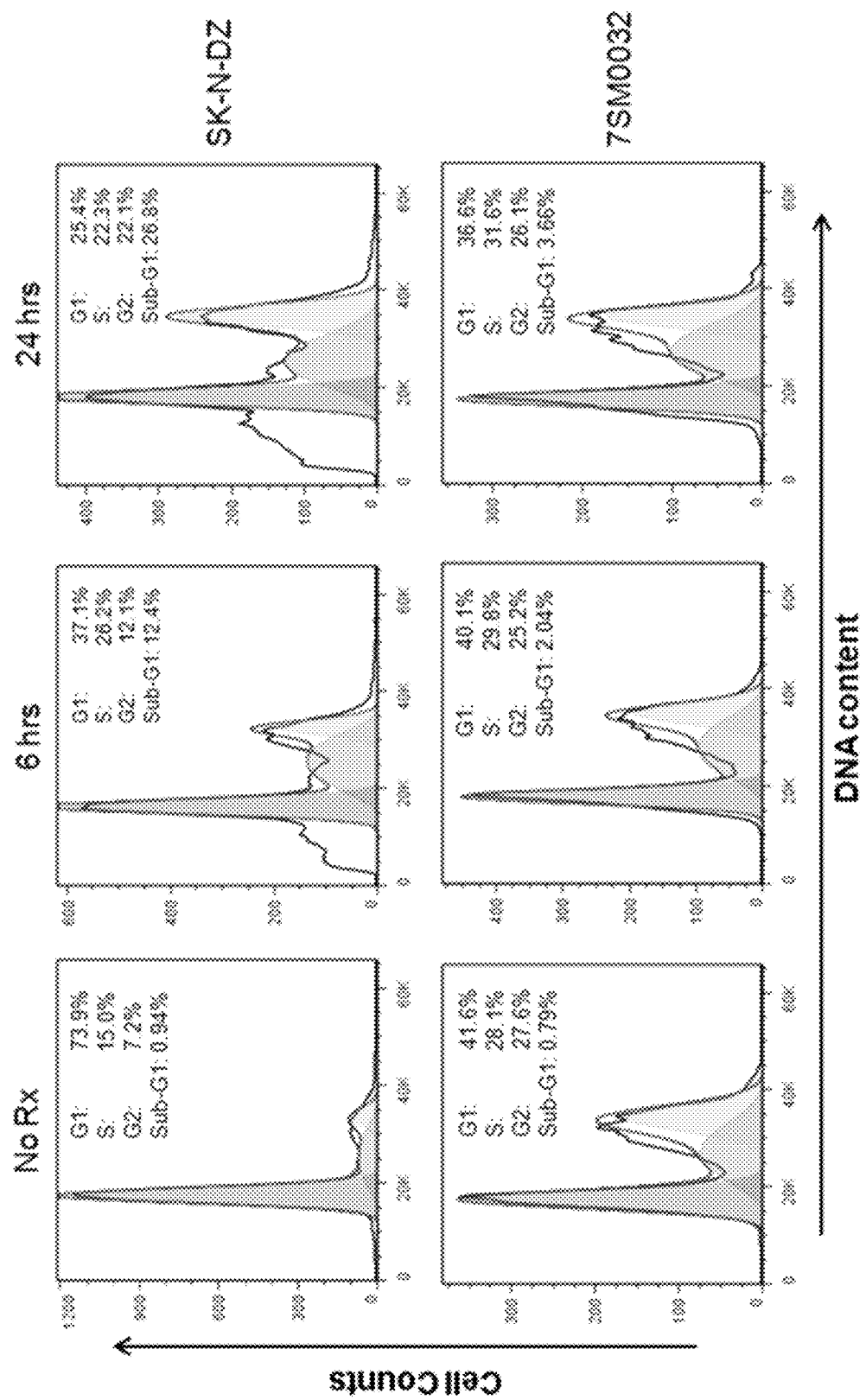
FIGS. 2A-2D depict data on the induction of cell cycle arrest, DNA damage, and apoptosis by AOH1160.
Figure 2B:
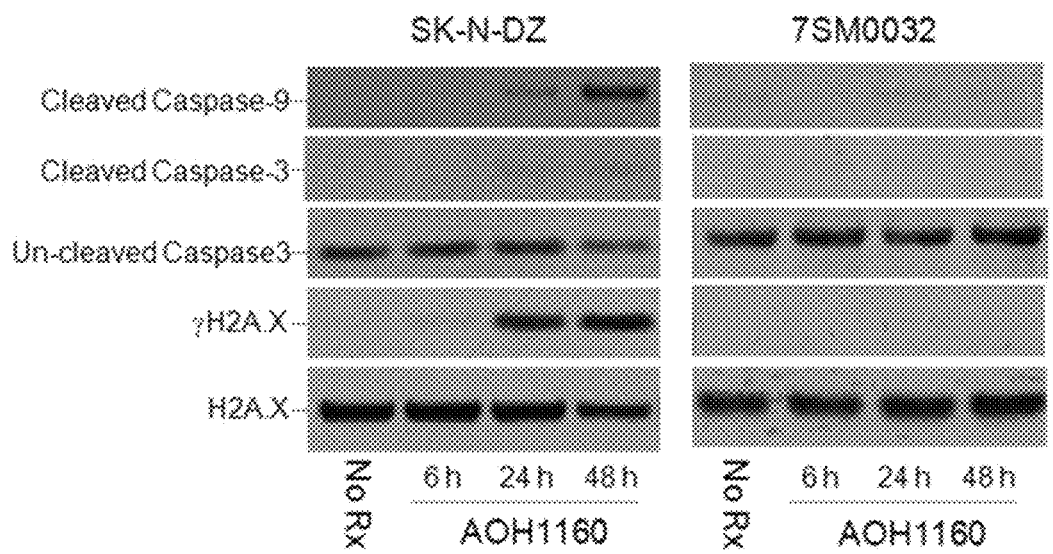
Figure 2C:
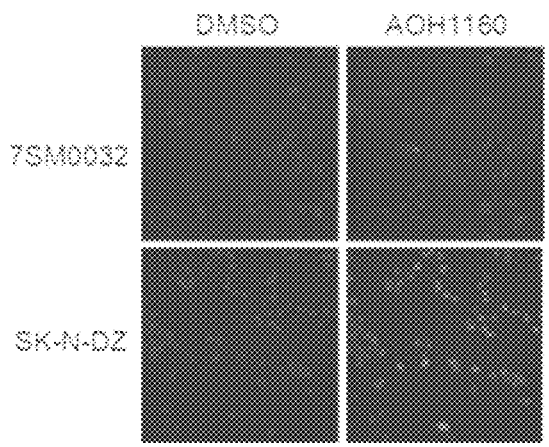
Figure 2D:
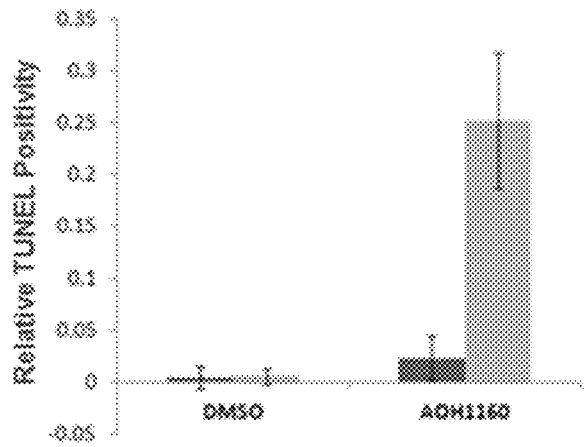

Example 13. AOH1160 Induces Cell Cycle Arrest, Accumulation of DNA Damage, and Apoptosis at Sub-Micromolar Concentrations AOH1160 causes cell cycle arrest (FIG. 2A), increases γH2A.X levels (FIG. 2B), and apoptosis as indicated by the increase in the sub-G1 population (FIG. 2A) and TUNEL positivity (FIG. 2B) in NB cells. The increase in apoptosis in NB cells coincides with activation of caspase-3 and caspase-9, suggesting the involvement of these two caspases in AOH1160-induced apoptosis. Consistent with its lack of toxicity to non-malignant cells in a cell viability assay, AOH1160 doesn't significantly change the cell cycle profiles of 7SM0032 cells (FIG. 2A). Nor does it increase intracellular γH2A.X level (FIG. 2B) or cause apoptosis in 7SM0032 cells (FIGS. 2C and 2D).

Figure 3A:
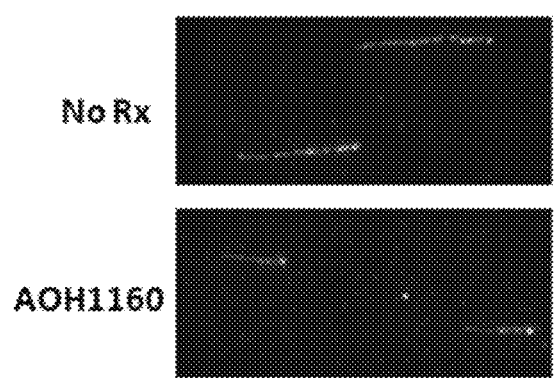
FIGS. 3A-3B.
Figure 3B:
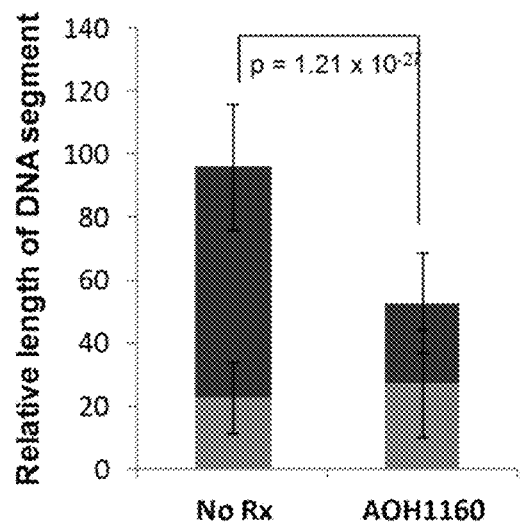
Figure 4:
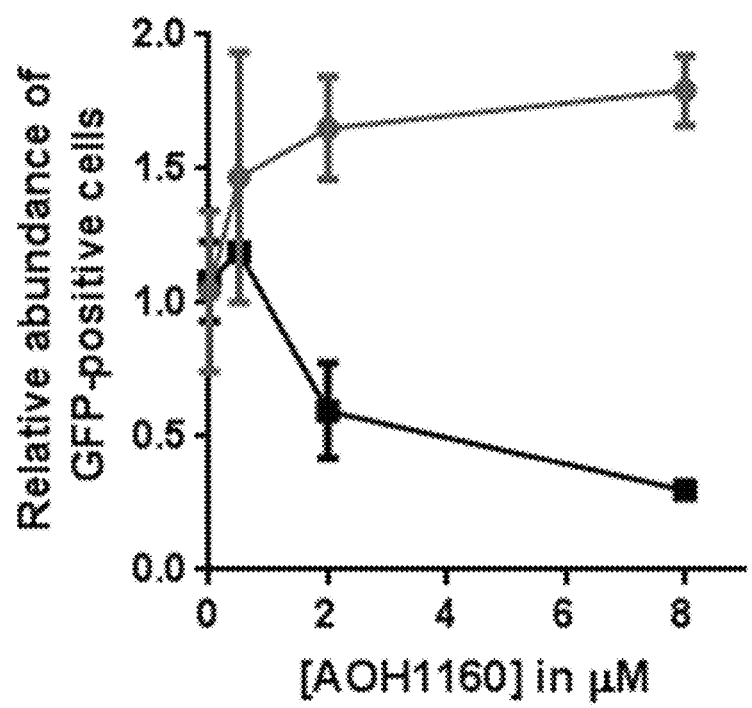
FIG. 4 depicts a line graph showing the inhibition of HR-mediated DSB repair. The DR-GFP (squares) and EJ5-GFP (circles) cell lines were transiently transfected by the pCBASce plasmid that expresses the I-SceI meganuclease. Three hours after transfection, cells were treated with various concentrations of AOH1160 in fresh growth medium. Cells treated with DMSO were used as control. The HR (homologous recombination) and EJ-mediated (end-joining mediated) DSB Double Stranded Break repair events, indicated by the restoration of a functional GFP gene in the respective cell lines, were quantified by measuring the relative abundance of GFP-positive cells by flow cytometry. Results in triplicates from each cell line and treatment condition relative to those from the control were averaged and graphed plus/minus standard deviations.
Figure 5:
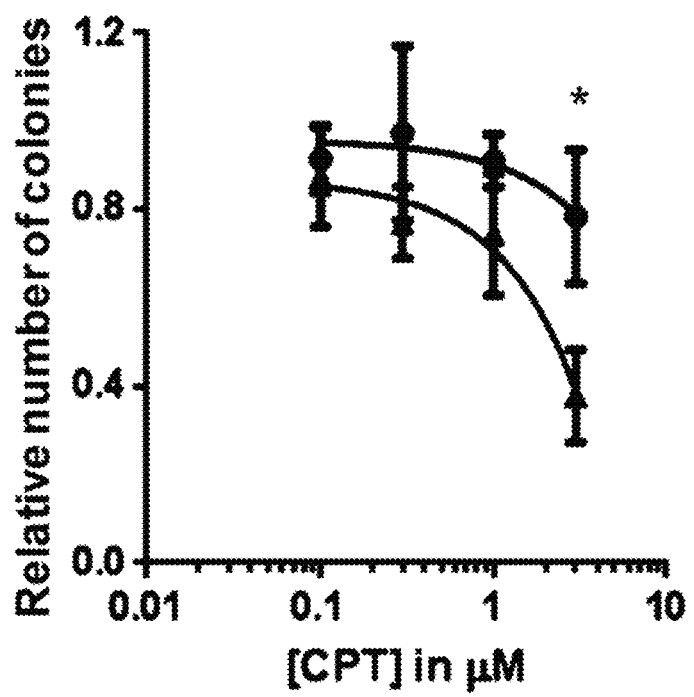
FIG. 5 depicts a line graph showing the enhanced sensitivity to cisplatin by AOH1160. Human SK-N-DZ NB cells were treated with or without various concentrations of cisplatin (CPT) in the presence or absence of 500 nM of AOH1160 for 18 h. Cells were washed twice with growth medium and were cultured in fresh medium for 3 weeks to allow colony formation. The colony counts in dishes treated by cisplatin without AOH1160 (circles) were normalized to the colony counts in dishes without cisplatin or AOH1160 treatment. The colony counts in dishes treated by both cisplatin and AOH1160 (triangles) were normalized to the colony counts in dishes treated by 500 nM AOH1160 only. The relative number of colonies in triplicates for each treatment condition were averaged and graphed plus/minus standard deviations. * indicates p<0.01.

Example 14. AOH1160 Inhibits HR-Mediated DSB Repair and Sensitizes NB Cells to Cisplatin AOH1160 blocks DNA repair in DR-GFP, but not in EJ5-GFP cells, indicating that it selectively inhibits HR-mediated DNA repair (FIGS. 3A and 3B). HR-mediated DNA repair plays an important role in repairing cross-linked DNA caused by chemotherapeutic drugs, such as cisplatin [27, 28]. A clonogenic assay was performed to investigate whether AOH1160 would increase NB cells' sensitivity to cisplatin. SK-N-DZ cells were treated with or without various concentrations of cisplatin in the presence or absence of 500 nM of AOH1160 for 18 hours. Cells were washed and cultured in fresh medium in the absence of either agent for 3 weeks to allow colony formation. As shown in FIG. 5, SK-N-DZ cells are more sensitive to cisplatin treatment in the presence of AOH1160 than in its absence, demonstrating the potential of combining AOH1160 with conventional chemotherapeutic drugs in treating NB patients.

Example 15. AOH1160 Inhibits Tumor Growth in Animals

Figure 6A:
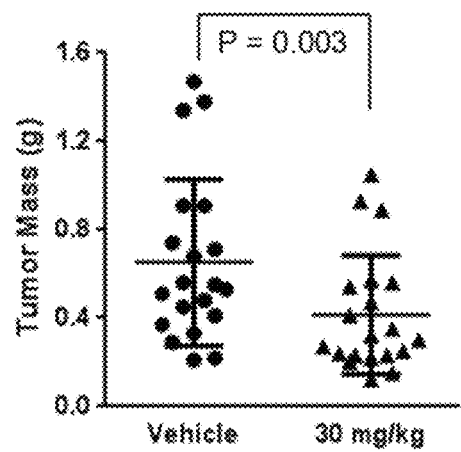
FIGS. 6A-6C.
Figure 6B:
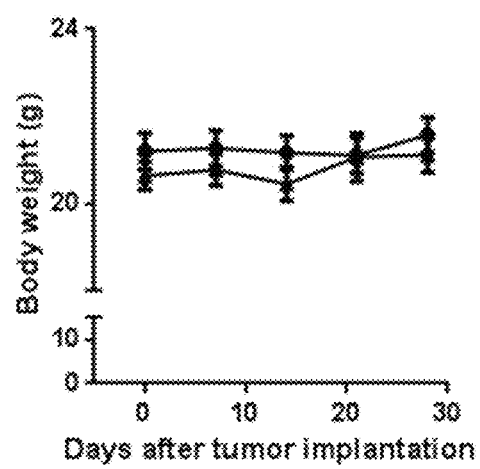
Figure 6C:
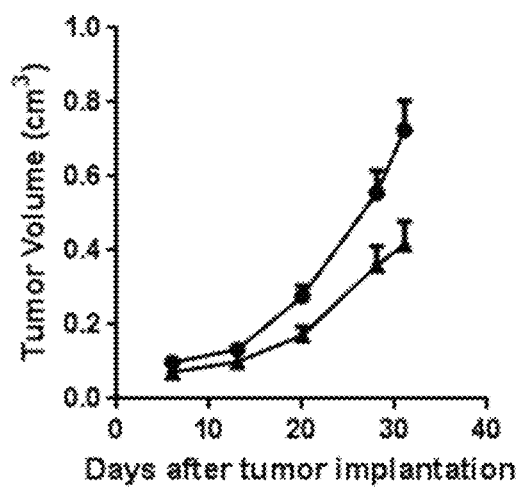

Given the potency and the favorable therapeutic properties of AOH1160, its efficacy was tested in nude mice bearing xenograft tumors derived from the SK-N-BE2(c) cells. AOH1160 was administered to mice at 30 mg/kg twice daily (BID) by oral gavages and the compound significantly reduced tumor burden (FIGS. 6A and 6B) in comparison to the control groups that were given vehicle only. Weight loss of the animals was monitored throughout the experiment as an indication of toxicity. AOH1160 did not cause any death or significant weight loss in the experimental animals (FIGS. 6A and 6B), including the non-tumor bearing control mice. These in vivo properties of AOH1160 prove the therapeutic potential of this compound in treating NB.

TABLE 2

Pharmacokinetics (PK) of AOH1160 in animals
Rat PO (dose: 20 mg/kg)

| Dosing | $T_{1/2}$ (hr) | $C_{max}$ (ng/ml) | $T_{max}$ (hr) | $AUC_{(0-inf)}$ (ng/mL * hr) | F (%) |
|---|---|---|---|---|---|
| Single | 3.8 ± 31 | 50 ± 31 | 3.3 ± 2.3 | 383 ± 110 | ND |
| BID | 4.3 ± 1.7 | 73 ± 23 | 6.0 ± 0.0 | 429 ± 195 | ND |

Example 16. Additional Analogues to Determine SAR

Specific analogs are envisioned, such as N substitutions on the benzene ring. For example an ortho-N substitution on the benzene ring together with the ortho-N on naphthalene. Additional analogs envisioned involve the 4-oxygen-pyridine position; a para-position might give more flexibility of the benzene ring A. It is interesting to move the phenyl ring A of AOH1160 from the ortho to the para position, having the formula:

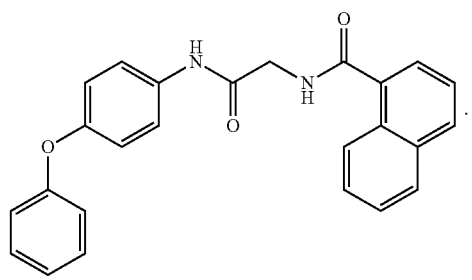 [SMILES: O=C(CNC(=O)c1cccc2ccccc12)Nc1ccc(Oc2ccccc2)cc1]

Figure 7:
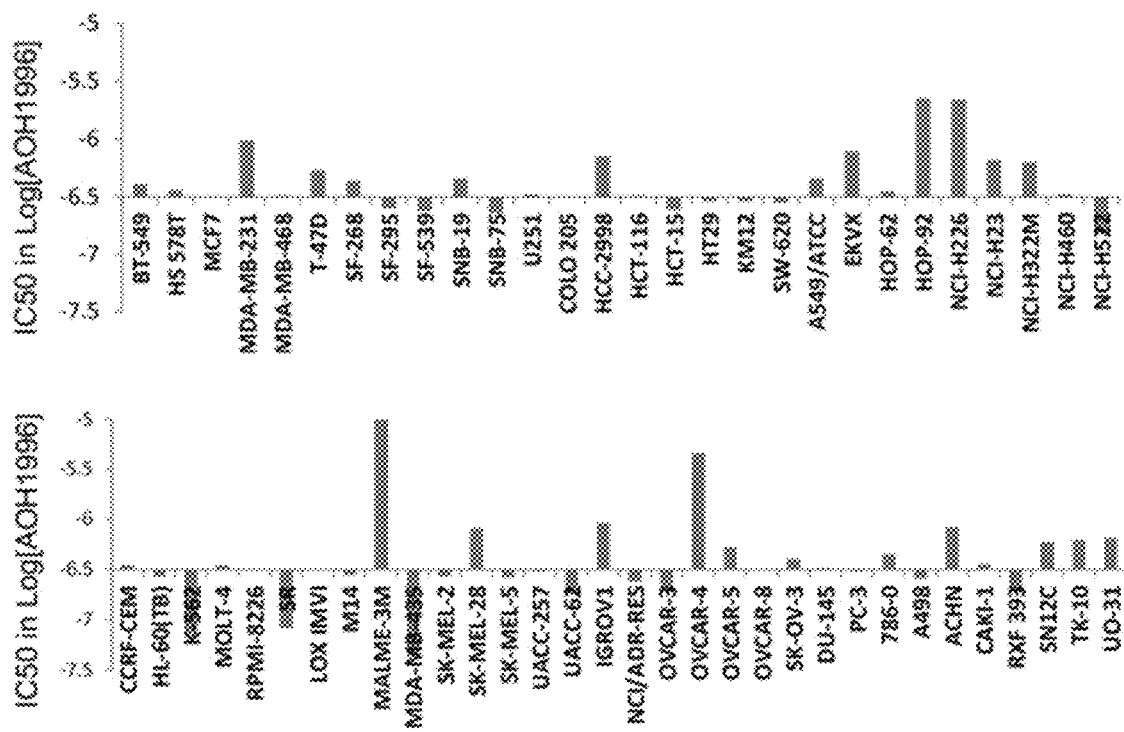
FIG. 7. NCI-60 panel test. The effect of AOH1160 on growth of the NCI-60 panel, which consists of 60 cancer cell lines representing 9 major cancer types, was tested in a 5-dose study. Shown are the Log IC50 values determined for each cell line. The median IC50 for this panel of cell lines is about 320 nM or $3.2×10^{-7}$M (the Log value of which corresponds to −6.5 on the graph). This study was performed by the National Institute of Cancer.

As observed in FIG. 7, the effect of AOH1160 on growth of the NCI-60 panel, which consists of 60 cancer cell lines representing 9 major cancer types, was tested in a 5-dose study. Shown are the Log IC50 values determined for each cell line. The median IC50 for this panel of cell lines is about 320 nM or $3.2\times10^{-7}$ M (the Log value of which corresponds to −6.5 on the graph).

Figure 8A:
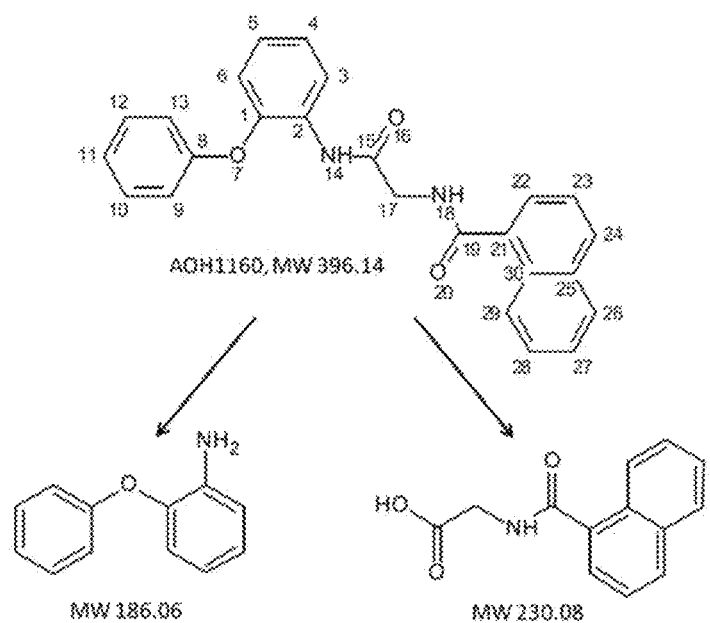
FIGS. 8A-8B.
Figure 8B:
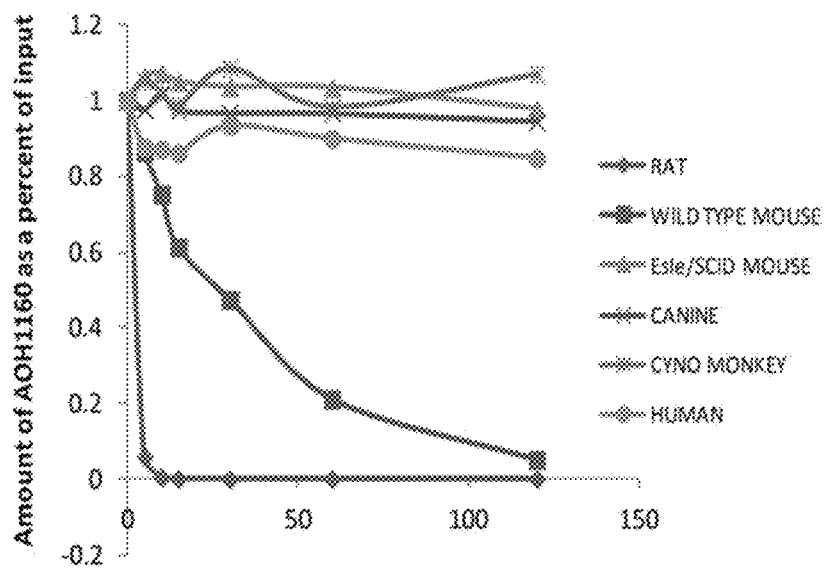

AOH1160 was degraded in the plasma collected from a wildtype Balb/c mouse, see FIGS. 8A-8B. Liquid chromatographymass spectrometry (LC-MS) analysis of AOH1160 metabolites found that the compound was degraded by amide cleavage as illustrated in the left panel. This amide cleavage was catalyzed by the carboxyl esterase, ES-1, which is highly expressed in rodents, but not significantly expressed in the blood of higher mammal species. AOH1160 is stable in the plasma of canine, monkey, and human, as well as in the plasma of ES-1-deficient mice (Es1e/SCID). The stability of AOH1160 in in Es1e/SCID mice not only proved that ES-1 was responsible for the quick degradation of AOH1160, but also identified a mouse model which mimics the human enzymatic environment for pharmacological study of AOH1160.

Figure 9:
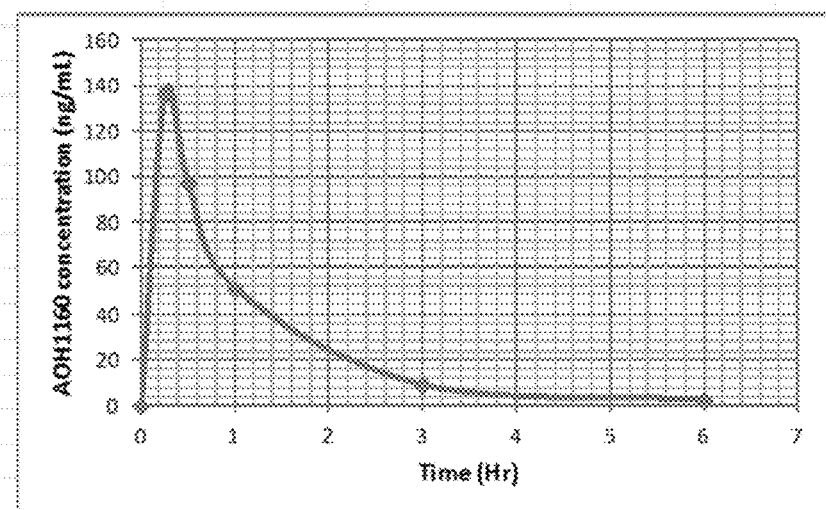
FIG. 9. Pharmacokinetic study of AOH1160. Pharmacokinetic study is important to determine how much drug/compound animals actually receive. In this study, the compound was given to Es1e/SCID mice orally in a newly designed formulation at 20 mg/kg. Plasmas were collected at 6 time points after dosing. Plasma concentration of AOH1160 was determined by MS.

Pharmacokinetic study is important to determine how much drug/compound animals actually receive. In this study, the compound was given to Es1e/SCID mice orally in a newly designed formulation at 20 mg/kg. Plasmas were collected at 6 time points after dosing. Plasma concentration of AOH1160 was determined by MS, as observed in FIG. 9.

Figure 10A:
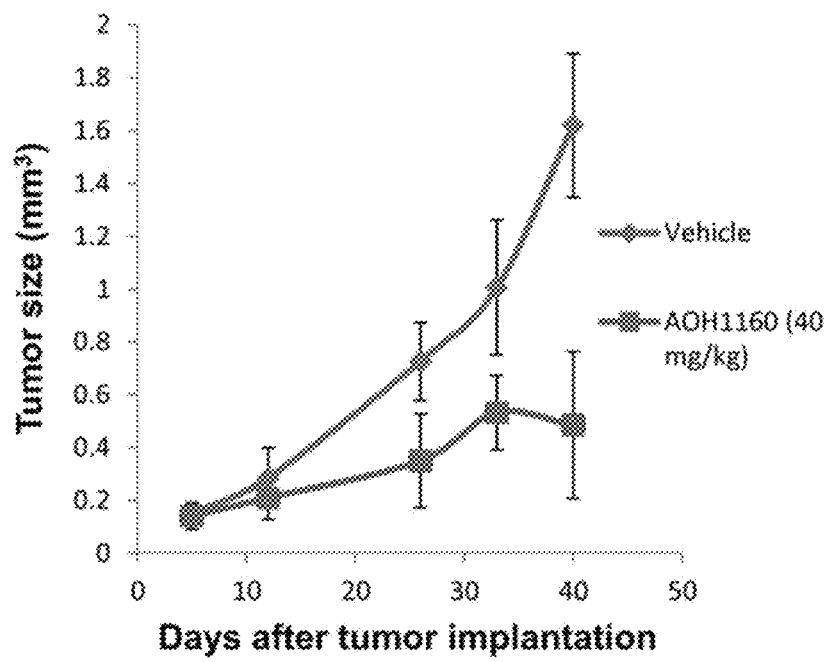
FIGS. 10A-10B. Inhibition of the growth xenograft tumor derived from a triple-negative breast cancer cell line (MDA-MB-436). Mice bearing xenograft tumors were given vehicle only or 40 mg/kg of AOH1160 through the study. Shown are tumor volumes (FIG. 10A) and mouse body weights (FIG. 10B) in the course of the study. The Es1e/SCID mice used in this study were treated by vehicle only (diamond) or by 40 mg/kg AOH1160 (square) once daily. AOH1160 inhibited tumor growth, but caused no significant weight loss.
Figure 10B:
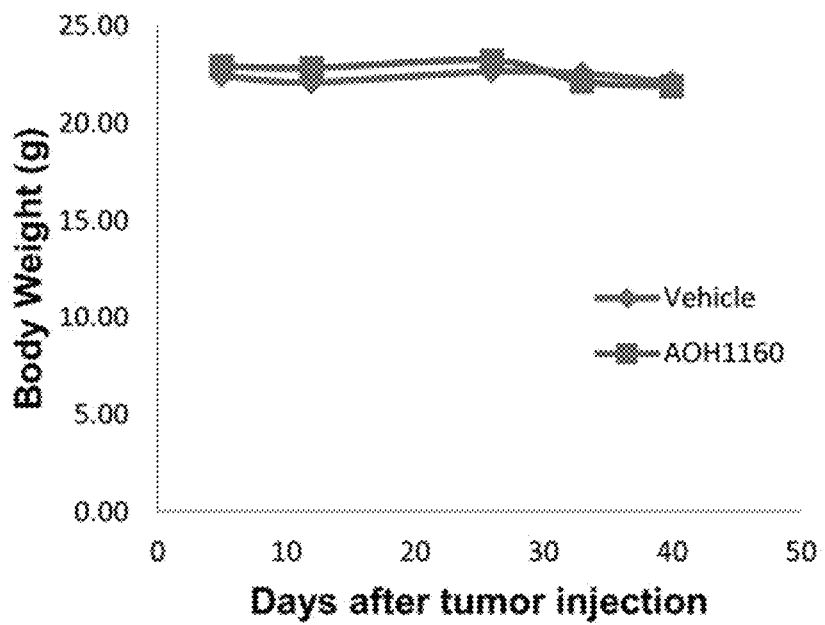

Inhibition of the growth xenograft tumor derived from a triple-negative breast cancer cell line (MDA-MB-436). Mice bearing xenograft tumors were given vehicle only or 40 mg/kg of AOH1160 through the study. Shown are tumor volumes (FIG. 10A) and mouse body weights (FIG. 10B) in the course of the study. The Es1e/SCID mice used in this study were treated by vehicle only (diamond) or by 40 mg/kg AOH1160 (square) once daily. AOH1160 inhibited tumor growth, but caused no significant weight loss.

Figure 11:
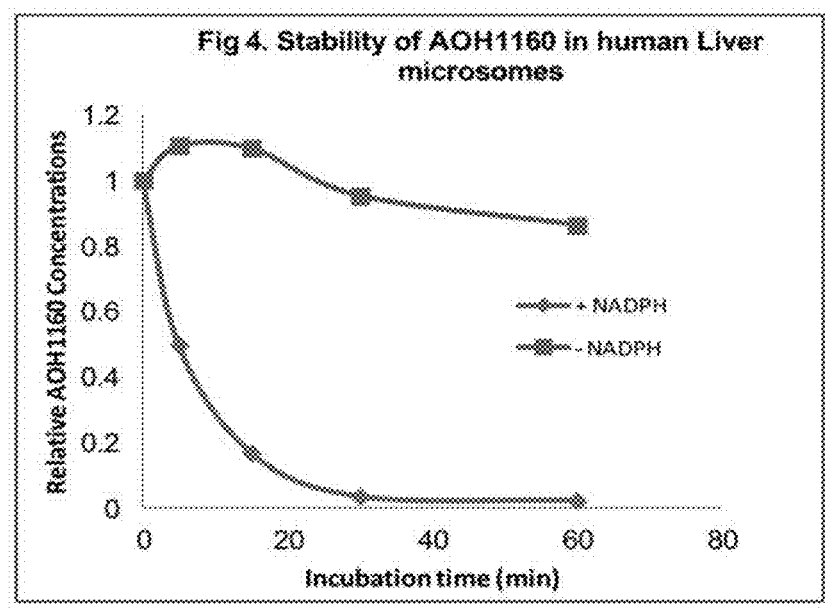
FIG. 11. AOH1160 stability in a liver microsome assay. Liver is a major organ responsible for drug metabolism. We tested the stability of AOH1160 in a liver microsome assay. By analyzing the metabolites, we determined a major pathway responsible for AOH1160 metabolism. AOH1160 was mainly metabolized through mono- and di-hydroxylation in a NADPH-dependent manner by human liver microsomes.
Figure 12:
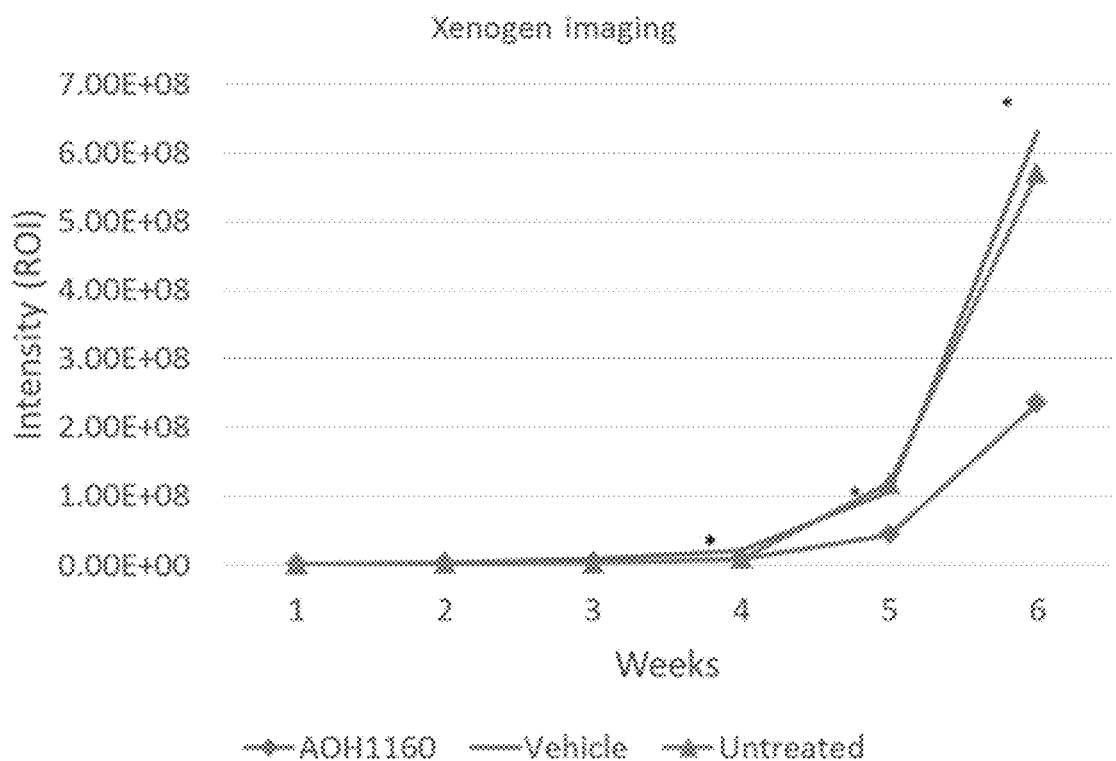
FIG. 12. Effects of AOH1160 on brain tumors in mice. The compound was given to tumor bearing mice once weekly. The brain cancer cells used in this study contains a luciferase. For measuring tumor growth, luciferin was injected into each mouse. The relative growth of the tumors in live mice was determined by measuring luminescent signals by a CCD camera. The compound inhibited brain tumor growth.

Liver is a major organ responsible for drug metabolism. We tested the stability of AOH1160 in a liver microsome assay (FIG. 11). By analyzing the metabolites, we determined a major pathway responsible for AOH1160 metabolism. AOH1160 was mainly metabolized through mono- and di-hydroxylation in a NADPH-dependent manner by human liver microsomes.

The compound (AOH1160) was give into tumor bearing mice once weekly. The brain cancer cells used in this study contains a luciferase. For measuring tumor growth, luciferin was injected into each mouse. The relative growth of the tumors in live mice was determined by measuring luminescent signals by a CCD camera. The compound inhibited brain tumor growth.

Figure 13A:
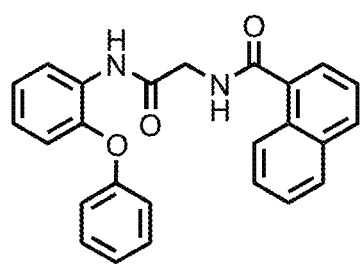
FIGS. 13A-13F. Identification of AOH1996, a stable analog of AOH1160. Since AOH1160 were found to be metabolized mainly through hydroxylation in liver, we synthesized several AOH1160 analogs, some of which mimic hydroxylated AOH1160 (FIGS. 13B and 13C). Other analogs have the corresponding hydroxylated sites blocked by o-methylation (FIGS. 13D and 13E). One o-methylated analog, AOH1996, is stable to NADPH dependent metabolism in a liver microsome assay (FIG. 13F).
Figure 13B:
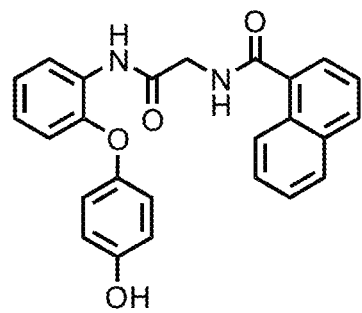
Figure 13C:
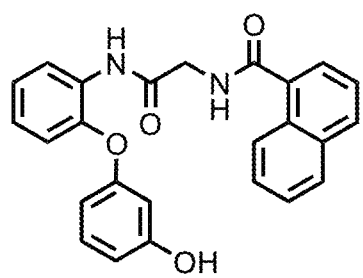
Figure 13D:
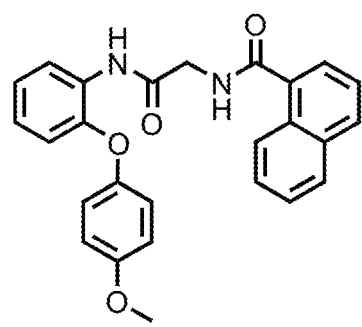
Figure 13E:
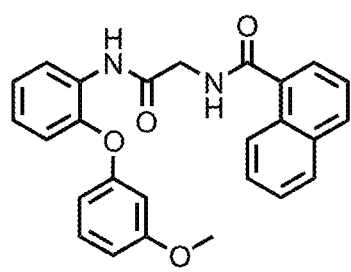
Figure 13F:
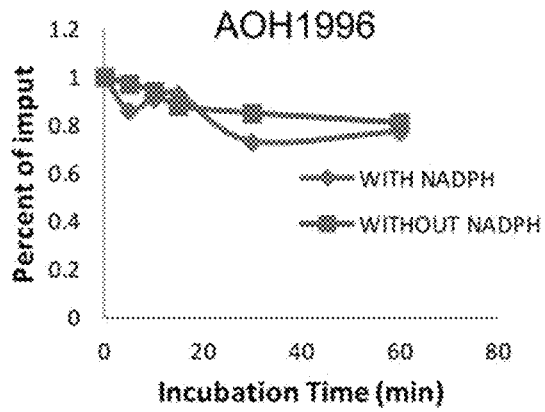

Since AOH1160 were found to be metabolized mainly through hydroxylation in liver, we synthesized several AOH1160 analogs, some of which mimic hydroxylated AOH1160. These analogs are being used as a standard to help identify where the hydroxyl group is attached in AOH1160 in liver. Interestingly, most hydroxylated AOH1160 analogs we tested so far had similar anti-cancer activities as AOH1160. We also synthesized several AOH1160 analogs, in which an o-methyl group was attached to AOH1160. One such analog, AOH1996, otherwise referred to as PCNA7, FIG. 13E, was found to be stable in a liver microsome assay.

Figure 14A:
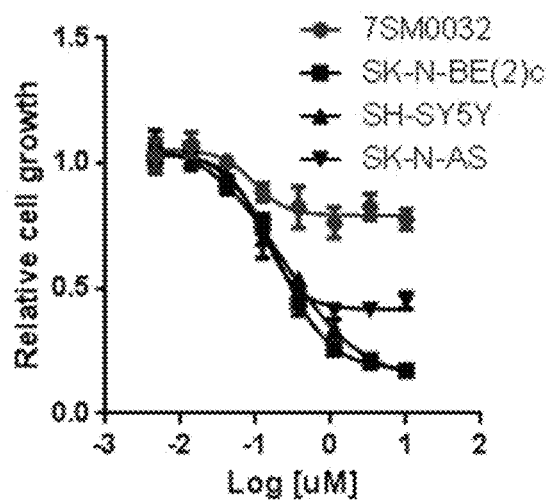
FIGS. 14A-14B: Like AOH1160, AOH1996 selectively kills neuroblastoma (FIG. 14A) and small cell lung cancer cells (FIG. 14B) at below micromolar concentrations. This compound has minimal toxicity to non-malignant cells, including neural crest stem cells (7SM0032), human small airway epithelial cells (hSAEC), and PBMCs.
Figure 14B:
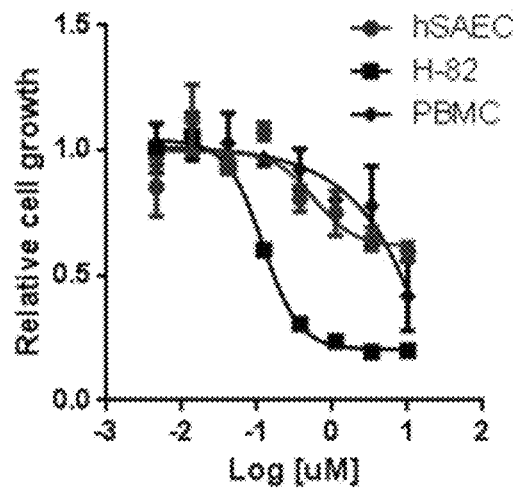
Figure 15A:
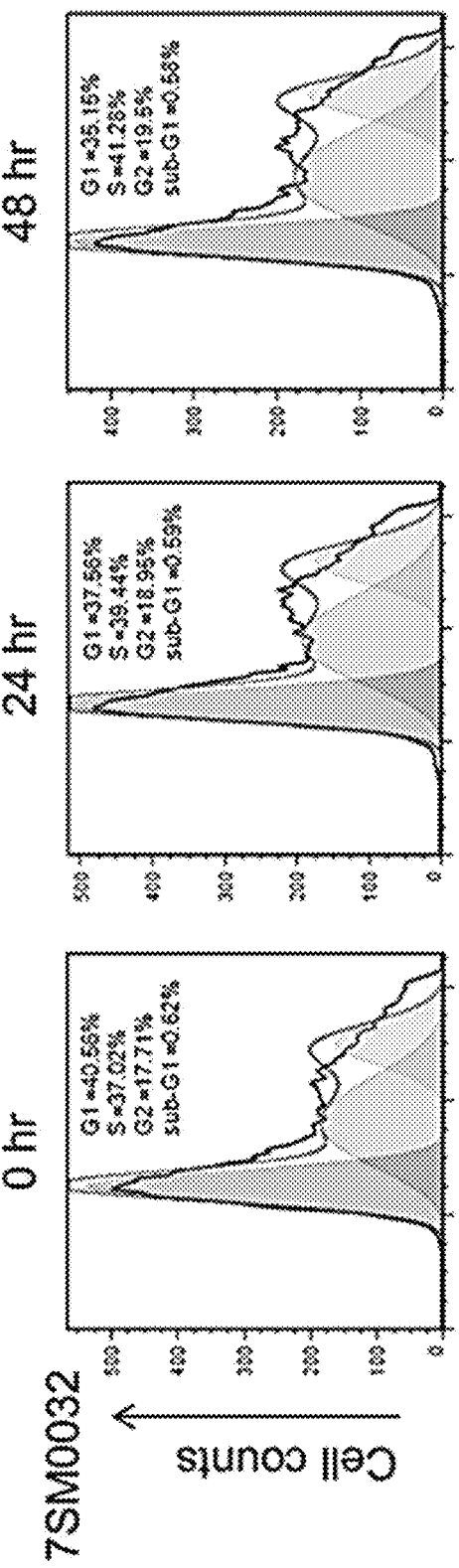
FIGS. 15A-15C. Like AOH1160, AOH1996 caused S/G2 cell cycle arrest in neuroblastoma cells (SH-SYSY and SK-N-BE(2)c), but exerted little effect on normal cells (7SM0032).
Figure 15B:
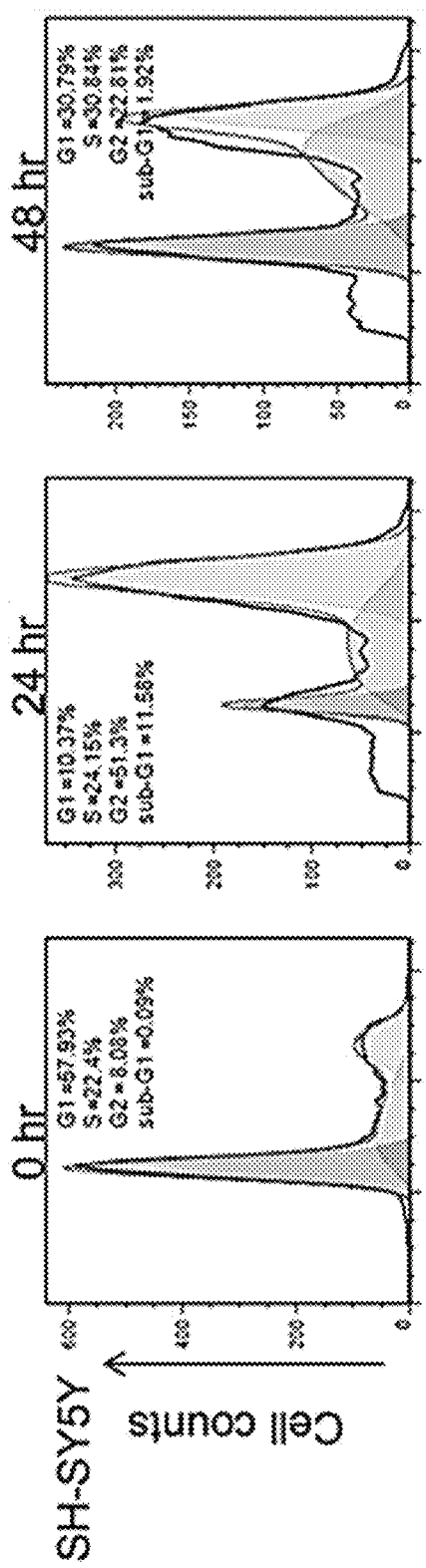
Figure 15C:
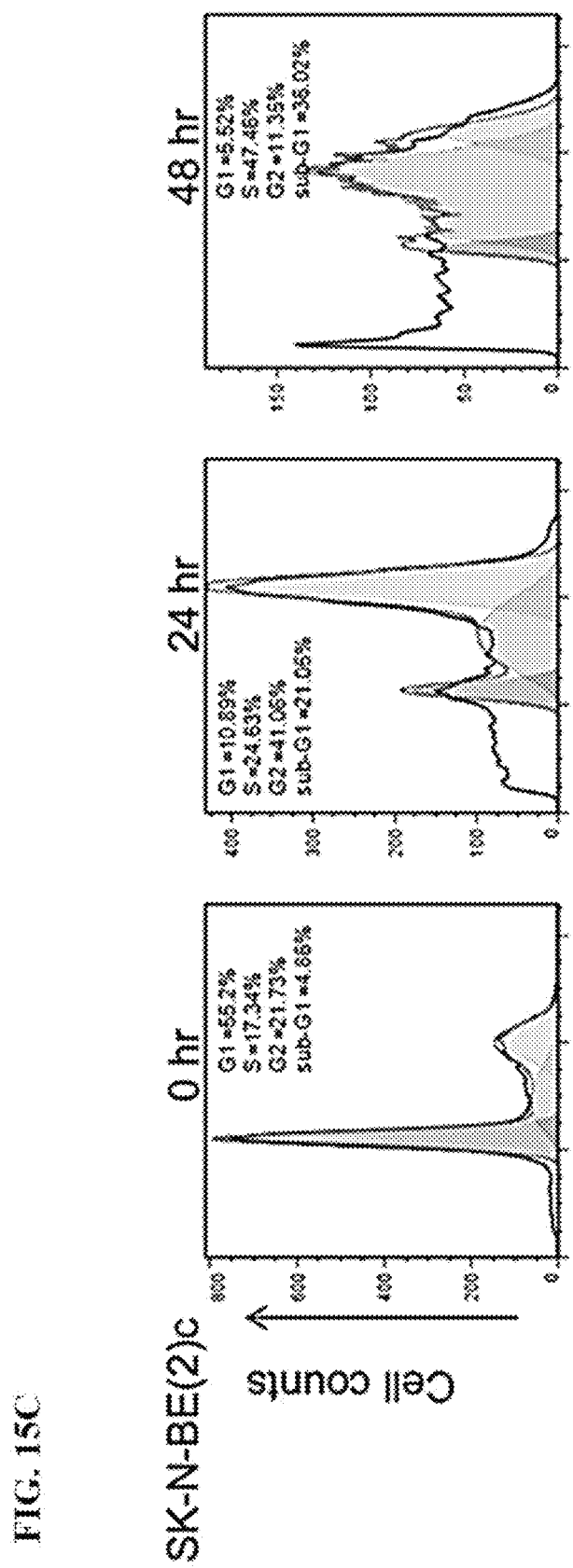

Like AOH1160, AOH1996 selectively kills neuroblastoma (FIG. 14A) and small cell lung cancer cells (FIG. 14B) at below micromolar concentrations. This compound has minimal toxicity to non-malignant cells, including neural crest stem cells (7SM0032), human small airway epithelial cells (hSAEC), and PBMCs. Additionally, similar to AOH1160, AOH1996 caused S/G2 cell cycle arrest in neuroblastoma cells (SH-SY5Y and SK-N-BE(2)c), but exerted little effect on normal cells (7SM0032).

TABLE 3

| Compound ID | Structures | IC50 (nM) | | | | |
|---|---|---|---|---|---|---|
| | | SK-N-BE(2)c | SK-N-DZ | SK-N-AS | PBMC | 7SM0032 |
| AOH1160 | 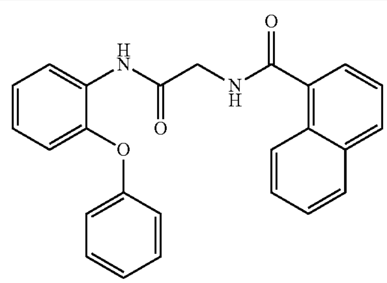 [SMILES: O=C(CNC(=O)c1cccc2ccccc12)Nc1ccccc1Oc1ccccc1] | 325.5 | 237.75 | 107.65 | >20000 | >20000 |
| PCNA1 | 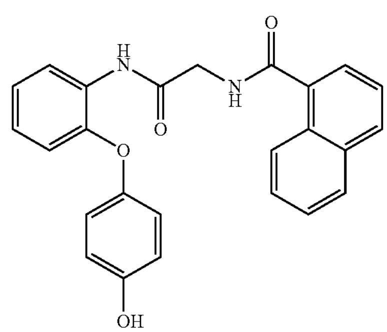 [SMILES: O=C(CNC(=O)c1cccc2ccccc12)Nc1ccccc1Oc1ccc(O)cc1] | 490 | 467 | 156.85 | >20000 | ND |

TABLE 3-continued

| Compound ID | Structures | IC50 (nM) | | | | |
|---|---|---|---|---|---|---|
| | | SK-N-BE(2)c | SK-N-DZ | SK-N-AS | PBMC | 7SM0032 |
| PCNA2 | 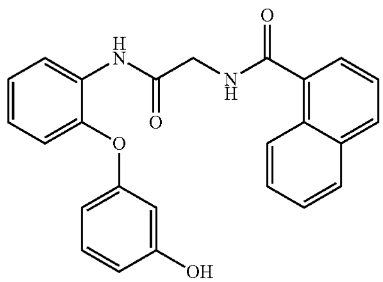 [SMILES: O=C(CNC(=O)c1cccc2ccccc12)Nc1ccccc1Oc1cccc(O)c1] | 485 | 539 | 192 | > 20000 | ND |
| PCNA3 | 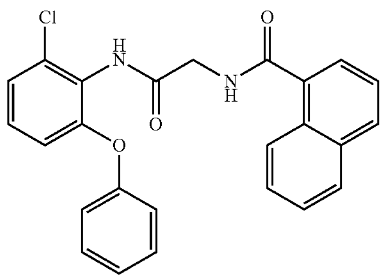 [SMILES: O=C(CNC(=O)c1cccc2ccccc12)Nc1c(Cl)cccc1Oc1ccccc1] | | | | | |
| PCNA3A | 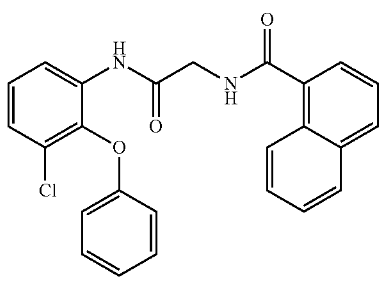 [SMILES: O=C(CNC(=O)c1cccc2ccccc12)Nc1cccc(Cl)c1Oc1ccccc1] | | | | | |
| PCNA4 | 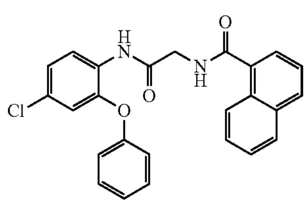 [SMILES: O=C(CNC(=O)c1cccc2ccccc12)Nc1ccc(Cl)cc1Oc1ccccc1] | 500 | 447.2 | 185.35 | > 20000 | ND |
| PCNA6 | 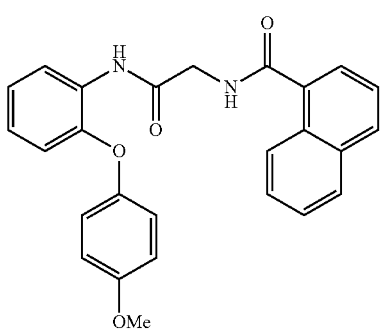 [SMILES: COc1ccc(Oc2ccccc2NC(=O)CNC(=O)c2cccc3ccccc23)cc1] | 234 | 271 | 91 | > 20000 | ND |

TABLE 3-continued

| Compound ID | Structures | IC50 (nM) SK-N-BE(2)c | SK-N-DZ | SK-N-AS | PBMC | 7SM0032 |
|---|---|---|---|---|---|---|
| PCNA7/ AOH1996 | 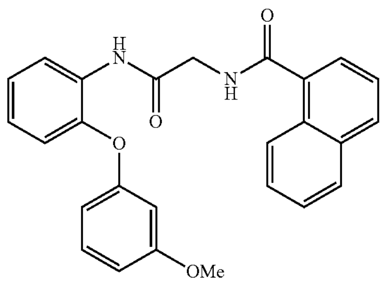 [SMILES: COc1cccc(Oc2ccccc2NC(=O)CNC(=O)c2cccc3ccccc23)c1] | 236 | 288 | 125 | >20000 | ND |
| #1161 | IC50 = 21.6 μM | ND | ND | 21600 | ND | ND |
| #1162 | IC50 > 50 μM | ND | ND | >50000 | ND | ND |
| #1165 | IC50 = 35 μM | ND | ND | 35000 | ND | ND |
| #1166 | IC50 = 34 μM | ND | ND | >30000 | ND | ND |

TABLE 3-continued

| Compound ID | Structures | IC50 (nM) | | | | |
| --- | --- | --- | --- | --- | --- | --- |
| | | SK-N-BE(2)c | SK-N-DZ | SK-N-AS | PBMC | 7SM0032 |
| #1167 | IC50 = 4.2 μM | ND | ND | ND | ND | ND |
| #1175 | IC50 > 30 μM | ND | ND | > 30000 | ND | ND |
| #1176 | 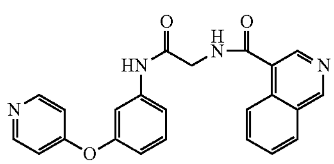 [SMILES: O=C(CNC(=O)c1cncc2ccccc12)Nc1cccc(Oc2ccncc2)c1] | ND | ND | > 30000 | ND | ND |
| #1177 | IC50 > 30 μM | ND | ND | ND | ND | ND |
| #1178 | IC50 = 1.10 μM | ND | ND | 1100 | ND | ND |

TABLE 3-continued

| Compound ID | Structures | IC50 (nM) | | | | |
|---|---|---|---|---|---|---|
| | | SK-N-BE(2)c | SK-N-DZ | SK-N-AS | PBMC | 7SM0032 |
| AOH1179 | IC50 > 30 μM | ND | ND | > 30000 | ND | ND |
| AOH1180 | IC50 > 30 μM | ND | ND | > 30000 | ND | ND |

ND = not determined

TABLE 4

| | AOH1160 IC$_{50}$ (nM) | Cancer type |
|---|---|---|
| HOP-62 | ND | Non-Small Cell Lung |
| EKVX | ND | Non-Small Cell Lung |
| SK-MEL-28 | ND | Melanoma |
| HCT-116 | 102 | Colon |
| NCI-H23 | 194 | Non-Small Cell Lung |
| DU-145 | 200 | Prostrate |
| NCI-H322M | 157 | Non-Small Cell Lung |
| HCT-15 | 133 | Colon |
| OVCAR-8 | 204 | Ovarian |
| A549 | 173 | Non-Small Cell Lung |
| HL-60 | 128 | Leukemia |

ND = not determined

TABLE 5

NCI-60 panel test. The GI$_{50}$sof the indicated compounds on the NCI-60 panel of cancer cell lines. The effect of the indicated compounds on growth of the NCI-60 panel, which consists of 60 cancer cell lines representing 9 major cancer types, was tested in a 5-dose study. Shown are the GI$_{50}$ (drug concentration yielding 50% growth inhibition) values (M) determined for each cell line.

| Cell Lines | AOH1160 | PCNA1 | PCNA2 | PCNA6 | PCNA7/AOH1996 |
|---|---|---|---|---|---|
| CCRF-CEM | 3.47E−07 | 9.33E−07 | 4.17E−06 | 9.12E−07 | 3.63E−07 |
| HL-60(TB) | 2.69E−07 | 7.08E−07 | 1.32E−06 | 6.17E−07 | 8.13E−08 |
| K-562 | 7.08E−08 | 5.01E−07 | 1.05E−06 | 1.45E−07 | 1.29E−07 |
| MOLT-4 | 3.47E−07 | 1.20E−06 | 4.90E−06 | 9.55E−07 | 6.61E−07 |
| RPMI-8226 | 3.16E−07 | 9.77E−07 | 8.13E−06 | 1.12E−06 | 9.55E−07 |
| SR | 8.32E−08 | 4.57E−07 | 1.05E−06 | 1.66E−07 | 1.15E−07 |
| A549/ATCC | 4.57E−07 | 1.48E−06 | 9.55E−06 | 1.26E−06 | 3.16E−07 |
| EKVX | 7.76E−07 | 1.17E−06 | 8.91E−06 | 1.38E−06 | 1.29E−06 |
| HOP-62 | 3.55E−07 | 1.35E−06 | 8.13E−06 | 7.24E−07 | 3.02E−07 |
| HOP-92 | 2.24E−06 | 2.51E−05 | 2.51E−05 | 2.51E−05 | 2.04E−07 |
| NCI-H226 | 2.19E−06 | 4.79E−06 | 2.51E−05 | 4.27E−06 | 2.51E−06 |

TABLE 5-continued

NCI-60 panel test. The $GI_{50}$s of the indicated compounds on the NCI-60 panel of cancer cell lines. The effect of the indicated compounds on growth of the NCI-60 panel, which consists of 60 cancer cell lines representing 9 major cancer types, was tested in a 5-dose study. Shown are the $GI_{50}$ (drug concentration yielding 50% growth inhibition) values (M) determined for each cell line.

| Cell Lines | AOH1160 | PCNA1 | PCNA2 | PCNA6 | PCNA7/AOH1996 |
|---|---|---|---|---|---|
| NCI-H23 | 6.61E−07 | 2.14E−06 | 1.58E−05 | 1.29E−06 | 7.41E−07 |
| NCI-H322M | 6.31E−07 | 1.15E−06 | 1.07E−05 | 1.23E−06 | 1.29E−06 |
| NCI-H460 | 3.31E−07 | 9.77E−07 | 5.75E−06 | 8.51E−07 | 2.95E−07 |
| NCI-H522 | 1.51E−07 | 8.51E−07 | 1.62E−06 | 1.95E−07 | 1.78E−07 |
| COLO 205 | 3.09E−07 | 7.94E−07 | 1.48E−05 | 6.46E−07 | 2.82E−07 |
| HCC-2998 | 7.08E−07 | 8.91E−06 | 2.51E−05 | 1.41E−06 | 1.26E−06 |
| HCT-116 | 3.24E−07 | 9.77E−07 | 1.38E−06 | 6.17E−07 | 9.55E−08 |
| HCT-15 | 2.45E−07 | 9.12E−07 | 3.16E−06 | 5.89E−07 | 1.29E−07 |
| HT29 | 2.88E−07 | 1.00E−06 | 2.14E−05 | 5.75E−07 | 1.10E−07 |
| KM12 | 2.88E−07 | 9.12E−07 | 2.19E−06 | 5.75E−07 | 1.91E−07 |
| SW-620 | 2.82E−07 | 9.12E−07 | 3.09E−06 | 6.76E−07 | 1.66E−07 |
| SF-268 | 4.37E−07 | 3.31E−06 | 2.09E−05 | 2.04E−06 | 5.50E−07 |
| SF-295 | 2.51E−07 | 6.17E−07 | 2.19E−06 | 3.98E−07 | 1.12E−07 |
| SF-539 | 2.40E−07 | 6.92E−07 | 4.07E−06 | 5.75E−07 | 2.24E−07 |
| SNB-19 | 4.57E−07 | 1.41E−06 | 8.71E−06 | 1.23E−06 | 6.17E−07 |
| SNB-75 | 2.29E−07 | 5.89E−07 | 3.31E−06 | | 1.29E−07 |
| U251 | 3.31E−07 | 1.41E−06 | 8.32E−06 | 1.05E−06 | 2.40E−07 |
| LOX IMVI | 3.09E−07 | 1.74E−06 | 1.51E−05 | 1.35E−06 | 2.69E−07 |
| MALME-3M | 1.00E−05 | | 5.89E−06 | 2.51E−05 | 1.70E−05 |
| M14 | 2.75E−07 | 6.92E−07 | 1.55E−06 | 5.50E−07 | 1.58E−07 |
| MDA-MB-435 | 4.27E−08 | 1.62E−07 | 7.59E−07 | 8.32E−08 | 7.08E−08 |
| SK-MEL-2 | 2.69E−07 | 2.51E−05 | 2.51E−05 | 2.29E−06 | 1.82E−07 |
| SK-MEL-28 | 8.13E−07 | 8.51E−07 | 1.86E−06 | 3.80E−07 | 4.37E−06 |
| SK-MEL-5 | 2.63E−07 | 2.51E−05 | 2.51E−05 | 2.51E−05 | 2.19E−07 |
| UACC-62 | 1.78E−07 | 1.17E−06 | 1.62E−06 | 5.62E−07 | 2.09E−07 |
| IGROV1 | 9.12E−07 | 2.34E−06 | 1.00E−05 | 1.58E−06 | 1.05E−06 |
| OVCAR-3 | 1.91E−07 | 7.41E−07 | 1.51E−06 | 3.89E−07 | 1.00E−07 |
| OVCAR-4 | 4.57E−06 | 2.82E−06 | 2.51E−05 | 2.24E−06 | 7.76E−07 |
| OVCAR-5 | 5.25E−07 | 6.31E−06 | 2.51E−05 | 2.00E−06 | 1.12E−06 |
| OVCAR-8 | 3.16E−07 | 1.32E−06 | 1.15E−05 | 1.15E−06 | 6.92E−07 |
| NCI/ADR-RES | 2.40E−07 | 1.20E−06 | 7.94E−06 | 4.27E−07 | 2.40E−07 |
| SK-OV-3 | 3.98E−07 | 1.58E−06 | 1.29E−05 | 1.02E−06 | 4.90E−07 |
| 786-0 | 4.47E−07 | 1.05E−06 | 1.00E−05 | 1.15E−06 | 1.82E−07 |
| A498 | 2.57E−07 | 1.02E−06 | 5.13E−06 | 5.62E−07 | 1.15E−07 |
| ACHN | 8.32E−07 | 1.86E−06 | 1.74E−05 | 1.51E−06 | 3.98E−07 |
| CAKI-1 | 3.55E−07 | | | | 9.12E−07 |
| RXF 393 | 1.86E−07 | 5.01E−07 | 4.17E−06 | 4.90E−07 | 1.66E−07 |
| SN12C | 5.89E−07 | 2.19E−06 | 2.51E−05 | 2.29E−06 | 1.45E−06 |
| TK-10 | 6.17E−07 | 1.70E−05 | 2.51E−06 | 2.14E−06 | 1.58E−06 |
| UO-31 | 6.46E−07 | 1.78E−06 | 1.66E−05 | 1.48E−06 | 1.82E−06 |
| PC-3 | 3.02E−07 | 1.32E−06 | 7.08E−06 | 1.05E−06 | 2.82E−07 |
| DU-145 | 3.24E−07 | 1.15E−06 | 9.55E−06 | 1.02E−06 | 7.08E−07 |
| MCF7 | 3.09E−07 | 8.51E−07 | 4.47E−06 | 2.57E−07 | 1.00E−07 |
| MDA-MB-231/ATCC | 9.77E−07 | 3.16E−06 | 1.78E−05 | 2.24E−06 | 7.76E−07 |
| HS 578T | 3.63E−07 | 1.35E−06 | 5.75E−06 | 1.70E−06 | 3.80E−07 |
| BT-549 | 4.07E−07 | 1.62E−06 | 2.51E−05 | 1.12E−06 | 2.95E−07 |
| T-47D | 5.37E−07 | 1.55E−06 | 9.77E−06 | 2.51E−06 | 1.38E−07 |
| MDA-MB-468 | 3.24E−07 | 5.50E−07 | 3.55E−06 | 4.57E−07 | 3.31E−07 |

TABLE 6

The cell lines of Table 5, categorized according to the cancer the cell line represents.

| Cancer | Cell line |
|---|---|
| Breast Cancer | BT-549, HS 578T, MCF7, MDA-MB-231/ATCC, MDA-MB-468, T-47D |
| Central Nervous System (CNS) Cancer | SF-268, SF-295, SF-539, SNB-19, SNB-75, U251 |
| Colon Cancer | COLO 208, HCC-2998, HCT-116, HCT-15, HT29, KM12, SW-620 |
| Leukemia/Myeloma | CCRF-CEM, HL-60(TB), K-562, MOLT-4, RPMI-8226, SR |
| Melanoma | LOX IMVI, MALME-3M, M14, MDA-MB-435, SK-MEL-2, SK-MEL-28, SK-MEL-5, UACC-257, UACC-62 |
| Non-Small Cell Lung Cancer | A549/ATCC, EKVX, HOP-62, HOP-92, NCI-H226, NCI-H23, NCI-H322M, NCI-H460, NCI-H522 |
| Ovarian Cancer | IGROV1, NCI/ADR-RES, OVCAR-3, OVCAR-4, OVCAR-5, OVCAR-8, SK-OV-3 |
| Prostate Cancer | DU-145, PC-3 |
| Renal Cancer | 786-0, A498, ACHN, CAKI-1, RXF 393, SN12C, TK-10, UO-31 |

References 1. Brodeur, G. M., Nat Rev Cancer, 2003. 3(3): p. 203-16. 2. De Bernardi, B., et al., J Clin Oncol, 2009. 27(7): p. 1034-40. 3. Bhatnagar, S. N. and Y. K. Sarin, Indian J Pediatr, 2012. 79(6): p. 787-92. 4. Armstrong, G. T., et al., J Clin Oncol, 2011. 29(22): p. 3056-64. 5. Maris, J. M., et al., Lancet, 2007. 369(9579): p. 2106-20. 6. Park, J. R., A. Eggert, and H. Caron, Hematol Oncol Clin North Am, 2010. 24(1): p. 65-86. 7. Aaltomaa, S., P. Lipponen, and K. Syrjanen, Anticancer Res, 1993. 13(2): p. 533-8. 8. Chu, J. S., C. S. Huang, and K. J. Chang, Cancer Lett, 1998. 131(2): p. 145-52. 9. Tahan, S. R., et al., Cancer, 1993. 71(11): p. 3552-9. 10. Strzalka, W. and A. Ziemienowicz, Ann Bot, 2011. 107(7): p. 1127-40. 11. Stoimenov, I. and T. Helleday, Biochem Soc Trans, 2009. 37(Pt 3): p. 605-13. 12. Krishna, T. S., et al., Cell, 1994. 79(7): p. 1233-43. 13. Waga, S., et al., Nature, 1994. 369(6481): p. 574-8. 14. Ducoux, M., et al., J Biol Chem, 2001. 276(52): p. 49258-66. 15. Warbrick, E., et al., Oncogene, 1997. 14(19): p. 2313-21. 16. Malkas, L. H., et al., Proc Natl Acad Sci USA, 2006. 103(51): p. 19472-7. 17. Hoelz, D. J., et al., Proteomics, 2006. 6(17): p. 4808-16. 18. Gu, L., et al., PLoS One, 2014. 9(4): p. e94773. 19. Punchihewa, C., et al., J Biol Chem, 2012. 287(17): p. 14289-300. 20. Friesner, R. A., et al., J Med Chem, 2006. 49(21): p. 6177-96. 21. Phillips, J. C., et al., J Comput Chem, 2005. 26(16): p. 1781-802. 22. Bennardo, N., et al., PLoS Genet, 2008. 4(6): p. e1000110. 23. Gunn, A., et al., J Biol Chem, 2011. 286(49): p. 42470-82. 24. Rothkamm, K., et al., Mol Cell Biol, 2003. 23(16): p. 5706-15. 25. Shibata, A., et al., EMBO J, 2011. 30(6): p. 1079-92. 26. Mayer, M. and B. Meyer, J Am Chem Soc, 2001. 123(25): p. 6108-17. 27. Al-Minawi, A. Z., et al., Nucleic Acids Res, 2009. 37(19): p. 6400-13. 28. Raschle, M., et al., Cell, 2008. 134(6): p. 969-80. 29. Capdeville, R., et al., Nat Rev Drug Discov, 2002. 1(7): p. 493-502. 30. Burris, H. A., 3rd, Oncologist, 2004. 9 Suppl 3: p. 10-5. 31. Flaherty, K. T., et al., N Engl J Med, 2012. 367(18): p. 1694-703. 32. Santoro, A., et al., Lancet Oncol, 2013. 14(1): p. 55-63. 33. Verstovsek, S., et al., N Engl J Med, 2012. 366(9): p. 799-807. 34. Vogel, C. L., et al., J Clin Oncol, 2002. 20(3): p. 719-26. 35. Von Hoff, D. D., et al., N Engl J Med, 2009. 361(12): p. 1164-72. 36. Bardelli, A. and S. Siena, J Clin Oncol, 2010. 28(7): p. 1254-61. 37. Janne, P. A., N. Gray, and J. Settleman, Nat Rev Drug Discov, 2009. 8(9): p. 709-23. 38. Sierra, J. R., V. Cepero, and S. Giordano, Mol Cancer, 2010. 9: p. 75. 39. Muller, R., et alPLoS One, 2013. 8(7): p. e70430. 40. Tan, Z., et al., Mol Pharmacol, 2012. 81(6): p. 811-9. 41. Yu, Y. L., et al., PLoS One, 2013. 8(4): p. e61362. 42. Zhao, H., et al., Mol Cancer Ther, 2011. 10(1): p. 29-36.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A compound having the formula:

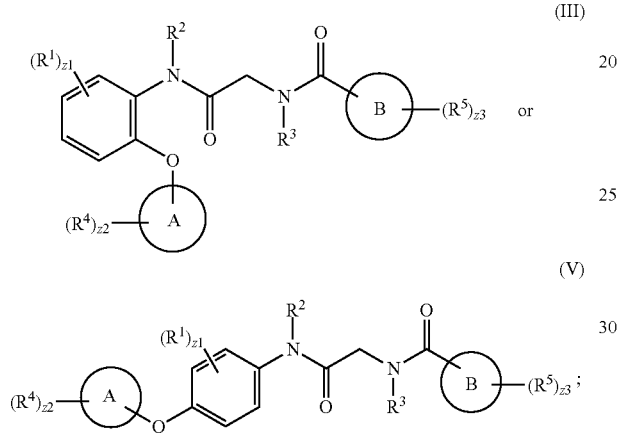

wherein

Ring A is phenyl or 5 to 6 membered heteroaryl;

Ring B is 1-naphthyl or isoquinolinyl;

$R^1$ is independently a halogen, $-CX^1_3$, $-CHX^1_2$, $-CH_2X$, $-CN$, $-SO_{n1}R^{10}$, $-SO_{v1}NR^7R^8$, $-NHNH_2$, $-ONR^7R^8$, $-NHC=(O)NHNH_2$, $-NHC=(O)NR^7R^8$, $-N(O)_{m1}$, $-NR^7R^8$, $-C(O)R^9$, $-C(O)-OR^9$, $-C(O)NR^7R^8$, $-OR^{10}$, $-NR^7SO_2R^{10}$, $-NR^7C=(O)R^9$, $-NR^7C(O)-OR^9$, $-NR^7OR^9$, $-OCX^1_3$, $-OCHX^1_2$, $-OCH_2X^1$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; or two adjacent $R^1$ substituents may optionally be joined to form a substituted or unsubstituted cycloalkyl, substituted or unsubstituted heterocycloalkyl, substituted or unsubstituted aryl, or substituted or unsubstituted heteroaryl;

$R^2$ is independently hydrogen, halogen, $-CX^2_3$, $-CHX^2_2$, $-CH_2X^2$, $-CN$, $-COOH$, $-CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^3$ is independently hydrogen, halogen, $-CX^3_3$, $-CHX^3_2$, $-CH_2X^3$, $-CN$, $-COOH$, $-CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^4$ is independently a halogen, $-CX^4_3$, $-CHX^4_2$, $-CH_2X^4$, $-CN$, $-SO_{n4}R^{14}$, $-SO_{v4}NR^{11}R^{12}$, $-NHNR^{11}R^{12}$, $-ONR^{11}R^{12}$, $-NHC=(O)NHNR^{11}R^{12}$, $-NHC=(O)NR^{11}R^{12}$, $-N(O)_{m4}$, $-NR^{11}R^{12}$, $-C(O)R^{13}$, $-C(O)-OR^{13}$, $-C(O)NR^{11}R^{12}$, $-OR^{14}$, $-NR^{11}SO_2R^{14}$, $-NR^{11}C=(O)R^{13}$, $-NR^{11}C(O)-OR^{13}$, $-NR^{11}OR^{13}$, $-OCX^4_3$, $-OCHX^4_2$, $-OCH_2X^4$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; or two adjacent $R^4$ substituents may optionally be joined to form a substituted or unsubstituted cycloalkyl, substituted or unsubstituted heterocycloalkyl, substituted or unsubstituted aryl, or substituted or unsubstituted heteroaryl;

$R^5$ is independently a halogen, $-CX^5_3$, $-CHX^5_2$, $-CH_2X^5$, $-CN$, $-SO_{n5}R^{18}$, $-SO_{v5}NR^{15}R^{16}$, $-NHNR^{15}R^{16}$, $-ONR^{15}R^{16}$, $-NHC=(O)NHNR^{15}R^{16}$, $-NHC=(O)NR^{15}R^{16}$, $-N(O)_{m5}$, $-NR^{15}R^{16}$, $-C(O)R^{17}$, $-C(O)-OR^{17}$, $-C(O)NR^{15}R^{16}$, $-OR^{18}$, $-NR^{15}SO_2R^{18}$, $-NR^{15}C=(O)R^{17}$, $-NR^{15}C(O)-OR^{17}$, $-NR^{15}OR^{17}$, $-OCX^5_3$, $-OCHX^5_2$, $-OCH_2X^5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; or two adjacent $R^5$ substituents may optionally be joined to form a substituted or unsubstituted cycloalkyl, substituted or unsubstituted heterocycloalkyl, substituted or unsubstituted aryl, or substituted or unsubstituted heteroaryl;

$R^7$, $R^8$, $R^9$, and $R^{10}$ are independently hydrogen, halogen, $-CX^A_3$, $-CHX^A_2$, $-CH_2X^A$, $-CN$, $-COOH$, $-CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; or $R^7$ and $R^8$ substituents bonded to the same nitrogen atom may optionally be joined to form a substituted or unsubstituted heterocycloalkyl or substituted or unsubstituted heteroaryl;

$R^{11}$, $R^{12}$, $R^{13}$, and $R^{14}$ are independently hydrogen, halogen, $-CX^B_3$, $-CHX^B_2$, $-CH_2X$, $-CN$, $-COOH$, $-CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; or $R^{11}$ and $R^{12}$ substituents bonded to the same nitrogen atom may optionally be joined to form a substituted or unsubstituted heterocycloalkyl or substituted or unsubstituted heteroaryl;

$R^{15}$, $R^{16}$, $R^{17}$, and $R^{18}$ are independently hydrogen, halogen, —$CX^C_3$, —$CHX^C_2$, —$CH_2X^C$, —CN, —COOH, —$CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; or $R^{15}$ and $R^{16}$ substituents bonded to the same nitrogen atom may optionally be joined to form a substituted or unsubstituted heterocycloalkyl or substituted or unsubstituted heteroaryl;

z1 is independently an integer from 0 to 4;

z2 is independently an integer from 0 to 5;

z3 is independently an integer from 0 to 7;

m1, m4, m5, v1, v4, and v5 are independently 1 or 2;

n1, n4, and n5 are independently an integer from 0 to 4; and $X^1$, $X^2$, $X^3$, $X^4$, $X^5$, $X^A$, $X^B$, and $X^C$ are independently —Cl, —Br, —I, or —F.

2. The compound of claim 1, wherein $R^1$ is independently halogen, —$CF_3$, —OH, —$NH_2$, —SH, substituted or unsubstituted $C_1$-$C_4$ alkyl, substituted or unsubstituted 2 to 4 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl.

3. The compound of claim 1, wherein $R^4$ is independently halogen, —$CF_3$, —OH, —$NH_2$, —SH, substituted or unsubstituted $C_1$-$C_4$ alkyl, substituted or unsubstituted 2 to 4 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl.

4. The compound of claim 1, wherein $R^4$ is independently —$OR^{14}$, and $R^{14}$ is hydrogen or unsubstituted $C_1$-$C_5$ alkyl.

5. The compound of claim 1, wherein $R^5$ is independently halogen, —$CF_3$, —OH, —$NH_2$, —SH, substituted or unsubstituted $C_1$-$C_4$ alkyl, substituted or unsubstituted 2 to 4 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl.

6. The compound of claim 1, wherein $R^2$ is hydrogen, unsubstituted methyl, unsubstituted ethyl, or unsubstituted isopropyl; and $R^3$ is hydrogen, unsubstituted methyl, unsubstituted ethyl, or unsubstituted isopropyl.

7. The compound of claim 1, wherein Ring A is phenyl.

8. The compound of claim 1, wherein Ring A is a 2-thienyl, 3-thienyl, 2-pyridyl, 3-pyridyl, or 4-pyridyl.

9. The compound of claim 1, wherein Ring B is a 1-naphthyl.

10. The compound of claim 1, wherein Ring B is a 1-isoquinolinyl, 3-isoquinolinyl, or 4-isoquinolinyl.

11. The compound of claim 1, having the formula:

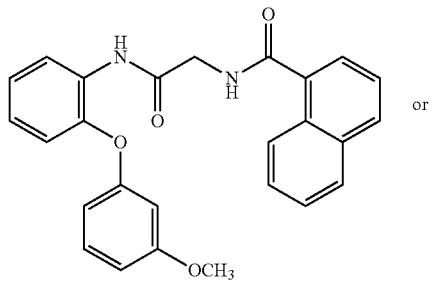

or

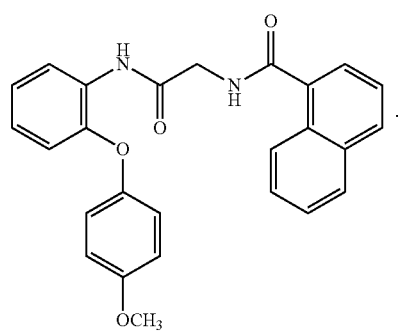

12. The compound of claim 1, having the formula:

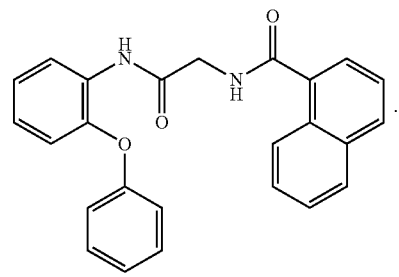 [SMILES: O=C(CNC(=O)c1cccc2ccccc12)Nc1ccccc1Oc1ccccc1]

13. The compound of claim 1, having the formula:

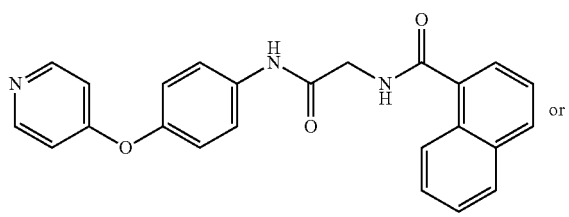

or

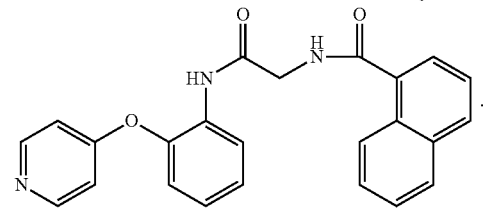

14. A pharmaceutical composition comprising a compound of claim 1, or a pharmaceutically acceptable salt thereof, and a pharmaceutically acceptable excipient.

15. The pharmaceutical composition of claim 14, further comprising an anti-cancer agent, wherein the anti-cancer agent is a cisplatin.

16. A method of treating a disease associated with PCNA activity in a patient having said disease, said method comprising administering a therapeutically effective amount of a compound of claim 1, or a pharmaceutically acceptable salt thereof.

17. A method of treating cancer in a patient having said cancer, said method comprising administering a therapeutically effective amount of a compound of claim 1, or a pharmaceutically acceptable salt thereof.

18. A compound having the formula:

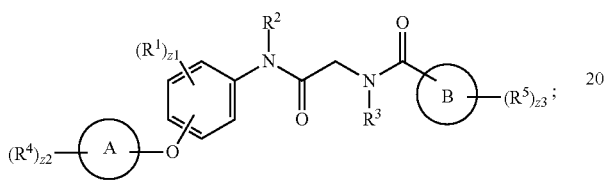

(II)

wherein
Ring A is phenyl or 5 membered heteroaryl;
Ring B is quinolinyl;
$R^1$ is independently a halogen, $-CX^1_3$, $-CHX^1_2$, $-CH_2X^1$, $-CN$, $-SO_{n1}R^{10}$, $-SO_{v1}NR^7R^8$, $-NHNH_2$, $-ONR^7R^8$, $-NHC=(O)NHNH_2$, $-NHC=(O)NR^7R^8$, $-N(O)_{m1}$, $-NR^7R^8$, $-C(O)R^9$, $-C(O)-OR^9$, $-C(O)NR^7R^8$, $-OR^{10}$, $-NR^7SO_2R^{10}$, $-NR^7C=(O)R^9$, $-NR^7C(O)-OR^9$, $-NR^7OR^9$, $-OCX^1_3$, $-OCHX^1_2$, $-OCH_2X^1$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; or two adjacent $R^1$ substituents may optionally be joined to form a substituted or unsubstituted cycloalkyl, substituted or unsubstituted heterocycloalkyl, substituted or unsubstituted aryl, or substituted or unsubstituted heteroaryl;
$R^2$ is independently hydrogen, halogen, $-CX^2_3$, $-CHX^2_2$, $-CH_2X^2$, $-CN$, $-COOH$, $-CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^3$ is independently hydrogen, halogen, $-CX^3_3$, $-CHX^3_2$, $-CH_2X^3$, $-CN$, $-COOH$, $-CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^4$ is independently a halogen, $-CX^4_3$, $-CHX^4_2$, $-CH_2X^4$, $-CN$, $-SO_{n4}R^{14}$, $-SO_{v4}NR^{11}R^{12}$, $-NHNR^{11}R^{12}$, $-ONR^{11}R^{12}$, $-NHC=(O)NHNR^{11}R^{12}$, $-NHC=(O)NR^{11}R^{12}$, $-N(O)_{m4}$, $-NR^{11}R^{12}$, $-C(O)R^{13}$, $-C(O)-OR^{13}$, $-C(O)NR^{11}R^{12}$, $-OR^{14}$, $-NR^{11}SO_2R^{14}$, $-NR^{11}C=(O)R^{13}$, $-NR^{11}C(O)-OR^{13}$, $-NR^{11}OR^{13}$, $-OCX^4_3$, $-OCHX^4_2$, $-OCH_2X^4$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; or two adjacent $R^4$ substituents may optionally be joined to form a substituted or unsubstituted cycloalkyl, substituted or unsubstituted heterocycloalkyl, substituted or unsubstituted aryl, or substituted or unsubstituted heteroaryl;
$R^5$ is independently a halogen, $-CX^5_3$, $-CHX^5_2$, $-CH_2X^5$, $-CN$, $-SO_{n5}R^{18}$, $-SO_{v5}NR^{15}R^{16}$, $-NHNR^{15}R^{16}$, $-ONR^{15}R^{16}$, $-NHC=(O)NHNR^{15}R^{16}$, $-NHC=(O)NR^{15}R^{16}$, $-N(O)_{m5}$, $-NR^{15}R^{16}$, $-C(O)R^{17}$, $-C(O)-OR^{17}$, $-C(O)NR^{15}R^{16}$, $-OR^{18}$, $-NR^{15}SO_2R^{18}$, $-NR^{15}C=(O)R^{17}$, $-NR^{15}C(O)-OR^{17}$, $-NR^{15}OR^{17}$, $-OCX^5_3$, $-OCHX^5_2$, $-OCH_2X^5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; or two adjacent $R^5$ substituents may optionally be joined to form a substituted or unsubstituted cycloalkyl, substituted or unsubstituted heterocycloalkyl, substituted or unsubstituted aryl, or substituted or unsubstituted heteroaryl;
$R^7$, $R^8$, $R^9$, and $R^{10}$ are independently hydrogen, halogen, $-CX^A_3$, $-CHX^A_2$, $-CH_2X^A$, $-CN$, $-COOH$, $-CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; or $R^7$ and $R^8$ substituents bonded to the same nitrogen atom may optionally be joined to form a substituted or unsubstituted heterocycloalkyl or substituted or unsubstituted heteroaryl;
$R^{11}$, $R^{12}$, $R^{13}$, and $R^{14}$ are independently hydrogen, halogen, $-CX^B_3$, $-CHX^B_2$, $-CH_2X^B$, $-CN$, $-COOH$, $-CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; or $R^{11}$ and $R^{12}$ substituents bonded to the same nitrogen atom may optionally be joined to form a substituted or unsubstituted heterocycloalkyl or substituted or unsubstituted heteroaryl;
$R^{15}$, $R^{16}$, $R^{17}$, and $R^{18}$ are independently hydrogen, halogen, $-CX^C_3$, $-CHX^C_2$, $-CH_2X^C$, $-CN$, $-COOH$, $-CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; or $R^{15}$ and $R^{16}$ substituents bonded to the same nitrogen atom may optionally be joined to form a substituted or unsubstituted heterocycloalkyl or substituted or unsubstituted heteroaryl;
z1 is independently an integer from 0 to 4;
z2 is independently an integer from 0 to 5;
z3 is independently an integer from 0 to 6;
m1, m4, m5, v1, v4, and v5 are independently 1 or 2;
n1, n4, and n5 are independently an integer from 0 to 4; and
$X^1$, $X^2$, $X^3$, $X^4$, $X^5$, $X^A$, $X^B$, and $X^C$ are independently $-Cl$, $-Br$, $-I$, or $-F$.

19. The compound of claim 18, wherein $R^1$ is independently halogen, —$CF_3$, —OH, —$NH_2$, —SH, substituted or unsubstituted $C_1$-$C_4$ alkyl, substituted or unsubstituted 2 to 4 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl.

20. The compound of claim 18, wherein $R^4$ is independently halogen, —$CF_3$, —OH, —$NH_2$, —SH, substituted or unsubstituted $C_1$-$C_4$ alkyl, substituted or unsubstituted 2 to 4 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl.

21. The compound of claim 18, wherein $R^4$ is independently —$OR^{14}$, and $R^{14}$ is hydrogen or unsubstituted $C_1$-$C_5$ alkyl.

22. The compound of claim 18, wherein $R^5$ is independently halogen, —$CF_3$, —OH, —$NH_2$, —SH, substituted or unsubstituted $C_1$-$C_4$ alkyl, substituted or unsubstituted 2 to 4 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl.

23. The compound of claim 18, wherein
$R^2$ is hydrogen, unsubstituted methyl, unsubstituted ethyl, or unsubstituted isopropyl; and
$R^3$ is hydrogen, unsubstituted methyl, unsubstituted ethyl, or unsubstituted isopropyl.

24. The compound of claim 18, wherein Ring A is phenyl.

25. The compound of claim 18, wherein Ring A is a 5 membered heteroaryl.

26. The compound of claim 18, wherein Ring A is a 2-thienyl or 3-thienyl.

27. A pharmaceutical composition comprising a compound of claim 18, or a pharmaceutically acceptable salt thereof, and a pharmaceutically acceptable excipient.

28. The pharmaceutical composition of claim 27, further comprising an anti-cancer agent, wherein the anti-cancer agent is a cisplatin.

29. A method of treating a disease associated with PCNA activity in a patient having said disease, said method comprising administering a therapeutically effective amount of a compound of claim 18, or a pharmaceutically acceptable salt thereof.

30. A method of treating cancer in a patient having said cancer, said method comprising administering a therapeutically effective amount of a compound of claim 18, or a pharmaceutically acceptable salt thereof.

31. A compound having the formula:

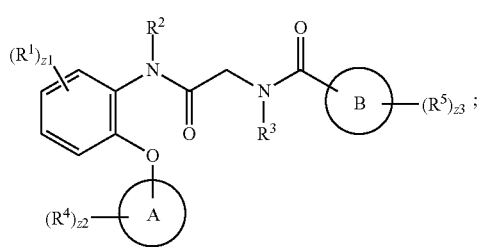

(III)

wherein
Ring A is phenyl or 5 to 6 membered heteroaryl;
Ring B is quinolinyl;

$R^1$ is independently a halogen, —$CX^1_3$, —$CHX^1_2$, —$CH_2X^1$, —CN, —$SO_{n1}R^{10}$, —$SO_{v1}NR^7R^8$, —$NHNH_2$, —$ONR^7R^8$, —$NHC$=$(O)NHNH_2$, —$NHC$=$(O)NR^7R^8$, —$N(O)_{m1}$, —$NR^7R^8$, —$C(O)R^9$, —$C(O)$—$OR^9$, —$C(O)NR^7R^8$, —$OR^{10}$, —$NR^7SO_2R^{10}$, —$NR^7C$=$(O)R^9$, —$NR^7C(O)$—$OR^9$, —$NR^7OR^9$, —$OCX^1_3$, —$OCHX^1_2$, —$OCH_2X^1$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; or two adjacent $R^1$ substituents may optionally be joined to form a substituted or unsubstituted cycloalkyl, substituted or unsubstituted heterocycloalkyl, substituted or unsubstituted aryl, or substituted or unsubstituted heteroaryl;

$R^2$ is independently hydrogen, halogen, —$CX^2_3$, —$CHX^2_2$, —$CH_2X^2$, —CN, —COOH, —$CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^3$ is independently hydrogen, halogen, —$CX^3_3$, —$CHX^3_2$, —$CH_2X^3$, —CN, —COOH, —$CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^4$ is independently a halogen, —$CX^4_3$, —$CHX^4_2$, —$CH_2X^4$, —CN, —$SO_4R^{14}$, —$SO_{v4}NR^{11}R^{12}$, —$NHNR^{11}R^{12}$, —$ONR^{11}R^{12}$, —$NHC$=$(O)NHNR^{11}R^{12}$, —$NHC$=$(O)NR^{11}R^{12}$, —$N(O)_{m4}$, —$NR^{11}R^{12}$, —$C(O)R^{13}$, —$C(O)$—$OR^{13}$, —$C(O)NR^{11}R^{12}$, —$OR^{14}$, —$NR^{11}SO_2R^{14}$, —$NR^{11}C$=$(O)R^{13}$, —$NR^{11}C(O)$—$OR^{13}$, —$NR^{11}OR^{13}$, —$OCX^4_3$, —$OCHX^4_2$, —$OCH_2X^4$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; or two adjacent $R^4$ substituents may optionally be joined to form a substituted or unsubstituted cycloalkyl, substituted or unsubstituted heterocycloalkyl, substituted or unsubstituted aryl, or substituted or unsubstituted heteroaryl;

$R^5$ is independently a halogen, —$CX^5_3$, —$CHX^5_2$, —$CH_2X^5$, —CN, —$SO_{n5}R^{18}$, —$SO_{v5}NR^{15}R^{16}$, —$NHNR^{15}R^{16}$, —$ONR^{15}R^{16}$, —$NHC$=$(O)NHNR^{15}R^{16}$, —$NHC$=$(O)NR^{15}R^{16}$, —$N(O)_{m5}$, —$NR^{15}R^{16}$, —$C(O)R^{17}$, —$C(O)$—$OR^{17}$, —$C(O)NR^{15}R^{16}$, —$OR^{18}$, —$NR^{15}SO_2R^{18}$, —$NR^{15}C$=$(O)R^{17}$, —$NR^{15}C(O)$—$OR^{17}$, —$NR^{15}OR^{17}$, —$OCX^5_3$, —$OCHX^5_2$, —$OCH_2X^5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; or two adjacent $R^5$ substituents may optionally be joined to form a substituted or unsubstituted cycloalkyl, substituted or unsubstituted heterocycloalkyl, substituted or unsubstituted aryl, or substituted or unsubstituted heteroaryl;

$R^7$, $R^8$, $R^9$, and $R^{10}$ are independently hydrogen, halogen, —$CX^A_3$, —$CHX^A_2$, —$CH_2X^A$, —CN, —COOH, —$CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; or $R^7$ and $R^8$ substituents bonded to the same nitrogen atom may optionally be joined to form a substituted or unsubstituted heterocycloalkyl or substituted or unsubstituted heteroaryl;

$R^{11}$, $R^{12}$, $R^{13}$, and $R^{14}$ are independently hydrogen, halogen, —$CX^B_3$, —$CHX^B_2$, —$CH_2X^B$, —CN, —COOH, —$CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; or $R^{11}$ and $R^{12}$ substituents bonded to the same nitrogen atom may optionally be joined to form a substituted or unsubstituted heterocycloalkyl or substituted or unsubstituted heteroaryl;

$R^{15}$, $R^{16}$, $R^{17}$, and $R^{18}$ are independently hydrogen, halogen, —$CX^C_3$, —$CHX^C_2$, —$CH_2X^C$, —CN, —COOH, —$CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; or $R^{15}$ and $R^{16}$ substituents bonded to the same nitrogen atom may optionally be joined to form a substituted or unsubstituted heterocycloalkyl or substituted or unsubstituted heteroaryl;

z1 is independently an integer from 0 to 4;
z2 is independently an integer from 0 to 5;
z3 is independently an integer from 0 to 6;
m1, m4, m5, v1, v4, and v5 are independently 1 or 2;
n1, n4, and n5 are independently an integer from 0 to 4; and
$X^1$, $X^2$, $X^3$, $X^4$, $X^5$, $X^A$, $X^B$, and $X^C$ are independently —Cl, —Br, —I, or —F.

32. The compound of claim 31, wherein $R^1$ is independently halogen, —$CF_3$, —OH, —$NH_2$, —SH, substituted or unsubstituted $C_1$-$C_4$ alkyl, substituted or unsubstituted 2 to 4 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl.

33. The compound of claim 31, wherein $R^4$ is independently halogen, —$CF_3$, —OH, —$NH_2$, —SH, substituted or unsubstituted $C_1$-$C_4$ alkyl, substituted or unsubstituted 2 to 4 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl.

34. The compound of claim 31, wherein $R^4$ is independently —$OR^{14}$, and $R^{14}$ is hydrogen or unsubstituted $C_1$-$C_5$ alkyl.

35. The compound of claim 31, wherein $R^5$ is independently halogen, —$CF_3$, —OH, —$NH_2$, —SH, substituted or unsubstituted $C_1$-$C_4$ alkyl, substituted or unsubstituted 2 to 4 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl.

36. The compound of claim 31, wherein
$R^2$ is hydrogen, unsubstituted methyl, unsubstituted ethyl, or unsubstituted isopropyl; and
$R^3$ is hydrogen, unsubstituted methyl, unsubstituted ethyl, or unsubstituted isopropyl.

37. The compound of claim 31, wherein Ring A is phenyl.

38. The compound of claim 31, wherein Ring A is a 2-thienyl, 3-thienyl, 2-pyridyl, 3-pyridyl, or 4-pyridyl.

39. A pharmaceutical composition comprising a compound of claim 31, or a pharmaceutically acceptable salt thereof, and a pharmaceutically acceptable excipient.

40. The pharmaceutical composition of claim 39, further comprising an anti-cancer agent, wherein the anti-cancer agent is a cisplatin.

41. A method of treating a disease associated with PCNA activity in a patient having said disease, said method comprising administering a therapeutically effective amount of a compound of claim 31, or a pharmaceutically acceptable salt thereof.

42. A method of treating cancer in a patient having said cancer, said method comprising administering a therapeutically effective amount of a compound of claim 31, or a pharmaceutically acceptable salt thereof.

* * * * *

UNITED STATES PATENT AND TRADEMARK OFFICE
CERTIFICATE OF CORRECTION

Page 1 of 2

PATENT NO. : 10,913,706 B2
APPLICATION NO. : 16/714062
DATED : February 9, 2021
INVENTOR(S) : Linda H. Malkas et al.

It is certified that error appears in the above-identified patent and that said Letters Patent is hereby corrected as shown below:

In the Claims

Column 167, Line 54, Claim 1 delete "independently".

Column 167, Line 61, Claim 1 delete "independently".

Column 168, Line 55, Claim 1 delete "$R^{13}$,and" and insert -- $R^{13}$, and --, therefor.

Column 169, Line 18, Claim 1 delete "z1 is independently" and insert -- z1 is --, therefor.

Column 169, Line 19, Claim 1 delete "z2 is independently" and insert -- z2 is --, therefor.

Column 169, Line 20, Claim 1 delete "z3 is independently" and insert -- z3 is --, therefor.

Column 171, Line 45, Claim 18 delete "independently".

Column 171, Line 52, Claim 18 delete "independently".

Column 172, Line 38, Claim 18 delete "$R^{13}$,and" and insert -- $R^{13}$, and --, therefor.

Column 172, Line 60, Claim 18 delete "z1 is independently" and insert -- z1 is --, therefor.

Column 172, Line 61, Claim 18 delete "z2 is independently" and insert -- z2 is --, therefor.

Column 172, Line 62, Claim 18 delete "z3 is independently" and insert -- z3 is --, therefor.

Column 174, Line 17, Claim 31 delete "independently".

Column 174, Line 24, Claim 31 delete "independently".

Signed and Sealed this
Thirtieth Day of November, 2021

Drew Hirshfeld
*Performing the Functions and Duties of the*
*Under Secretary of Commerce for Intellectual Property and*
*Director of the United States Patent and Trademark Office*

Column 175, Line 9, Claim 31 delete "$R^{13}$,and" and insert -- $R^{13}$, and --, therefor.

Column 175, Line 31, Claim 31 delete "z1 is independently" and insert -- z1 is --, therefor.

Column 175, Line 32, Claim 31 delete "z2 is independently" and insert -- z2 is --, therefor.

Column 175, Line 33, Claim 31 delete "z3 is independently" and insert -- z3 is --, therefor.

SEQUENCE LISTING

```
<160> NUMBER OF SEQ ID NOS: 4

<210> SEQ ID NO 1
<211> LENGTH: 1355
<212> TYPE: DNA
<213> ORGANISM: Homo sapiens

<400> SEQUENCE: 1
ggatggccgg agctggcgcc ctggttctgg aggtaaccgg ttactgaggg cgagaagcgc     60
cacccggagg ctctagcctg acaaatgctt gctgacctgg gccagagctc ttcccttacg    120
caagtctcag ccggtcgtcg cgacgttcgc ccgctcgctc tgaggctcct gaagccgaaa    180
ccagctagac tttcctcctt cccgcctgcc tgtagcggcg ttgttgccac tccgccacca    240
tgttcgaggc gcgcctggtc cagggctcca tcctcaagaa ggtgttggag gcactcaagg    300
acctcatcaa cgaggcctgc tgggatatta gctccagcgg tgtaaacctg cagagcatgg    360
actcgtccca cgtctctttg gtgcagctca ccctgcggtc tgagggcttc gacacctacc    420
gctgcgaccg caacctggcc atgggcgtga acctcaccag tatgtccaaa atactaaaat    480
gcgccggcaa tgaagatatc attacactaa gggccgaaga taacgcggat accttggcgc    540
tagtatttga agcaccaaac caggagaaag tttcagacta tgaaatgaag ttgatggatt    600
tagatgttga acaacttgga attccagaac aggagtacag ctgtgtagta aagatgcctt    660
ctggtgaatt tgcacgtata tgccgagatc tcagccatat tggagatgct gttgtaattt    720
cctgtgcaaa agacggagtg aaattttctg caagtggaga acttggaaat ggaaacatta    780
aattgtcaca gacaagtaat gtcgataaag aggaggaagc tgttaccata gagatgaatg    840
aaccagttca actaactttt gcactgaggt acctgaactt ctttacaaaa gccactccac    900
tctcttcaac ggtgacactc agtatgtctg cagatgtacc ccttgttgta gagtataaaa    960
ttgcggatat gggacactta aaatactact tggctcccaa gatcgaggat gaagaaggat   1020
cttaggcatt cttaaaattc aagaaaataa aactaagctc tttgagaact gcttctaaga   1080
```

```
tgccagcata tactgaagtc ttttctgtca ccaaatttgt acctctaagt acatatgtag   1140
atattgtttt ctgtaaataa cctattttt tctctattct ctgcaatttg tttaaagaat   1200
aaagtccaaa gtcagatctg gtctagttaa cctagaagta tttttgtctc ttagaaatac   1260
ttgtgatttt tataatacaa aagggtcttg actctaaatg cagttttaag aattgttttt   1320
gaatttaaat aaagttactt gaatttcaaa catca                             1355
```

<210> SEQ ID NO 2
<211> LENGTH: 261
<212> TYPE: PRT
<213> ORGANISM: Homo sapiens

<400> SEQUENCE: 2

```
Met Phe Glu Ala Arg Leu Val Gln Gly Ser Ile Leu Lys Lys Val Leu
1               5                   10                  15

Glu Ala Leu Lys Asp Leu Ile Asn Glu Ala Cys Trp Asp Ile Ser Ser
            20                  25                  30

Ser Gly Val Asn Leu Gln Ser Met Asp Ser Ser His Val Ser Leu Val
        35                  40                  45

Gln Leu Thr Leu Arg Ser Glu Gly Phe Asp Thr Tyr Arg Cys Asp Arg
    50                  55                  60

Asn Leu Ala Met Gly Val Asn Leu Thr Ser Met Ser Lys Ile Leu Lys
65                  70                  75                  80

Cys Ala Gly Asn Glu Asp Ile Ile Thr Leu Arg Ala Glu Asp Asn Ala
                85                  90                  95

Asp Thr Leu Ala Leu Val Phe Glu Ala Pro Asn Gln Glu Lys Val Ser
            100                 105                 110

Asp Tyr Glu Met Lys Leu Met Asp Leu Asp Val Glu Gln Leu Gly Ile
        115                 120                 125

Pro Glu Gln Glu Tyr Ser Cys Val Val Lys Met Pro Ser Gly Glu Phe
    130                 135                 140

Ala Arg Ile Cys Arg Asp Leu Ser His Ile Gly Asp Ala Val Val Ile
145                 150                 155                 160

Ser Cys Ala Lys Asp Gly Val Lys Phe Ser Ala Ser Gly Glu Leu Gly
                165                 170                 175

Asn Gly Asn Ile Lys Leu Ser Gln Thr Ser Asn Val Asp Lys Glu Glu
            180                 185                 190

Glu Ala Val Thr Ile Glu Met Asn Glu Pro Val Gln Leu Thr Phe Ala
        195                 200                 205

Leu Arg Tyr Leu Asn Phe Phe Thr Lys Ala Thr Pro Leu Ser Ser Thr
    210                 215                 220

Val Thr Leu Ser Met Ser Ala Asp Val Pro Leu Val Val Glu Tyr Lys
225                 230                 235                 240

Ile Ala Asp Met Gly His Leu Lys Tyr Tyr Leu Ala Pro Lys Ile Glu
                245                 250                 255

Asp Glu Glu Gly Ser
            260
```

<210> SEQ ID NO 3
<211> LENGTH: 13
<212> TYPE: PRT
<213> ORGANISM: Homo sapiens

<400> SEQUENCE: 3

```
Leu Asp Val Glu Gln Leu Gly Ile Pro Glu Gln Glu Tyr
1               5                   10
```

```
<210> SEQ ID NO 4
<211> LENGTH: 8
<212> TYPE: PRT
<213> ORGANISM: Homo sapiens

<400> SEQUENCE: 4

Leu Gly Ile Pro Glu Gln Glu Tyr
1               5
```